US010449211B2

(12) United States Patent
Katibah et al.

(10) Patent No.: US 10,449,211 B2
(45) Date of Patent: Oct. 22, 2019

(54) COMPOSITIONS AND METHODS FOR ACTIVATING "STIMULATOR OF INTERFERON GENE"—DEPENDENT SIGNALLING

(71) Applicant: ADURO BIOTECH, INC., Berkeley, CA (US)

(72) Inventors: George Edwin Katibah, Fremont, CA (US); David Kanne, Corte Madera, CA (US); Leonard Sung, San Mateo, CA (US); Kelsey Gauthier, Alameda, CA (US); Laura Hix Glickman, Oakland, CA (US); Justin Leong, Union City, CA (US); Sarah M. McWhirter, Albany, CA (US); Thomas W. Dubensky, Jr., Berkeley, CA (US)

(73) Assignee: ADURO BIOTECH, INC., Berkeley, CA (US)

( * ) Notice: Subject to any disclaimer, the term of this patent is extended or adjusted under 35 U.S.C. 154(b) by 12 days.

(21) Appl. No.: 15/556,982

(22) PCT Filed: Mar. 9, 2016

(86) PCT No.: PCT/US2016/021597
§ 371 (c)(1),
(2) Date: Sep. 8, 2017

(87) PCT Pub. No.: WO2016/145102
PCT Pub. Date: Sep. 15, 2016

(65) Prior Publication Data

US 2018/0064745 A1 Mar. 8, 2018

Related U.S. Application Data

(60) Provisional application No. 62/131,235, filed on Mar. 10, 2015.

(51) Int. Cl.

| | |
|---|---|
| ***A01N 43/04*** | (2006.01) |
| ***A61K 31/70*** | (2006.01) |
| ***A61K 31/7084*** | (2006.01) |
| ***C07H 21/02*** | (2006.01) |
| ***C07H 21/00*** | (2006.01) |
| ***A61K 39/39*** | (2006.01) |
| ***C07H 19/213*** | (2006.01) |
| ***A61P 37/06*** | (2006.01) |
| ***A61P 29/00*** | (2006.01) |
| ***A61P 35/00*** | (2006.01) |
| ***A61P 11/06*** | (2006.01) |
| ***A61P 3/10*** | (2006.01) |

(52) U.S. Cl.
CPC .......... *A61K 31/7084* (2013.01); *A61K 39/39* (2013.01); *A61P 3/10* (2018.01); *A61P 11/06* (2018.01); *A61P 29/00* (2018.01); *A61P 35/00* (2018.01); *A61P 37/06* (2018.01); *C07H 19/213* (2013.01); *C07H 21/00* (2013.01); *C07H 21/02* (2013.01); *Y02A 50/463* (2018.01)

(58) Field of Classification Search
None
See application file for complete search history.

(56) References Cited

U.S. PATENT DOCUMENTS

| | | | |
|---|---|---|---|
| 4,978,672 | A | 12/1990 | Bowman et al. |
| 5,547,941 | A | 8/1996 | Battistini et al. |
| 5,637,483 | A | 6/1997 | Dranoff et al. |
| 5,698,432 | A | 12/1997 | Oxford |
| 5,811,097 | A | 9/1998 | Allison et al. |
| 5,904,920 | A | 5/1999 | Dranoff et al. |
| 5,985,290 | A | 11/1999 | Jaffee et al. |
| 6,033,674 | A | 3/2000 | Jaffee et al. |
| 6,277,368 | B1 | 8/2001 | Hiserodt et al. |
| 6,350,445 | B1 | 2/2002 | Jaffee et al. |
| 6,464,973 | B1 | 10/2002 | Levitsky et al. |
| 6,689,607 | B2 | 2/2004 | Ni et al. |
| 7,169,791 | B2 | 1/2007 | Breitenstein et al. |
| 7,473,761 | B2 | 1/2009 | Albert et al. |
| 7,482,367 | B2 | 1/2009 | Alkawa et al. |
| 7,569,555 | B2 | 8/2009 | Karaolis |

(Continued)

FOREIGN PATENT DOCUMENTS

| | | | |
|---|---|---|---|
| CN | 102199183 | A | 9/2011 |
| CN | 102199183 | B | 12/2013 |

(Continued)

OTHER PUBLICATIONS

Shanahan et al. Biochemistry (2013), vol. 52, pp. 365-377.*

(Continued)

*Primary Examiner* — Patrick T Lewis

(74) *Attorney, Agent, or Firm* — Actuity Law Group, PC; Michael A. Whittaker

(57) ABSTRACT

The present invention provides highly active cyclic-di-nucleotide (CDN) immune stimulators that activate DCs via a recently discovered cytoplasmic receptor known as STING (Stimulator of Interferon Genes), In particular, the CDNs of the present invention are provided in the form of a composition comprising one or more cyclic purine dinucleotides induce human STING-dependent type I interferon production, wherein the cyclic purine dinucleotides present in the composition are 2'-fluoro substituted, bis-3',5'CDNs, and most preferably one or more 2',2"-diF-Rp,Rp, bis-3', 5'CDNs.

10 Claims, 16 Drawing Sheets

Specification includes a Sequence Listing.

(56) References Cited

U.S. PATENT DOCUMENTS

| | | | |
|---|---|---|---|
| 7,592,326 | B2 | 9/2009 | Karaolis |
| 7,598,257 | B2 | 10/2009 | Rodgers et al. |
| 7,618,632 | B2 | 11/2009 | Collins et al. |
| 7,709,458 | B2 | 5/2010 | Karaolis |
| 7,767,675 | B2 | 8/2010 | Zhuo et al. |
| 7,812,135 | B2 | 10/2010 | Smith et al. |
| 7,867,493 | B2 | 1/2011 | Damiano et al. |
| 7,943,743 | B2 | 5/2011 | Korman et al. |
| 8,008,449 | B2 | 8/2011 | Korman et al. |
| 8,012,469 | B2 | 9/2011 | Levitsky et al. |
| 8,039,479 | B2 | 10/2011 | Michellys et al. |
| 8,178,563 | B2 | 5/2012 | Gao et al. |
| 8,263,635 | B2 | 9/2012 | Bock et al. |
| 8,354,509 | B2 | 1/2013 | Carven |
| 8,367,716 | B2 | 2/2013 | Karaolis |
| 8,372,858 | B2 | 2/2013 | Michellys et al. |
| 8,388,967 | B2 | 3/2013 | Smith et al. |
| 8,415,355 | B2 | 4/2013 | Besong et al. |
| 8,420,645 | B2 | 4/2013 | Weng et al. |
| 8,450,310 | B2 | 5/2013 | Drysdale et al. |
| 8,519,129 | B2 | 8/2013 | Marsilje et al. |
| 8,546,336 | B2 | 10/2013 | Charest et al. |
| 8,552,002 | B2 | 10/2013 | Ding et al. |
| 8,552,003 | B2 | 10/2013 | Chen et al. |
| 8,552,156 | B2 | 10/2013 | Takayanagi et al. |
| 8,562,997 | B2 | 10/2013 | Jaiswal et al. |
| 8,563,556 | B2 | 10/2013 | Giron et al. |
| 8,586,023 | B2 | 11/2013 | Shiku et al. |
| 8,591,886 | B2 | 11/2013 | Ponath et al. |
| 8,609,089 | B2 | 12/2013 | Langermann et al. |
| 8,685,980 | B2 | 4/2014 | Besong et al. |
| 8,709,424 | B2 | 4/2014 | Schebye et al. |
| 8,728,476 | B2 | 5/2014 | Van Den Berg |
| 8,735,551 | B2 | 5/2014 | Elis et al. |
| 8,895,705 | B2 | 11/2014 | Medema et al. |
| 9,090,646 | B2 | 7/2015 | Jones et al. |
| 9,549,944 | B2 | 1/2017 | Dubensky et al. |
| 9,597,391 | B2 | 3/2017 | Ebensen et al. |
| 9,695,212 | B2 | 7/2017 | Dubensky, Jr. et al. |
| 9,718,848 | B2 | 8/2017 | Adams et al. |
| 9,724,408 | B2 | 8/2017 | Dubensky, Jr. et al. |
| 9,840,533 | B2 | 12/2017 | Patel et al. |
| 9,994,607 | B2 | 6/2018 | Adams et al. |
| 10,011,630 | B2 | 7/2018 | Vernejoul et al. |
| 10,047,115 | B2 | 8/2018 | Biggadike et al. |
| 10,092,644 | B2 | 10/2018 | Yan et al. |
| 10,106,574 | B2 | 10/2018 | Altman et al. |
| 10,131,686 | B2 | 11/2018 | Patel et al. |
| 10,189,873 | B2 | 1/2019 | Dubensky et al. |
| 2007/0142401 | A1 | 6/2007 | Auberson et al. |
| 2008/0286296 | A1* | 11/2008 | Ebensen ............ A61K 37/7084 424/194.1 |
| 2010/0028330 | A1 | 2/2010 | Collins et al. |
| 2010/0056576 | A1 | 3/2010 | Burger et al. |
| 2010/0105667 | A1 | 4/2010 | Furet et al. |
| 2010/0150946 | A1 | 6/2010 | Jooss et al. |
| 2010/0310602 | A1 | 12/2010 | Reed et al. |
| 2011/0150892 | A1 | 6/2011 | Thudium et al. |
| 2012/0039906 | A1 | 2/2012 | Olive |
| 2012/0114649 | A1 | 5/2012 | Langermann et al. |
| 2012/0252785 | A1 | 10/2012 | Griffin et al. |
| 2013/0225574 | A1 | 8/2013 | Caravatti et al. |
| 2014/0044728 | A1 | 2/2014 | Takayanagi et al. |
| 2014/0072566 | A1 | 3/2014 | Kwon |
| 2014/0155345 | A1 | 6/2014 | Jones et al. |
| 2014/0205653 | A1 | 7/2014 | Dubensky, Jr. et al. |
| 2014/0341976 | A1 | 11/2014 | Dubensky et al. |
| 2015/0210769 | A1 | 7/2015 | Freeman et al. |
| 2015/0218274 | A1 | 8/2015 | Sabatos-Peyton et al. |
| 2015/0259420 | A1 | 9/2015 | Triebel et al. |
| 2017/0283454 | A1 | 10/2017 | Dubensky, Jr. et al. |
| 2018/0064745 | A1 | 3/2018 | Katibah et al. |
| 2018/0118777 | A1 | 5/2018 | Patel et al. |

FOREIGN PATENT DOCUMENTS

| | | | |
|---|---|---|---|
| EP | 0296122 | A2 | 12/1988 |
| EP | 1611112 | A1 | 1/2006 |
| EP | 1682103 | A1 | 7/2006 |
| EP | 1441737 | B1 | 8/2006 |
| EP | 1870399 | A1 | 12/2007 |
| EP | 2099447 | B1 | 11/2012 |
| EP | 2051990 | B1 | 2/2013 |
| EP | 2021328 | B1 | 4/2013 |
| EP | 2581113 | A1 | 4/2013 |
| EP | 1866339 | B1 | 5/2013 |
| EP | 2445903 | B1 | 3/2014 |
| EP | 2344474 | B1 | 9/2015 |
| EP | 2474545 | B1 | 11/2016 |
| EP | 2606070 | B1 | 12/2016 |
| WO | 9749395 | A1 | 12/1997 |
| WO | 9806842 | A1 | 2/1998 |
| WO | 9835958 | A1 | 8/1998 |
| WO | 9903854 | A1 | 1/1999 |
| WO | 9920758 | A1 | 4/1999 |
| WO | 9940196 | A1 | 8/1999 |
| WO | 0103720 | A2 | 1/2001 |
| WO | 0210192 | A2 | 2/2002 |
| WO | 0222577 | A2 | 3/2002 |
| WO | 03037347 | A1 | 5/2003 |
| WO | 03077914 | A1 | 9/2003 |
| WO | 2004005281 | A1 | 1/2004 |
| WO | 2004045532 | A2 | 6/2004 |
| WO | 2004060319 | A2 | 7/2004 |
| WO | 2004072051 | A1 | 8/2004 |
| WO | 2005007190 | A1 | 1/2005 |
| WO | 2005039549 | A1 | 5/2005 |
| WO | 2005055808 | A2 | 6/2005 |
| WO | 2005073224 | A2 | 8/2005 |
| WO | 2005115451 | A2 | 12/2005 |
| WO | 2006083289 | A2 | 8/2006 |
| WO | 2006121168 | A1 | 11/2006 |
| WO | 2006122806 | A2 | 11/2006 |
| WO | 2007005874 | A2 | 1/2007 |
| WO | 2007024945 | A1 | 3/2007 |
| WO | 2007030377 | A1 | 3/2007 |
| WO | 2007070514 | A1 | 6/2007 |
| WO | 2007084786 | A1 | 7/2007 |
| WO | 2007131201 | A2 | 11/2007 |
| WO | 2007133822 | A1 | 11/2007 |
| WO | 2008016893 | A1 | 2/2008 |
| WO | 2008073687 | A2 | 6/2008 |
| WO | 2008106692 | A1 | 9/2008 |
| WO | 2009101611 | A1 | 8/2009 |
| WO | 2009114335 | A2 | 9/2009 |
| WO | 2009115562 | A2 | 9/2009 |
| WO | 2009141386 | A1 | 11/2009 |
| WO | 2010002655 | A2 | 1/2010 |
| WO | 2010003118 | A1 | 1/2010 |
| WO | 2010007120 | A1 | 1/2010 |
| WO | 2010019570 | A2 | 2/2010 |
| WO | 2010026124 | A1 | 3/2010 |
| WO | 2010027827 | A2 | 3/2010 |
| WO | 2010029082 | A1 | 3/2010 |
| WO | 2010060937 | A2 | 6/2010 |
| WO | 2010077634 | A1 | 7/2010 |
| WO | 2010101849 | A1 | 9/2010 |
| WO | 2010104883 | A1 | 9/2010 |
| WO | 2010149755 | A1 | 12/2010 |
| WO | 2011003025 | A1 | 1/2011 |
| WO | 2011025927 | A1 | 3/2011 |
| WO | 2011028683 | A1 | 3/2011 |
| WO | 2011051726 | A2 | 5/2011 |
| WO | 2011066342 | A2 | 6/2011 |
| WO | 2011076786 | A1 | 6/2011 |
| WO | 2011090754 | A1 | 7/2011 |
| WO | 2011101409 | A1 | 8/2011 |
| WO | 2011155607 | A1 | 12/2011 |
| WO | 2012004367 | A1 | 1/2012 |
| WO | 2012022814 | A1 | 2/2012 |
| WO | 2012068360 | A1 | 5/2012 |
| WO | 2013039954 | A1 | 3/2013 |
| WO | 2013079174 | A1 | 6/2013 |

(56) References Cited

FOREIGN PATENT DOCUMENTS

| | | | |
|---|---|---|---|
| WO | 2013111105 A1 | | 8/2013 |
| WO | 2013124826 A1 | | 8/2013 |
| WO | 2013166000 A1 | | 11/2013 |
| WO | 2013171639 A1 | | 11/2013 |
| WO | 2013171640 A1 | | 11/2013 |
| WO | 2013171641 A1 | | 11/2013 |
| WO | 2013171642 A1 | | 11/2013 |
| WO | 2013184757 A1 | | 12/2013 |
| WO | 2014008218 A1 | | 1/2014 |
| WO | 2014012479 A1 | | 1/2014 |
| WO | 2014018632 A1 | | 1/2014 |
| WO | 2014072493 A1 | | 5/2014 |
| WO | 2014085318 A1 | | 6/2014 |
| WO | 2014093936 A1 | | 6/2014 |
| WO | 2014141104 A1 | | 9/2014 |
| WO | 2014151616 A1 | | 9/2014 |
| WO | 2014160160 A2 | | 10/2014 |
| WO | 2014179335 A1 | | 11/2014 |
| WO | 2014179760 | | 11/2014 |
| WO | 2014189805 A1 | | 11/2014 |
| WO | 2014189806 | | 11/2014 |
| WO | 2015017652 | | 2/2015 |
| WO | 2015026684 | | 2/2015 |
| WO | 2015066188 | | 5/2015 |
| WO | 2015074145 A1 | | 5/2015 |
| WO | 2015077354 A1 | | 5/2015 |
| WO | 2015185565 | | 12/2015 |
| WO | 2016/096174 A1 | † | 6/2016 |
| WO | 2016096174 A1 | | 6/2016 |
| WO | 2016096577 A1 | | 6/2016 |
| WO | 2016120305 A1 | | 8/2016 |
| WO | 2017027645 A1 | | 2/2017 |
| WO | 2017027646 A1 | | 2/2017 |
| WO | 2017093933 A1 | | 6/2017 |
| WO | 2017123657 A1 | | 7/2017 |
| WO | 2017123669 A1 | | 7/2017 |

OTHER PUBLICATIONS

Karaolis et al. Biochemical and Biophysical Research Communications (2005), vol. 329, pp. 40-45.*

Eckstein Nucleic Acid Therapeutics (2014), vol. 24, No. 6, pp. 374-387.*

International Search Report and Written Opinion issued in PCT/US2016/021597 dated Jun. 10, 2016, Applicant Aduro Biotech, Inc. (10 pages).

Fu et al., STING agonist formulated cancer vaccines can cure established tumors resistant to PD-1 blockade. Sci Transl Med. Apr. 15, 2015;7(283):283ra52 (+ Supplementary materials, 25 pp total).

Li et al., Hydrolysis of 2'3'-cGAMP by ENPP1 and design of nonhydrolyzable analogs. Nat Chem Biol. Dec. 2014;10(12):1043-1048.

Lioux et al., Design, Synthesis, and Biological Evaluation of Novel Cyclic Adenosine-Inosine Monophosphate (cAIMP) Analogs That Activate Stimulator of Interferon Genes (STING). J Med Chem. Nov. 23, 2016;59(22):10253-10267.

Ablasser et al., cGAS produces 2'-5'-linked cdn second messenger that activates STING. Nature. Jun. 20, 2013;498(7454):380-384.

Aslandis and , de Jong, Ligation-independent cloning of PCR products (LIC-PCR). Nucleic Acids Res. Oct. 25, 1990;18(20):6069-6074.

Bala et al., PLGA Nanoparticles in Drug Delivery: The State of the Art. Crit Rev Ther Drug Cartier Syst. 2004;21(5):387-422.

Barber, Cytoplasmic DNA innate immune pathways. Immunol Rev. Sep. 2011;243(1):99-108.

Battistini et al., Stereoselective Synthesis of Cyclic Dinucleotide Phosphorothioates. Tetrahedron, 1993;49(5):1115-1132.

Burdette and Vance, STING and the innate immune response to nucleic acids in the cytosol. Nat Immunol. Jan. 2013;14(1):19-26.

Burdette et al., STING is a direct innate immune sensor of cyclic di-GMP. Nature. Sep. 25, 2011;478(7370):515-518 doi:10.1038/nature10429.

Caskey et al., Synthetic double-stranded RNA induces innate immune responses similar to a live viral vaccine in humans. J Exp Med. Nov. 21, 2011;208(12):2357-2366.

Civril et al., Structural mechanism of cytosolic DNA sensing by cGAS. Nature. Jun. 20, 2013;498(7454):332-337.

Coffman et al., Vaccine adjuvants: putting innate immunity to work. Immunity. Oct. 29, 2010;33(4):492-503.

Conlon et al., Mouse, but not Human STING, Binds and Signals in Response to the Vascular Disrupting Agent 5,6-Dimethylxanthenone-4-Acetic Acid. J Immunol. May 15, 2013;190(10):5216-5225.

Crimmins et al., Listeria monocytogenes multidrug resistance transporters activate a cytosolic surveillance pathway of innate immunity. Proc Natl Acad Sci U S A. Jul. 22, 2008;105(29):10191-10196.

Danilchanka and Mekalanos, Cyclic Dinucleotides and the Innate Immune Response. Cell. Aug. 29, 2013;154(5):962-970.

Davies et al., Coordinated Regulation of Accessory Genetic Elements Produces Cyclic Di-Nucleotides for V. cholerae Virulence. Cell. Apr. 13, 2012;149(2):358-370.

Dessureault et al., A phase-I Trial Using a Universal GM-CSF-producing and CD40L-expressing Bystander Cell Line (GM.CD40L) in the Formulation of Autologous Tumor Cell-based Vaccines for Cancer Patients with Stage IV disease. Ann Surg Oncol. Feb. 2007;14(2):869-884.

Diner et al., The Innate Immune DNA Sensor cGAS Produces a Noncanonical Cyclic Dinucleotide that Activates Human STING. Cell Rep. May 30, 2013;3(5):1355-1361.

Dubensky et al., Abstract 4573: A novel tumor vaccine with cyclic dinucleotides—can induce potent anti-tumor responses in vivo. Cancer Res. Apr. 15, 2013;73(8 Suppl):4573-4573.

Dubensky et al., Rationale, progress, and development of vaccines utilizing STING-activating cyclic dinucleotide adjuvants. Ther Adv Vaccines. Nov. 2013;1(4):131-143.

Dubensky and Reed, Adjuvants for cancer vaccines. Semin Immunol. Jun. 2010;22(3):155-161.

Dubensky, oral slide presentation "Development of Cyclic Dinucleotides as STING-Targeted Molecular Adjuvants." Immunological Mechanisms of Vaccination seminar, Fairmont Chateau Laurier, Ottawa, Ontario Canada Dec. 14, 2012:13 pages.

Dubensky, Jr. et al., 2013 Annual Meeting of the Society for Immunotherapy of Cancer presented Nov. 9, 2013. "Modified STING-Activating Cyclic Dinucleotide Derivatives Significantly Enhance the Anti-Tumor Activity of Therapeutic Vaccines." (24 pages).

Dubensky, Jr. et al., 2014 Keystone Vaccines Symposia presented Oct. 9, 2014 "Development of Human STING-Activating Synthetic Cyclic Dinucleotide Derivatives as Adjuvants for Cancer Immunotherapy and Infectious Disease." (30 pages).

Eager and Nemunaitis, GM-CSF Gene-Transduced Tumor Vaccines. Mol Ther. Jul. 2005;12(1):18-27.

Ebensen et al., Bis-(3',5')-cyclic dimeric adenosine monophosphate: strong Th1/Th2/Th17 promoting mucosal adjuvant. Vaccine. Jul. 18, 2011;29(32):5210-5220.

Einstein et al., Comparison of the immunogenicity and safety of Cervarix and Gardasil human papillomavirus (HPV) cervical cancer vaccines in healthy women aged 18-45 years. Hum Vaccin. Oct. 2009;5(10):705-719.

Fitzgerald et al., IKKepsilon and TBK1 are essential components of the IRF3 signaling pathway. Nat Immunol. May 2003;4(5):491-496.

Gao et al., Cyclic [G(20,50)pA(30,50)p] Is the Metazoan Second Messenger Produced by DNA-Activated Cyclic GMP-AMP Synthase. Cell. May 23, 2013;153(5):1094-1107.

Gao et al., Structure-Function Analysis of STING Activation by c[G(2',5')pA(3',5')p] and Targeting by Antiviral DMXAA. Cell. Aug. 15, 2013;154(4):748-762.

Hamid et al., Safety and Tumor Responses with Lambrolizumab (Anti-PD-1) in Melanoma. N Engl J Med. Jul. 11, 2013;369(2):134-144.

Hughes, Nanostructure-mediated drug delivery. Nanomedicine. Mar. 2005;1(1):22-30.

Ireton and Gale, RIG-I Like Receptors in Antiviral Immunity and Therapeutic Applications. Viruses. Jun. 2011;3(6):906-919.

(56) References Cited

OTHER PUBLICATIONS

Ishikawa and Barber, STING an Endoplasmic Reticulum Adaptor that Facilitates Innate Immune Signaling. Nature. Oct. 2, 2008;455(7213):674-678.
Iwasaki and Medzhitov, Regulation of adaptive immunity by the innate immune system. Science. Jan. 15, 2010;327(5963):291-295.
Jin et al., Identification and characterization of a loss-of-function human MPYS variant. Genes Immun. Jun. 2011;12(4):263-269.
Kastenmuller et al., Protective T cell immunity in mice following protein-TLR7/8 agonist-conjugate immunization requires aggregation, type I IFN, and multiple DC subsets. J Clin Invest. May 2011;121(5):1782-1796.
Kranzusch et al., Structure of Human cGAS Reveals a Conserved Family of Second-Messenger Enzymes in Innate Immunity. Cell Rep. May 30, 2013;3(5):1362-1368.
Leber et al., Distinct TLR- and NLR-Mediated Transcriptional Responses to an Intracellular Pathogen. PLoS Pathog. Jan. 2008;4(1):e6.
Luo et al, Selective binding of 2'-F-c-di-GMP to Ct-E88 and Cb-E43, new class I riboswitches from Clostridium tetani and Clostridium botulinum respectively. Mol Biosyst. Jun. 2013;9(6):1535-1539.
McCune et al., Active specific immunotherapy with tumor cells and Corynebacterium parvum: A phase I study. Cancer. May 1979;43(5):1619-1623.
McWhirter et al., A host type I interferon response is induced by cytosolic sensing of the bacterial second messenger cyclic-di-GMP. J Exp Med. Aug. 31, 2009;206(9):1899-1911.
Meehan et al. Nuclease-Resistant c-di-AMP Derivatives That Differentially Recognize RNA and Protein Receptors. Biochemistry. Feb. 16, 2016;55(6):837-849.
Muderhwa et al., Oil-in-water liposomal emulsions: Characterization and potential use in vaccine delivery. J Pharm Sci. Dec. 1999;88(12):1332-1339.
Nelson and Griswold, A computer program for calculating antibody affinity constants. Comput Methods Programs Biomed. Jul.-Aug. 1988;27(1):65-68.
Pandey et. al., Microbial Sensing by Toll-Like Receptors and Intracellular Nucleic Acid Sensors. Cold Spring Harb Perspect Biol. Oct. 9, 2014;7(1):a016246.
Pulendran and Ahmed el al., Immunological mechanisms of vaccination. Nature Immunol. 12: 509-17, 2011.
Reed et al., New horizons in adjuvants for vaccine development. Trends Immunol. Jan. 2009;30(1):23-32.
Römling et al., Cyclic di-GMP: the First 25 Years of a Universal BacterialSecond Messenger. Microbiol Mol Biol Rev. Mar. 2013;77(1):1-52.
Sauer et al., The N-Ethyl-N-Nitrosourea-Induced Goldenticket Mouse Mutant Reveals an Essential Function of Sting in the In Vivo Interferon Response to Listeria monocytogenes and Cyclic Dinucleotides. Infect Immun. Feb. 2011;79(2):688-694.
Shanahan et al., Differential analogue binding by two classes of c-di-GMP riboswitches. J Am Chem Soc. Oct. 5, 2011;133(39):15578-15592.
Shu et al., Structure of STING bound to cyclic di-GMP reveals the mechanism of cyclic dinucleotide recognition by the immune system. Nat Struct Mol Biol. Jun. 24, 2012;19(7):722-724.
Office Action issued by the USPTO in U.S. Appl. No. 15/630,741 dated Nov. 13, 2018 (7 pages total).
Strbo et al., Secreted heat shock protein gp96-Ig: next-generation vaccines for cancer and infectious diseases. Immunol Res. Dec. 2013;57(1-3):311-325.
Sun et al., Cyclic GMP-AMP Synthase Is a Cytosolic DNA Sensor That Activates the Type I Interferon Pathway. Science. Feb. 15, 2013;339(6121):786-791.
Tchigvintsev et al., Structural Insight into the Mechanism of c-di-GMP Hydrolysis by EAL Domain Phosphodiesterases. J Mol Biol. Sep. 24, 2010;402(3):524-538.
Tezuka et al., Synthesis of 2'-Modified Cyclic Bis(3'-5')diadenylic Acids (c-di-AMPs) and Their Promotion of Cell Division in a Freshwater Green Alga. Chem Lett. 2012;41:1723-1725.
Van Erp et al., Application of a sol particle immunoassay to the determination of affinity constants of monoclonal antibodies. J Immunoassay. 1991;12(3):425-443.
Vance et al., Patterns of Pathogenesis: Discrimination of Pathogenic and Nonpathogenic Microbes by the Innate Immune System. Cell Host Microbe. Jul. 23, 2009;6(1):10-21.
Ward et al., Binding activities of a repertoire of single immunoglobulin variable domains secreted from *Escherichia coli*. Nature. Oct. 12, 1989;341(6242):544-546.
Wilson et al., Simplified conjugation chemistry for coupling peptides to F(ab') fragments: autologous red cell agglutination assay for HIV-1 antibodies. J Immunol Methods. Oct. 14, 1994;175(2):267-273.
Witte et al., Cyclic di-AMP Is Critical for Listeria monocytogenes Growth, Cell Wall Homeostasis, and Establishment of Infection. MBio. May 28, 2013;4(3):e00282-13 (10 pages).
Woodward et al., c-di-AMP secreted by intracellular Listeria monocytogenes activates a host type I interferon response. Science. Jun. 25, 2010;328(5986):1703-1705.
Woodward et al., Supporting online material May 27, 2010 on Science Express DOI: 10.1126/science.1189801 (15 pages).
Wu et al., Cyclic GMP-AMP Is an Endogenous Second Messenger in Innate Immune Signaling by Cytosolic DNA. Science. Feb. 15, 2013;339(6121):826-830—includes supplemental material (15 pages total).
Wu et al., Corrected Supplemental Materials for Cyclic GMP-AMP is an Endogeneous Second Messenger in Innate Immune Signaling by Cytosolic DNA. Science, Jan. 10, 2013 :21 pages.
Xiao and Fitzgerald, The cGAS-STING Pathway for DNA Sensing. Mol Cell. Jul. 25, 2013;51(2):135-139.
Yamazaki et al., Cutting Edge: Tumor Secreted Heat Shock-Fusion Protein Elicits CD8 Cells for Rejection. J Immunol. Nov. 15, 1999;163(10):5178-5182.
Yan et al., Synthesis and immunostimulatory properties of the phosphorothioate analogues of cdiGMP. Bioorg Med Chem Lett. Oct. 15, 2008;18(20):5631-5634.
Yarmush et al., Coupling of antibody-binding fragments to solid-phase supports: site-directed binding of F(ab')2 fragments. J Biochem Biophys Methods. Dec. 1992;25(4):285-297.
Yi et al., Single Nucleotide Polymorphisms of Human STING Can Affect Innate Immune Response to Cyclic Dinucleotides. PLoS One. Oct. 21, 2013;8(10):e77846.
Zhang et al., Cyclic GMP-AMP Containing Mixed Phosphodiester Linkages Is an Endogenous High-Affinity Ligand for STING. Mol Cell. Jul. 25, 2013;51(2):226-235.
Zhao et al., Thiophosphate Analogs of c-di-GMP: Impact on Polymorphism. Nucleosides Nucleotides Nucleic Acids. May 2009;28(5):352-378.
Zhou et al., Potent suppression of c-di-GMP synthesis via I-site allosteric inhibition of diguanylate cyclases with 2'-F-c-di-GMP. Bioorg Med Chem. Jul. 15, 2013;21(14):4396-4404.
Zhou et al., Endo-S-c-di-GMP analogues-polymorphism and binding studies with class I riboswitch. Molecules. Nov. 9, 2012;17(11):13376-13389.
Extended European Search Report issued in EP 16762447 dated Sep. 27, 2018 (6 pages total).
Office Action issued in Panama Patent Application No. 91768-01 dated Jul. 16, 2018 (10 pages total)—Engl translation only.
U.S. Appl. No. 62/131,235.†

* cited by examiner
† cited by third party

FIG. 1
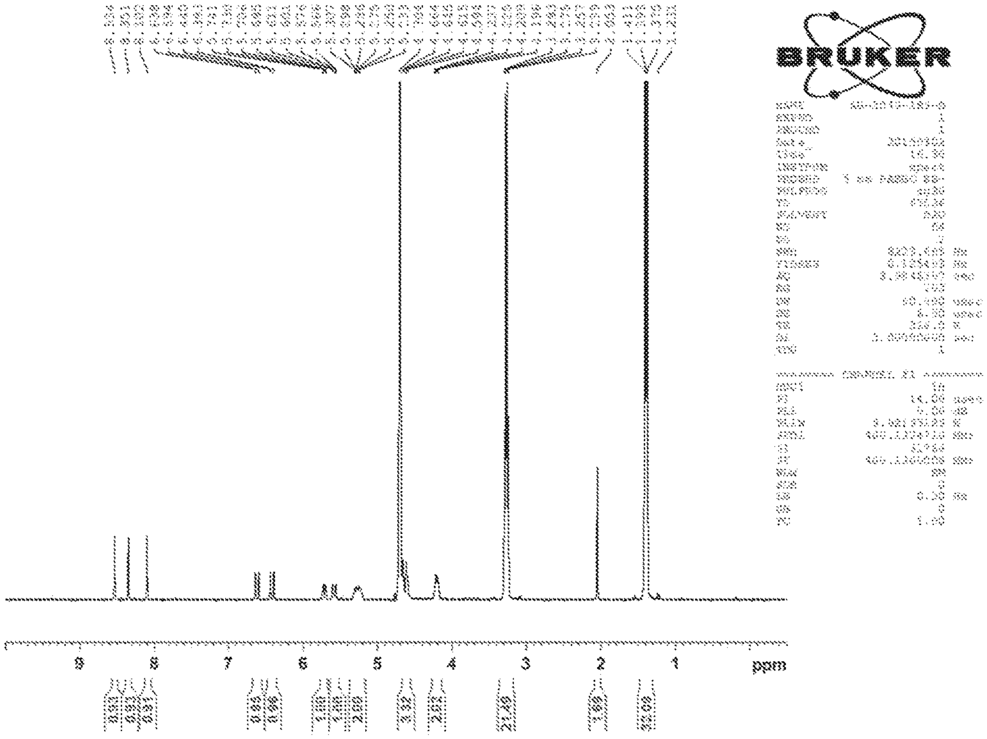
LC conditions: 2-50% acetonitrile in 10 mM TEAA – 5 micron column
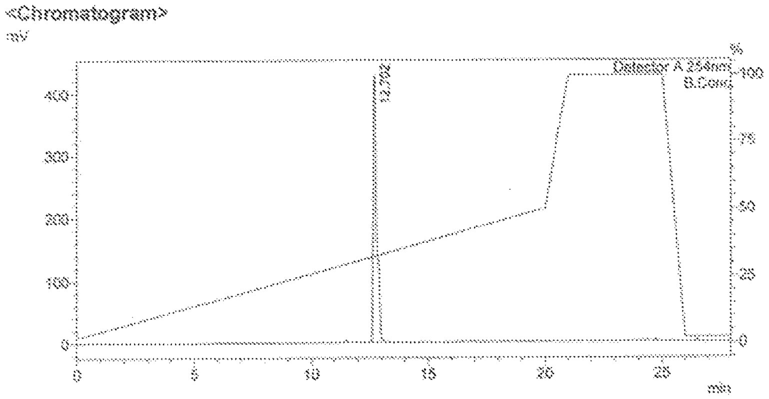

FIG. 4

```
1    mphsslhpsi  pcprghgaqk  aalvllsacl  vtlwglgepp  ehtlrylvlh  laslqlglll
61   ngvcslaeel  rhihsryrgs  ywrtvraclg  cplrrgalll  lsiyfyyslp  navgppftwm
121  lallglsqal  nillglkgla  paeisavcek  gnfnvahgla  wsyyigylrl  ilpelqarir
181  tynqhynnll  rgavsqrlyi  llpldcgvpd  nlsmadpnir  fldklpqqtg  dhagikdrvy
241  snsiyellen  gqragtcvle  yatplqtlfa  msqysqagfs  redrleqakl  fcrtledila
301  dapesqnncr  liayqepadd  ssfslsqevl  rhlrqeekee  vtvgslktsa  vpststmsqe
361  pellisgmek  plplrtdfs (SEQ ID NO: 1)
```

COMPOSITIONS AND METHODS FOR ACTIVATING "STIMULATOR OF INTERFERON GENE"—DEPENDENT SIGNALLING

The present invention is filed under 35 U.S.C. § 371 as the U.S. national phase of International Patent Application No. PCT/US2016/021597, filed Mar. 9, 2016, which designated the United States and claims the benefit of priority to U.S. Provisional Application No. 62/131,235 filed Mar. 10, 2015, each of which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Sep. 8, 2017, is named ADR_1004_US_SeqListing.txt and is 22 kilobytes in size.

BACKGROUND OF THE INVENTION

The following discussion of the background of the invention is merely provided to aid the reader in understanding the invention and is not admitted to describe or constitute prior art to the present invention.

New insights into the mechanisms underlying immune-evasion, together with combination treatment regimens that potentiate the potency of therapeutic vaccination-either directly or indirectly-through combination with immune checkpoint inhibitors or other therapies, have served as a basis for the development of vaccines or immune modulators that can prime or boost an effective adaptive immune response, consisting of tumor-specific $CD4^+$ and $CD8^+$ T cells specific for a targeted malignancy, resulting in an antitumor response and clinical benefit. How the innate immune system is engaged by targeted ligands shapes the development of an adaptive response and lends itself to the design of vaccines and immunomodulators (Reed et al., Trends Immunol., 30: 23-32, 2009; Dubensky and Reed, Semin. Immunol., 22: 155-61, 2010; Kastenmuller et al., J. Clin. Invest., 121: 1782-1796, 2011; Coffman et al., Immunity, 33: 492-503, 2010).

The cyclic dinucleotides CDNs cyclic-di-AMP (produced by *Listeria monocytogenes* and other bacteria) and its analogs cyclic-di-GMP and cyclic-GMP-AMP (cGAMP) are recognized by the host cell as a pathogen associated molecular pattern (PAMP), which bind to the pathogen recognition receptor (PRR) known as Stimulator of INterferon Genes (STING). STING is an adaptor protein in the cytoplasm of host mammalian cells which activates the TANK binding kinase (TBK1)-IRF3 and the NF-κB signaling axis, resulting in the induction of IFN-β and other gene products that strongly activate innate immunity. It is now recognized that STING is a component of the host cytosolic surveillance pathway (Vance et al., 2009), that senses infection with intracellular pathogens and in response induces the production of IFN-β, leading to the development of an adaptive protective pathogen-specific immune response consisting of both antigen-specific CD4 and CD8 T cells as well as pathogen-specific antibodies. Examples of cyclic purine dinucleotides are described in some detail in, for example: U.S. Pat. Nos. 7,709,458 and 7,592,326; patent applications WO2007/054279, WO2014/093936, and WO2014/189805; and Yan et al., Bioorg. Med. Chem Lett. 18: 5631 (2008).

An uncharacterized mouse gene with significant structural homology to the catalytic domain of human oligoadenylate synthase cyclic GMP-AMP synthase was reported to be the enzyme responsible for producing STING-binding CDNs in mammalian cells. Sun et al., Science 339(6121):786-91, 2013. Termed cyclic GMP-AMP Synthase (cGAS), this enzyme catalyzes the synthesis of cGAMP from ATP and GTP in the presence of DNA. This cGAMP then functions as a second messenger that binds to and activates STING. These cGAS-produced CDNs differed structurally from the bacterially produced CDNs in that they possess an unusual phosphodiester linkage. Thus, while the bacterially produced CDNs contain a bis-3',5' linkage between the two nucleotides, mammalian CDNs contained one 2',5' linkage and one 3',5' linkage, or a so-called "mixed linkage (ML) or non-canonical CDNs. These 2',5'-3',5' molecules bind STING with nM affinity, some 300-fold better than bacterial c-di-GMP.

Human STING (hSTING) also has known polymorphisms, including alleles encoding histidine at position 232, which are refractory to bis-3',5' (canonical) CDNs, but not 2',5'-3',5' (non-canonical, mixed linkage) CDNs (Diner et al., Cell Reports 3, 1355-61, 2013; Jin et al., Genes and Immunity, 12: 263-9, 2011). Single nucleotide polymorphisms in the hSTING gene have been reported to affect the responsiveness to bacterial-derived canonical CDNs (Diner et al., 2013: Gao et al., Cell 154, 748-762, 2013; Conlon et. al., J. Immunol. 190: 5216-5225, 2013). Five haplotypes of hSTING have been reported (WT, REF, HAQ, AQ and Q alleles), which vary at amino acid positions 71, 230, 232 and 293 (Jin et al., 2011; Yi et al., PLOS One 8: e77846, 2013). Cells expressing hSTING reportedly respond poorly to stimulation with bacterial CDNs cGAMP, c-di-AMP and c-di-GMP having bis-(3',5') linkages, but are responsive to the endogenously produced cGAS product, ML cGAMP (Diner et al., 2013). Thus, it has been suggested that the 2',5'-3',5' molecules represent much more potent physiological ligands in terms of hSTING targeting (Zhang et al., Mol. Cell. 51:226-35, 2013; Xiao and Fitzgerald, Mol. Cell 51: 135-39, 2013).

SUMMARY OF THE INVENTION

It is an object of the present invention to provide compositions and methods which modulate immune responses to diseases. It is a further object of the invention to provide compositions and methods which provide cyclic purine dinucleotide analogs that exhibit improved characteristics when employed for activation of mammalian, and preferably human, STING. It is yet a further object of the invention to provide compositions and methods for the treatment of cancer.

In a first aspect, the present invention provides compositions comprising: one or more mono- or di-fluoro substituted bis-3',5' cyclic purine dinucleotides ("mono- or di-F-CDN compounds"), or prodrugs, pharmaceutically acceptable salts, pharmaceutically acceptable solvates or pharmaceutically acceptable hydrates thereof, that bind to STimulator of INterferon Genes ("STING") and stimulate STING-dependent type I interferon production at concentrations at least 10-fold lower than one or more (and preferably each of) of bis-3',5' c-di-GMP (i.e. 3',3'-(G)(G)), bis-3',5' c-di-AMP (i.e. 3',3'-(A)(A) or CDA), or bis-3',5' c-GMP-AMP (i.e. 3',3'-(G)(A) or cGAMP) when measured using at least one human (h) STING allele. Preferably, this is measured using the hSTING(REF) allele described in Ishikawa, H., and Barber, G. N. (2008). *Nature* 455, 674-678, the protein sequence of which is NCBI Reference Sequence NP_938023 (SEQ ID NO: 1; FIG. 6). This is most preferably measured in vitro using a mammalian cell line (e.g., HEK293T cells) which does not express a functional STING endogenously, but has been modified to stably express the hSTING(REF) allele as described hereinafter (e.g. see Example 12).

In a related aspect, the present invention provides compositions comprising: one or more mono- or di-F-CDN compounds that bind at least one human STING allelic protein product with an affinity at least 10-fold higher than one or more of bis-3',5' c-di-GMP (i.e. 3',3'-(G)(G)), bis-3',5' c-di-AMP (i.e. 3',3'-(A)(A) or CDA), or bis-3',5' c-GMP-AMP (i.e. 3',3'-(G)(A) or cGAMP when measured using at least one human STING protein. Preferably, this is measured using isolated the protein encoded by the hSTING(REF) allele described (Ishikawa, H., and Barber, G. N. (2008). *Nature* 455, 674-678), the protein sequence of which is NCBI Reference Sequence NP_938023 using a method such as differential scanning fluorometry as described hereinafter (e.g. see Example 11).

As described hereinafter, substitution of one or both of the free 2'-hydroxyls with fluoro on the bis-3',5' cyclic purine dinucleotides of the present invention substantially improve their binding to human STING. A number of 2'-fluoro substituted CDNs find use in the present invention. Preferred 2'-fluoro substituted CDNs include, but are not limited to, those derived by substitution of one or both 2'-hydroxyls on c-di-AMP, c-di-GMP, c-di-IMP, c-AMP-GMP, c-AMP-IMP, c-GMP-IMP, and analogs, or prodrugs or pharmaceutically acceptable salts thereof. This list is not meant to be limiting. Additional aspects and embodiments of mono- or di-F-CDN compounds are described hereinafter.

In a second aspect, the present invention provides a mono- or di-fluoro substituted 3',5'-3',5' cyclic purine dinucleotide (mono- or di-F-CDN) compound of Formula I:

Formula I

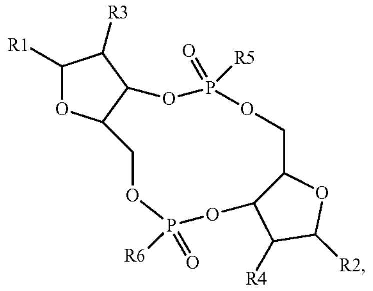

or a prodrug, pharmaceutically acceptable salt, pharmaceutically acceptable solvate or pharmaceutically acceptable hydrate thereof, wherein each R1 and R2 is independently a purine; each R3 and R4 is independently H, OH or F, provided that one or both of R3 and R4 are F; and each R5 and R6 is independently OH or SH.

In certain embodiments of the second aspect, each R5 and R6 is SH. In preferred embodiments when each R5 and R6 is SH, the compositions comprise one or more substantially pure Sp,Sp, Rp,Rp, Sp,Rp, or Rp,Sp stereoisomers. In some embodiments the compositions comprise one or more substantially pure Rp,Rp stereoisomers.

Purines R1 and R2 that may find use in the compounds described herein have the following general structures:

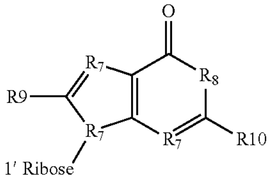

or

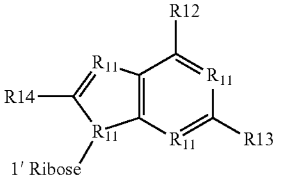

wherein:

each R7 or R11 is independently —CR— or —N—; R8 is —$C(R)_2$—, —O—, or —NR—;

each R9, R10, R12, R13, or R14 is independently selected from the group consisting of hydrogen, halogen, —CN, —OR, —SR, —$N(R)_2$, —C(O)R, —$CO_2R$, —S(O)R, —$S(O)_2R$, —$C(O)N(R)_2$, —$SO_2N(R)_2$, —OC(O)R, —N(R)C(O)R, —N(R)$N(R)_2$, —C═NOR, —N(R)C(O)$N(R)_2$, —N(R)$SO_2N(R)_2$, —N(R)$SO_2R$, —OC(O)$N(R)_2$ or an optionally substituted substituent selected from the group consisting of $C_{1-12}$ aliphatic, phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, and a 5-6 membered heteroaryl ring having 1-3 heteroatoms independently selected from nitrogen, oxygen, or sulfur, wherein each R is independently an optionally substituted substituent selected from the group consisting of $C_{1-12}$ aliphatic, phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, and a 5-6 membered heteroaryl ring having 1-3 heteroatoms independently selected from nitrogen, oxygen, or sulfur, or two R groups on the same nitrogen are taken together with their intervening atoms to form an optionally substituted 3-7 membered saturated, partially unsaturated, or heteroaryl ring having 1-4 heteroatoms independently selected from nitrogen, oxygen, or sulfur. Each $C_{1-12}$ aliphatic, phenyl, 3-7 membered saturated or partially unsaturated monocyclic carbocyclic ring, 7-10 membered saturated or partially unsaturated bicyclic carbocyclic ring, 3-7 membered saturated or partially unsaturated heterocyclic ring, 7-10 membered saturated or partially unsaturated bicyclic heterocyclic ring, and 5-6 membered heteroaryl ring, or two R groups on the same nitrogen taken together to form 3-7 membered saturated, partially unsaturated, or heteroaryl ring is optionally substituted with 1 to 5, 1 to 4, 1 to 3, 1 to 2, or 1 independently selected substituents selected from the group consisting of halogen, —CN, —$NO_2$, —OH, ═O, —$NH_2$, $C_{1-6}$ alkyl, $C_{1-6}$ alkoxy, $C_{1-6}$ alkylamino, and $C_{1-6}$ di-alkylamino.

In certain embodiments of the second aspect and embodiments thereof, each of R1 and R2 are independently selected from the group consisting of adenine, guanine, isoguanine, hypoxanthine, and xanthine or analogs thereof. In some embodiments, each of R1 and R2 are independently adenine or guanine. In some embodiments, one of R1 or R2 is adenine, and the other of R1 or R2 is guanine; each of R and R2 are adenine; or each of R1 and R2 are Guanine, or in each case or analogs thereof. In a preferred embodiment, R1 and R2 are independently adenine or guanine, provided that R1 and R2 are not both guanine, or analogs thereof.

In some embodiments of the second aspect and embodiments thereof, each R5 and R6 is SH and R1 and R2 are independently:

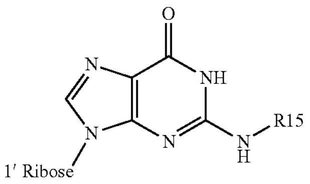

or

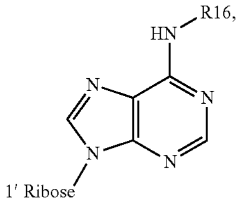

wherein R15 and R16 are independently H or —C(O)R', wherein R' is $C_{1-6}$ alkyl or phenyl. In some embodiments, R15 is H or —C(O)-isopropyl and R16 is H or —C(O)-phenyl.

In some embodiments of the second aspect and embodiments thereof, the compound of Formula I is selected from the group consisting of:

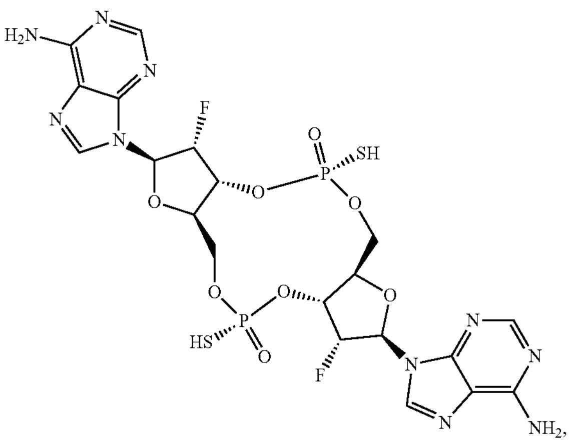

-continued

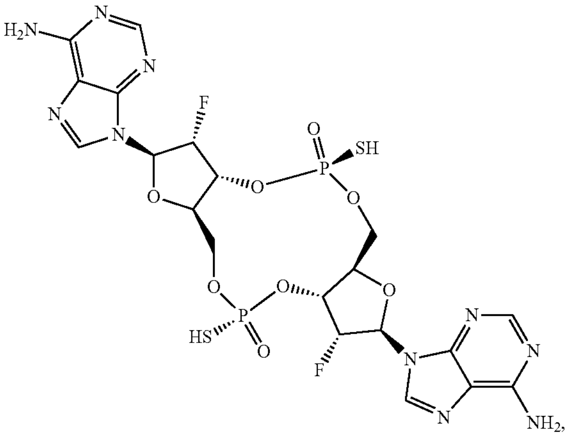

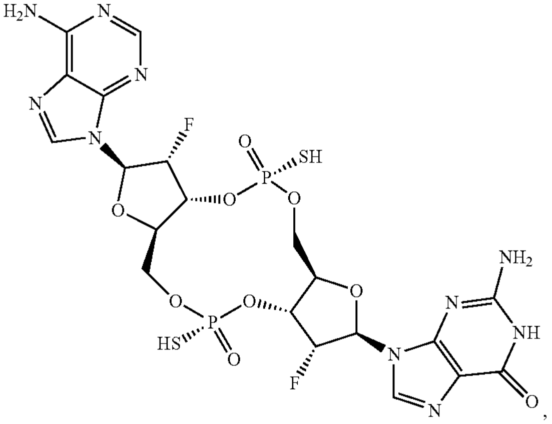

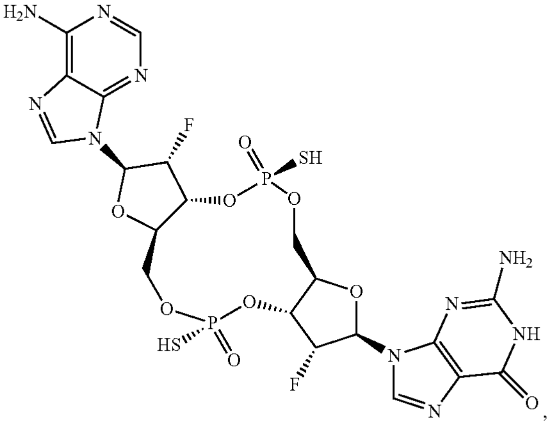

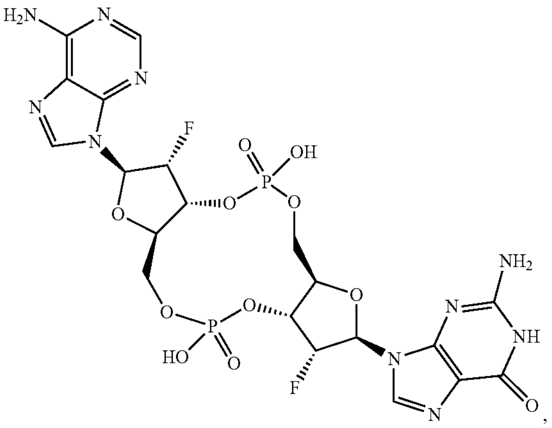

-continued
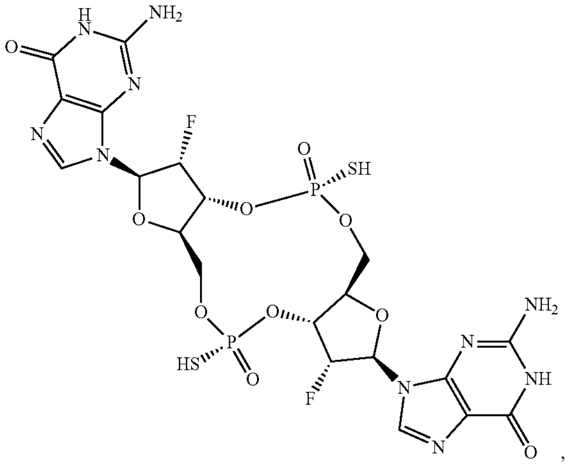
,
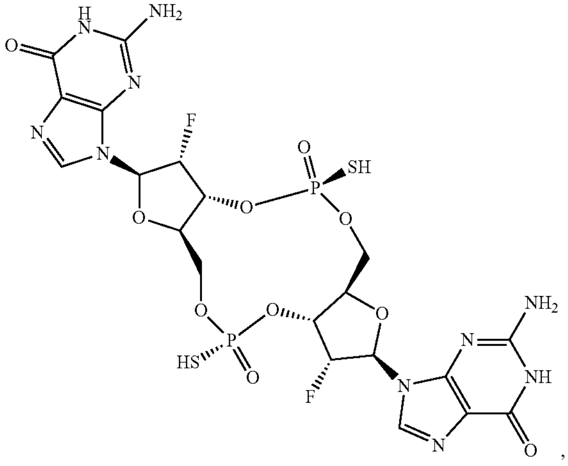
,
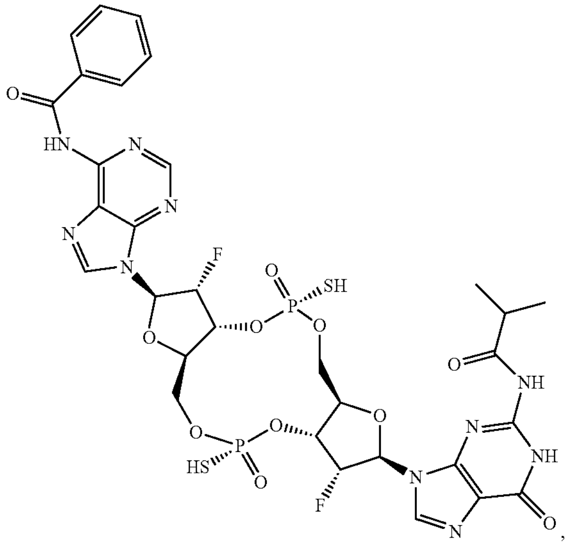
,
-continued
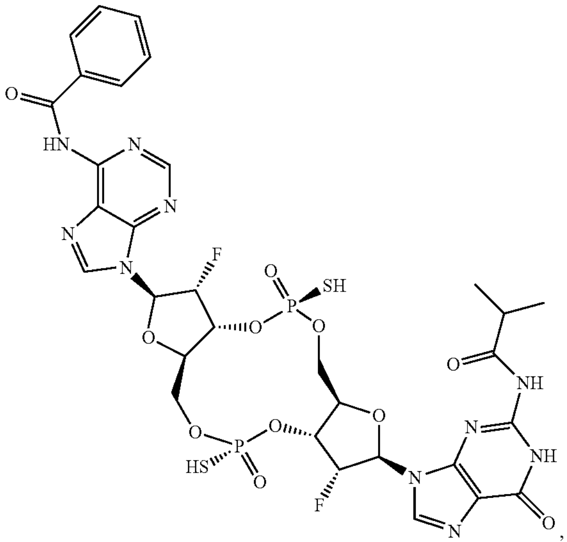
,
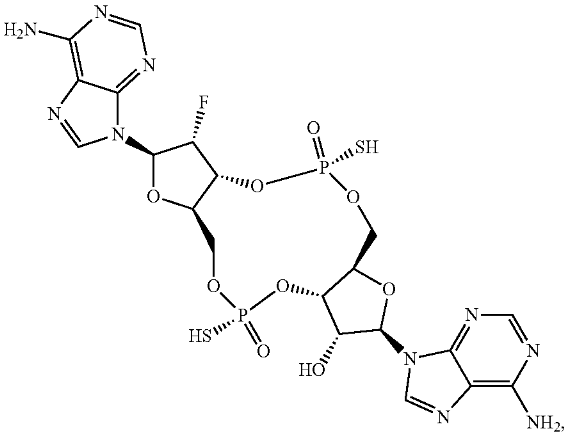
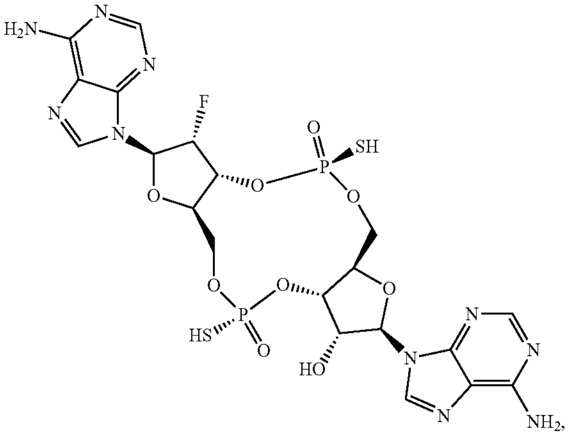

-continued
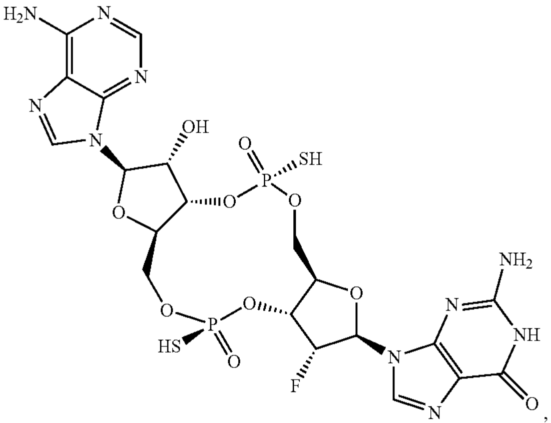
,
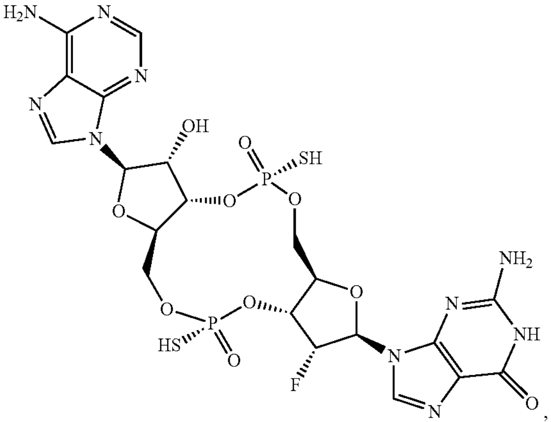
,
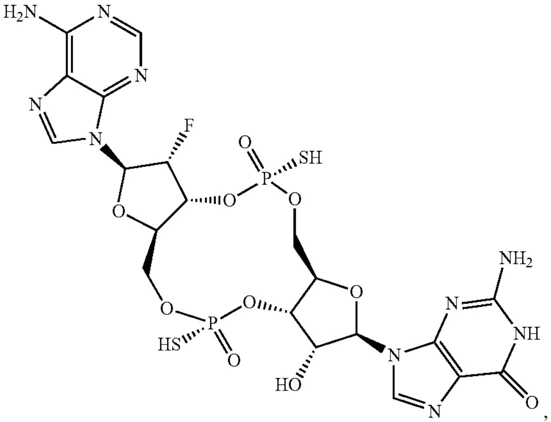
,
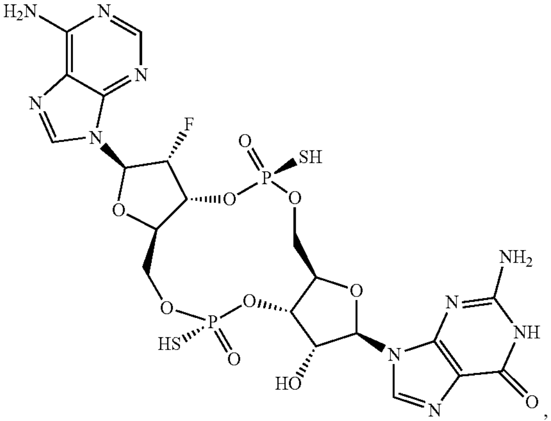 [SMILES: Nc1nc2c(ncn2[C@@H]2O[C@@H]3CO[P@](=O)(S)O[C@H]4[C@@H](F)[C@H](n5cnc6c(N)ncnc65)O[C@@H]4CO[P@@](=O)(S)O[C@H]3[C@H]2O)c(=O)[nH]1]
,
-continued
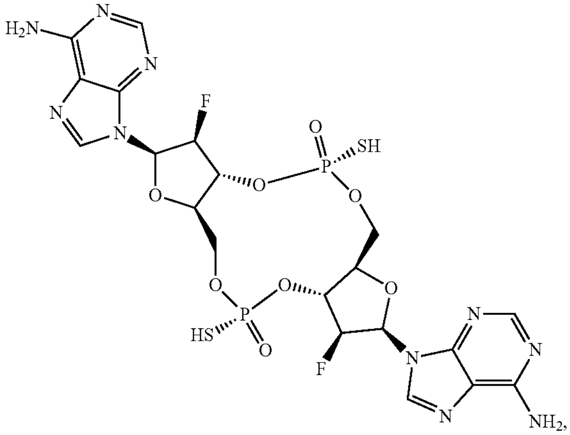
,
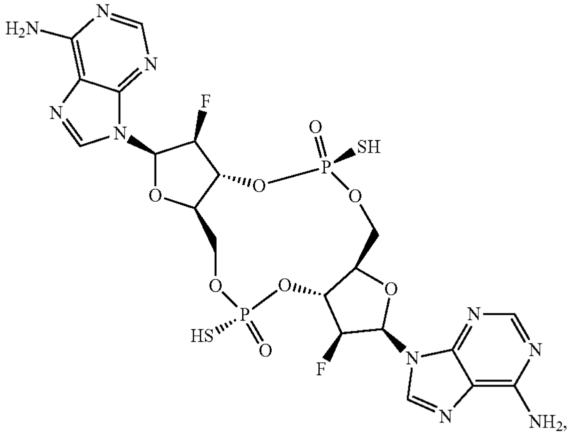
,
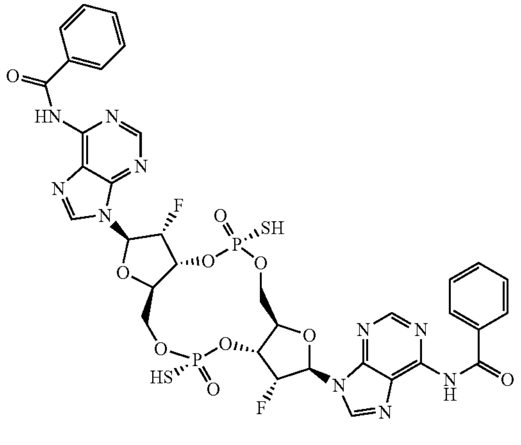
and -continued

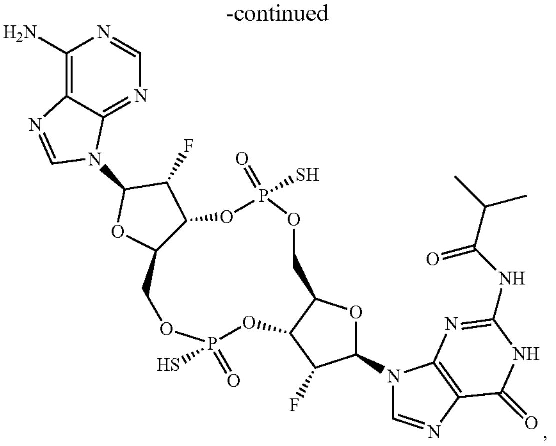

or a prodrug, pharmaceutically acceptable salt, pharmaceutically acceptable solvate or pharmaceutically acceptable hydrate thereof.

In preferred embodiments of the second aspect and embodiments thereof, each of R3 and R4 is F. This is referred to herein as 2',2"-diF or di-2'F.

In some embodiments the one or more compounds are 2',2"-diF-Rp,Rp cyclic purine dinucleotides (thus in which each R5 and R6 is SH), including, but not limited to, 2',2"-diF-Rp,Rp-c-di-AMP (also referred to herein as 2',2"-diF-R,R-CDA or 3',3'-RR-(2'F-A)(2'F-A)), 2',2"-diF-Rp,Rp-c-di-GMP (also referred to herein as 2',2"-diF-R,R-CDG or 3',3'-RR-(2'F-G)(2'F-G)), 2',2"-diF-Rp,Rp-c-di-IMP (also referred to herein as 2',2"-diF-R,R-CDI or 3',3'-RR-(2'F-I)(2'F-I)), 2',2"-diF-Rp,Rp-c-AMP-GMP (also referred to herein as 2',2"-diF-R,R-cGAMP or 3',3'-RR-(2'F-G)(2'F-A)), 2',2"-diF-Rp,Rp-c-AMP-IMP (also referred to herein as 2',2"-diF-R,R-cIAMP or 3',3'-RR-(2'F-I)(2'F-A)), 2',2"-diF-Rp,Rp-c-GMP-IMP (also referred to herein as 2',2"-diF-R,R-cGIMP or 3',3'-RR-(2'F-G)(2'F-I)), and analogs thereof.

In a preferred embodiment of the second aspect, and any embodiments thereof, the compound is not one of the following:

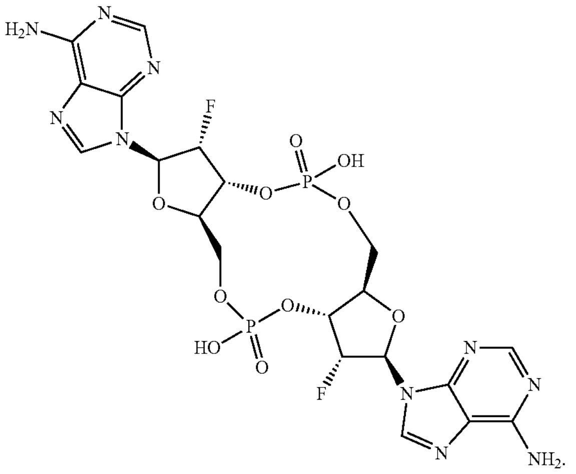

-continued

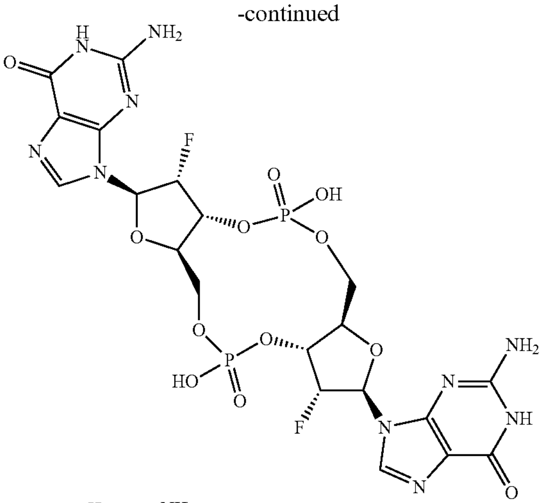

or

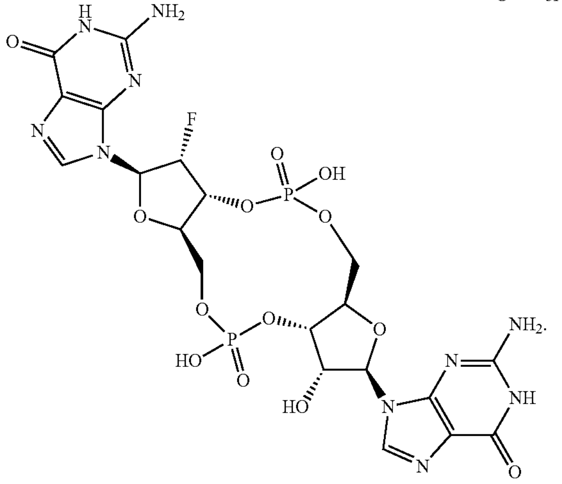

In a third aspect, the present invention provides a mono- or di-F-CDN compound of Formula II:

Formula II

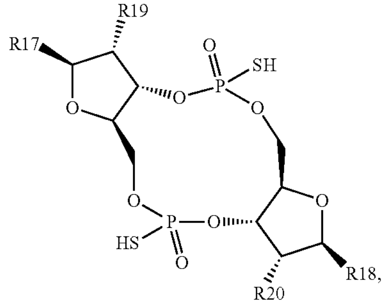

or a prodrug, pharmaceutically acceptable salt, pharmaceutically acceptable solvate or pharmaceutically acceptable hydrate thereof.

wherein:

R17 and R18 are independently a guanine or adenine bound to the structure via the N9 position, wherein the 6 position amine of adenine is optionally substituted with a benzoyl group and wherein the 2 position amine of guanine is optionally substituted with an isobutyryl group;

R19 and R20 are independently OH or F, provided that at least one of R19 and R20 is F.

In a first embodiment of the third aspect, the compound of Formula II is a compound of Formula IIa, a compound of Formula IIb or a compound of Formula IIc:

Formula IIa

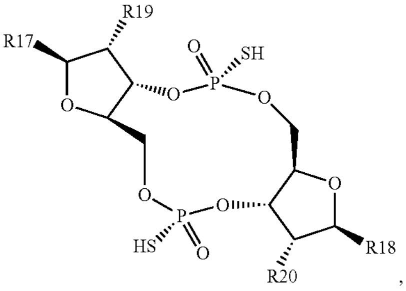

,

Formula IIb

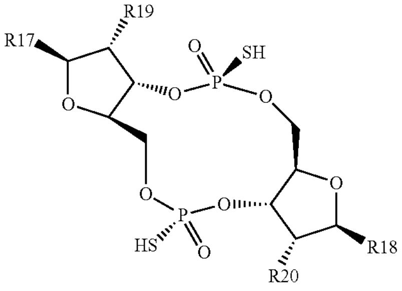

or

IIc

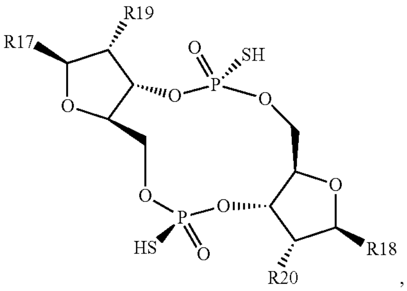

, or a prodrug, pharmaceutically acceptable salt, pharmaceutically acceptable solvate or pharmaceutically acceptable hydrate thereof, wherein R17, R18, R19 and R20 are as defined for Formula II.

In a second embodiment of the third aspect or first embodiment thereof, R17 and R18 are independently adenine or guanine. In some embodiments, R17 and R18 are independently adenine or guanine, provided that R17 and R18 are not both guanine. In some embodiments, R17 and R18 are both adenine. In some embodiments. R17 and R18 are both guanine. In some embodiments, one of R17 and R18 is adenine and the other of R17 and R18 is guanine.

In some embodiments of the third aspect, and first or second embodiments thereof, one of R19 and R20 is F and the other of R19 and R20 is OH. In some embodiments. R19 and R20 are both F. In some embodiments, R19 and R20 are both F and the compound is a compound of Formula IIa.

In some embodiments of the third aspect, the mono- or di-F-CDN compound is selected from the group consisting of:

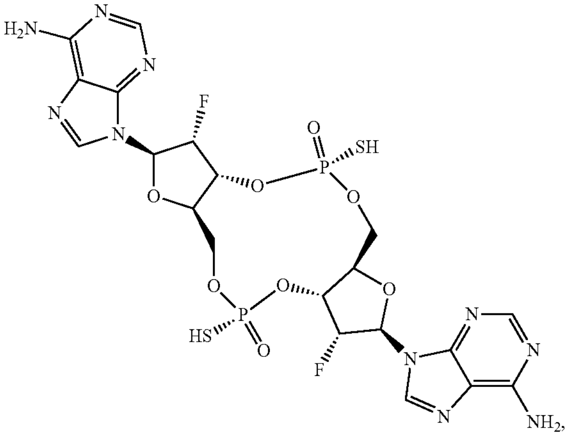

,

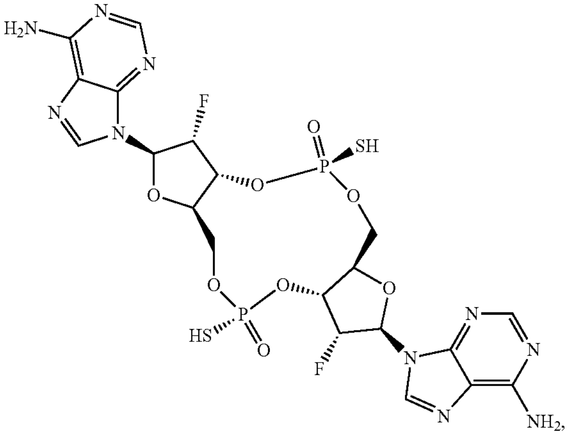

,

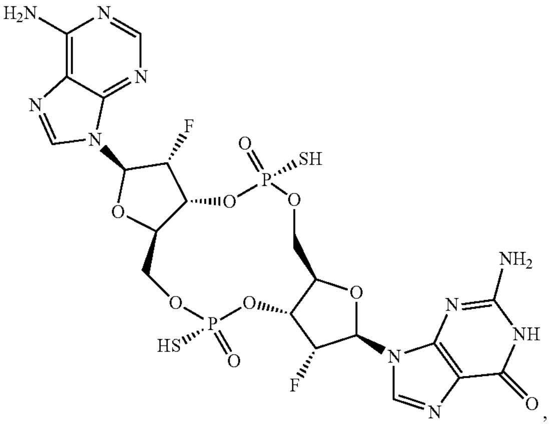

,

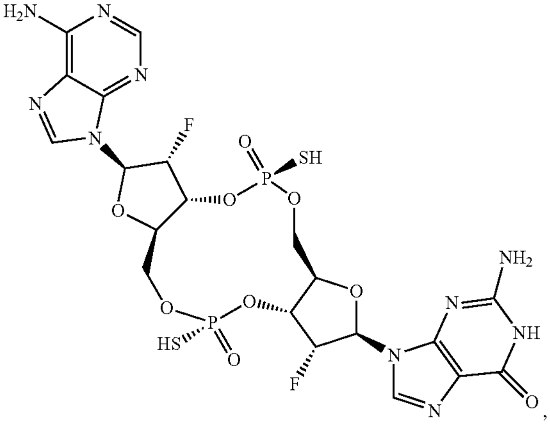

,

-continued
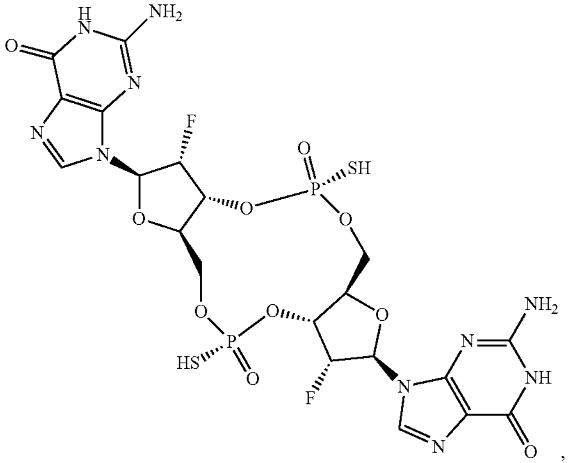
,
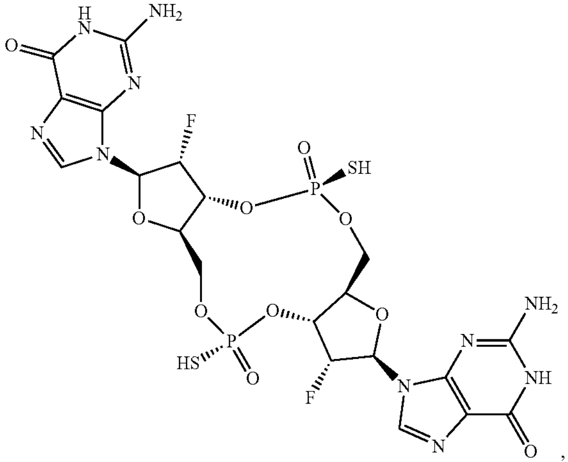
,
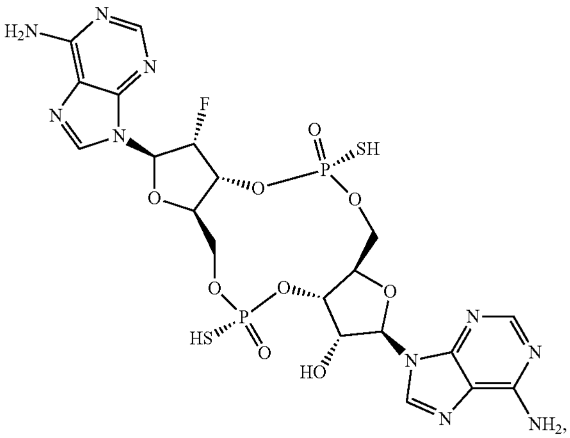
,
-continued
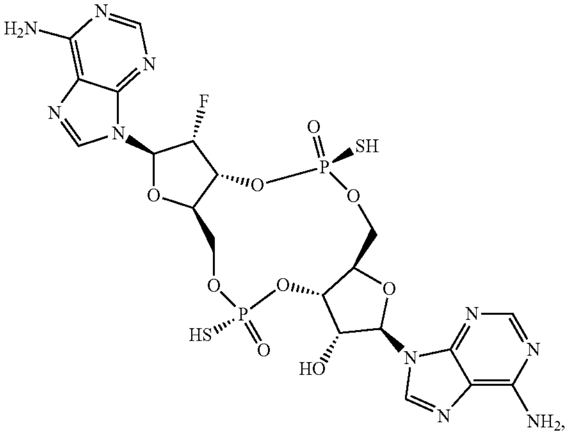
,
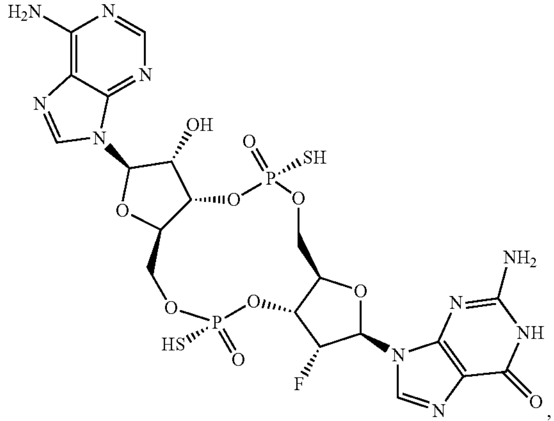
,
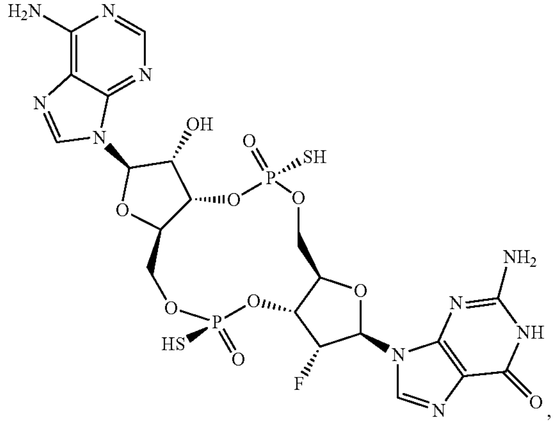
,
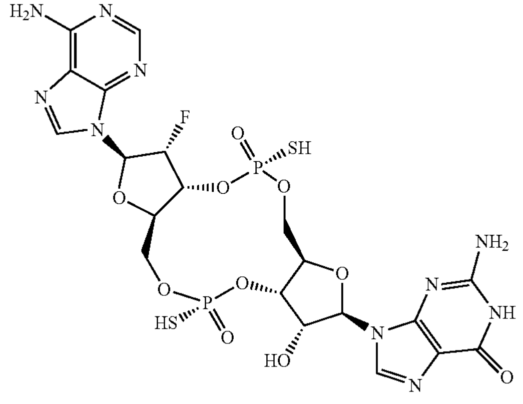
and -continued
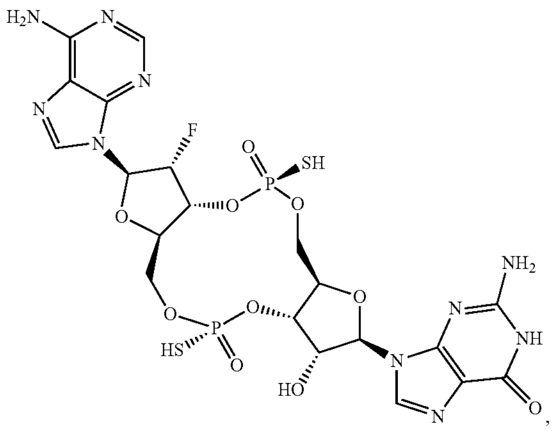 [SMILES: Nc1nc2c(ncn2[C@@H]2O[C@@H]3CO[P@](=O)(S)O[C@H]4[C@@H](F)[C@H](n5cnc6c(N)ncnc65)O[C@@H]4CO[P@@](=O)(S)O[C@H]3[C@H]2O)c(=O)[nH]1]
,
or a prodrug, pharmaceutically acceptable salt, pharmaceutically acceptable solvate or pharmaceutically acceptable hydrate thereof.
In some embodiments of the third aspect, the mono- or di-F-CDN compound is selected from the group consisting of:
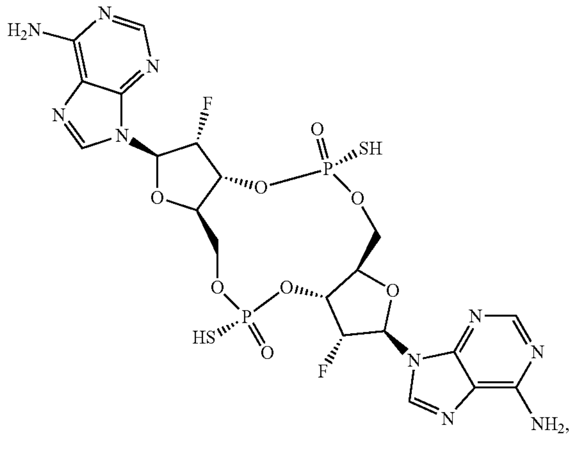
,
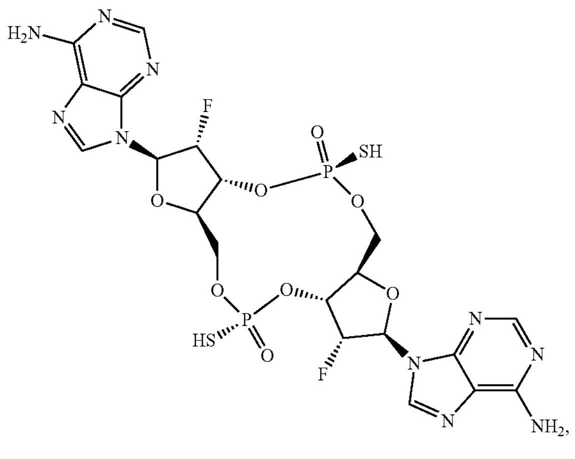
,
-continued
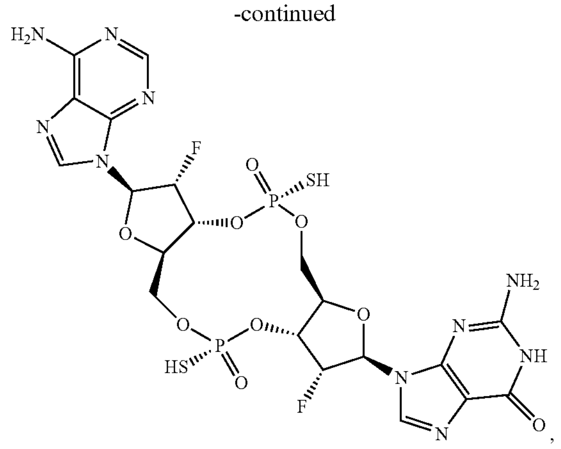
,
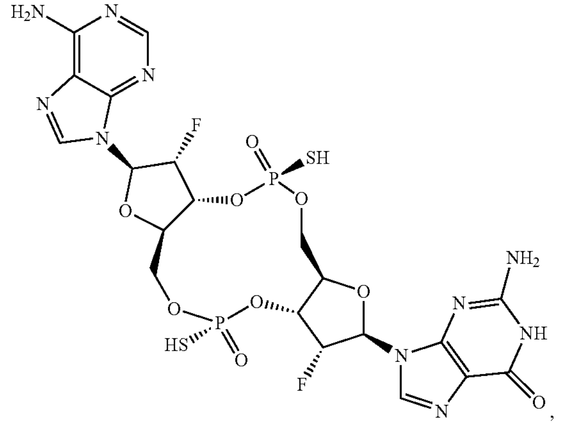
,
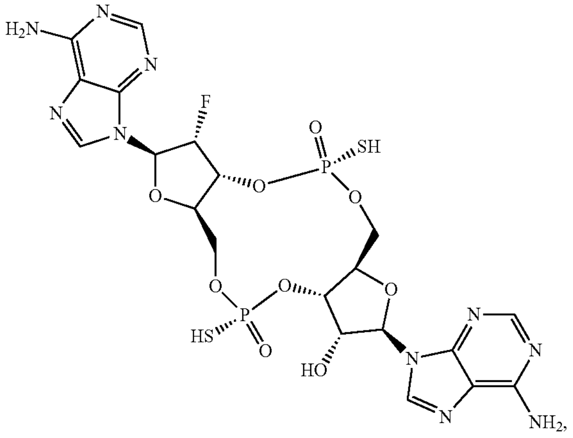
,
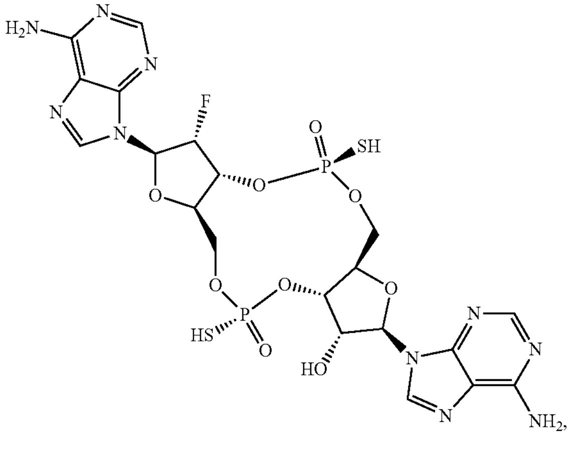
, -continued

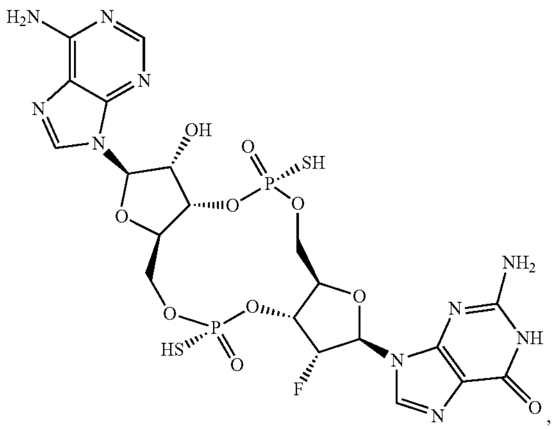

,

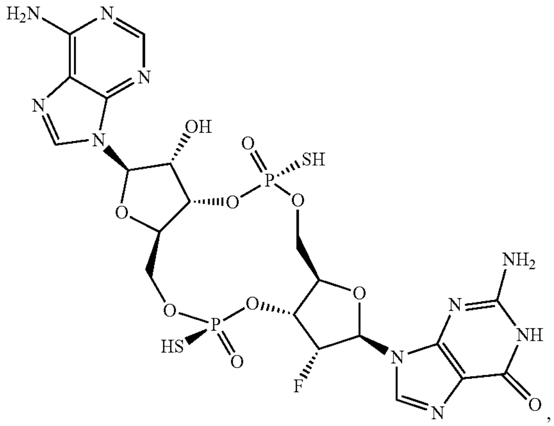

,

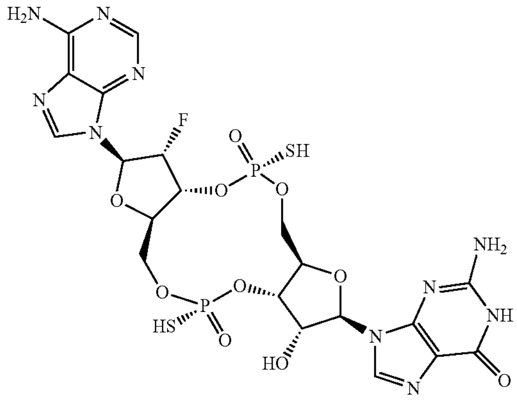

and

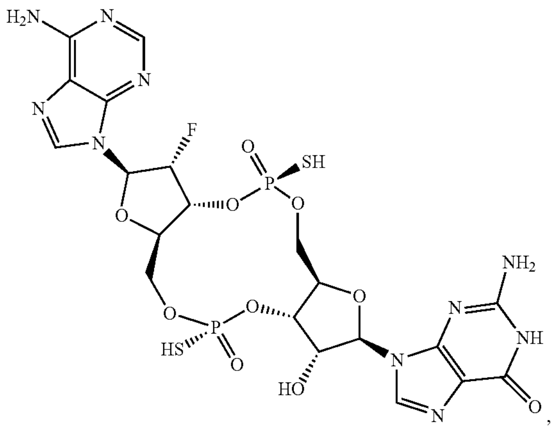

, or a prodrug, pharmaceutically acceptable salt, pharmaceutically acceptable solvate or pharmaceutically acceptable hydrate thereof.

In a fourth aspect, the present invention provides a di-F-CDN compound of Formula III:

Formula III

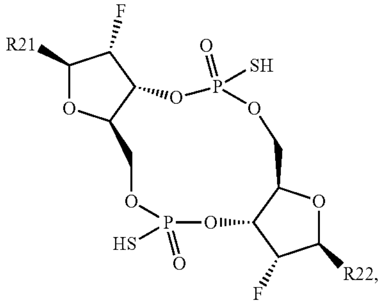

or a prodrug, pharmaceutically acceptable salt, pharmaceutically acceptable solvate or pharmaceutically acceptable hydrate thereof, wherein R21 and R22 are independently a guanine or adenine bound to the structure via the N9 position.

In a first embodiment of the fourth aspect, the compound of Formula III is a compound of Formula IIIa or a compound of Formula IIIb:

Formula IIIa

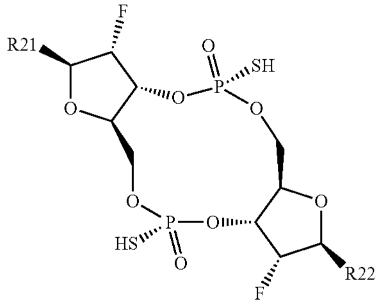

or

Formula IIIb

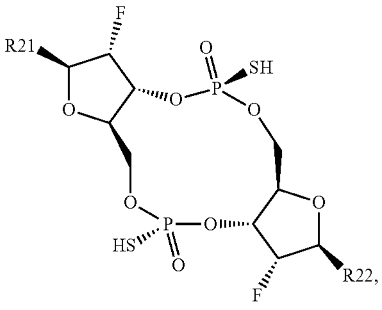

or a prodrug, pharmaceutically acceptable salt, pharmaceutically acceptable solvate or pharmaceutically acceptable hydrate thereof, wherein R21 and R22 are as defined for Formula III.

In a second embodiment of the fourth aspect or first embodiment thereof, R21 and R22 are independently a guanine or adenine, provided that R21 and R22 are not both guanine. In some embodiments, R21 and R22 are both adenine. In some embodiments. R21 is adenine and R22 is guanine.

In some embodiments of the fourth aspect, or the first or second embodiments thereof, the compound is a compound of Formula IIIa.

In some embodiments of the fourth aspect, the di-F-CDN compound is selected from the group consisting of:

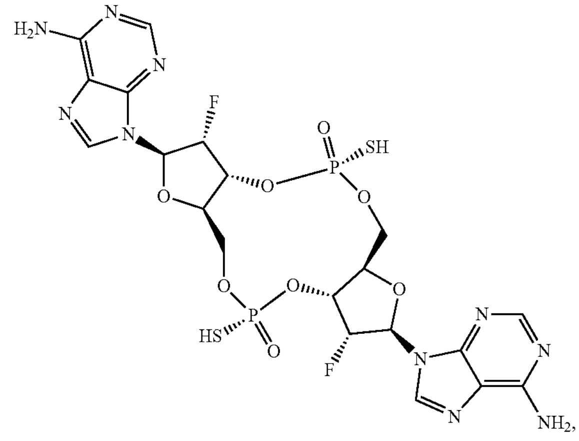

,

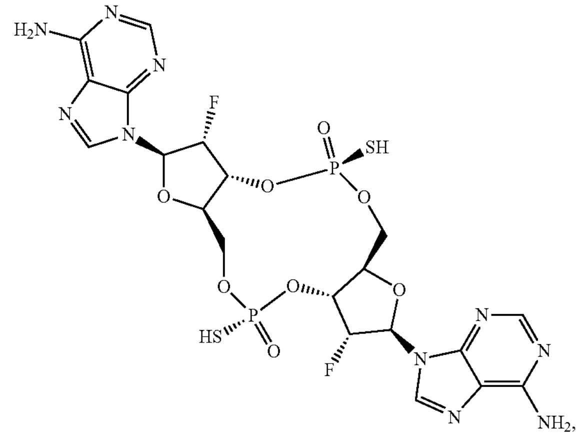

,

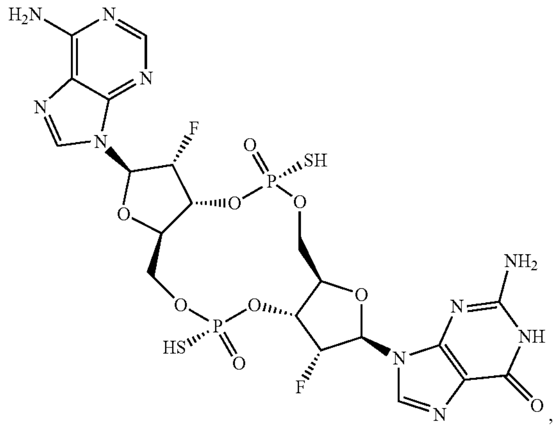

,

-continued

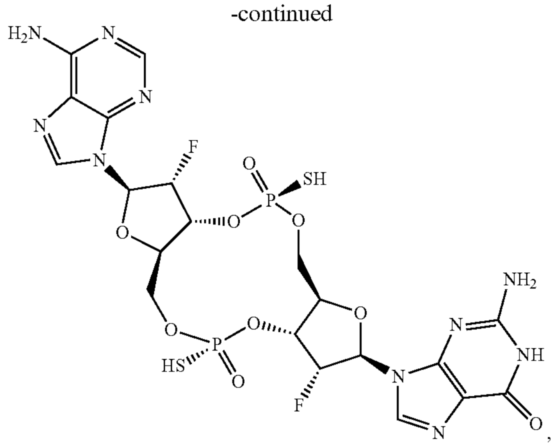

,

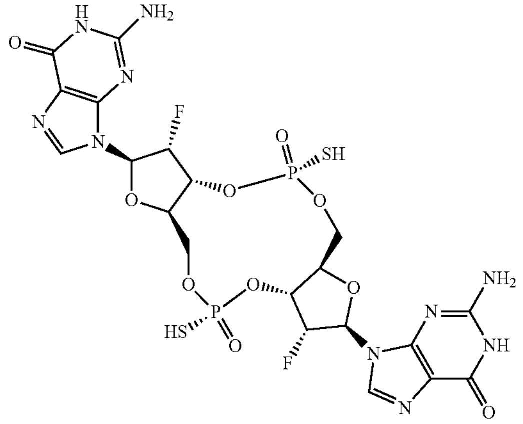

and

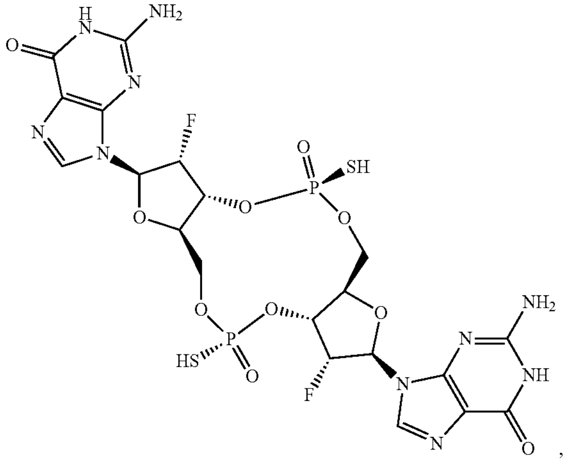

, or a prodrug, pharmaceutically acceptable salt, pharmaceutically acceptable solvate or pharmaceutically acceptable hydrate thereof.

In some embodiments of the fourth aspect, the di-F-CDN compound is selected from the group consisting of:

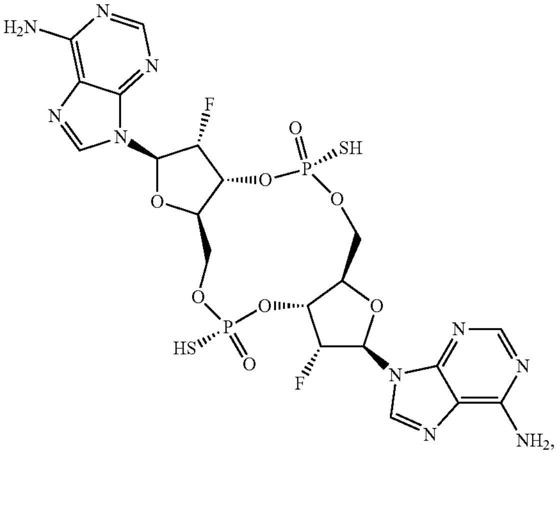
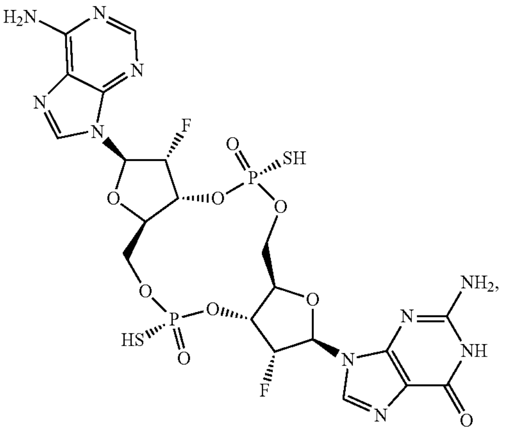
and
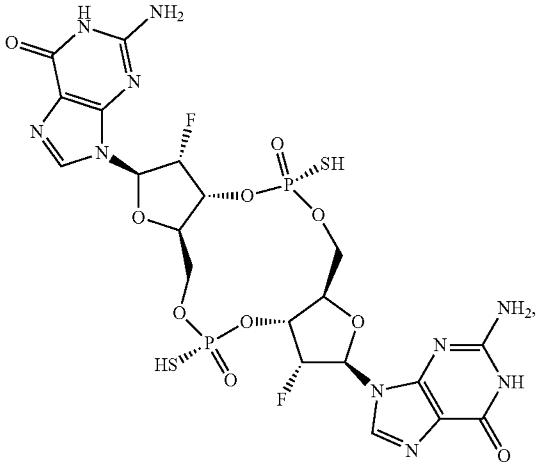
or a prodrug, pharmaceutically acceptable salt, pharmaceutically acceptable solvate or pharmaceutically acceptable hydrate thereof.
In some embodiments of the fourth aspect, the di-F-CDN compound is selected from the group consisting of:
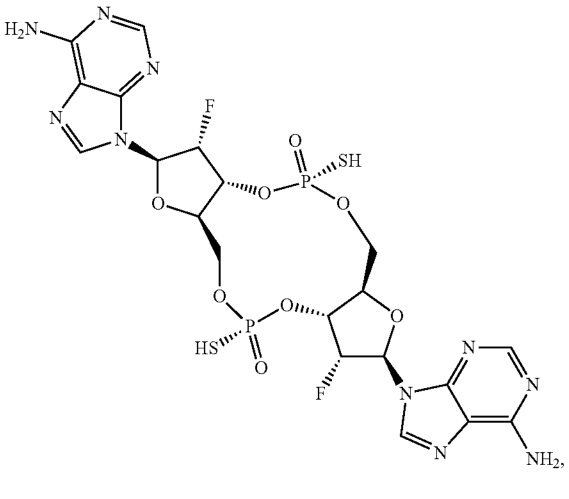
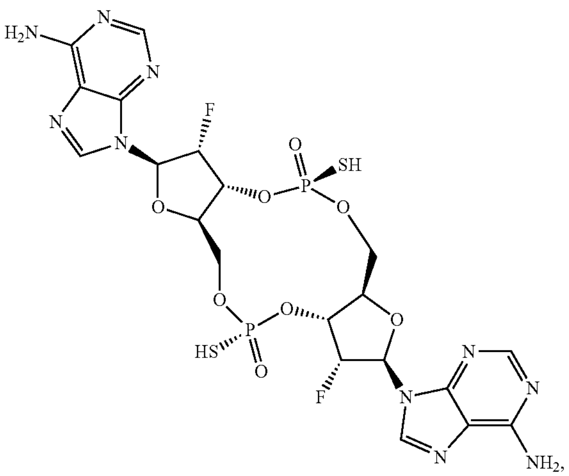
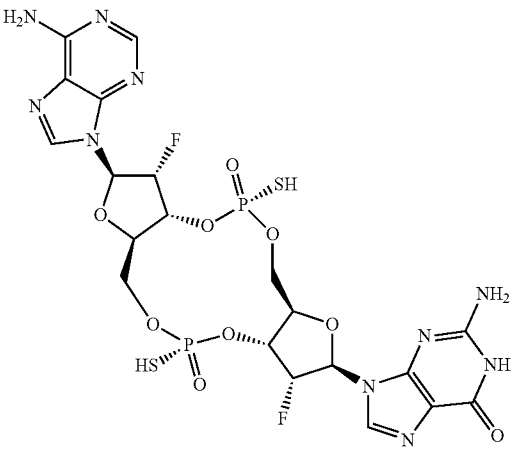
and -continued

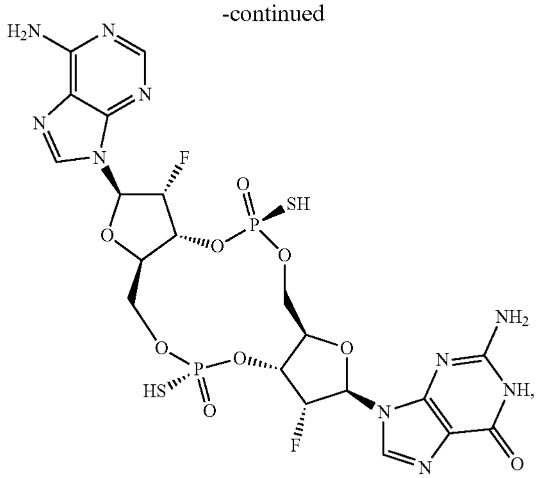

or a prodrug, pharmaceutically acceptable salt, pharmaceutically acceptable solvate or pharmaceutically acceptable hydrate thereof.

In some embodiments of the fourth aspect, the di-F-CDN compound is selected from the group consisting of:

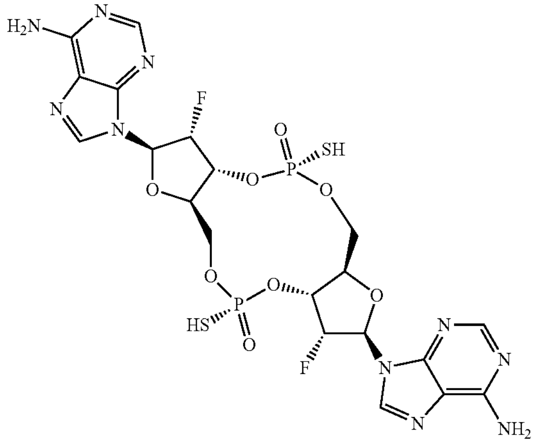

and

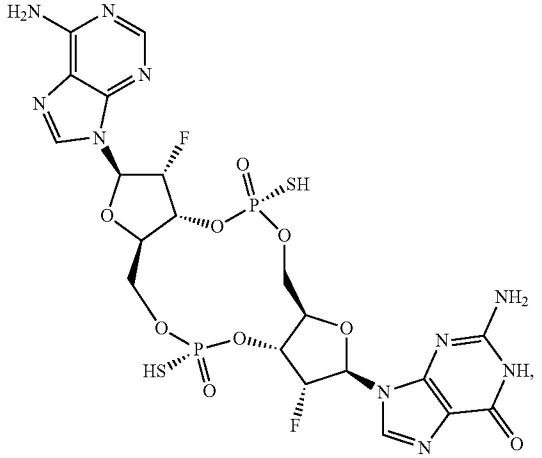

or a prodrug, pharmaceutically acceptable salt, pharmaceutically acceptable solvate or pharmaceutically acceptable hydrate thereof.

In a fifth aspect, the present invention provides a mono-F-CDN compound of Formula IV:

Formula IV

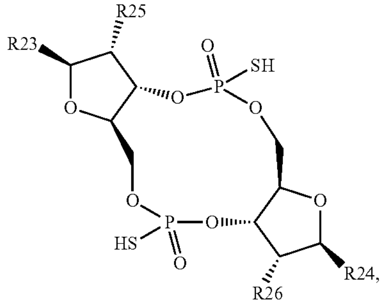

or a prodrug, pharmaceutically acceptable salt, pharmaceutically acceptable solvate or pharmaceutically acceptable hydrate thereof, wherein:

R23 and R24 are independently a guanine or adenine bound to the structure via the N9 position; and one of R25 and R26 is OH and the other of R25 and R26 is F.

In a first embodiment of the fifth aspect, the compound of Formula IV is a compound of Formula IVa, a compound of Formula IVb or a compound of Formula IVc:

Formula IVa

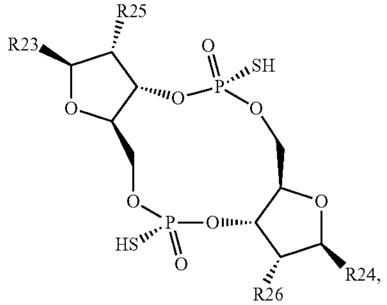

Formula IVb

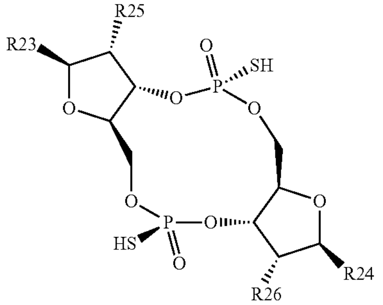

or

Formula IVc

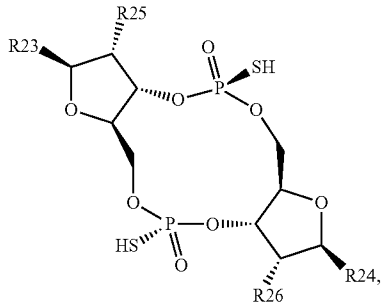

or a prodrug, pharmaceutically acceptable salt, pharmaceutically acceptable solvate or pharmaceutically acceptable hydrate thereof, wherein R23, R24, R25 and R26 are as defined for Formula IV.

In second embodiment of the fifth aspect or first embodiment thereof, R23 and R24 are independently adenine or guanine provided that R23 and R24 are not both guanine. In some embodiments, R23 and R24 are both adenine. In some embodiments, one of R23 and R24 is adenine and the other of R23 and R24 is guanine.

In some embodiments of the fifth aspect, or the first or second embodiments thereof, the compound is a compound of Formula IVa.

In some embodiments of the fifth aspect, the mono-F-CDN compound is selected from the group consisting of:

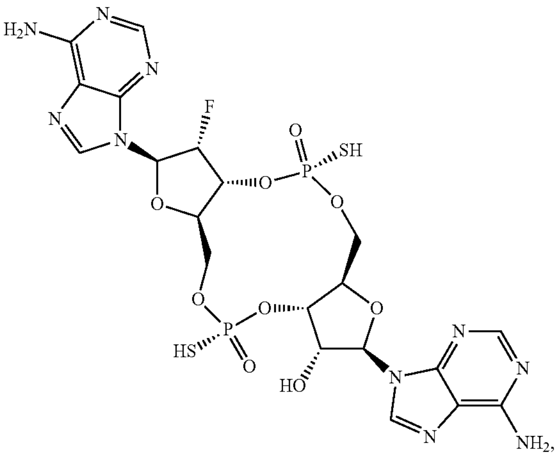

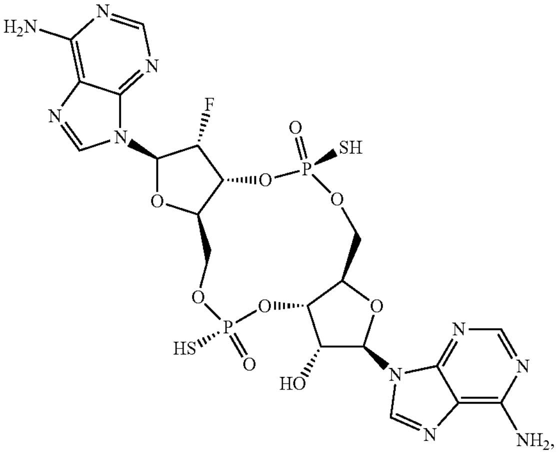

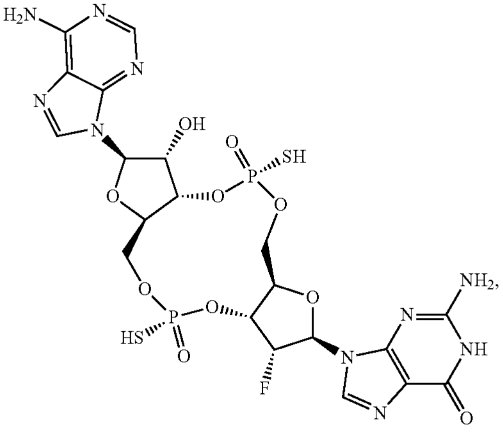

-continued

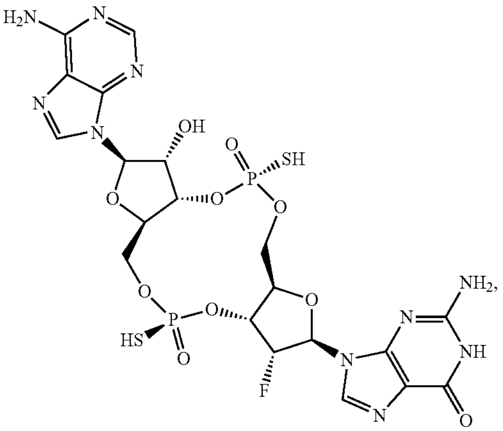

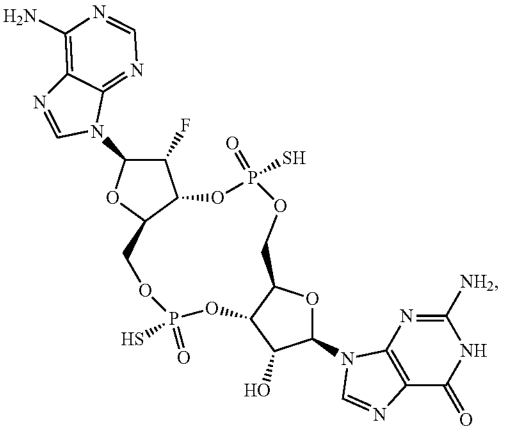

and

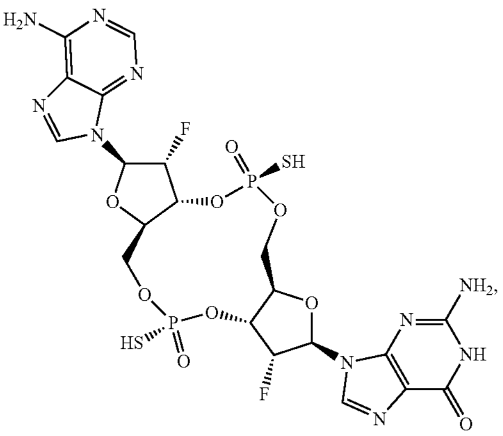

or a prodrug, pharmaceutically acceptable salt, pharmaceutically acceptable solvate or pharmaceutically acceptable hydrate thereof.

In a sixth aspect, the present invention provides a mono- or di-F cyclic di-adenine compound of Formula V:

Formula V

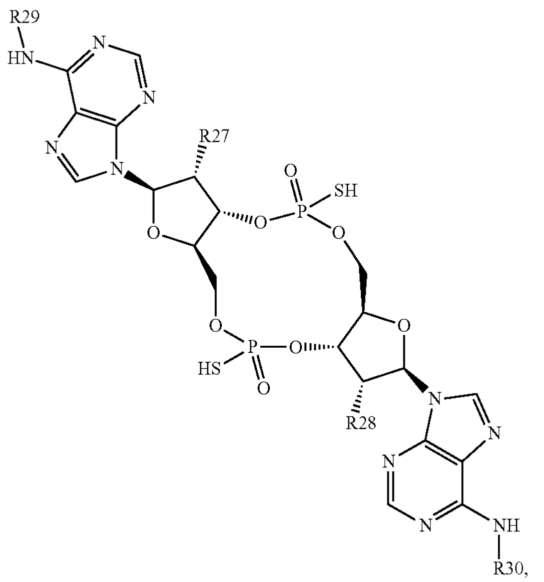

or a prodrug, pharmaceutically acceptable salt, pharmaceutically acceptable solvate or pharmaceutically acceptable hydrate thereof, wherein:

R27 and R28 are independently OH or F, provided that at least one of R27 and R28 is F; and R29 and R30 are independently H or benzoyl.

In a first embodiment of the sixth aspect, the compound of Formula V is a compound of Formula Va or a compound of Formula Vb:

Formula Va

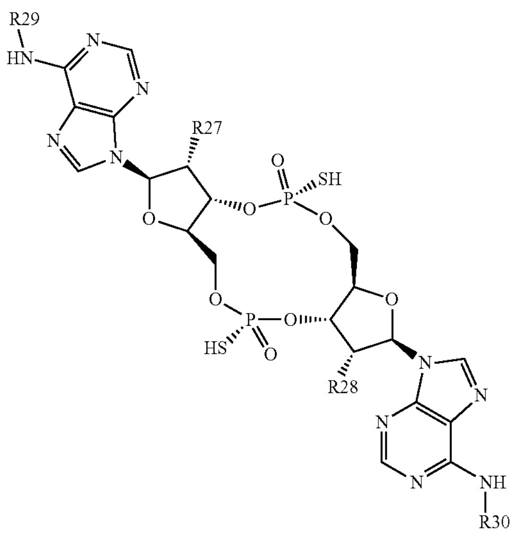

or

-continued

Formula Vb

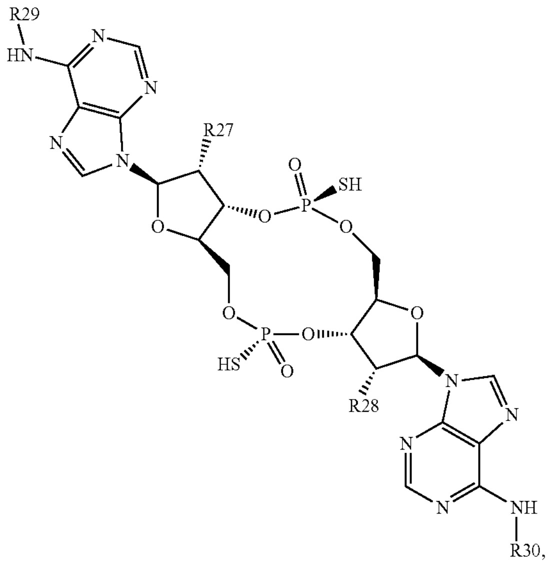

or a prodrug, pharmaceutically acceptable salt, pharmaceutically acceptable solvate or pharmaceutically acceptable hydrate thereof, wherein R27. R28, R29 and R30 are as defined for Formula V.

In second embodiment of the sixth aspect or first embodiment thereof. R29 and R30 are both H. In some embodiments, R29 and R30 are both benzoyl. In some embodiments, one of R29 and R30 is benzoyl and the other of R29 and R30 is H.

In some embodiments of the sixth aspect, and first or second embodiments thereof, R27 and R28 are both F. In some embodiments, one of R27 and R28 is F and the other of R27 and R28 is OH.

In some embodiments of the sixth aspect, R27 and R28 are both F, and R29 and R30 are both H. In some embodiments, the compound is a compound of Formula Va, R27 and R28 are both F, and R29 and R30 are both H.

In some embodiments of the sixth aspect, the mono- or di-F cyclic di-adenine compound is selected from the group consisting of:

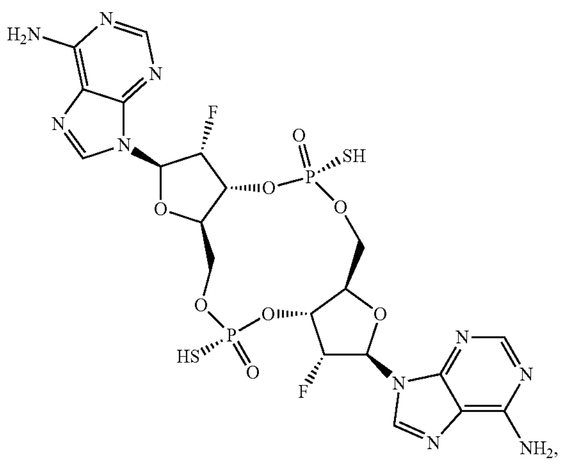

-continued

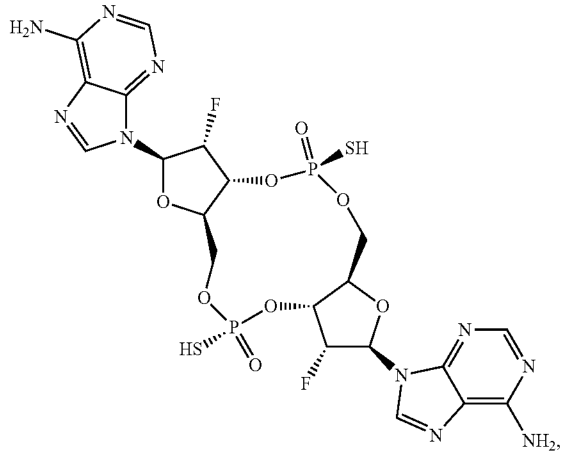

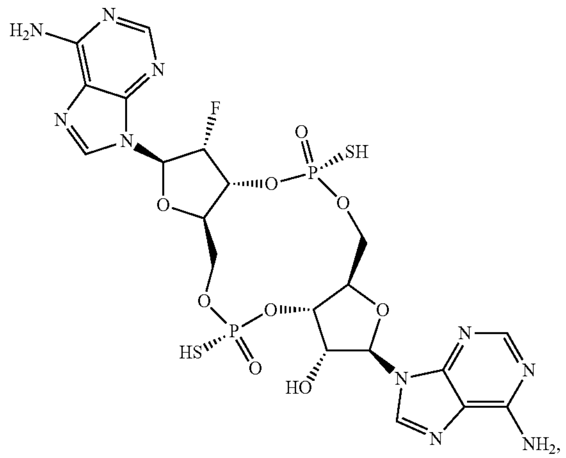

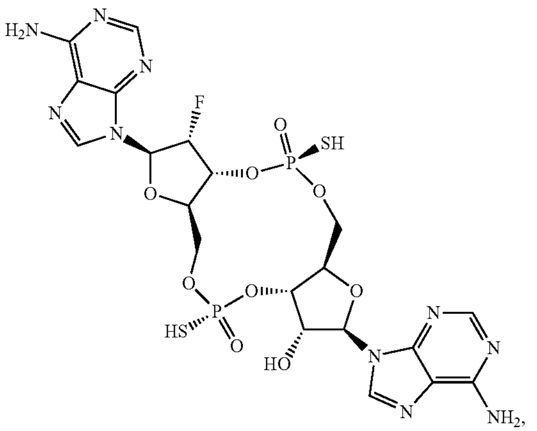

and

-continued

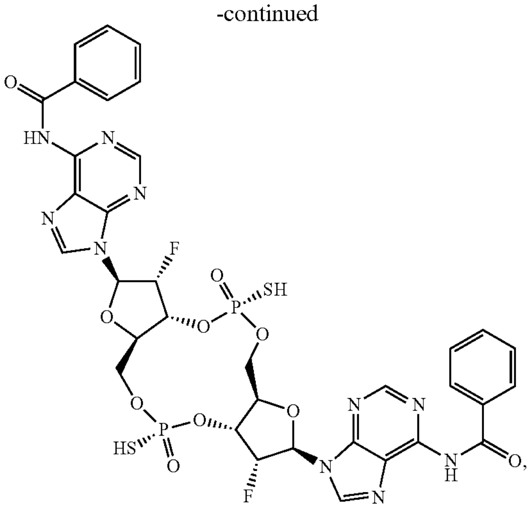

or a prodrug, pharmaceutically acceptable salt, pharmaceutically acceptable solvate or pharmaceutically acceptable hydrate thereof.

In some embodiments of the sixth aspect, the mono- or di-F cyclic di-adenine compound is selected from the group consisting of:

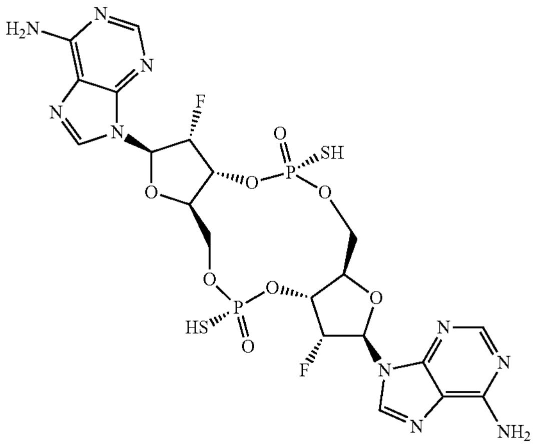

and

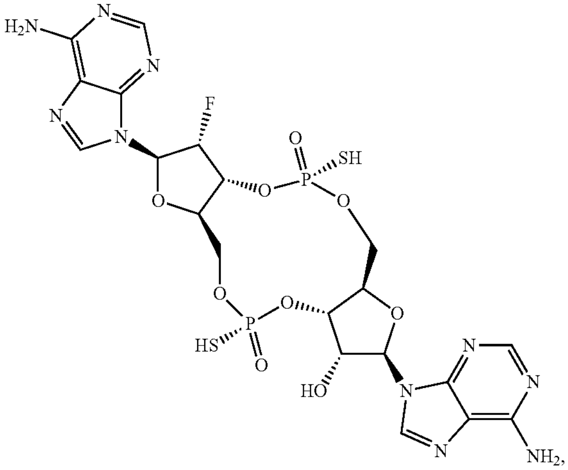

or a prodrug, pharmaceutically acceptable salt, pharmaceutically acceptable solvate or pharmaceutically acceptable hydrate thereof.

In a seventh aspect, the present invention provides a mono- or di-F cyclic di-guanine compound of Formula VI:

Formula VI

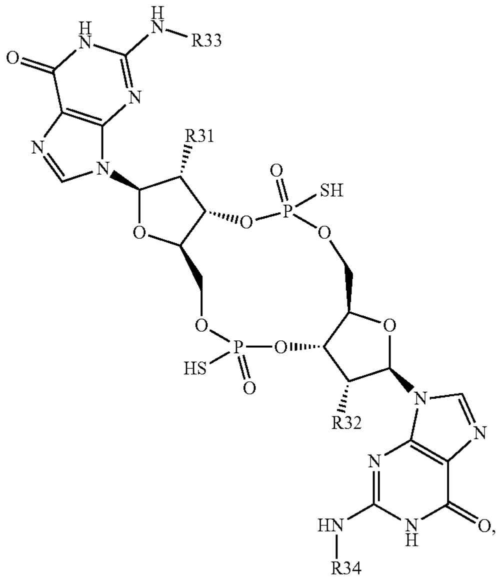

or a prodrug, pharmaceutically acceptable salt, pharmaceutically acceptable solvate or pharmaceutically acceptable hydrate thereof, wherein:

R31 and R32 are independently OH or F, provided that at least one of R31 and R32 is F;

R33 and R34 are independently H or butyryl.

In a first embodiment of the seventh aspect, the compound of Formula VI is a compound of Formula VIa or a compound of Formula VIb:

Formula VIa

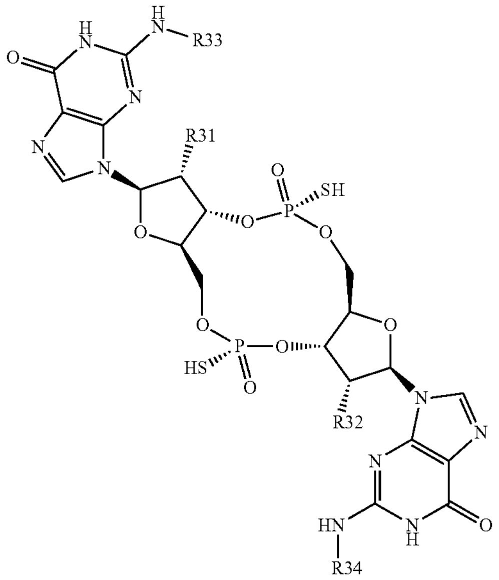

or

-continued

Formula VIb

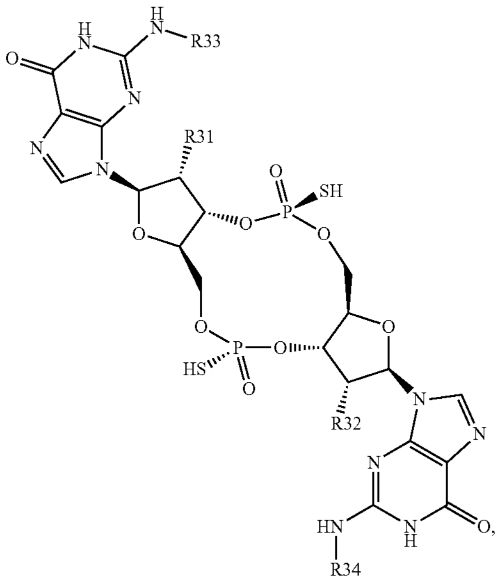

or a prodrug, pharmaceutically acceptable salt, pharmaceutically acceptable solvate or pharmaceutically acceptable hydrate thereof, wherein R31, R32, R33 and R34 are as defined for Formula VI.

In second embodiment of the seventh aspect or first embodiment thereof, R33 and R34 are both H. In some embodiments. R33 and R34 are both butyryl. In some embodiments, one of R33 and R34 is butyryl and the other of R33 and R34 is H.

In some embodiments of the seventh aspect, and first or second embodiments thereof. R31 and R32 are both F. In some embodiments, one of R31 and R32 is F and the other of R31 and R32 is OH.

In some embodiments of the sixth aspect, R31 and R32 are both F, and R33 and R34 are both H. In some embodiments, the compound is a compound of Formula VIa, R31 and R32 are both F, and R33 and R34 are both H.

In some embodiments of the seventh aspect, the mono- or di-F cyclic di-guanine compound is selected from the group consisting of:

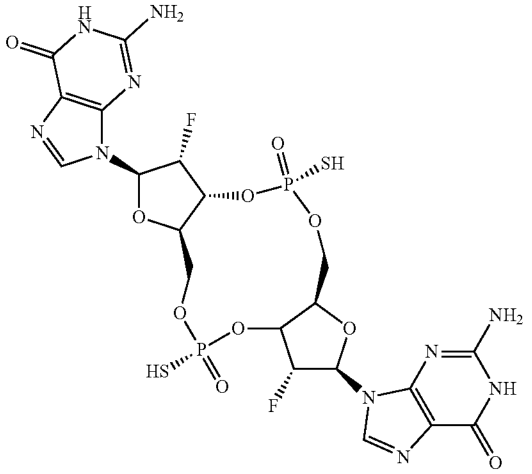

and

-continued

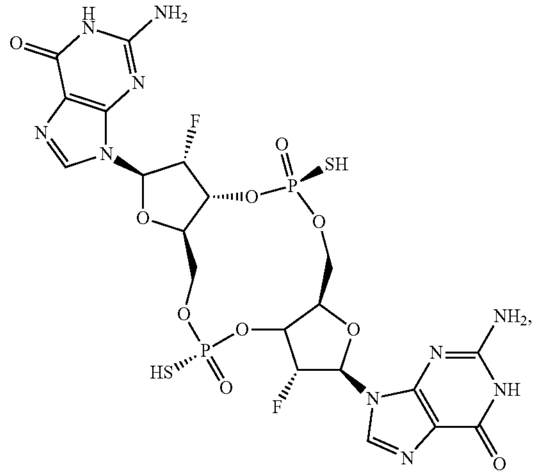

or a prodrug, pharmaceutically acceptable salt, pharmaceutically acceptable solvate or pharmaceutically acceptable hydrate thereof.

In an eighth aspect, the present invention provides a mono- or di-F cyclic guanine and adenine dinucleotide compound of Formula VII:

Formula VII

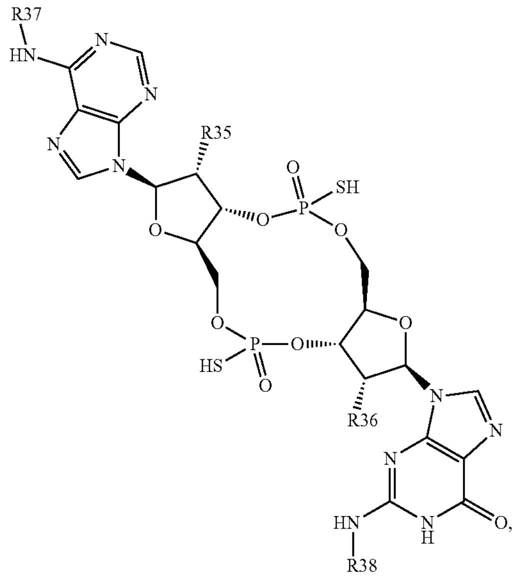

or a prodrug, pharmaceutically acceptable salt, pharmaceutically acceptable solvate or pharmaceutically acceptable hydrate thereof, wherein:

R35 and R36 am independently OH or F, provided that at least one of R35 and R36 is F;

R37 is H or benzoyl; and

R38 is H or butyryl.

In a first embodiment of the eighth aspect, the compound of Formula VII is a compound of Formula VIIa, a compound of Formula VIIb or a compound of Formula VIIc:

Formula VIIa

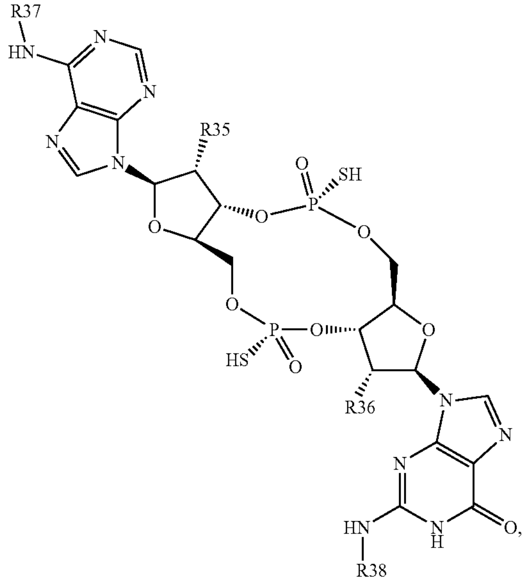

Formula VIIb

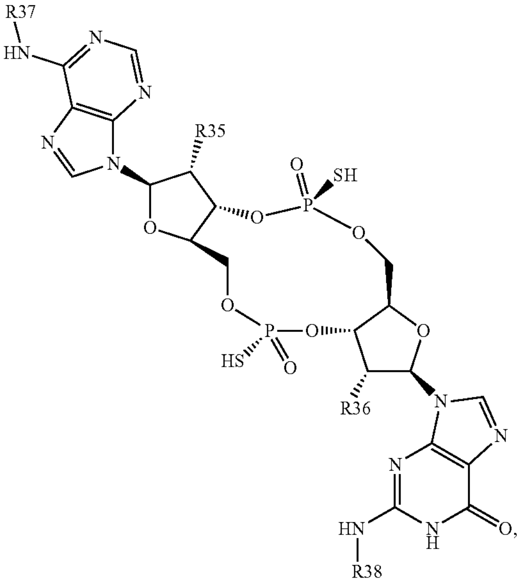

or

-continued

Formula VIIc

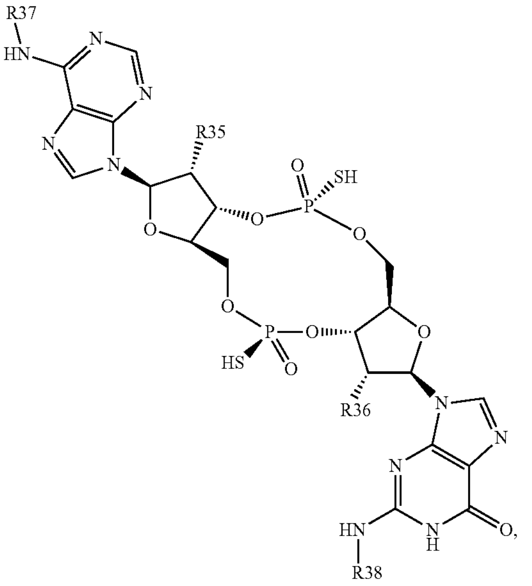

or a prodrug, pharmaceutically acceptable salt, pharmaceutically acceptable solvate or pharmaceutically acceptable hydrate thereof, wherein R35, R36. R37 and R38 are as defined for Formula VII.

In second embodiment of the eighth aspect or first embodiment thereof, R37 and R38 are both H. In some embodiments, R37 is benzoyl and R38 is butyryl. In some embodiments, R37 is H and R38 is butyryl. In some embodiments. R37 is benzoyl and R38 is H.

In some embodiments of the eighth aspect, and first or second embodiments thereof. R35 and R36 are both F. In some embodiments, one of R35 and R36 is F and the other of R35 and R36 is OH. In some embodiments R35 and R36 are both F and the compound is a compound of Formula VIIa.

In some embodiments of the eight aspect and first embodiment thereof. R35 and R36 are both F and R37 and R38 are both H. In some embodiments, R35 and R36 are both F, R37 is H and R38 is butyryl. In some embodiments, R35 and R36 are both F. R37 is benzoyl and R38 is H. In some embodiments, R35 and R36 are both F. R37 is benzoyl and R38 is butyryl. In some embodiments, R35 and R36 are both F, R37 and R38 are both H, and the compound is a compound of Formula VIIa.

In some embodiments of the eight aspect and first embodiment thereof, R35 is F, R36 is OH and R37 and R38 are both H. In some embodiments. R35 is F. R36 is OH, R37 is H and R38 is butyryl. In some embodiments, R35 is F, R36 is OH, R37 is benzoyl and R38 is H. In some embodiments, R35 is F, R36 is OH. R37 is benzoyl and R38 is butyryl. In some embodiments. R35 is F, R36 is OH. R37 and R38 are both H, and the compound is a compound of Formula VIIa.

In some embodiments of the eight aspect and first embodiment thereof, R35 is OH, R36 is F and R37 and R38 are both H. In some embodiments, R35 is OH, R36 is F, R37 is H and R38 is butyryl. In some embodiments, R35 is OH. R36 is F, R37 is benzoyl and R38 is H. In some embodiments, R35 is OH, R36 is F, R37 is benzoyl and R38 is butyryl. In some embodiments, R35 is OH, R36 is F, R37 and R38 are both H, and the compound is a compound of Formula VIIa.

In some embodiments of the eighth aspect, the mono- or di-F cyclic guanine and adenine dinucleotide compound is selected from the group consisting of:

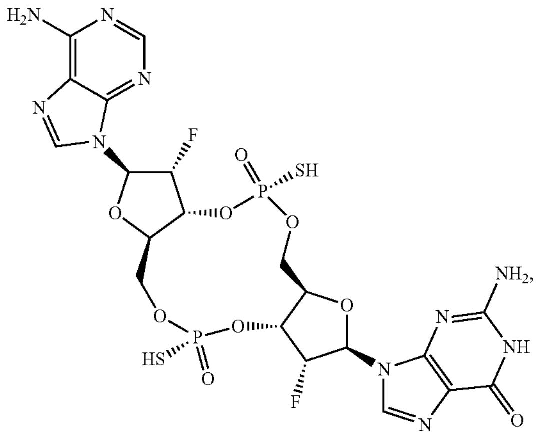

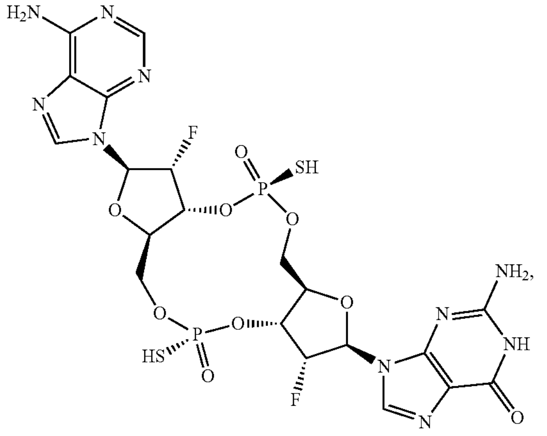

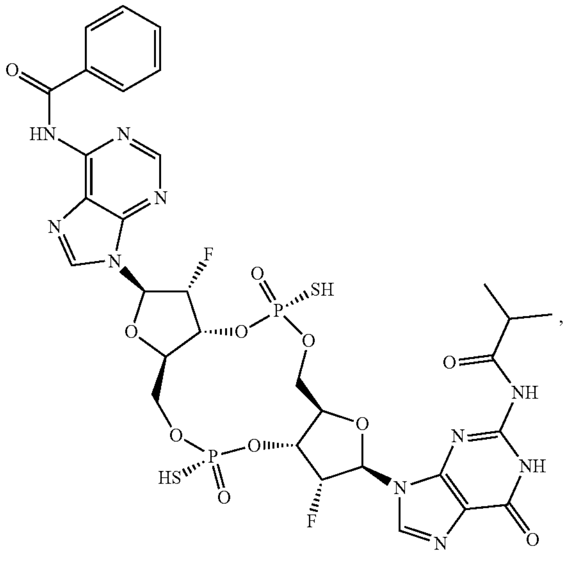

-continued
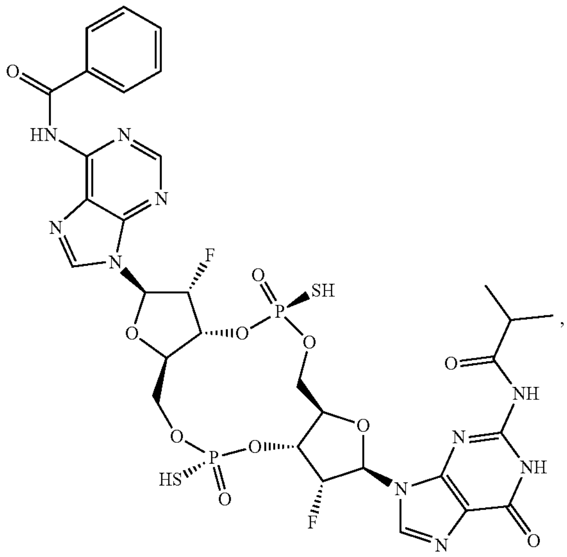
,
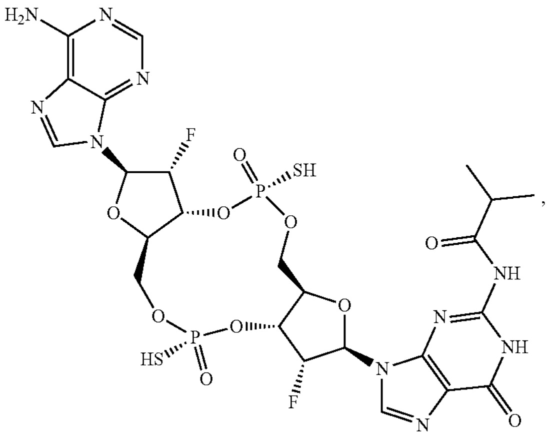
,
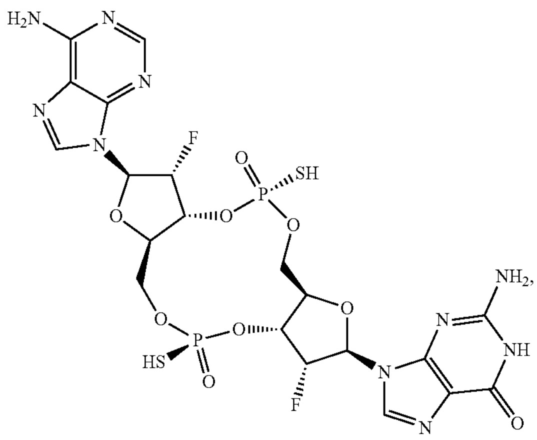
-continued
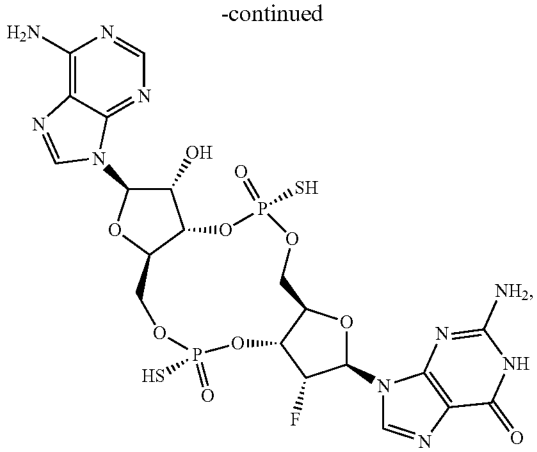
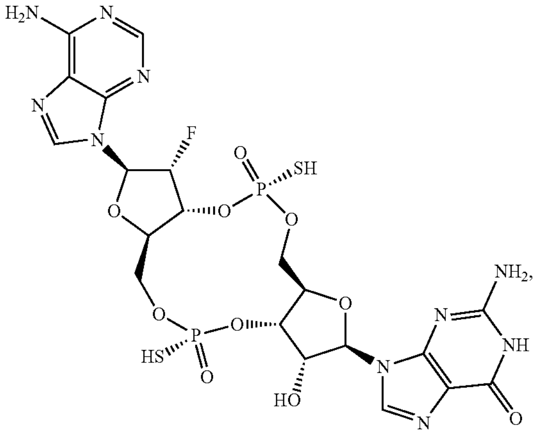
and
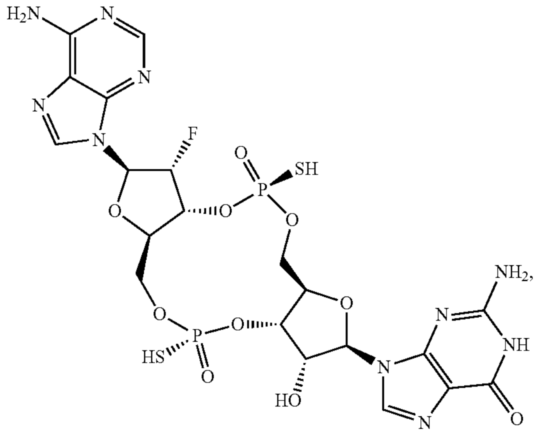
or a prodrug, pharmaceutically acceptable salt, pharmaceutically acceptable solvate or pharmaceutically acceptable hydrate thereof.
In some embodiments of the eighth aspect, the mono- or di-F cyclic guanine and adenine dinucleotide compound is selected from the group consisting of:

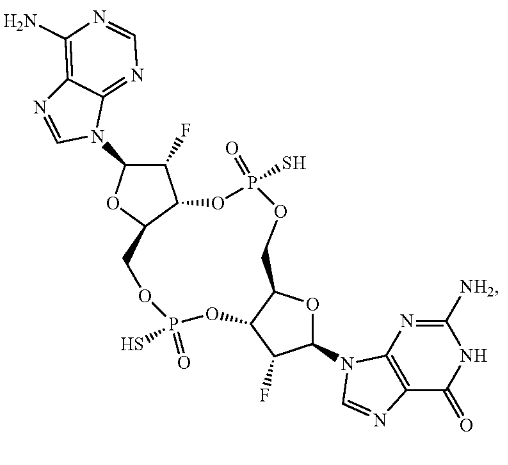

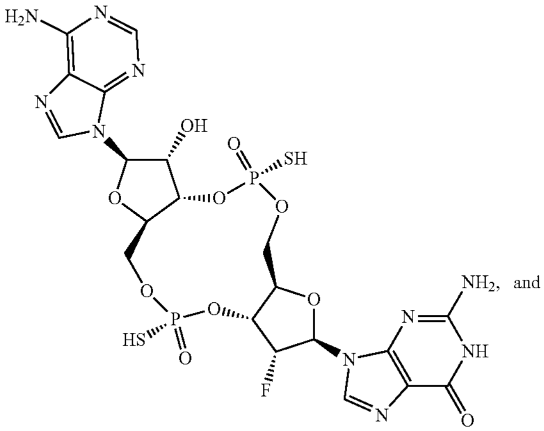

and

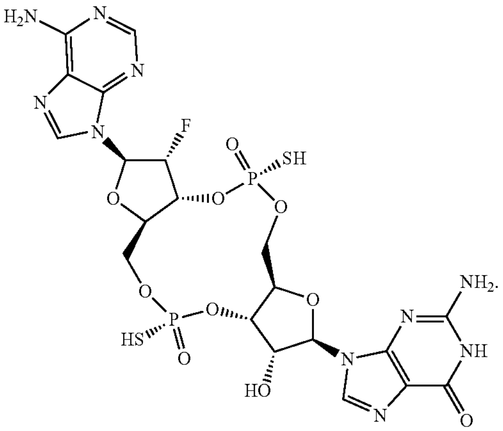

or a prodrug, pharmaceutically acceptable salt, pharmaceutically acceptable solvate or pharmaceutically acceptable hydrate thereof.

In a ninth aspect, a compound 3',3'-RR-(2'F-A)(2'F-A) is provided, having the structure:

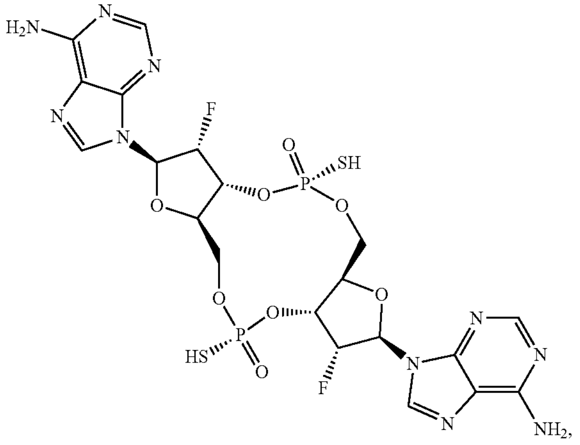 [SMILES: Nc1ncnc2c1ncn2[C@@H]1O[C@@H]2CO[P@@](=O)(S)O[C@H]3[C@@H](F)[C@H](n4cnc5c(N)ncnc54)O[C@@H]3CO[P@@](=O)(S)O[C@H]2[C@H]1F]

or a prodrug, pharmaceutically acceptable salt, pharmaceutically acceptable solvate or pharmaceutically acceptable hydrate thereof.

In a tenth aspect, a compound 3',3'-RS-(2'F-A)(2'F-A) is provided, having the structure:

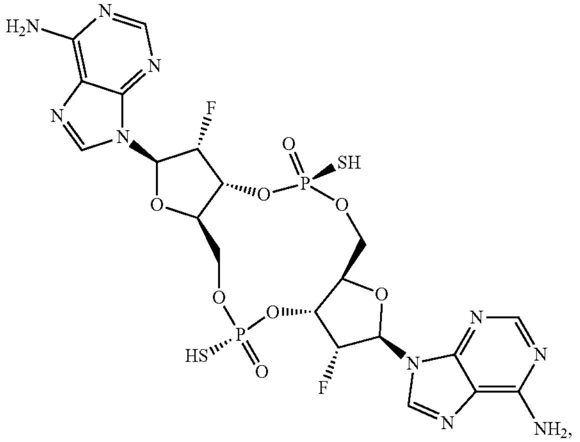 [SMILES: Nc1ncnc2c1ncn2[C@@H]1O[C@@H]2CO[P@@](=O)(S)O[C@H]3[C@@H](F)[C@H](n4cnc5c(N)ncnc54)O[C@@H]3CO[P@](=O)(S)O[C@H]2[C@H]1F]

or a prodrug, pharmaceutically acceptable salt, pharmaceutically acceptable solvate or pharmaceutically acceptable hydrate thereof.

In an eleventh aspect, a compound 3',3'-RR-(2'F-G)(2'F-A) is provided, having the structure:

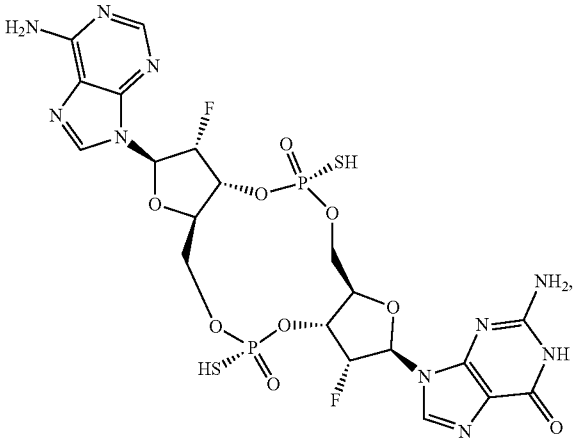 [SMILES: Nc1nc2c(ncn2[C@@H]2O[C@@H]3CO[P@@](=O)(S)O[C@H]4[C@@H](F)[C@H](n5cnc6c(N)ncnc65)O[C@@H]4CO[P@@](=O)(S)O[C@H]3[C@H]2F)c(=O)[nH]1]

or a prodrug, pharmaceutically acceptable salt, pharmaceutically acceptable solvate or pharmaceutically acceptable hydrate thereof.

In a twelfth aspect, a compound 3',3'-RS-(2'F-G)(2'F-A) is provided, having the structure:

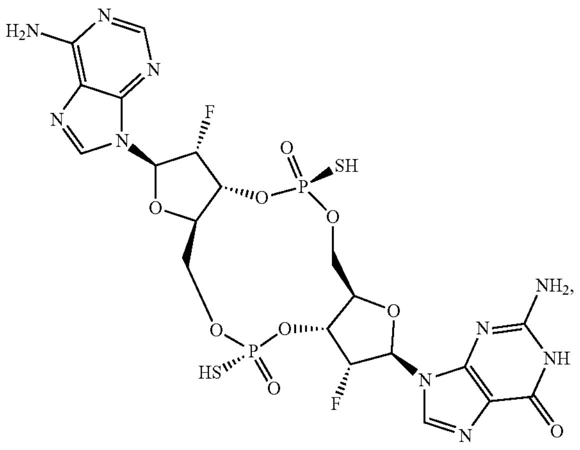 [SMILES: Nc1nc2c(ncn2[C@@H]2O[C@@H]3CO[P@](=O)(S)O[C@H]4[C@@H](F)[C@H](n5cnc6c(N)ncnc65)O[C@@H]4CO[P@@](=O)(S)O[C@H]3[C@H]2F)c(=O)[nH]1]

or a prodrug, pharmaceutically acceptable salt, pharmaceutically acceptable solvate or pharmaceutically acceptable hydrate thereof.

In a thirteenth aspect, a compound 3',3'-RR-(2'F-G)(2'F-G) is provided, having the structure:

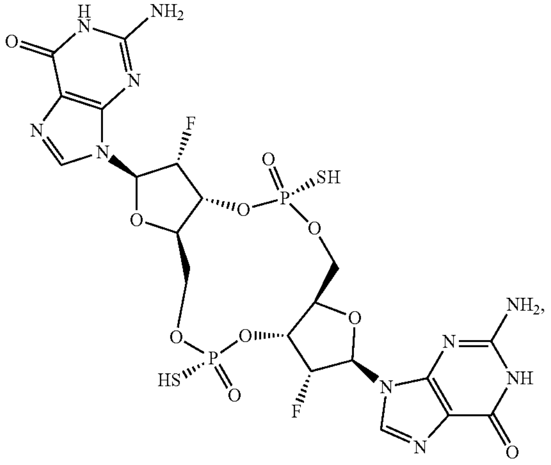 [SMILES: Nc1nc2c(ncn2[C@@H]2O[C@@H]3CO[P@@](=O)(S)O[C@H]4[C@@H](F)[C@H](n5cnc6c(=O)[nH]c(N)nc65)O[C@@H]4CO[P@@](=O)(S)O[C@H]3[C@H]2F)c(=O)[nH]1]

or a prodrug, pharmaceutically acceptable salt, pharmaceutically acceptable solvate or pharmaceutically acceptable hydrate thereof.

In a fourteenth aspect, a compound 3',3'-RS-(2'F-G)(2'F-G) is provided, having the structure:

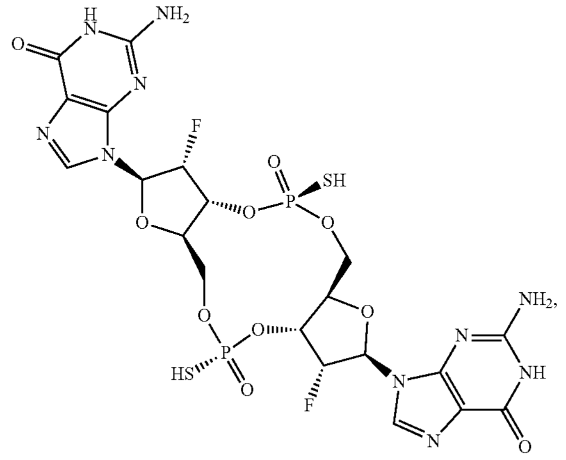 [SMILES: Nc1nc2c(ncn2[C@@H]2O[C@@H]3CO[P@@](=O)(S)O[C@H]4[C@@H](F)[C@H](n5cnc6c(=O)[nH]c(N)nc65)O[C@@H]4CO[P@](=O)(S)O[C@H]3[C@H]2F)c(=O)[nH]1]

or a prodrug, pharmaceutically acceptable salt, pharmaceutically acceptable solvate or pharmaceutically acceptable hydrate thereof.

In a fifteenth aspect, a compound 3',3'-RR-(2'F-iBuG)(2'F-BzA) is provided, having the structure:

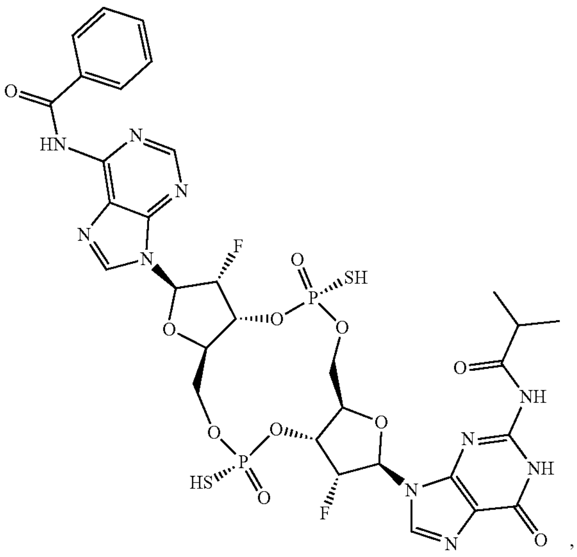 [SMILES: CC(C)C(=O)Nc1nc2c(ncn2[C@@H]2O[C@@H]3CO[P@@](=O)(S)O[C@H]4[C@@H](F)[C@H](n5cnc6c(NC(=O)c7ccccc7)ncnc65)O[C@@H]4CO[P@@](=O)(S)O[C@H]3[C@H]2F)c(=O)[nH]1 ; ","]

or a prodrug, pharmaceutically acceptable salt, pharmaceutically acceptable solvate or pharmaceutically acceptable hydrate thereof.

In a sixteenth aspect, a compound 3',3'-RS-(2'F-iBuG)(2'F-BzA) is provided, having the structure:

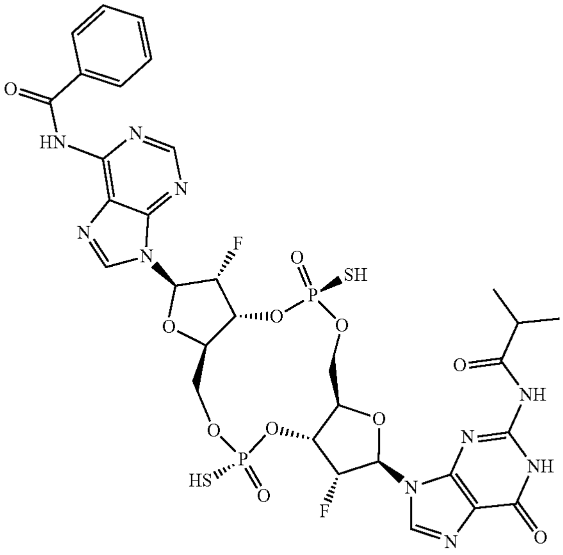
, or a prodrug, pharmaceutically acceptable salt, pharmaceutically acceptable solvate or pharmaceutically acceptable hydrate thereof.

In a seventeenth aspect, a compound 3',3'-RR-(2'F-BzA)(2'F-BzA) is provided, having the structure:

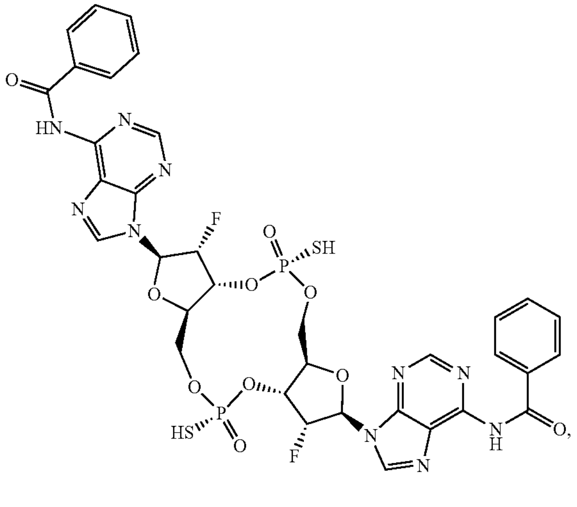 [SMILES: O=C(Nc1ncnc2c1ncn2[C@@H]1O[C@@H]2CO[P@@](=O)(S)O[C@H]3[C@@H](F)[C@H](n4cnc5c(NC(=O)c6ccccc6)ncnc54)O[C@@H]3CO[P@@](=O)(S)O[C@H]2[C@H]1F)c1ccccc1]

or a prodrug, pharmaceutically acceptable salt, pharmaceutically acceptable solvate or pharmaceutically acceptable hydrate thereof.

In an eighteenth aspect, a compound 3',3'-RR-(2'F-iBuG)(2'F-A) is provided, having the structure:

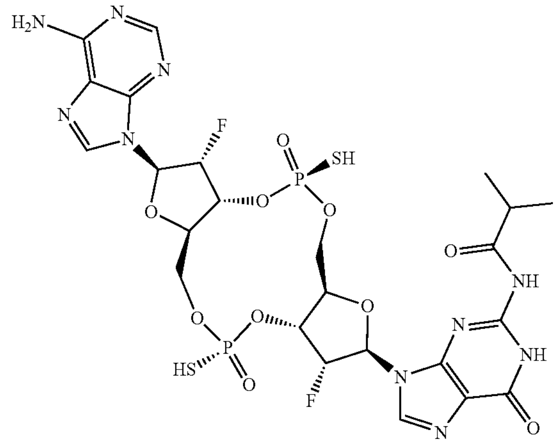
, or a prodrug, pharmaceutically acceptable salt, pharmaceutically acceptable solvate or pharmaceutically acceptable hydrate thereof.

In a nineteenth aspect, a compound 3',3'-RR-(A)(2'F-A) is provided, having the structure:

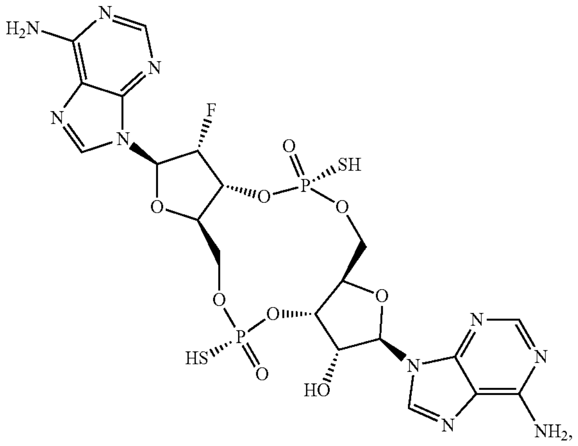 [SMILES: Nc1ncnc2c1ncn2[C@@H]1O[C@@H]2CO[P@@](=O)(S)O[C@H]3[C@@H](F)[C@H](n4cnc5c(N)ncnc54)O[C@@H]3CO[P@@](=O)(S)O[C@H]2[C@H]1O]

or a prodrug, pharmaceutically acceptable salt, pharmaceutically acceptable solvate or pharmaceutically acceptable hydrate thereof.

In a twentieth aspect, a compound 3',3'-RS-(A)(2'F-A) is provided, having the structure:

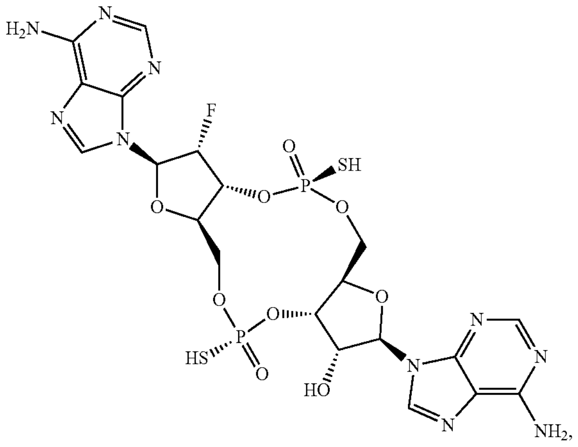 [SMILES: Nc1ncnc2c1ncn2[C@@H]1O[C@@H]2CO[P@](=O)(S)O[C@H]3[C@@H](F)[C@H](n4cnc5c(N)ncnc54)O[C@@H]3CO[P@@](=O)(S)O[C@H]2[C@H]1O]

or a prodrug, pharmaceutically acceptable salt, pharmaceutically acceptable solvate or pharmaceutically acceptable hydrate thereof.

In a twenty-first aspect, a compound 3',3'-RR-(2'F-G)(A) is provided, having the structure:

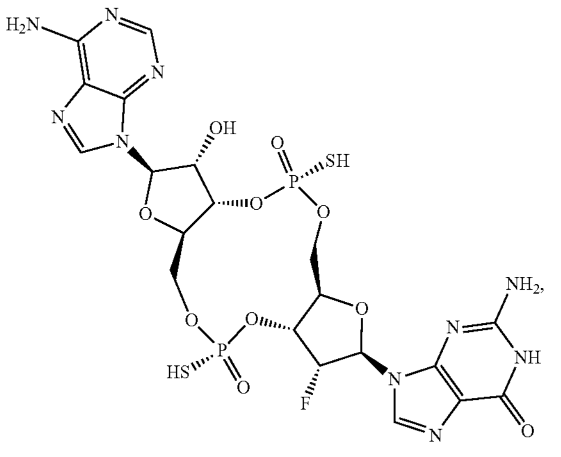 [SMILES: Nc1nc2c(ncn2[C@@H]2O[C@@H]3CO[P@@](=O)(S)O[C@H]4[C@@H](O)[C@H](n5cnc6c(N)ncnc65)O[C@@H]4CO[P@@](=O)(S)O[C@H]3[C@H]2F)c(=O)[nH]1]

or a prodrug, pharmaceutically acceptable salt, pharmaceutically acceptable solvate or pharmaceutically acceptable hydrate thereof.

In a twenty-second aspect, a compound 3',3'-SR-(2'F-G)(A) is provided, having the structure:

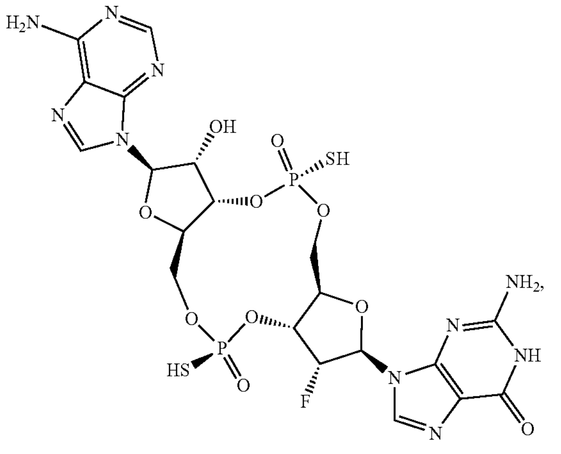 [SMILES: Nc1nc2c(ncn2[C@@H]2O[C@@H]3CO[P@@](=O)(S)O[C@H]4[C@@H](O)[C@H](n5cnc6c(N)ncnc65)O[C@@H]4CO[P@](=O)(S)O[C@H]3[C@H]2F)c(=O)[nH]1]

or a prodrug, pharmaceutically acceptable salt, pharmaceutically acceptable solvate or pharmaceutically acceptable hydrate thereof.

In a twenty-third aspect, a compound 3',3'-RR-(G)(2'F-A) is provided, having the structure:

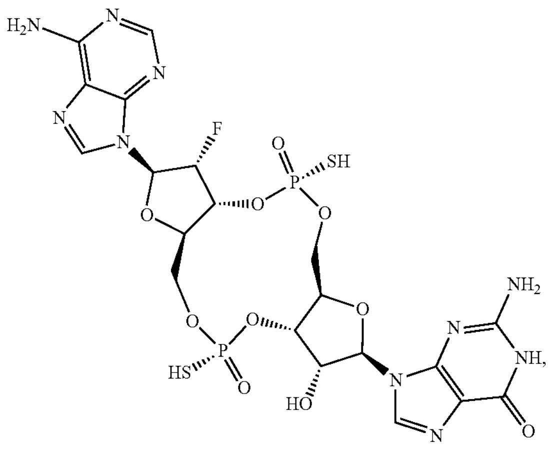 [SMILES: Nc1nc2c(ncn2[C@@H]2O[C@@H]3CO[P@@](=O)(S)O[C@H]4[C@@H](F)[C@H](n5cnc6c(N)ncnc65)O[C@@H]4CO[P@@](=O)(S)O[C@H]3[C@H]2O)c(=O)[nH]1]

or a prodrug, pharmaceutically acceptable salt, pharmaceutically acceptable solvate or pharmaceutically acceptable hydrate thereof.

In a twenty-fourth aspect, a compound 3',3'-RS-(G)(2'F-A) is provided, having the structure:

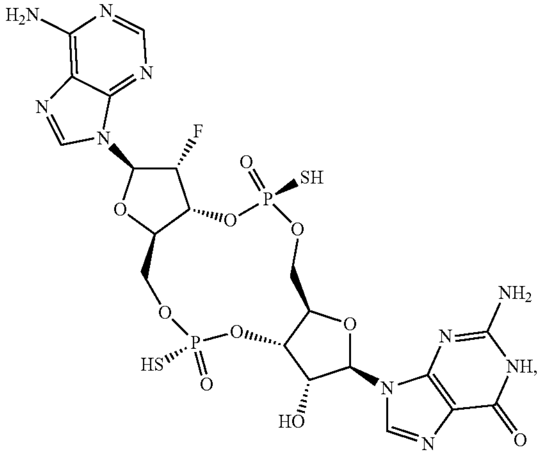 [SMILES: Nc1nc2c(ncn2[C@@H]2O[C@@H]3CO[P@](=O)(S)O[C@H]4[C@@H](F)[C@H](n5cnc6c(N)ncnc65)O[C@@H]4CO[P@@](=O)(S)O[C@H]3[C@H]2O)c(=O)[nH]1]

or a prodrug, pharmaceutically acceptable salt, pharmaceutically acceptable solvate or pharmaceutically acceptable hydrate thereof.

In a twenty-fifth aspect, a compound 3',3'-(2'F-G)(2'F-A) is provided, having the structure:

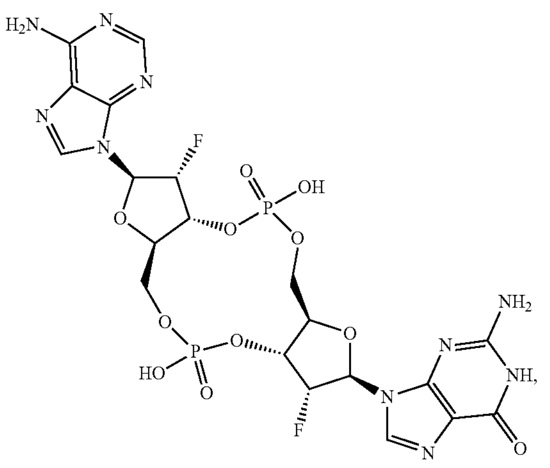 [SMILES: Nc1nc2c(ncn2[C@@H]2O[C@@H]3COP(=O)(O)O[C@H]4[C@@H](F)[C@H](n5cnc6c(N)ncnc65)O[C@@H]4COP(=O)(O)O[C@H]3[C@H]2F)c(=O)[nH]1]

or a prodrug, pharmaceutically acceptable salt, pharmaceutically acceptable solvate or pharmaceutically acceptable hydrate thereof.

In a twenty-sixth aspect, a compound 3',3'-RR-(2'βF-A)(2'βF-A) is provided, having the structure:

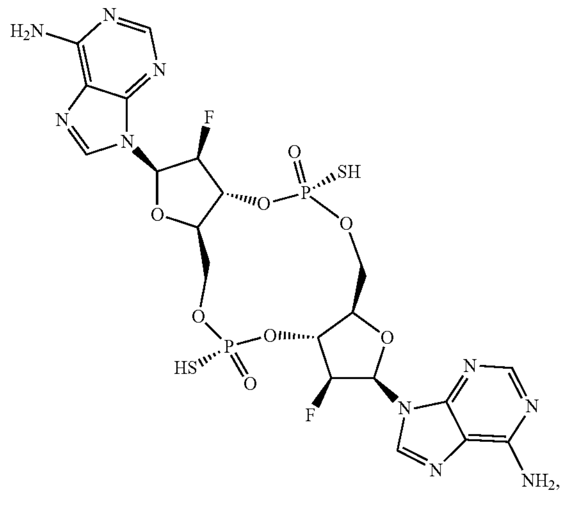 [SMILES: Nc1ncnc2c1ncn2[C@@H]1O[C@@H]2CO[P@@](=O)(S)O[C@H]3[C@H](F)[C@H](n4cnc5c(N)ncnc54)O[C@@H]3CO[P@@](=O)(S)O[C@H]2[C@@H]1F]

or a prodrug, pharmaceutically acceptable salt, pharmaceutically acceptable solvate or pharmaceutically acceptable hydrate thereof.

In a twenty-seventh aspect, a compound 3',3'-RS-(2'βF-A)(2'βF-A) is provided, having the structure:

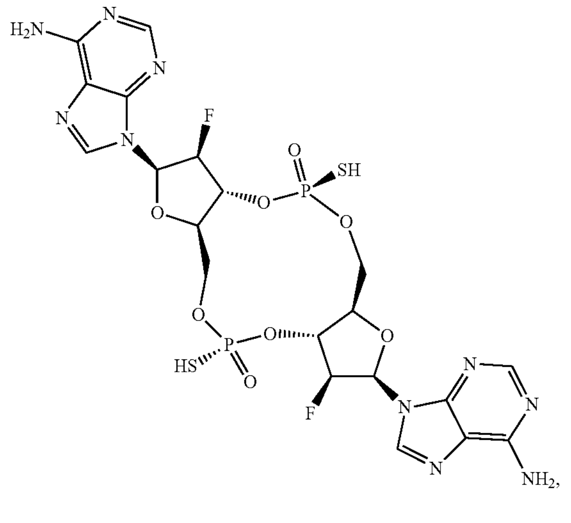 [SMILES: Nc1ncnc2c1ncn2[C@@H]1O[C@@H]2CO[P@@](=O)(S)O[C@H]3[C@H](F)[C@H](n4cnc5c(N)ncnc54)O[C@@H]3CO[P@](=O)(S)O[C@H]2[C@@H]1F]

or a prodrug, pharmaceutically acceptable salt, pharmaceutically acceptable solvate or pharmaceutically acceptable hydrate thereof.

In any of the mono- or di-F-CDN compounds of any of the above aspects and embodiments thereof, the structure is preferably a thiophosphate at each of the phosphate linkers (e.g. R5 and R6 or Formula I are both SH), more preferably wherein the stereochemistry at each phosphorus is R, and the compound is substantially pure.

In some embodiments of any of the above aspects and embodiments thereof, the mono- or di-F-CDN compounds include prodrugs, pharmaceutically acceptable salts, pharmaceutically acceptable solvates or pharmaceutically acceptable hydrates thereof, including pharmaceutically acceptable salts, pharmaceutically acceptable solvates or pharmaceutically acceptable hydrates of any prodrugs thereof, and including any pharmaceutically acceptable solvates or pharmaceutically acceptable hydrates of any pharmaceutically acceptable salts thereof. In some embodiments, the mono- or di-F-CDN compounds include pharmaceutically acceptable solvates, pharmaceutically acceptable hydrates or pharmaceutically acceptable salts thereof. In some embodiments, the mono- or di-F-CDN compound is a pharmaceutically acceptable salt, or a pharmaceutically acceptable solvate or pharmaceutically acceptable hydrate thereof. In some embodiments, the mono- or di-F-CDN compound is a pharmaceutically acceptable salt thereof.

In some embodiments of any of the above aspects and embodiments thereof, the mono- or di-F-CDN compounds include pharmaceutically acceptable salts thereof. In some embodiments, the pharmaceutically acceptable salt is selected from the group consisting of the sodium, potassium, calcium, magnesium, zinc, aluminum, ammonium, diethylamine, isopropylamine, olamine, benzathine, benethamine, tromethamine (2-amino-2-(hydroxymethyl)propane-1,3-diol), morpholine, epolamine, piperidine, piperazine, picoline, dicyclohexylamine, N,N'-dibenzylethylenediamine, 2-hydroxyethylamine, tri-(2-hydroxyethyl)amine, chloroprocaine, choline, deanol, imidazole, diethanolamine, ethylenediamine, meglumine (N-methylglucamine), procaine, dibenzylpiperidine, dehydroabietylamine, glucamine, collidine, quinine, quinolone, erbumine, lysine and arginine salt.

In one embodiment of any of the above aspects or embodiments thereof, the mono- or di-F-CDN compounds are provided as the disodium salt thereof. In some embodiments, the mono- or di-F-CDN compounds are provided as the disodium salt thereof, or a pharmaceutically acceptable solvate or pharmaceutically acceptable hydrate thereof.

In some embodiments of any of the above aspects and embodiments thereof, the mono- or di-F-CDN compound is more active in a cellular assay that measures the induction of human STING dependent IFN-β production as compared to one or more reference compounds. In some embodiments, the one or more reference compounds are selected from the group consisting of 3',3'-(G)(G) (i.e. cyclic-[G(3',5')p-G(3',5')p]), 3',3'-(A)(A) (i.e. cyclic-[A(3',5')p-A(3',5')p]), 3',3'-(G)(A) (i.e. cyclic-[G(3',5')p-A(3',5')p]), 3',3'-RR-(A)(A) (i.e. dithio-(Rp,Rp)-cyclic-[A(3',5')p-A(3',5')p]), 3',3'-RR-(G)(G) (i.e. dithio-(Rp,Rp)-cyclic-[G(3',5')p-G(3',5')p]), and 3',3'-RR-(G)(A) (i.e. dithio-(Rp,Rp)-cyclic-[G(3',5')p-A(3',5')p]). In some embodiments, the mono- or di-F-CDN compound is a mono- or di-F-RR-CDN compound and the one or more reference compounds are selected from the group consisting of 3',3'-RR-(A)(A), 3',3'-RR-(G)(G) and 3',3'-RR-(G)(A). In some embodiments, the reference compound is the di-OH reference compound. In some embodiments, the cellular assay is an hPBMC assay, for example the assay as described in Example 13. In some embodiments, the cellular assay is a THP1 assay, for example the assay as described in Example 14. In a preferred embodiment, the cellular assay is performed without the addition of an agent that enhances uptake of the mono- or di-F-CDN compound or reference compound by the assay cells or an agent that enhances the permeability of the mono- or di-F-CDN compound or reference compound to the assay cells. In some embodiments, the cellular assay is a THP1 cellular assay performed without the addition of an agent that enhances uptake of the mono- or di-F-CDN compound or reference compound by the assay cells or an agent that enhances the permeability of the mono- or di-F-CDN compound or reference compound to the assay cells, in which the mono- or di-F-CDN compound has an EC50 of less than 40 μM, less than 30 μM, less than 20 μM, less than 15 μM, or less than 10 μM. In some embodiments the mono- or di-F-CDN compound has an EC50 of less than 40 μM, less than 30 μM, less than 20 μM, less than 15 μM, or less than 10 μM in a cellular assay that measures induction of human STING dependent IFN-β production, wherein the cellular assay is performed without the addition of an agent that enhances uptake of the mono- or di-F-CDN compound by the assay cells or an agent that enhances the permeability of the mono- or di-F-CDN compound to the assay cells. In one embodiment the cellular assay is a THP1 cellular assay as described in Example 14, wherein the assay is performed without addition of digitonin. In some embodiments, the mono- or di-F-CDN compound has an EC50 that is less than the EC50 of one or more reference compounds selected from the group consisting of 3',3'-(G)(G) (i.e. cyclic-[G(3',5')p-G(3',5')p]), 3',3'-(A)(A) (i.e. cyclic-[A(3',5')p-A(3',5')p]), 3',3'-(G)(A) (i.e. cyclic-[G(3',5')p-A(3',5')p]), 3',3'-RR-(A)(A) (i.e. dithio-(Rp,Rp)-cyclic-[A(3',5')p-A(3',5')p]), 3',3'-RR-(G)(G) (i.e. dithio-(Rp,Rp)-cyclic-[G(3',5')p-G(3',5')p]), and 3',3'-RR-(G)(A) (i.e. dithio-(Rp,Rp)-cyclic-[G(3',5')p-A(3',5')p]) in a cellular assay that measures induction of human STING dependent IFN-β production, preferably wherein the cellular assay is performed without the addition of an agent that enhances uptake of the mono- or di-F-CDN compound or reference compound by the assay cells or an agent that enhances the permeability of the mono- or di-F-CDN compound or reference compound to the assay cells. In some embodiments, the mono- or di-F-CDN compound has an EC50 that is less than the EC50 of a di-OH reference compound in a THP1 cellular assay as described in Example 14, preferably wherein the assay is performed without addition of digitonin. In some embodiments, the mono- or di-F-CDN compound has an EC50 that is at least 2-fold, at least 3-fold, at least 4-fold, at least 5-fold, at least 6-fold, at least 7-fold, or at least 8-fold lower than the EC50 of the di-OH reference compound in the THP1 cellular assay as described in Example 14, wherein the assay is performed without addition of digitonin.

As described hereinafter, a cyclic purine dinucleotide composition according to the present invention, wherein one or more mono- or di-F-CDN compounds present in the composition can induce STING-dependent type I interferon production at least 2-fold, and more preferably 5-fold or 10-fold, or more, at concentrations at least 10-fold, 50-fold, or 100-fold lower than one or more of bis-3',5' c-di-GMP (i.e. 3',3'-(G)(G)), bis-3',5' c-di-AMP (i.e. 3',3'-(A)(A) or CDA), or bis-3',5' c-GMP-AMP (i.e. 3',3'-(G)(A) or cGAMP) (meaning lacking the 2'-F substitution(s)). As noted herein, most preferably, the STING is human STING. In preferred embodiments, a composition comprising a mono- or di-F-CDN compound according to the present invention activates human STING but the corresponding bis-3',5' cyclic purine dinucleotide (having the same purines and lacking the 2'-F substitution(s)) does not.

As also described hereinafter, is a composition comprising a mono- or di-F-CDN compound according to the present invention, wherein one or more mono- or di-F-CDN compounds present in the composition bind STING with an affinity at least 10-fold, 50-fold, or 100-fold higher one or more of bis-3',5' c-di-GMP (i.e. 3',3'-(G)(G)), bis-3',5' c-di-AMP (i.e. 3',3'-(A)(A) or CDA), or bis-3',5' c-GMP-AMP (i.e. 3',3'-(G)(A) or cGAMP) (meaning lacking the 2'-F substitution(s)). As noted herein, most preferably, the STING is human STING. In preferred embodiments, a cyclic purine dinucleotide composition according to the present invention binds STING with an affinity at least 10-fold, 50-fold, or 100-fold higher than the corresponding bis-(3',5') cyclic purine dinucleotide (having the same purines and lacking the 2'-F substitution(s)).

In some embodiments of any of the above aspects and embodiments thereof, the mono- or di-F-CDN compound binds at least one human STING allelic protein product (including any one of WT, REF. HAQ, AQ and Q alleles) with a greater affinity than one or more reference compounds selected from the group consisting of 3',3'-(G)(G) (i.e. cyclic-[G(3',5')p-G(3',5')p]), 3',3'-(A)(A) (i.e. cyclic-[A(3',5')p-A(3',5')p]), 3',3'-(G)(A) (i.e. cyclic-[G(3',5')p-A(3',5')p]), 3',3'-RR-(A)(A) (i.e. dithio-(Rp,Rp)-cyclic-[A(3',5')p-A(3',5')p]), 3',3'-RR-(G)(G) (i.e. dithio-(Rp,Rp)-cyclic-[G(3',5')p-G(3',5')p]), and 3',3'-RR-(G)(A) (i.e. dithio-(Rp,Rp)-cyclic-[G(3',5')p-A(3',5')p]) when measured using at least one human STING protein. In some embodiments of any of the above aspects and embodiments thereof, the mono- or di-F-CDN compound binds at least one human STING allelic protein product with an affinity greater than a di-OH reference compound. Preferably, this is measured using the isolated protein encoded by the hSTING (WT), hSTING (HAQ) or hSTING (REF) allele (Ishikawa, H., and Barber, G. N. (2008). *Nature* 455, 674-678; Yi et al., 2013, PLos One 2013 Oct. 21, 8(10):e77846; the protein sequence of the REF allele is NCBI Reference Sequence NP_938023) using a method such as differential scanning fluorometry (DSF) as described hereinafter and in Example 11.

In a twenty-eighth aspect, the present invention provides pharmaceutical compositions comprising one or more mono- or di-F-CDN compounds, as described in the second through twenty-seventh aspects and any embodiments thereof as described herein above, including any prodrugs, pharmaceutically acceptable salts, pharmaceutically acceptable solvates, or pharmaceutically acceptable hydrates thereof, and a delivery vehicle which enhances cellular uptake and/or stability of the compound. In some embodiments, the delivery vehicle comprises one or more agents selected from the group consisting of adjuvants, lipids, liposomes, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

In a twenty-ninth aspect, the present invention provides pharmaceutical compositions comprising one or more mono- or di-F-CDN compounds, as described in the second through twenty-seventh aspects and any embodiments thereof as described herein above, including any prodrugs, pharmaceutically acceptable salts, pharmaceutically acceptable solvates, or pharmaceutically acceptable hydrates thereof, and a pharmaceutically acceptable excipient.

In a first embodiment of the twenty-ninth aspect, the pharmaceutical composition does not include an agent that enhances cellular permeability of the one or more mono- or di-F-CDN compounds.

In a second embodiment of the twenty-ninth aspect, the pharmaceutical composition does not include an agent that enhances cellular uptake of the one or more mono- or di-F-CDN compounds.

In a third embodiment of the twenty-ninth aspect, the pharmaceutical composition further comprises a delivery vehicle which enhances cellular uptake and/or stability of the compound. In some embodiments, the delivery vehicle comprises one or more agents selected from the group consisting of adjuvants, lipids, liposomes, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

In some embodiments of the twenty-eighth aspect and embodiments thereof or twenty-ninth aspect and first, second or third embodiments thereof, the pharmaceutical composition further comprises one or more additional pharmaceutically active components selected from the group consisting of an immune checkpoint inhibitor (e.g. CTLA-4, PD-1, Tim-3. Vista. BTLA, LAG-3 and TIGIT pathway antagonists; PD-1 pathway blocking agents; PD-L1 inhibitors; including without limitation anti-PD-1 antibodies nivolumab, pembrolizumab or pidilizumab; PD-1 inhibitor AMP-224; anti-CTLA-4 antibody ipilimumab; and anti-PD-L1 antibodies BMS-936559. MPDL3280A, MED14736, or avelumab); a TLR agonist (e.g. CpG or monophosphoryl lipid A); an inactivated or attenuated bacteria which induce innate immunity (e.g., inactivated or attenuated *Listeria* monocytogenes); a composition that mediates innate immune activation via Toll-like Receptors (TLRs), via (NOD)-like receptors (NLRs), via Retinoic acid inducible gene-based (RIG)-I-like receptors (RLRs), via C-type lectin receptors (CLRs), or via pathogen-associated molecular patterns (PAMPs); and a chemotherapeutic agent. In some embodiments, the immune checkpoint inhibitor is selected from the group consisting of a CTLA-4 pathway antagonist, a PD-1 pathway antagonist, a Tim-3 pathway antagonist, a Vista pathway antagonist, a BTLA pathway antagonist, a LAG-3 pathway antagonist, and a TIGIT pathway antagonist. In some embodiments, the immune checkpoint inhibitor is an anti-PD-1 antibody, an anti-PD-L1 antibody, an anti-CTLA-4 antibody, an anti-TIM-3 antibody, an anti-BTLA antibody or an anti-LAG-3 antibody. In some embodiments, the immune checkpoint inhibitor is selected from the group consisting of nivolumab, pembrolizumab, pidilizumab, AMP-224, ipilimumab, BMS-936559, MPDL3280A, MEDI4736, and avelumab. In some embodiments, the TLR agonist is CpG or monophosphoryl lipid A.

In some embodiments of the twenty-eighth aspect or twenty-ninth aspect and any of the above embodiments thereof, the pharmaceutical composition further comprises an inactivated tumor cell which expresses and secretes one or more cytokines which stimulate dendritic cell induction, recruitment and/or maturation, or which expresses and secretes one or more heat shock proteins, including gp96-Ig fusion proteins. In some embodiments, the one or more cytokines is selected from the group consisting of GM-CSF, CCL20, CCL3, IL-12p70 and FLT-3 ligand. In some embodiments, the tumor cell is inactivated by treatment with radiation. In some embodiments, the one or more cytokines is selected from the group consisting of GM-CSF. CCL20, CCL3, IL-12p70 and FLT-3 ligand, and the tumor cell is inactivated by treatment with radiation. In some embodiments, the inactivated tumor cell expresses and secretes a gp96-Ig fusion protein.

In some embodiments of the twenty-eighth aspect or twenty-ninth aspect and any of the above embodiments thereof, the pharmaceutical composition further comprises one or more antigens selected for the purposes of inducing an immune response against said one or more antigen(s) when the composition is administered to an individual. In some embodiments, the antigen is a recombinant protein antigen. In some embodiments, the antigen is a recombinant protein antigen related to an infectious disease, a malignancy, or an allergan. In some embodiments, the one or more antigens is one or more antigens in Table 1.

In some embodiments of the twenty-eighth aspect or twenty-ninth aspect and any of the above embodiments thereof, the pharmaceutical compositions are formulated as aqueous or oil-in-water emulsions.

In a thirtieth aspect, the invention provides a method for treating an individual suffering from a cancer, wherein the method comprises administering to the individual in need thereof an effective amount of one or more mono- or di-F-CDN compounds, as described in the second through twenty-seventh aspects and any embodiments thereof as described herein above, including any prodrugs, pharmaceutically acceptable salts, pharmaceutically acceptable solvates, or pharmaceutically acceptable hydrates thereof, or compositions thereof as described in the twenty-eighth and twenty-ninth aspects and any embodiments thereof as described herein above. In some embodiments, the one or more mono- or di-F-CDN compounds or composition thereof is administered non-parenterally or parenterally. In some embodiments, the administration is subcutaneous, intramuscular, intradermal, mucosal, vaginal, cervical, peri-tumoral, intra-tumoral, or directly into the tumor-draining lymph node(s). In some embodiments, the administration is mucosal, preferably oral.

In a first embodiment of the thirtieth aspect, the individual receiving such treatment may be suffering from a cancer selected from the group consisting of a colorectal cancer, an aero-digestive squamous cancer, a lung cancer, a brain cancer, a liver cancer, a stomach cancer, a bladder cancer, a thyroid cancer, an adrenal cancer, a gastrointestinal cancer, an oropharyngeal cancer, an esophageal cancer, a head and neck cancer, an ovarian cancer, a uterine cancer, a cervical cancer, an endometrial cancer, a breast cancer, a melanoma, a prostate cancer, a pancreatic carcinoma, a renal carcinoma, a sarcoma, a leukemia, a lymphoma and a multiple myeloma.

In a second embodiment of the thirtieth aspect and of the first embodiment thereof, the method for treating an individual suffering from a cancer further comprises administering one or more additional cancer therapies. In some embodiments, the one or more additional cancer therapies comprises radiation therapy, surgery, a chemotherapy, or an immunotherapy (for example, without limitation, an immunomodulator, an immune checkpoint inhibitor, a cellular immunotherapy, or a cancer vaccine). In some embodiments, the one or more additional cancer therapies comprises an inactivated tumor cell that expresses and secretes one or more cytokines or one or more heat shock proteins. In some embodiments, the cytokine is selected from the group consisting of GM-CSF. CCL20, CCL3, IL-12p70, and FLT-3 ligand. In some embodiments the heat shock protein is a gp96-Ig protein. In some embodiments, the method comprises administering one or more additional cancer therapies selected from the group consisting of a chemotherapeutic agent; an immune checkpoint inhibitor; a TLR agonist; a vaccine selected to stimulate an immune response to one or more cancer antigens, a therapeutic antibody that induces antibody-dependent cellular cytotoxicity; an immunomodulatory cell line; an inactivated or attenuated bacteria that induces innate immunity; an antigen selected for the purpose of inducing an immune response, and a composition that mediates innate immune activation via Toll-like Receptors (TLRs), (NOD)-like receptors (NLRs), Retinoic acid inducible gene-based (RIG)-I-like receptors (RLRs), C-type lectin receptors (CLRs) or pathogen-associated molecular patterns ("PAMPs"). In some embodiments, the immune checkpoint inhibitor is an anti-PD-1 antibody, an anti-PD-L1 antibody, an anti-CTLA-4 antibody, an anti-TIM-3 antibody, an anti-BTLA antibody or an anti-LAG-3 antibody. In some embodiments, the TLR agonist is CpG or monophosphoryl lipid A. In some embodiments, the therapeutic antibody that induces antibody-dependent cellular cytotoxicity is rituximab, ibritumomab, tositumomab, cetuximab, trastuzumab, brentuximab vedotin, alemtuzumab, oncolym, ibilimumab, vitaxin, or bevacizumab.

In some embodiments of the thirtieth aspect and first and second embodiments thereof, the individual suffers from a cancer expressing a cancer antigen, and the method for treating said individual further comprises administering to the individual a primary therapy to remove or kill cancer cells expressing the cancer antigen, wherein the administration of the primary therapy is simultaneously with, prior to or following administration of the mono- or di-F-CDN compound or composition thereof. In some embodiments, the mono- or di-F-CDN compound or composition thereof is administered as a neoadjuvant therapy to the primary therapy. In preferred embodiments, the mono- or di-F-CDN compound or composition thereof is administered following the primary therapy. In some embodiments, the primary therapy comprises surgery to remove the cancer cells from the mammal, radiation therapy to kill the cancer cells in the mammal, or both surgery and radiation therapy.

In a thirty-first aspect, the invention provides a method of treating a disease in an individual, comprising administering to the individual in need thereof i) an effective amount of one or more mono- or di-F-CDN compounds, as described in the second through twenty-seventh aspects and any embodiments thereof as described herein above, including any prodrugs, pharmaceutically acceptable salts, pharmaceutically acceptable solvates, or pharmaceutically acceptable hydrates thereof, or compositions thereof as described in the twenty-eighth and twenty-ninth aspects and any embodiments thereof as described herein above; and ii) an effective amount of one or more therapeutic antibodies that induce antibody-dependent cellular cytotoxicity, wherein the disease is selected from the group consisting of a cancer, acute rejection of an organ transplant. Type I diabetes mellitus, rheumatoid arthritis, psoriasis. Crohn's disease, restenosis and allergic asthma. In some embodiments, the cancer is selected from the group consisting of lymphoma (e.g. B-cell lymphoma), breasts cancer, chronic lymphocytic leukemia, colorectal cancer, melanoma, non-small cell lung carcinoma, small cell lung cancer, bladder cancer, prostate cancer and other solid tumors. In some embodiments, the therapeutic antibody is selected from the group consisting of muromonab-CD3, infliximab, daclizumab, omalizumab, abciximab, rituximab, ibritumomab, tositumomab, cetuximab, trastuzumab, brentuximab vedotin, alemtuzumab, oncolym, ibilimumab, vitaxin, and bevacizumab.

In a thirty-second aspect, the invention provides a method for the treatment of disorders in which shifting of Th1 to Th2 immunity confers clinical benefit, wherein the method comprises administering to the individual in need thereof one or more mono- or di-F-CDN compounds, as described in the second through twenty-seventh aspects and any embodiments thereof as described herein above, including any prodrugs, pharmaceutically acceptable salts, pharmaceutically acceptable solvates, or pharmaceutically acceptable hydrates thereof, or compositions thereof as described in the twenty-eighth and twenty-ninth aspects and any embodiments thereof as described herein above. Cell-mediated immunity (CMI) is associated with TH1 CD4+ T lymphocytes producing cytokines IL-2, interferon (IFN)-γ and tumor necrosis factor (TNF)-α. In contrast, humoral immunity is associated with TH2 CD4+ T lymphocytes producing IL-4. IL-6 and IL-10. Immune deviation towards TH1 responses typically produces activation of cytotoxic T-cell lymphocytes (CTL), natural killer (NK) cells, macrophages and monocytes. Generally, Th1 responses are more effective against intracellular pathogens (viruses and bacteria that are inside host cells) and tumors, while Th2 responses are more effective against extracellular bacteria, parasites including helminths and toxins. In addition, the activation of innate immunity is expected to normalize the T-helper type 1 and 2 (Th1/Th2) immune system balance and to suppress the excessive reaction of Th2 type responses that cause immunoglobulin (Ig) E-dependent allergies and allergic asthma.

The mono- or di-F-CDN compounds, as described in the second through twenty-seventh aspects and any embodiments thereof as described herein above, including any prodrugs, pharmaceutically acceptable salts, pharmaceutically acceptable solvates, or pharmaceutically acceptable hydrates thereof, or compositions thereof as described in the twenty-eighth and twenty-ninth aspects and any embodiments thereof as described herein above, may be administered to individuals in need thereof, as described in the methods of the thirtieth through thirty-second aspects and any embodiments thereof as described herein above, by a variety of parenteral and non-parenteral routes in formulations containing pharmaceutically acceptable excipients (e.g. carriers, adjuvants, vehicles and the like). Preferred non-parenteral routes include mucosal (e.g., oral, vaginal, nasal, cervical, etc.) routes. Preferred parenteral routes include but, are not limited to, one or more of subcutaneous, intravenous, intramuscular, intraarterial, intradermal, intrathecal and epidural administrations. Preferably administration is by subcutaneous, intra-tumoral or peri-tumoral routes, more preferably subcutaneous administration.

The mono- or di-F-CDN compounds, as described in the second through twenty-seventh aspects and any embodiments thereof as described herein above, including any prodrugs, pharmaceutically acceptable salts, pharmaceutically acceptable solvates, or pharmaceutically acceptable hydrates thereof, or compositions thereof as described in the twenty-eighth and twenty-ninth aspects and any embodiments thereof as described herein may be co-administered to individuals in need thereof, as described in the methods of the thirtieth through thirty-second aspects and any embodiments thereof as described herein above, with one or more additional pharmaceutically active components such as adjuvants, lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers, immune checkpoint inhibitors (e.g. CTLA-4, PD-1. Tim-3, Vista. BTLA, LAG-3 and TIGIT pathway antagonists; PD-1 pathway blocking agents; PD-L1 inhibitors; including without limitation anti-PD-1 antibodies nivolumab, pembrolizumab or pidilizumab; PD-1 inhibitor AMP-224; anti-CTLA-4 antibody ipilimumab; and anti-PD-L1 antibodies BMS-936559, MPDL3280A, MEDI4736, or avelumab), inactivated or attenuated bacteria which induce innate immunity (e.g., inactivated or attenuated *Listeria monocytogenes*), compositions which mediate innate immune activation via Toll-like Receptors (TLRs), (NOD)-like receptors (NLRs). Retinoic acid inducible gene-based (RIG)-I-like receptors (RLRs). C-type lectin receptors (CLRs), or pathogen-associated molecular patterns ("PAMPs"), or chemotherapeutic agents.

In a thirty-third aspect, the invention provides one or more mono- or di-F-CDN compounds, as described in the second through twenty-seventh aspects and any embodiments thereof as described herein above, including any prodrugs, pharmaceutically acceptable salts, pharmaceutically acceptable solvates, or pharmaceutically acceptable hydrates thereof, or compositions thereof as described in the twenty-eighth and twenty-ninth aspects and any embodiments thereof as described herein above, for use as adjuvants in combination with a therapeutic or prophylactic vaccine. In some embodiments, the vaccine is selected to stimulate an immune response to one or more predetermined antigens. In some embodiments, the vaccine comprises one or more antigens, including a recombinant protein antigen related to an infectious disease, a malignancy, or an allergan. In some embodiments, the one or more mono- or di-F-CDN compound or composition thereof is used simultaneously with, prior to or following the vaccine. In some embodiments, the one or more mono- or di-F-CDN compound or composition thereof is formulated in the same composition as the vaccine.

In a first embodiment of the thirty-third aspect, the vaccine comprises an inactivated or attenuated bacteria or virus comprising the one or more antigens of interest, one or more purified antigens, live viral or bacterial delivery vectors recombinantly engineered to express and/or secrete the one or more antigens, antigen presenting cell (APC) vectors comprising cells that are loaded with the one or more antigens or transfected with a composition comprising a nucleic acid encoding the one or more antigens, liposomal antigen delivery vehicles, or naked nucleic acid vectors encoding the one or more antigens. In some embodiments, the vaccine is an anti-bacterial, anti-viral, or anti-cancer therapeutic or prophylactic vaccine. In some embodiments, the one or more antigens is one or more antigens selected from the group consisting of a viral antigen, a bacterial antigen and a cancer antigen.

In some embodiments of the thirty-third aspect and first embodiment thereof, the vaccine comprises an inactivated tumor cell that expresses and secretes one or more cytokines. In some embodiments, the cytokine is selected from the group consisting of GM-CSF, CCL20, CCL3, IL-12p70, and FLT-3 ligand.

In some embodiments of the thirty-third aspect and first embodiment thereof, the vaccine comprises an inactivated tumor cell that expresses and secretes one or more heat shock proteins. In some embodiments, the heat shock protein is gp96-Ig fusion protein.

In a thirty-fourth aspect, the invention provides a method for treating an individual suffering from a chronic infectious disease, wherein the method comprises administering to the individual in need thereof an effective amount of one or more mono- or di-F-CDN compounds, as described in the second through twenty-seventh aspects and any embodiments thereof as described herein above, including any prodrugs, pharmaceutically acceptable salts, pharmaceutically acceptable solvates, or pharmaceutically acceptable hydrates thereof, or compositions thereof as described in the twenty-eighth and twenty-ninth aspects and any embodiments thereof as described herein above. In some embodiments, the one or more mono- or di-F-CDN compounds or composition thereof is administered in combination with another agent for use in treating the chronic infectious disease. In some embodiments, the chronic infectious disease is selected from the group consisting of HBV infection, HCV infection, HPV infection, HSV infection and hepatocellular cancer.

In a thirty-fifth aspect, the invention provides one or more mono- or di-F-CDN compounds, as described in the second through twenty-seventh aspects and any embodiments thereof as described herein above, including any prodrugs, pharmaceutically acceptable salts, pharmaceutically acceptable solvates, or pharmaceutically acceptable hydrates thereof, or compositions thereof as described in the twenty-eighth and twenty-ninth aspects and any embodiments thereof as described herein above, for use in treating a disease or indication as described in any of the thirtieth through thirty-fourth aspects and any embodiments thereof as described herein above. In a preferred embodiment, the one or more mono- or di-F-CDN compounds are for use in treating a cancer. In some embodiments, the cancer is selected from the group consisting of a colorectal cancer, an aero-digestive squamous cancer, a lung cancer, a brain cancer, a liver cancer, a stomach cancer, a bladder cancer, a thyroid cancer, an adrenal cancer, a gastrointestinal cancer, an oropharyngeal cancer, an esophageal cancer, a head and neck cancer, an ovarian cancer, a uterine cancer, a cervical cancer, an endometrial cancer, a breast cancer, a melanoma, a prostate cancer, a pancreatic carcinoma, a renal carcinoma, a sarcoma, a leukemia, a lymphoma and a multiple myeloma.

In a thirty-sixth aspect, the invention provides one or more mono- or di-F-CDN compounds, as described in the second through twenty-seventh aspects and any embodiments thereof as described herein above, including any prodrugs, pharmaceutically acceptable salts, pharmaceutically acceptable solvates, or pharmaceutically acceptable hydrates thereof, or compositions thereof as described in the twenty-eighth and twenty-ninth aspects and any embodiments thereof as described herein above, for use the preparation of a medicament for the treatment of a disease or indication as described in any of the thirtieth through thirty-fourth aspects and any embodiments thereof as described herein above. In a preferred embodiment, the one or more mono- or di-F-CDN compounds are for use in preparation of a medicament for the treatment of a cancer. In some embodiments, the cancer is selected from the group consisting of a colorectal cancer, an aero-digestive squamous cancer, a lung cancer, a brain cancer, a liver cancer, a stomach cancer, a bladder cancer, a thyroid cancer, an adrenal cancer, a gastrointestinal cancer, an oropharyngeal cancer, an esophageal cancer, a head and neck cancer, an ovarian cancer, a uterine cancer, a cervical cancer, an endometrial cancer, a breast cancer, a melanoma, a prostate cancer, a pancreatic carcinoma, a renal carcinoma, a sarcoma, a leukemia, a lymphoma and a multiple myeloma.

In a thirty-seventh aspect, the invention provides a kit that includes one or more mono- or di-F-CDN compounds, as described in the second through twenty-seventh aspects and any embodiments thereof as described herein above, including any prodrugs, pharmaceutically acceptable salts, pharmaceutically acceptable solvates, or pharmaceutically acceptable hydrates thereof, or compositions thereof as described in the twenty-eighth and twenty-ninth aspects and any embodiments thereof as described herein above. In some embodiments, one or more mono- or di-F-CDN compounds or compositions thereof is packaged, e.g., in a vial, bottle or similar container, which may be further packaged, e.g., within a box, envelope, or similar container. In some embodiments, one or more mono- or di-F-CDN compounds or compositions thereof is approved by the U.S. Food and Drug Administration or similar regulatory agency for administration to a mammal, e.g., a human. In one embodiment, such a kit includes written instructions for use and/or other indication that the one or more mono- or di-F-CDN compounds or compositions thereof is suitable or approved for administration to a mammal. e.g., a human, for a suitable disease or condition. In some embodiments, the compound or composition is packaged in unit dose or single dose form, e.g., single dose pills, capsules, or the like.

In some embodiments of the pharmaceutical compositions of the twenty-eighth and twenty-ninth aspects and any embodiments thereof as described herein above, and of the methods for the treatment of diseases or indications as described in any of the thirtieth through thirty-fourth aspects and any embodiments thereof as described herein above, and the compounds for use in treating diseases as described in the thirty-fifth aspect, or for use in preparing a medicament as described in the thirty-sixth aspect as described herein above, the compound is a compound selected from the group consisting of:

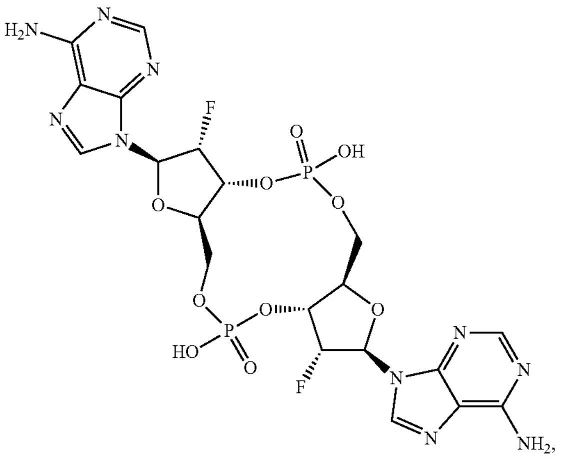

,

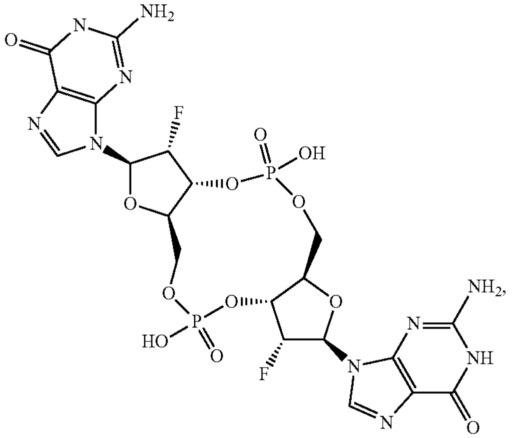

and

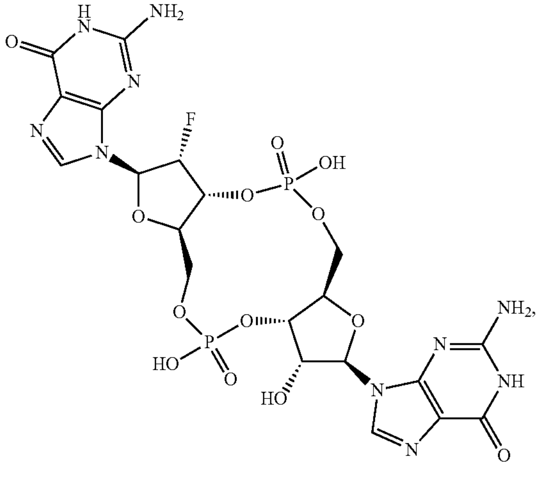

, or a prodrug, pharmaceutically acceptable salt, pharmaceutically acceptable solvate or pharmaceutically acceptable hydrate thereof.

BRIEF DESCRIPTION OF THE FIGURES

FIG. 1A-B depicts analytical data NMR (1A) and LC (1B) for 3',3'-RR-(2'F-G)(2'F-A) (dithio-(Rp,Rp)-cyclic-[2'F-G (3',5')p-2'F-A(3',5')p]).

FIG. 4 depicts the protein sequence of hSTING(REF).

DETAILED DESCRIPTION OF THE INVENTION

Figure 2:
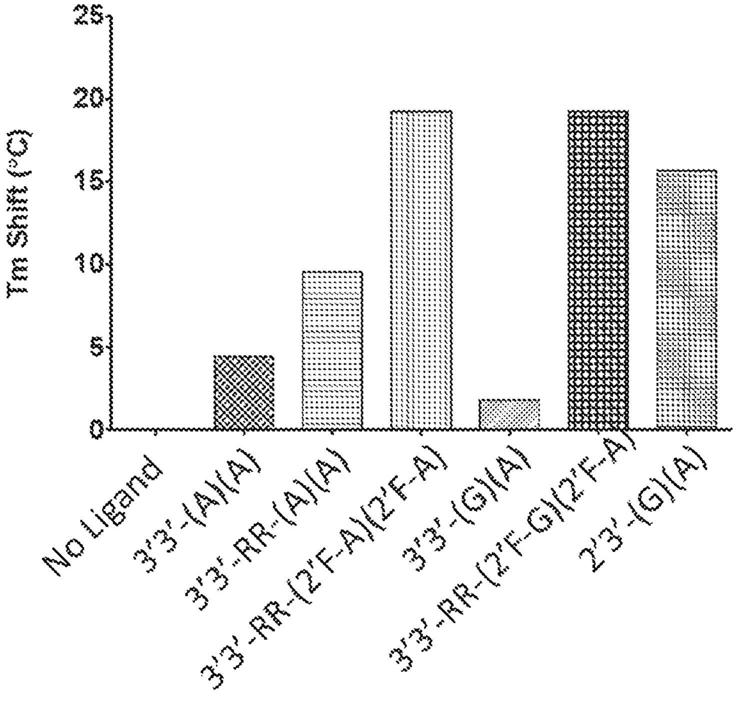
FIG. 2 depicts binding of mono- or di-F CDNs to human STING REF protein.

The present invention relates to the production and use of mono- or di-fluoro substituted bis-3',5' cyclic-di-nucleotide (mono- or di-F-CDN) immune stimulators that activate DCs via a cytoplasmic receptor known as STING (Stimulator of Interferon Genes). In particular, the CDNs of the present invention are provided in the form of a composition comprising one or more mono- or di-F-CDN, and most preferably one or more dithio Rp,Rp di-F-CDNs.

Conserved microbial structures known as Pathogen-Associated Molecular Patterns (PAMPs) are sensed by host cell Pattern Recognition Receptors (PRRs with germ-line encoded specificity), triggering a downstream signaling cascade resulting in the induction of cytokines and chemokines, and initiation of a specific adaptive immune response (Iwasaki and Medzhitov, Science 327, 291-5, 2010). How the innate immune system is engaged by PAMPs presented from an infectious agent shapes the development of an adaptive response appropriate to combat the invading pathogen from causing disease.

One objective in the design of immune modulators and adjuvants is to select defined PAMPs or synthetic molecules which activate designated PRRs and initiate a desired response. Adjuvants such as monophosphoryl lipid A (MPL) and CpG are microbial-derived PAMPs recognized by Toll-like receptors (TLRs), a class of PRRs that signal through MyD88 and TRIF adaptor molecules and mediate induction of NF-kB dependent proinflammatory cytokines (Pandey et. al., Cold Spring Harb Perspect Biol 2015; 7: a016246). MPL (TLR-4 agonist) and CpG (TLR-9 agonist) are the most clinically advanced adjuvants, and are components of vaccines that are approved or pending approval by the FDA (Einstein et al., Human Vaccines, 5: 705-19, 2009; Ahmed et al., Nature Immunol. 12: 509-17, 2011). While TLRs present on the cell surface (e.g., TLR-4) and endosomes (e.g., TLR-9) sense extracellular and vacuolar pathogens, the productive growth cycle of multiple pathogens including viruses and intracellular bacteria occurs in the cytosol. The compartmentalization of extracellular, vacuolar, and cytosolic PRRs has led to the hypothesis that the innate immune system can sense productively replicating pathogenic microbes by monitoring the cytosol (Vance et al., Cell Host & Microbe 6: 10-21, 2009). This provides a rationale for the use of agonists that activate PRRs comprising the cytosolic surveillance pathway and may be an effective strategy for the design of effective vaccines for eliciting cellular immunity, an immune correlate of protection against intracellular pathogens and therapeutic benefit in cancer.

Type I interferons (IFN-α, IFN-β) are the signature cytokines induced by two distinct TLR-independent cytosolic signaling pathways. In the first pathway, various forms of single-stranded and double-stranded (ds) RNA are sensed by RNA helicases, including retinoic acid-inducible gene I (RIG-I) and melanoma differentiation-associated gene 5 (MDA-5), and through the IFN-β promoter stimulator 1 (IPS-1) adaptor protein mediate phosphorylation of the IRF-3 transcription factor, leading to induction of IFN-β (Ireton and Gale, Viruses 3: 906-19, 2011). IPS-$1^{-/-}$ deficient mice have increased susceptibility to infection with RNA viruses. Sensors that signal through the IPS-1 pathway are directly targeted for inactivation by various viral proteins, demonstrating a requirement of this cytosolic host defense pathway to control productive virus infection. Synthetic dsRNA, such as polyinosinic:polycytidylic acid (poly (I:C) and poly ICLC, an analog that is formulated with poly L lysine to resist RNase digestion, is an agonist for both TLR3 and MDA5 pathways, is a powerful inducer of IFN-β, and is currently being evaluated in several diverse clinical settings (Caskey et al., J. Exp. Med. 208: 2357-77, 2011).

STING (Stimulator of Interferon Genes) is a central mediator for the second cytosolic pathway that triggers type 1 interferon, in response to sensing cytosolic double-stranded (ds) DNA from infectious pathogens or aberrant host cells (Danger Associated Molecular Patterns. DAMPS) (Barber, Immunol. Rev 243: 99-108, 2011). Alternatively known as TMEM 173, MITA, ERIS, and MPYS. STING was discovered using cDNA expression cloning methods as a MyD88-independent host cell defense factor expressed in macrophages, dendritic cells (DCs) and fibroblasts was found to induce expression of IFN-β and NF-κB dependent pro-inflammatory cytokines in response to sensing cytoplasmic DNA, in response to infection with herpes simplex virus (Ishikawa and Barber. Nature 455: 674-79, 2008).

Cyclic dinucleotides (CDNs) have been studied as ubiquitous small molecule second messengers synthesized by bacteria which regulate diverse processes including motility and formation of biofilms (Romling et al., Micrb. Mol. Biol. Rev., 77: 1-52, 2013). CDNs are also a ligand for STING (Burdette et al., Nature 478: 515-18, 2011). In response to binding CDNs, STING activates signaling through the TBK-1/IRF-3 axis and NF-κB axis and induces the expression of IFN-β and other co-regulated genes (Burdette and Vance. Nat Immunol. 14: 19-26, 2013; McWhirter et al., J. Exp. Med. 206: 1899-1911, 2009). Cyclic (c)-di-AMP is secreted by multidrug resistance efflux pumps from the intracellular bacterium *Listeria monocytogenes* into the cytosol of infected host antigen presenting cells, and is correlated with $CD4^+$ and CD8+ T cell-mediated protection in the mouse listeriosis model (Woodward et al., Science 328, 1703-05, 2010; Crimmins et al., Proc. Natl. Acad. Sci. USA 105: 10191-10196, 2008). Induction of IFN-β in Lm-infected macrophages is dependent upon activation of the STING signaling pathway, and the level of type I IFN induced by c-di-AMP in macrophages from $MyD88^{-/-}$ $Trif^{-/-}$ or C57BL/6 parental mice is indistinguishable (Leber et al., PLoS Pathog 4(1): e6. doi:10.1371, 2008; Witte et al., mBio 4: e00282-13, 2012). In contrast, IFN-β is not induced by CDNs in macrophages derived from goldenticket (gt) mice encoding a nonfunctional mutant STING protein (Sauer et al., Infect. Immun. 79: 688-94, 2011). The extracellular bacterium. *Vibrio cholera*, produces a hybrid c-GMP-AMP (cGAMP) molecule, which also induces the STING pathway (Davies et al., Cell 149: 358-70, 2012). The activation of innate immunity with these ubiquitous second messengers suggests that sensing CDNs may be integral to host defense against bacterial infection.

While STING was discovered as being the critical sensor for inducing the production of IFN-β in response to infection with herpes simplex virus, how the DNA from this viral pathogen was detected in the cytoplasm initially remained elusive. This conundrum was solved with the discovery of cyclic GMP-AMP synthase (cGAS), a host cell nucleotidyl transferase that directly binds dsDNA, and in response synthesizes a second messenger, cyclic GMP-AMP (cGAMP), which activates the STING pathway and induces IFN-β expression (Sun et al., Science 339: 786-91, 2013; Wu et al., Science 339: 826-30, 2013). Cells without a functional cGAS are unable to express IFN-β in response to stimulation with cytosolic DNA. It was later shown that cells expressing a particular STING allele were non-responsive to stimulation by CDNs, but responsive to stimulation with dsDNA in a cGAS-dependent and TLR9 (MyD88)-independent manner (Diner et. al., 2013). This observation was incompatible with a mechanism defined by cGAS synthesizing STING-activating CDN ligands in response to sensing cytosolic dsDNA. This apparent paradox was resolved by several independent investigators, who demonstrated that cGAS produces a non-canonical CDN (c-GMP-AMP; cGAMP) that activates STING alleles that are non-responsive to canonical CDNs (Civril et al., Nature 498: 332-37, 2013, Diner et al., 2013, Gao et al., 2013, Ablasser et al., Nature 498: 380-84, 2013, Kranzusch et al., Cell Reports 3: 1362-68, 2013, Zhang et al., Mol. Cell. 51: 226-35, 2013). cGAMP thus functions as a second messenger that binds to and activates STING. Unlike the CDN second messengers produced by bacteria, in which the two purine nucleosides are joined by a phosphate bridge with bis-(3',5') linkages, the internucleotide phosphate bridge in the cyclic-GMP-AMP synthesized by cGAS is joined by non-canonical 2',5' and 3',5' linkages (alternatively termed "mixed" linkages or ML), represented as c[G(2',5')pA(3',5')p]. These 2',5'-3',5' molecules bind STING with nM affinity, some 300-fold better than bacterial c-di-GMP. Thus, it has been suggested that the 2',5'-3',5' molecules represent much more potent physiological ligands in terms of STING targeting. Zhang et al., 2013; see also, Xiao and Fitzgerald. Mol. Cell 51: 135-39, 2013. The differences in internucleotide phosphate bridge structures between CDNs produced by bacteria [canonical bis-(3',5') linkages] and by host cell cGAS (non-canonical 2',5' and 3',5' linkages) indicates that the STING receptor evolved to distinguish between CDNs produced by bacteria or by host cell cGAS.

Human STING has known polymorphisms, including alleles encoding histidine at position 232, which are refractory to canonical CDNs, but not non-canonical CDNs (Diner et al., 2013, Jin et al., 2011). Single nucleotide polymorphisms in the hSTING gene have been shown to affect the responsiveness to bacterial-derived canonical CDNs (Diner et al., 2013; Gao et al., 2013; Conlon et. al., 2013). Five haplotypes of hSTING have been identified (WT, REF. HAQ, AQ and Q alleles), which vary at amino acid positions 71, 230, 232 and 293 (Jin et al., 2011; Yi et al., 2013). Cells expressing hSTING respond poorly to stimulation with bacterial CDNs cGAMP, c-di-AMP and c-di-GMP having bis-(3',5') linkages, but are responsive to the endogenously produced cGAS product. ML cGAMP (Diner et al., 2013). Surprisingly, the mono- or di-fluoro substituted bis-3',5' linked CDNs of the present invention, in particular the di-F-CDNs, stimulate the hSTING REF allele comparably to the endogenously produced ML cGAMP. Examples of cyclic purine dinucleotides are described in some detail in, e.g., U.S. Pat. Nos. 7,709,458 and 7,592,326; WO2007/054279, WO2014/093936 and WO2014/189805; and Yan et al., Bioorg. Med. Chem Lett. 18: 5631 (2008).

Native CDN molecules are sensitive to degradation by phosphodiesterases that are present in host cells, for example in antigen presenting cells, which take up vaccine formulations that contain said native CDN molecules. The potency of a defined adjuvant may be diminished by such degradation, as the adjuvant would be unable to bind and activate its defined PRR target. Lower adjuvant potency could be measured, for example by a lower amount of induced expression of a signature molecule of innate immunity (e.g., IFN-β), correlated with weaker vaccine potency, as defined by the magnitude of a measured antigen-specific immune response.

In the present invention, substantially pure mono- or di-fluoro CDNs, and particularly dithio-diphosphate derivatives of mono- or di-fluoro CDNs are provided. The synthesis process for said dithio-diphosphate derivatives of c-di-AMP, c-GAMP and c-di-GMP molecules results in a mixture of diastereomers, including Rp,Rp, Sp,Sp, SpRp, and Rp,Sp dithio-diphosphate molecules. These individual species may be separated, and exhibit substantial differences in their pharmaceutical characteristics, wherein the Rp,Rp diastereomer is preferred.

Definitions

"Administration" as it is used herein with regard to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer. e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell. By "administered together" or "co-administered" it is not meant to be implied that two or more agents be administered as a single composition. Although administration as a single composition is contemplated by the present invention, such agents may be delivered to a single subject as separate administrations, which may be at the same or different time, and which may be by the same route or different routes of administration. By "administered simultaneously" it is meant to be implied that two or more agents be administered at essentially the same time, although not necessarily administered as a single composition or by the same route of administration.

An "agonist," as it relates to a ligand and receptor, comprises a molecule, combination of molecules, a complex, or a combination of reagents, that stimulates the receptor. For example, an agonist of granulocyte-macrophage colony stimulating factor (GM-CSF) receptor can encompass GM-CSF, a mutein or derivative of GM-CSF, a peptide mimetic of GM-CSF, a small molecule that mimics the biological function of GM-CSF, or an antibody that stimulates GM-CSF receptor.

An "antagonist," as it relates to a ligand and receptor, comprises a molecule, combination of molecules, or a complex, that inhibits, counteracts, downregulates, and/or desensitizes the receptor. "Antagonist" encompasses any reagent that inhibits a constitutive activity of the receptor. A constitutive activity is one that is manifest in the absence of a ligand/receptor interaction. "Antagonist" also encompasses any reagent that inhibits or prevents a stimulated (or regulated) activity of a receptor. By way of example, an antagonist of GM-CSF receptor includes, without implying any limitation, an antibody that binds to the ligand (GM-CSF) and prevents it from binding to the receptor, or an antibody that binds to the receptor and prevents the ligand from binding to the receptor, or where the antibody locks the receptor in an inactive conformation.

The term "antibody" as used herein refers to a peptide or polypeptide derived from, modeled after or substantially encoded by an immunoglobulin gene or immunoglobulin genes, or fragments thereof, capable of specifically binding an antigen or epitope. See. e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

The term "di-OH reference compound" as used herein refers to a known CDN compound lacking any 2' and/or 2"

fluoro substituent of the mono- or di-F-CDN compounds as described herein, instead having an —OH substituent at these positions. Preferably, the known di-OH reference compound for the mono- or di-F-CDN compounds as described herein has the same bases as the mono- or di-F-CDN compound, and has the same phosphodiester linkage (e.g. phosphodiester or the thiophosphate analog). For example, the di-OH reference compound for 3',3'-RR-(2'F-A)(2'F-A), 3',3'-RR-(2'F-A)(A), 3',3'-RR-(A)(2'F-A), and 3',3'-RR-(2'βF-A)(2'βF-A) is 3',3'-RR-(A)(A); the di-OH reference compound for 3',3'-RR-(G)(2'F-A), 3',3'-RR-(2'F-G)(2'F-A), and 3',3'-RR-(2'F-G)(A) is 3',3'-RR-(G)(A); and the di-OH reference compound for 3',3'-RR-(2'F-G)(2'F-G) is 3',3'-RR-(G)(G). The di-OH reference compounds 3',3'-RR-(A)(A), 3',3'-RR-(G)A) and 3',3'-RR-(G)(G) are described, for example, in PCT publication WO 2014/093936.

By "an agent that enhances permeability" or "an agent that enhances uptake" as used herein as it relates to cell permeability or uptake of compound by cells, is an agent that enhances the permeability of a cell to a compound or enhances the uptake of a compound by the cell, either in vitro, or in vivo. The mono- or di-F-CDN compounds as described herein, or di-OH reference compound can be compared in an in vitro cell based assay, wherein the assay may be performed with or without an agent, such as digitonin, that allows for the compound to be taken up by the cell. The mono- or di-F-CDN compounds as described herein are surprisingly active in such cell based assays without the need for such an agent that enhances permeability of the cell or enhances uptake of the compound by the cell, for example in the THP-1 cell assay as described herein. Compositions comprising the mono- or di-F-CDN compounds as described herein can be formulated without an agent that enhances permeability of the cell or enhances uptake of the compound by the cell, for example without a delivery vehicle that enhances permeability of the cell or enhances cellular uptake. Such additives or delivery vehicles include, without limitation, lipid or lipid-like adjuvants, liposomes, interbilayer crosslinked multilamellar vesicles, nanocarriers, nanoparticles and the like, such as nanoparticles comprising Poly(lactic acid) (PLA), Poly(glycolic acid) (PGA), and/or their copolymers such as biodegradeable poly(D,L-lactic-co-glycolic acid) [PLGA]-based or poly anhydride-based nanoparticles or microparticles.

By "substantially purified" with regard to CDNs of the invention is meant that a specified species accounts for at least 50%, more often accounts for at least 60%, typically accounts for at least 70%, more typically accounts for at least 75%, most typically accounts for at least 80%, usually accounts for at least 85%, more usually accounts for at least 90%, most usually accounts for at least 95%, and conventionally accounts for at least 98% by weight, or greater, of the CDN activity present in a composition. The weights of water, buffers, salts, detergents, reductants, protease inhibitors, stabilizers (including an added protein such as albumin), and excipients are generally not used in the determination of purity.

"Specifically" or "selectively" binds, when referring to a ligand/receptor, nucleic acid/complementary nucleic acid, antibody/antigen, or other binding pair (e.g., a cytokine to a cytokine receptor) (each generally referred to herein as a "target biomolecule" or a "target") indicates a binding reaction which is related to the presence of the target in a heterogeneous population of proteins and other biologics. Specific binding can mean, e.g., that the binding compound, nucleic acid ligand, antibody, or binding composition derived from the antigen-binding site of an antibody, of the contemplated method binds to its target with an affinity that is often at least 25% greater, more often at least 50% greater, most often at least 100% (2-fold) greater, normally at least ten times greater, more normally at least 20-times greater, and most normally at least 100-times greater than the affinity with a non-target molecule.

"Ligand" refers to a small molecule, nucleic acid, peptide, polypeptide, saccharide, polysaccharide, glycan, glycoprotein, glycolipid, or combinations thereof that binds to a target biomolecule. While such ligands may be agonists or antagonists of a receptor, a ligand also encompasses a binding agent that is not an agonist or antagonist, and has no agonist or antagonist properties. Specific binding of a ligand for its cognate target is often expressed in terms of an "Affinity." In preferred embodiments, the ligands of the present invention bind with affinities of between about $10^4$ $M^{-1}$ and about $10^8$ $M^{-1}$. Affinity is calculated as $K_d=k_{off}/k_{on}$ ($k_{off}$ is the dissociation rate constant, $K_{on}$ is the association rate constant and $K_d$ is the equilibrium constant).

Affinity can be determined at equilibrium by measuring the fraction bound (r) of labeled ligand at various concentrations (c). The data are graphed using the Scatchard equation: $r/c=K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988. In an alternative, affinity can be measured by isothermal titration calorimetry (ITC). In a typical ITC experiment, a solution of ligand is titrated into a solution of its cognate target. The heat released upon their interaction (ΔH) is monitored over time. As successive amounts of the ligand are titrated into the ITC cell, the quantity of heat absorbed or released is in direct proportion to the amount of binding. As the system reaches saturation, the heat signal diminishes until only heats of dilution are observed. A binding curve is then obtained from a plot of the heats from each injection against the ratio of ligand and binding partner in the cell. The binding curve is analyzed with the appropriate binding model to determine $K_B$, n and ΔH. Note that $K_B=1/K_d$.

The term "prodrug" as used herein refers to a modification of contemplated compounds, wherein the modified compound exhibits less pharmacological activity (as compared to the modified compound) and wherein the modified compound is converted within the body (e.g., in a target cell or target organ) back into the unmodified form through enzymatic or non-enzymatic reactions. In certain embodiments, the hydroxyl on one ribose comprises a prodrug leaving group. Prodrugs can modify the physicochemical, biopharmaceutic, and pharmacokinetic properties of drugs. Traditional prodrugs are classified as drugs that are activated by undergoing transformation in vivo to form the active drug. Reasons for prodrug development are typically poor aqueous solubility, chemical instability, low oral bioavailability, lack of blood brain barrier penetration, and high first pass metabolism associated with the parent drug. Suitable prodrug moieties are described in, for example, "Prodrugs and Targeted Delivery," J. Rautico, Ed., John Wiley & Sons, 2011. Examples include, but are not limited to, leaving groups removed by cellular esterases, a C6 to C18 fatty acid ester, a myristoyl ester, a pentanoyl ester, a hexanoyl ester, and a heptanoyl ester. For example, the mono-2'F-CDN compounds as described herein can include substitution at the remaining 2' hydroxyl, to form such esters.

The term "subject" or "individual" as used herein refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology. Preferred are subjects who have an existing diagnosis of a particular cancer which is being targeted by the compositions and methods of the present invention. Preferred cancers for treatment with the compositions described herein include, but are not limited to prostate cancer, renal carcinoma, melanoma, pancreatic cancer, cervical cancer, ovarian cancer, colon cancer, head & neck cancer, lung cancer and breast cancer.

"Therapeutically effective amount" is defined as an amount of a reagent or pharmaceutical composition that is sufficient to show a patient benefit. i.e., to cause a decrease, prevention, or amelioration of the symptoms of the condition being treated. When the agent or pharmaceutical composition comprises a diagnostic agent, a "diagnostically effective amount" is defined as an amount that is sufficient to produce a signal, image, or other diagnostic parameter. Effective amounts of the pharmaceutical formulation will vary according to factors such as the degree of susceptibility of the individual, the age, gender, and weight of the individual, and idiosyncratic responses of the individual. "Effective amount" encompasses, without limitation, an amount that can ameliorate, reverse, mitigate, prevent, or diagnose a symptom or sign of a medical condition or disorder or a causative process thereof. Unless dictated otherwise, explicitly or by context, an "effective amount" is not limited to a minimal amount sufficient to ameliorate a condition.

"Treatment" or "treating" (with respect to a condition or a disease) is an approach for obtaining beneficial or desired results including and preferably clinical results. For purposes of this invention, beneficial or desired results with respect to a disease include, but are not limited to, one or more of the following: preventing a disease, improving a condition associated with a disease, curing a disease, lessening severity of a disease, delaying progression of a disease, alleviating one or more symptoms associated with a disease, increasing the quality of life of one suffering from a disease, and/or prolonging survival. Likewise, for purposes of this invention, beneficial or desired results with respect to a condition include, but are not limited to, one or more of the following: preventing a condition, improving a condition, curing a condition, lessening severity of a condition, delaying progression of a condition, alleviating one or more symptoms associated with a condition, increasing the quality of life of one suffering from a condition, and/or prolonging survival. For instance, in embodiments where the compositions described herein are used for treatment of cancer, the beneficial or desired results include, but are not limited to, one or more of the following: reducing the proliferation of (or destroying) neoplastic or cancerous cells, reducing metastasis of neoplastic cells found in cancers, shrinking the size of a tumor, decreasing symptoms resulting from the cancer, increasing the quality of life of those suffering from the cancer, decreasing the dose of other medications required to treat the disease, delaying the progression of the cancer, and/or prolonging survival of patients having cancer. Depending on the context, "treatment" of a subject can imply that the subject is in need of treatment, e.g., in the situation where the subject comprises a disorder expected to be ameliorated by administration of a reagent.

"Vaccine" encompasses preventative vaccines. Vaccine also encompasses therapeutic vaccines, e.g., a vaccine administered to a mammal that comprises a condition or disorder associated with the antigen or epitope provided by the vaccine.

Cyclic Purine Dinucleotides

Prokaryotic as well as eukaryotic cells use various small molecules for cell signaling and intra- and intercellular communication. Cyclic nucleotides like cGMP, cAMP, etc. are known to have regulatory and initiating activity in pro- and eukaryotic cells. Unlike eukaryotic cells, prokaryotic cells also use cyclic purine dinucleotides as regulatory molecules. In prokaryotes, the condensation of two GTP molecules is catalyzed by the enzyme diguanylate cyclase (DGC) to give c-diGMP, which represents an important regulator in bacteria.

Recent work suggests that cyclic diGMP or analogs thereof can also stimulate or enhance immune or inflammatory response in a patient or can enhance the immune response to a vaccine by serving as an adjuvant in mammals. Cytosolic detection of pathogen-derived DNA requires signaling through TANK binding kinase 1 (TBK1) and its downstream transcription factor, IFN-regulatory factor 3 (IRF3). A transmembrane protein called STING (stimulator of IFN genes; also known as MITA, ERIS, MPYS and TMEM 173) functions as the signaling receptor for these cyclic purine dinucleotides, causing stimulation of the TBK1-IRF3 signalling axis and a STING-dependent type I interferon response. See, e.g., FIG. 1. Burdette et al., Nature 478: 515-18, 2011 demonstrated that STING binds directly to cyclic diguanylate monophosphate, but not to other unrelated nucleotides or nucleic acids.

Cyclic purine dinucleotides for use as precursors to derive the CDNs of the present invention are described in some detail in. e.g., Gao et al., Cell (2013) 153: doi: 10.1016/j.cell.2013.04.046; U.S. Pat. Nos. 7,709,458 and 7,592,326; WO2007/054279, WO2014/093936 and WO2014/189805; and Yan et al., Bioorg. Med. Chem Lett. 18: 5631 (2008). These CDNs may be modified using standard organic chemistry techniques in order to produce the CDNs of the present invention.

The mono- or di-F-CDN compounds of the present invention as described herein are potent STING agonists, and demonstrate unexpected improvement over known non-fluoro substituted CDN compounds, such as RR-(A)(A), or the endogenously produced cGAS product, ML cGAMP. The mono- or di-F-CDN compounds of the present invention are compared to known compounds that differ in the substitution of the 2' and 2" position, for example a di-OH reference compound such as 3',3'-(A)(A), 3',3'-(G)(A), 3',3'-RR-(A)(A) or 3',3'-RR-(G)(A). The properties of the mono- or di-F-CDN compounds are demonstrated in Examples 11-17 below, where the compounds demonstrate an improvement over the di-OH reference compound as having one or more of i) a higher $T_m$ shift in a DSF assay as described in Example 11 for one or more of hSTING (WT), hSTING (HAQ) or hSTING (REF); ii) a higher relative expression of IFN-β transcript in an hPBMC assay as described in Example 13 for one or more of hSTING (WT), hSTING (HAQ) or hSTING (REF); or iii) a lower EC50 in a THP1 cell assay as described in Example 14, where preferably the THP1 assay is performed in the absence of digitonin. In some embodiments, the mono- or di-F-CDN demonstrates an improvement over the di-OH reference compound as having two or more of i) a higher $T_m$ shift in a DSF assay as described in Example 14 for one or more of hSTING (WT), hSTING (HAQ) or hSTING (REF); ii) a higher relative expression of IFN-β transcript in an hPBMC assay as described in Example 13 for one or more of hSTING (WT), hSTING (HAQ) or hSTING (REF); or iii) a lower EC50 in a THP1 cell assay as described in Example 14, where preferably the THP1 assay is performed in the absence of digitonin. In some embodiments, the mono- or di-F-CDN demonstrates an improvement over the di-OH reference compound as having each of i) a higher $T_m$ shift in a DSF assay as described in Example 11 for one or more of hSTING (WT), hSTING (HAQ) or hSTING (REF); ii) a higher relative expression of IFN-3 transcript in an hPBMC assay as described in Example 13 for one or more of hSTING (WT), hSTING (HAQ) or hSTING (REF); or iii) a lower EC50 in a THP1 cell assay as described in Example 14, where preferably the THP1 assay is performed in the absence of digitonin. In some embodiments of the mono- or di-F-CDN compounds as described herein, the mono- or di-F-CDN compound has at least a 2-fold, at least a 5-fold, at least a 10-fold, at least a 50-fold, at least a 100-fold, at least a 500-fold, or at least a 1000-fold higher relative expression of IFN-β transcript in an hPBMC assay as described in Example 13 for hSTING REF allele as compared to 3',3'-RR-(A)(A). In some embodiments, the mono- or di-F-CDN compound has an EC50 in the THP1 assay described in Example 14 without addition of digitonin that is at least 2-fold, at least 3-fold, at least 4-fold, at least 5-fold, at least 6-fold, at least 7-fold, or at least 8-fold lower than the EC50 of a di-OH reference compound. In some embodiments, the mono- or di-F-CDN compound has an EC50 in the THP1 cell assay without addition of an agent that enhances the permeability of the compound to the cell or an agent that enhances the uptake of the compound by the cell that is less than 40 μM, less than 30 μM, less than 20 μM, less than 15 μM, or less than 10 μM. In some embodiments, the mono- or di-F-CDN compound has an EC50 in the THP1 assay described in Example 14 without addition of digitonin that is less than 40 μM, less than 30 μM, less than 20 μM, less than 15 μM, or less than 10 μM.

Preferred cyclic purine dinucleotides are phosphorothioate analogues, referred to herein as "thiophosphates". Phosphorothioates are a variant of normal nucleotides in which one of the nonbridging oxygens is replaced by a sulfur. The sulfurization of the internucleotide bond dramatically reduces the action of endo- and exonucleases, including 5' to 3' and 3' to 5' DNA POL 1 exonuclease, nucleases S1 and P1, RNases, serum nucleases and snake venom phosphodiesterase. In addition, the potential for crossing the lipid bilayer increases.

A phosphorothioate linkage is inherently chiral. The skilled artisan will recognize that the phosphates in this structure may each exist in R or S forms. Thus, Rp,Rp, Sp,Sp, Sp,Rp, and Rp,Sp forms are possible for the compounds of Formula I and all subformulae thereof. As noted above, cyclic purine dinucleotides of the present invention comprise 2'-F substituted forms of CDNs, and in particular CDN thiophosphates. Thus, 2'-F substituted Rp,Rp, Sp,Sp. Sp,Rp, and Rp,Sp forms may likewise be obtained. Preferred purines include, but are not limited to, adenine, guanine, inosine, hypoxanthine, xanthine, isoguanine, etc. The mono- or di-F-CDNs of the present invention are preferably phosphorothioate analogues, including substantially pure Sp,Sp, Rp,Rp, SpRp, or Rp,Sp stereoisomers thereof, and most preferably substantially pure Rp,Rp stereoisomers thereof.

The term "alkyl," as used herein, refers to a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms with from 1 to about 6 carbon atoms being more preferred. The term "lower alkyl" as used herein includes from 1 to about 6 carbon atoms. Alkyl groups as used herein may optionally include one or more further substituent groups.

The term "alkenyl," as used herein, refers to a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

The term "alkynyl," as used herein, refers to a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

The term "acyl," as used herein, refers to a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

The term "alicyclic" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

The term "alkoxy." as used herein, refers to a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

The term "aminoalkyl" as used herein, refers to an amino substituted C\-Cn alkyl radical. The alkyl portion of the radical forms a covalent bond with a parent molecule. The amino group can be located at any position and the aminoalkyl group can be substituted with a further substituent group at the alkyl and/or amino portions.

The terms "aralkyl" and "arylalkyl," as used herein, refer to an aromatic group that is covalently linked to a C\-Cn alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

The terms "aryl" and "aromatic," as used herein, refer to a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

The terms "halo" and "halogen." as used herein, refer to an atom selected from fluorine, chlorine, bromine and iodine.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

The term "heteroarylalkyl," as used herein, refers to a heteroaryl group as previously defined that further includes a covalently attached $C_1$-$C_{12}$ alkyl radical. The alkyl radical portion of the resulting heteroarylalkyl group is capable of forming a covalent bond with a parent molecule. Examples include without limitation, pyridinylmethyl, pyrimidinylethyl, napthyridinylpropyl and the like. Heteroarylalkyl groups as used herein may optionally include further substituent groups on one or both of the heteroaryl or alkyl portions.

As noted above, the mono- or di-F CDN compounds also include prodrug forms of the CDNs, and in particular CDN thiophosphates. Prodrugs can modify the physicochemical, biopharmaceutic, and pharmacokinetic properties of drugs. Traditional prodrugs are classified as drugs that are activated by undergoing transformation in vivo to form the active drug. Reasons for prodrug development are typically poor aqueous solubility, chemical instability, low oral bioavailability, lack of blood brain barrier penetration, and high first pass metabolism associated with the parent drug. Suitable prodrug moieties are described in, for example, "Prodrugs and Targeted Delivery," J. Rautico, Ed., John Wiley & Sons, 2011.

The term "substantially pure" as used herein with regard to dithio-diphosphate cyclic purine dinucleotides refers to an Rp,Rp or Rp,Sp form which is at least 75% pure relative to other possible stereochemistries at the chiral phosphorus centers indicated in the mono- or di-F—RR-CDN compounds as described herein, such as compounds of Formula II. By way of example, a "substantially pure 3',3'-RR-(2'F-A)(2'F-A)" would be at least 75% pure with regard to the Rp,Sp and Sp,Sp forms, i.e. with respect to 3',3'-RS-(2'F-A)(2'F-A) and 3',3'-SS-(2'F-A)(2'F-A). In preferred embodiments, a substantially pure cyclic purine dinucleotide is at least 85% pure, at least 90% pure, at least 95% pure, at least 97% pure, and at least 99% pure. While a substantially pure cyclic purine dinucleotide preparation of the invention is "stereochemically pure," this is not meant to indicate that all CDNs within the preparation having a particular stereochemistry at these chiral centers are otherwise identical. For example, a substantially pure cyclic purine dinucleotide preparation may contain a combination of 3',3'-RR-(2'F-A)(2'F-A) and 3',3'-RR-(2'F-G)(2'F-A) and still be a substantially pure cyclic purine dinucleotide preparation. Such a preparation may also include other components as described hereinafter that are advantageous for patient treatment, provided that all CDNs within the preparation having a particular stereochemistry at these chiral centers.

The mono- or di-F-CDN compounds and compositions thereof described herein can be administered to a host, either alone or in combination with a pharmaceutically acceptable excipient, in an amount sufficient to induce, modify, or stimulate an appropriate immune response. The immune response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression. In certain embodiments, the mono- or di-F-CDN compounds and compositions thereof described herein are administered in conjunction with one or more additional compositions including vaccines intended to stimulate an immune response to one or more predetermined antigens; adjuvants; CTLA-4 and PD-1 pathway antagonists, lipids, liposomes, chemotherapeutic agents, immunomodulatory cell lines, etc.

The mono- or di-F-CDN compounds and compositions thereof described herein may be administered before, after, and/or simultaneously with an additional therapeutic or prophylactic composition or modality. These include, without limitation, B7 costimulatory molecule, interleukin-2, interferon-γ, GM-CSF, CTLA-4 antagonists, OX-40/OX-40 ligand, CD40/CD40 ligand, sargramostim, levamisol, vaccinia virus. Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Carriers for inducing a T cell immune response which preferentially stimulate a cytolytic T cell response versus an antibody response are preferred, although those that stimulate both types of response can be used as well. In cases where the agent is a polypeptide, the polypeptide itself or a polynucleotide encoding the polypeptide can be administered. The carrier can be a cell, such as an antigen presenting cell (APC) or a dendritic cell. Antigen presenting cells include such cell types as macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used. Examples of facultative antigen-presenting cells include astrocytes, follicular cells, endothelium and fibroblasts. The carrier can be a bacterial cell that is transformed to express the polypeptide or to deliver a polynucleotide which is subsequently expressed in cells of the vaccinated individual. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR2, TLR4, TLR5. TLR7, TLR8. TLR9, including lipoprotein, LPS, monophosphoryl lipid A, lipoteichoic acid, imiquimod, resiquimod, and in addition retinoic acid-inducible gene I (RIG-I) agonists such as poly I:C, used separately or in combination with the described compositions are also potential adjuvants. Other representative examples of adjuvants include the synthetic adjuvant QS-21 comprising a homogeneous saponin purified from the bark of *Quillaja saponaria* and *Corynebacterium parvum* (McCune et al., Cancer, 1979; 43:1619). It will be understood that the adjuvant is subject to optimization. In other words, the skilled artisan can engage in routine experimentation to determine the best adjuvant to use.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott. Williams & Wilkins, Phila., Pa.; Chabner and Longo (eds.) (2001) Cancer Chemotherapy and Biotherapy, Lippincott, Williams & Wilkins, Phila., Pa.). Generally, co-administration or administration together indicates treating a subject with two or more agents, where the agents can be administered simultaneously or at different times. For example, such agents may be delivered to a single subject as separate administrations, which may be at essentially the same time or different times, and which may be by the same route or different routes of administration. Such agents may be delivered to a single subject in the same administration (e.g. same formulation) such that they are administered at the same time by the same route of administration.

Because of the adjuvant properties of the compounds of the present invention, their use may also combined with other therapeutic modalities including other vaccines, adjuvants, antigen, antibodies, and immune modulators. Examples are provided below.

Adjuvants

In addition to the mono- or di-F-CDN compounds and compositions thereof described herein, the compositions or methods of the present invention may further comprise one or more additional substances which, because of their nature, can act to stimulate or otherwise utilize the immune system to respond to the cancer antigens present on the targeted tumor cell(s). Such adjuvants include, but are not limited to, lipids, liposomes, inactivated bacteria which induce innate immunity (e.g., inactivated or attenuated *Listeria monocytogenes*), compositions which mediate innate immune activation via Toll-like Receptors (TLRs), (NOD)-like receptors (NLRs), Retinoic acid inducible gene-based (RIG)-I-like receptors (RLRs), C-type lectin receptors (CLRs) and/or pathogen-associated molecular patterns ("PAMPS"). Examples of PAMPs include lipoproteins, lipopolypeptides, peptidoglycans, zymosan, lipopolysaccharide, neisserial porins, flagellin, profillin, galactoceramide, muramyl dipeptide. Peptidoglycans, lipoproteins, and lipoteichoic acids are cell wall components of Gram-positive. Lipopolysaccharides are expressed by most bacteria, with MPL being one example. Flagellin refers to the structural component of bacterial flagella that is secreted by pathogenic and commensal bacterial. α-Galactosylceramide (α-GalCer) is an activator of natural killer T (NKT) cells. Muramyl dipeptide is a bioactive peptidoglycan motif common to all bacteria. This list is not meant to be limiting. Preferred adjuvant compositions are described below.

Immune Checkpoint Inhibitors

The mono- or di-F-CDN compounds as described herein can be used in combination with an immune checkpoint inhibitor, such as an immune checkpoint inhibitor selected from the group consisting of a CTLA-4 pathway antagonist, a PD-1 pathway antagonist, a Tim-3 pathway antagonist, a Vista pathway antagonist, a BTLA pathway antagonist, a LAG-3 pathway antagonist, or a TIGIT pathway antagonist. In some embodiments, the immune checkpoint inhibitor is selected from the group consisting of an anti-CTLA-4 antibody, an anti-PD-1 antibody, an anti-Tim-3 antibody, an anti-Vista antibody, an anti-BTLA antibody, an anti-LAG-3 antibody, or an anti-TIGIT antibody.

The mono- or di-F-CDN compounds as described herein can be used in combination with CTLA-4 pathway antagonists. In some embodiments, the combination is used to treat a solid tumor or a hematologic malignancy. CTLA-4 is thought to be an important negative regulator of the adaptive immune response. Activated T cells upregulate CTLA-4, which binds CD80 and CD86 on antigen-presenting cells with higher affinity than CD28, thus inhibiting T-cell stimulation, IL-2 gene expression and T-cell proliferation. Antitumor effects of CTLA4 blockade have been observed in murine models of colon carcinoma, metastatic prostate cancer, and metastatic melanoma. In some embodiments, the CTLA-4 pathway antagonist is an anti-CTLA-4 antibody molecule selected from the group consisting of tremelimumab and ipilimumab. In some embodiments, the anti-CTLA-4 antibody is an anti-CTLA-4 antibody as disclosed in e.g., U.S. Pat. No. 5,811,097.

Ipilimumab (Yervoy™, a CTLA-4 antibody, also known as MDX-010, CAS No. 477202-00-9) and tremelimumab (IgG2 monoclonal antibody available from Pfizer, formerly known as ticilimumab, CP-675,206) are humanized monoclonal antibodies that bind to human CTLA4 and prevent its interaction with CD80 and CD86. Phase I and II studies using ipilimumab and tremelimumab have demonstrated clinical activity in cancer patients. Other negative immune regulators which may be targeted by a similar strategy include programmed cell death 1 (PD-1), B and T lymphocyte attenuator, transforming growth factor beta β, interleukin-10, and vascular endothelial growth factor.

In some embodiments, the mono- or di-F-CDN compounds as described herein can be used in combination with an anti-CTLA-4 antibody and an anti-PD-1 antibody. In one embodiment, the combination includes an anti-PD-1 antibody molecule, e.g., as described herein, and an anti-CTLA-4 antibody, e.g., ipilimumab. Exemplary doses that can be use include a dose of anti-PD-1 antibody molecule of about 1 to 10 mg/kg, e.g., 3 mg/kg, and a dose of an anti-CTLA-4 antibody. e.g., ipilimumab, of about 3 mg/kg.

The mono- or di-F-CDN compounds as described herein can be used in combination with PD-1 pathway antagonists. In some embodiments, the combination is used to treat a solid tumor or a hematologic malignancy. PD-1 is another negative regulator of adaptive immune response that is expressed on activated T-cells. PD-1 binds to B7-H1 and B7-DC, and the engagement of PD-1 suppresses T-cell activation. Anti-tumor effects have been demonstrated with PD-1 pathway blockade. Anti-PD-1 antibody molecules (e.g. Nivolumab (Opdivo™), pembrolizumab (Keytruda™), and pidilizumab), and AMP-224 have been reported in the literature to be examples of PD-1 pathway blockers which may find use in the present invention. In some embodiments, the PD-1 pathway antagonist is an anti-PD-1 antibody molecule selected from the group consisting of nivolumab, pembrolizumab or pidilizumab.

In some embodiments, the anti-PD-1 antibody is nivolumab. Alternative names for nivolumab include MDX-1106, MDX-1106-04, ONO-4538, or BMS-936558. In some embodiments, the anti-PD-1 antibody is nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO2006/121168. In one embodiment, the inhibitor of PD-1 is nivolumab, and having a sequence disclosed herein (or a sequence substantially identical or similar thereto, e.g., a sequence at least 85%, 90%, 95% identical or higher to the sequence specified).

The heavy chain amino acid sequence of nivolumab is as follows:

(SEQ ID NO: 2)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLKTKTYTCNVDH

KPSNTKVDKRVESKYGPPCPPCPAPEFLGGPSVFLVPPKPKDTLMISRTP

-continued

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGK

The light chain amino acid sequence of nivolumab is as follows:

(SEQ ID NO: 3)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

In some embodiments, the anti-PD-1 antibody is pembrolizumab. Pembrolizumab (also referred to as lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) *New England Journal of Medicine* 369 (2): 134-44, U.S. Pat. No. 8,354,509 and WO2009/114335. In one embodiment, the inhibitor of PD-1 is pembrolizumab, and having a sequence disclosed herein (or a sequence substantially identical or similar thereto, e.g., a sequence at least 85%, 90%, 95% identical or higher to the sequence specified).

The heavy chain amino acid sequences of pembrolizumab is as follows:

(SEQ ID NO: 4)
QVQLVQSGVE VKKPGASVKV SCKASGYTFT NYYMYWVRQA PGQLGEWMGG 50

INPSNGGTNF NEKFKNRVTL TTDSSTTTAY MELKSLQFDD TAVYYCARRD 100

YRFDMGFDYW GQGTTVTVSS ASTKGPSVFP LAPCSRSTSE STAALGCLVK 150

DYFPEPVTVS WNSGALTSGV HTFPAVLQSS GLYSLSSVVT VPSSSLGTKT 200

YTCNVDHKPS NTKVDKRVES KYGPPCPPCP APEFLGGPSV FLFPPKPKDT 250

LMISRTPEVT CVVVDVSQED PEVQFNWYVD GVEVHNAKTK PREEQFNSTY 300

RVVSVLTVLH QDWLNGKEYK CKVSNKGLPS SIEKTISKAK GQPREPQVYT 350

LPPSQEEMTK NQVSLTCLVK GFYPSDIAVE WESNGQPENN YKTTPPVLDS 400

DGSFFLYSRL TVDKSRWQEG NVFSCSVMHE ALHNHYTQKS LSLSLGK 447

The light chain amino acid sequences of pembrolizumab is as follows:

(SEQ ID NO: 5)
EIVLTQSPAT LSLSPGERAT LSCRASKGVS TSGYSYLHWY QQKPGQAPRL 50

LIYLASYLES GVPARFSGSG SGTDFTLTIS SLEPEDFAVY YCQHSRDLPL 100

TFGGGTKVEI KRTVAAPSVF IFPPSDEQLK SGTASVVCLL NNFYPREAKV 150

QWKVDNALQS GNSQESVTEQ DSKDSTYSLS STLTLSKADY EKHKVYACEV 200

THQGLSSPVT KSFNRGEC 218

In some embodiments, the anti-PD-1 antibody is pidilizumab. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611.

In some embodiments, the anti-PD-1 antibody is AMP 514 (Amplimmune), or an anti-PD-1 antibody as disclosed in U.S. Pat. No. 8,609,089, US 2010028330, and/or US 20120114649.

In some embodiments the PD-1 pathway antagonist is an anti-PD-1 antibody molecule disclosed in US 2015/0210769, published on Jul. 30, 2015, entitled "Antibody Molecules to PD-1 and Uses Thereof".

In one embodiment, the anti-PD-1 antibody molecule includes at least one or two heavy chain variable domain (optionally including a constant region), at least one or two light chain variable domain (optionally including a constant region), or both, comprising the amino acid sequence of BAP049-Clone-A. BAP049-Clone-B, BAP049-Clone-C, BAP049-Clone-D, or BAP049-Clone-E; or as described in Table 1 of US 2015/0210769, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences. The anti-PD-1 antibody molecule, optionally, comprises a leader sequence from a heavy chain, a light chain, or both, as shown in Table 4 of US 2015/0210769; or a sequence substantially identical thereto. The disclosure of US 2015/0210769 is hereby incorporated by reference as it relates to the amino acid sequences and nucleotide sequences in Table 4 therein.

In yet another embodiment, the anti-PD-1 antibody molecule includes at least one, two, or three complementarity determining regions (CDRs) from a heavy chain variable region and/or a light chain variable region of an antibody described in US 2015/0210769, e.g., an antibody chosen from any of BAP049-hum01, BAP049-hum02, BAP049-hum03, BAP049-hum04, BAP049-hum05, BAP049-hum06, BAP049-hum07. BAP049-hum08, BAP049-hum09. BAP049-hum10. BAP049-hum11. BAP049-hum12, BAP049-hum13. BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1 therein, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule includes at least one, two, or three CDRs (or collectively all of the CDRs) from a heavy chain variable region comprising an amino acid sequence shown in Table 1 of US 2015/0210769, or encoded by a nucleotide sequence shown in Table 1 therein. In one embodiment, one or more of the CDRs (or collectively all of the CDRs) have one, two, three, four, five, six or more changes. e.g., amino acid substitutions or deletions, relative to the amino acid sequence shown in Table 1, or encoded by a nucleotide sequence shown in Table 1 therein.

In yet another embodiment, the anti-PD-1 antibody molecule includes at least one, two, or three CDRs (or collectively all of the CDRs) from a light chain variable region comprising an amino acid sequence shown in Table 1 of US 2015/0210769, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1 therein, or encoded by a nucleotide sequence shown in Table 1 therein. In certain embodiments, the anti-PD-1 antibody molecule includes a substitution in a light chain CDR, e.g., one or more substitutions in a CDR1, CDR2 and/or CDR3 of the light chain. In one embodiment, the anti-PD-1 antibody molecule includes a substitution in the light chain CDR3 at position 102 of the light variable region, e.g., a substitution of a cysteine to tyrosine, or a cysteine to serine residue, at position 102 of the light variable region according to Table 1 (e.g., SEQ ID NO: 16 or 24 for murine or chimeric, unmodified; or any of SEQ ID NOs: 34, 42, 46, 54, 58, 62, 66, 70, 74, or 78 for a modified sequence).

In another embodiment, the anti-PD-1 antibody molecule includes at least one, two, three, four, five or six CDRs (or collectively all of the CDRs) from a heavy and light chain variable region comprising an amino acid sequence shown in Table 1 of US 2015/0210769, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1 therein, or encoded by a nucleotide sequence shown in Table 1 therein.

In one embodiment, the anti-PD-1 antibody molecule includes: (a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33, each as disclosed in Table 1 of US 2015/0210769; (b) a VH comprising a VHCDR1 amino acid sequence chosen from SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32, each as disclosed in Table 1 of US 2015/0210769: (c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33, each as disclosed in Table 1 of US 2015/0210769; or (d) a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32, each as disclosed in Table 1 of US 2015/0210769.

In another embodiment, the anti-PD-1 antibody molecule comprises (i) a heavy chain variable region (VH) comprising a VHCDR1 amino acid sequence chosen from SEQ ID NO: 1, SEQ ID NO: 4, or SEQ ID NO: 224; a VHCDR2 amino acid sequence of SEQ ID NO: 2 or SEQ ID NO: 5; and a VHCDR3 amino acid sequence of SEQ ID NO: 3; and (ii) a light chain variable region (VL) comprising a VLCDR1 amino acid sequence of SEQ ID NO: 10 or SEQ ID NO: 13, a VLCDR2 amino acid sequence of SEQ ID NO: 11 or SEQ ID NO: 14, and a VLCDR3 amino acid sequence of SEQ ID NO: 32 or SEQ ID NO: 33, each as disclosed in Table 1 of US 2015/0210769.

In some embodiments the PD-1 pathway antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 inhibitor is AMP-224 (B7-DCIg; Amplimmune; e.g., disclosed in WO2010/027827 and WO2011/066342) is a PD-L2 Fc fusion soluble receptor that blocks the interaction between PD-1 and B7-H1.

In some embodiments the PD-1 pathway antagonist is a PD-L1 or PD-L2 inhibitor. In some embodiments the PD-L1 or PD-L2 inhibitor is an anti-PD-L1 antibody or an anti-PD-L2 antibody. In some embodiments, the anti-PD-L1 inhibitor is chosen from YW243.55.S70. MPDL3280A, MEDI-4736, MSB-0010718C, or MDX-1105. In some embodiments, the PD-L1 inhibitor is an anti-PD-L1 antibody MSB0010718C. MSB0010718C (also referred to as A09-246-2; Merck Serono) is a monoclonal antibody that binds to PD-L1. MSB0010718C and other humanized anti-PD-L1 antibodies are disclosed in WO2013/079174, and having a sequence disclosed therein (or a sequence substantially identical or similar thereto, e.g., a sequence at least 85%, 90%, 95% identical or higher to the sequence specified).

The heavy chain amino acid sequence (SEQ ID NO: 24 as disclosed in WO2013/079174) of MSB0010718C includes at least the following:

(SEQ ID NO: 6)
EVQLLESGGGLVQPGGSLRLSCAASGFTFSSYIMMWVRQAPGKGLEWVSS

IYPSGGITFYADKGRFTISRDNSKNTLYLQMNSLRAEDTAVYYCARIKLG

TVTTVDYWGQGTLVTVSS

The light chain amino acid sequence (SEQ ID NO: 25 as disclosed in WO2013/079174) of MSB0010718C includes at least the following:

(SEQ ID NO: 7)
QSALTQPASVSGSPGQSITISCTGTSSDVGGYNYVSWYQQHPGKAPKLMI

YDVSNRPSGVSNRFSGSKSGNTASLTISGLQAEDEADYYCSSYTSSSTRV

FGTGTKVTVL

In one embodiment, the PD-L1 inhibitor is YW243.55.S70. The YW243.55.S70 antibody is an anti-PD-L1 antibody as described in WO 2010/077634 (heavy and light chain variable region sequences shown in SEQ ID Nos. 20 and 21, respectively), and having a sequence disclosed therein (or a sequence substantially identical or similar thereto, e.g., a sequence at least 85%, 90%, 95% identical or higher to the sequence specified).

In one embodiment, the PD-L1 inhibitor is MDX-1105. MDX-1105, also known as BMS-936559, is an anti-PD-L1 antibody described in WO2007/005874, and having a sequence disclosed therein (or a sequence substantially identical or similar thereto. e.g., a sequence at least 85%, 90%, 95% identical or higher to the sequence specified).

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906.

In other embodiments, the PD-L2 inhibitor is AMP-224. AMP-224 is a PD-L2 Fc fusion soluble receptor that blocks the interaction between PD1 and B7-H1 (B7-DCIg; Amplimmune; e.g., disclosed in WO2010/027827 and WO2011/066342

The mono- or di-F-CDN compounds as described herein can be used in combination with TIM-3 pathway antagonists. In some embodiments, the combination is used to treat a solid tumor or a hematologic malignancy. In some embodiments, the TIM-3 pathway antagonist is an anti-TIM-3 antibody. In some embodiments, anti-TIM-3 antibody molecules are disclosed in US 2015/0218274, published on Aug. 6, 2015, entitled "Antibody Molecules to TIM-3 and Uses Thereof".

In one embodiment, the anti-TIM-3 antibody molecule includes at least one or two heavy chain variable domain (optionally including a constant region), at least one or two light chain variable domain (optionally including a constant region), or both, comprising the amino acid sequence of ABTIM3, ABTIM3-hum01, ABTIM3-hum02. ABTIM3-hum03. ABTIM3-hum04, ABTIM3-hum05, ABTIM3-hum06. ABTIM3-hum07, ABTIM3-hum08, ABTIM3-hum09, ABTIM3-hum10, ABTIM3-hum11, ABTIM3-hum12, ABTIM3-hum13. ABTIM3-hum14. ABTIM3-hum15, ABTIM3-hum16. ABTIM3-hum17, ABTIM3-hum18, ABTIM3-hum19. ABTIM3-hum20, ABTIM3-hum21. ABTIM3-hum22, ABTIM3-hum23; or as described in Tables 1-4 of US 2015/0218274; or encoded by the nucleotide sequence in Tables 1-4 therein; or a sequence substantially identical (e.g., at least 80%, 85%, 90%, 92%, 95%, 97%, 98%, 99% or higher identical) to any of the aforesaid sequences. The anti-TIM-3 antibody molecule, optionally, comprises a leader sequence from a heavy chain, a light chain, or both, as shown in US 2015/0218274; or a sequence substantially identical thereto. The disclosure of US 2015/0218274 is hereby incorporated by reference as it relates to the amino acid sequences and nucleotide sequences in Tables 1-4 therein.

In yet another embodiment, the anti-TIM-3 antibody molecule includes at least one, two, or three complementarity determining regions (CDRs) from a heavy chain variable region and/or a light chain variable region of an antibody described in US 2015/0218274. e.g., an antibody chosen from any of ABTIM3. ABTIM3-hum0, ABTIM3-hum02. ABTIM3-hum03, ABTIM3-hum04, ABTIM3-hum05. ABTIM3-hum06, ABTIM3-hum07, ABTIM3-hum08. ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21. ABTIM3-hum22. ABTIM3-hum23; or as described in Tables 1-4 of US 2015/0218274; or encoded by the nucleotide sequence in Tables 1-4 therein; or a sequence substantially identical (e.g., at least 80%, 85%, 90%, 92%, 95%, 97%, 98%, 99% or higher identical) to any of the aforesaid sequences.

In yet another embodiment, the anti-TIM-3 antibody molecule includes at least one, two, or three CDRs (or collectively all of the CDRs) from a heavy chain variable region comprising an amino acid sequence shown in Tables 1-4 of US 2015/0218274, or encoded by a nucleotide sequence shown in Tables 1-4 therein. In one embodiment, one or more of the CDRs (or collectively all of the CDRs) have one, two, three, four, five, six or more changes, e.g., amino acid substitutions or deletions, relative to the amino acid sequence shown in Tables 1-4 therein, or encoded by a nucleotide sequence shown in Table 1-4 therein.

In yet another embodiment, the anti-TIM-3 antibody molecule includes at least one, two, or three CDRs (or collectively all of the CDRs) from a light chain variable region comprising an amino acid sequence shown in Tables 1-4 of US 2015/0218274, or encoded by a nucleotide sequence shown in Tables 1-4 therein. In one embodiment, one or more of the CDRs (or collectively all of the CDRs) have one, two, three, four, five, six or more changes, e.g., amino acid substitutions or deletions, relative to the amino acid sequence shown in Tables 1-4 therein, or encoded by a nucleotide sequence shown in Tables 1-4 therein. In certain embodiments, the anti-TIM-3 antibody molecule includes a substitution in a light chain CDR, e.g., one or more substitutions in a CDR1. CDR2 and/or CDR3 of the light chain.

In another embodiment, the anti-TIM-3 antibody molecule includes at least one, two, three, four, five or six CDRs (or collectively all of the CDRs) from a heavy and light chain variable region comprising an amino acid sequence shown in Tables 1-4 of US 2015/0218274, or encoded by a nucleotide sequence shown in Tables 1-4 therein. In one embodiment, one or more of the CDRs (or collectively all of the CDRs) have one, two, three, four, five, six or more changes, e.g., amino acid substitutions or deletions, relative to the amino acid sequence shown in Tables 1-4 therein, or encoded by a nucleotide sequence shown in Tables 1-4 therein.

In one embodiment, the anti-TIM-3 antibody molecule includes: (a) a heavy chain variable region (VH) comprising a VHCDR1 amino acid sequence chosen from SEQ ID NO: 9; a VHCDR2 amino acid sequence of SEQ ID NO: 10; and a VHCDR3 amino acid sequence of SEQ ID NO: 5; and a light chain variable region (VL) comprising a VLCDR1 amino acid sequence of SEQ ID NO: 12, a VLCDR2 amino acid sequence of SEQ ID NO: 13, and a VLCDR3 amino acid sequence of SEQ ID NO: 14, each as disclosed in Tables 1-4 of US 2015/0218274; (b) a VH comprising a VHCDR1 amino acid sequence chosen from SEQ ID NO: 3; a VHCDR2 amino acid sequence of SEQ ID NO: 4; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each as disclosed in Tables 1-4 of US 2015/0218274; (c) a VH comprising a VHCDR1 amino acid sequence chosen from SEQ ID NO: 9; a VHCDR2 amino acid sequence of SEQ ID NO: 25; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14, each as disclosed in Tables 1-4 of US 2015/0218274; (d) a VH comprising a VHCDR1 amino acid sequence chosen from SEQ ID NO: 3; a VHCDR2 amino acid sequence of SEQ ID NO: 24; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each as disclosed in Tables 1-4 of US 2015/0218274; (e) a VH comprising a VHCDR1 amino acid sequence chosen from SEQ ID NO: 9; a VHCDR2 amino acid sequence of SEQ ID NO: 31; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14, each as disclosed in Tables 1-4 of US 2015/0218274; or (f) a VH comprising a VHCDR1 amino acid sequence chosen from SEQ ID NO: 3; a VHCDR2 amino acid sequence of SEQ ID NO: 30; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each as disclosed in Tables 1-4 of US 2015/0218274.

In some embodiments, the TIM-3 pathway antagonist is an anti-TIM-3 antibody as disclosed in U.S. Pat. No. 8,552, 156, WO 2011/155607, EP 2581113 or U.S Publication No.: 2014/044728.

The mono- or di-F-CDN compounds as described herein can be used in combination with LAG-3 pathway antagonists. In some embodiments, the combination is used to treat a solid tumor or a hematologic malignancy. In some embodiments, the LAG-3 pathway antagonist is an anti-LAG-3 antibody. In some embodiments the anti-LAG-3 antibody molecules are disclosed in US 2015/0259420, filed Mar. 13, 2015, entitled "Antibody Molecules to LAG-3 and Uses Thereof".

In one embodiment, the anti-LAG-3 antibody molecule includes at least one or two heavy chain variable domain (optionally including a constant region), at least one or two light chain variable domain (optionally including a constant region), or both, comprising the amino acid sequence of any of BAP050-hum01, BAP050-hum02, BAP050-hum03, BAP050-hum04. BAP050-hum05. BAP050-hum06. BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G. BAP050-Clone-H, BAP050-Clone-I, or BAP050-Clone-J; or as described in Table 1 of US 2015/0259420, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences. The disclosure of US 2015/0259420 is hereby incorporated by reference as it relates to the amino acid sequences and nucleotide sequences in Table 1 therein.

In yet another embodiment, the anti-LAG-3 antibody molecule includes at least one, two, or three complementarity determining regions (CDRs) from a heavy chain variable region and/or a light chain variable region of an antibody described herein, e.g., an antibody chosen from any of BAP050-hum01. BAP050-hum02, BAP050-hum03, BAP050-hum04. BAP050-hum05. BAP050-hum06. BAP050-hum07. BAP050-hum08. BAP050-hum09. BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser). BAP050-Clone-F. BAP050-Clone-G, BAP050-Clone-H, BAP050-Clone-I, or BAP050-Clone-J; or as described in Table 1 of US 2015/0259420, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences.

In yet another embodiment, the anti-LAG-3 antibody molecule includes at least one, two, or three CDRs (or collectively all of the CDRs) from a heavy chain variable region comprising an amino acid sequence shown in Table 1 of US 2015/0259420, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1 therein, or encoded by a nucleotide sequence shown in Table 1 therein.

In yet another embodiment, the anti-LAG-3 antibody molecule includes at least one, two, or three CDRs (or collectively all of the CDRs) from a light chain variable region comprising an amino acid sequence shown in Table 1 of US 2015/0259420, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1 therein, or encoded by a nucleotide sequence shown in Table 1 therein. In certain embodiments, the anti-PD-L1 antibody molecule includes a substitution in a light chain CDR. e.g., one or more substitutions in a CDR1, CDR2 and/or CDR3 of the light chain.

In another embodiment, the anti-LAG-3 antibody molecule includes at least one, two, three, four, five or six CDRs (or collectively all of the CDRs) from a heavy and light chain variable region comprising an amino acid sequence shown in Table 1 of US 2015/0259420, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1 therein, or encoded by a nucleotide sequence shown in Table 1 therein.

In one embodiment, the anti-LAG-3 antibody molecule includes: (i) a heavy chain variable region (VH) including a VHCDR1 amino acid sequence chosen from SEQ ID NO: 1. SEQ ID NO: 4 or SEQ ID NO: 286; a VHCDR2 amino acid sequence of SEQ ID NO: 2; and a VHCDR3 amino acid sequence of SEQ ID NO: 3, each as disclosed in Table 1 of US 2015/0259420; and (ii) a light chain variable region (VL) including a VLCDR1 amino acid sequence of SEQ ID NO: 10, a VLCDR2 amino acid sequence of SEQ ID NO: 11, and a VLCDR3 amino acid sequence of SEQ ID NO: 12, each as disclosed in Table 1 of US 2015/0259420.

In another embodiment, the anti-LAG-3 antibody molecule includes: (i) a heavy chain variable region (VH) including a VHCDR1 amino acid sequence chosen from SEQ ID NO: 1. SEQ ID NO: 4 or SEQ ID NO: 286; a VHCDR2 amino acid sequence of SEQ ID NO: 5, and a VHCDR3 amino acid sequence of SEQ ID NO: 3, each as disclosed in Table 1 of US 2015/0259420; and (ii) a light chain variable region (VL) including a VLCDR1 amino acid sequence of SEQ ID NO: 13, a VLCDR2 amino acid sequence of SEQ ID NO: 14, and a VLCDR3 amino acid sequence of SEQ ID NO: 15, each as disclosed in Table 1 of US 2015/0259420.

In one embodiment, the anti-LAG-3 antibody molecule comprises the VHCDR1 amino acid sequence of SEQ ID NO: 1 as disclosed in Table 1 of US 2015/0259420. In another embodiment, the anti-LAG-3 antibody molecule comprises the VHCDR1 amino acid sequence of SEQ ID NO: 4 as disclosed in Table 1 of US 2015/0259420. In yet another embodiment, the anti-LAG-3 antibody molecule comprises the VHCDR1 amino acid sequence of SEQ ID NO: 286, as disclosed in Table 1 of US 2015/0259420.

In some embodiments, the anti-LAG-3 antibody is BMS-986016. BMS-986016 (also referred to as BMS986016; Bristol-Myers Squibb) is a monoclonal antibody that binds to LAG-3. BMS-986016 and other humanized anti-LAG-3 antibodies are disclosed in US 2011/0150892, WO2010/019570, and WO2014/008218.

T-Cell Receptor Agonists

The mono- or di-F-CDN compounds as described herein can be used in combination with a T-cell receptor agonist, such as a CD28 agonist, an OX40 agonist, a GITR agonist, a CD137 agonist, a CD27 agonist or an HVEM agonist.

The mono- or di-F-CDN compounds as described herein can be used in combination with a CD27 agonist. Exemplary CD27 agonists include an anti-CD27 agonistic antibody, e.g. as described in PCT Publication No. WO 2012/004367.

The mono- or di-F-CDN compounds as described herein can be used in combination with a GITR agonist. In some embodiments, the combination is used to treat a solid tumor or a hematologic malignancy. Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No.: 0920505B1. U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. No. 7,812,135. U.S. Pat. No. 8,388,967. U.S. Pat. No. 8,591,886. European Patent No.: EP 1866339. PCT Publication No.: WO 2011/028683, U.S. Pat. No. 8,709,424, PCT Publication No.: WO 2013/039954. International Publication No.: WO2013/039954. U.S. Publication No.: US2014/0072566, International Publication NO.: WO2015/026684. PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, U.S. Pat. No. 6,689,607, PCT Publication No.: WO2006/083289, PCT Publication No.: WO 2005/115451, U.S. Pat. No. 7,618,632, PCT Publication No.: WO 2011/051726, International Publication No.: WO2004060319, and International Publication No.: WO2014012479.

In one embodiment, the mono- or di-F-CDN compounds as described herein is used in combination with a GITR agonist used in combination with a PD-1 inhibitor, e.g., as described in WO2015/026684.

In another embodiment, the mono- or di-F-CDN compounds as described herein is used in combination with a GITR agonist used in combination with a TLR agonist, e.g., as described in WO2004060319, and International Publication No.: WO2014012479.

TLR Agonists

The mono- or di-F-CDN compounds as described herein can be used in combination with a Toll like receptor agonist. The term "Toll like receptor" (or "TLR") as used herein refers to a member of the Toll-like receptor family of proteins or a fragment thereof that senses a microbial product and/or initiates an adaptive immune response. In one embodiment, a TLR activates a dendritic cell (DC). Toll like receptors (TLRs) are a family of pattern recognition receptors that were initially identified as sensors of the innate immune system that recognize microbial pathogens. TLRs comprise a family of conserved membrane spanning molecules containing an ectodomain of leucine-rich repeats, a transmembrane domain and an intracellular TIR (Toll/IL-1R) domain. TLRs recognize distinct structures in microbes, often referred to as "PAMPs" (pathogen associated molecular patterns). Ligand binding to TLRs invokes a cascade of intra-cellular signaling pathways that induce the production of factors involved in inflammation and immunity.

In humans, ten TLR have been identified. TLRs that are expressed on the surface of cells include TLR-1, -2, -4, -5, and -6, while TLR-3, -7/8, and -9 are expressed with the ER compartment. Human dendritic cell subsets can be identified on the basis of distinct TLR expression patterns. By way of example, the myeloid or "conventional" subset of DC (mDC) expresses TLRs 1-8 when stimulated, and a cascade of activation markers (e.g. CD80, CD86, MHC class I and II, CCR7), pro-inflammatory cytokines, and chemokines are produced. A result of this stimulation and resulting expression is antigen-specific CD4+ and CD8+ T cell priming. These DCs acquire an enhanced capacity to take up antigens and present them in an appropriate form to T cells. In contrast, the plasmacytoid subset of DC (pDC) expresses only TLR7 and TLR9 upon activation, with a resulting activation of NK cells as well as T-cells. As dying tumor cells may adversely affect DC function, it has been suggested that activating DC with TLR agonists may be beneficial for priming anti-tumor immunity in an immunotherapy approach to the treatment of cancer. It has also been suggested that successful treatment of breast cancer using radiation and chemotherapy requires TLR4 activation.

TLR agonists known in the art and finding use in the present invention include, but are not limited to, the following:

Pam3Cys, a TLR-1/2 agonist;
CFA, a TLR-2 agonist;
MALP2, a TLR-2 agonist;
Pam2Cys, a TLR-2 agonist;
FSL-1, a TLR-2 agonist;
Hib-OMPC, a TLR-2 agonist;
polyribosinic:polyribocytidic acid (Poly I:C), a TLR-3 agonist;
polyadenosine-polyuridylic acid (poly AU), a TLR-3 agonist;
Polyinosinic-Polycytidylic acid stabilized with poly-L-lysine and carboxymethylcellulose (Hiltonol®), a TLR-3 agonist;
monophosphoryl lipid A (MPL), a TLR-4 agonist;
LPS, a TLR-4 agonist;
bacterial flagellin, a TLR-5 agonist;
sialyl-Tn (STn), a carbohydrate associated with the MUC1 mucin on a number of human cancer cells and a TLR-4 agonist;
imiquimod, a TLR-7 agonist;
resiquimod, a TLR-7/8 agonist:
loxoribine, a TLR-7/8 agonist; and
unmethylated CpG dinucleotide (CpG-ODN), a TLR-9 agonist.

Because of their adjuvant qualities. TLR agonists are preferably used in combinations with other vaccines, adjuvants and/or immune modulators, and may be combined in various combinations. Thus, in certain embodiments, the mono- or di-F-CDN compounds that bind to STING and induce STING-dependent TBK1 activation and an inactivated tumor cell which expresses and secretes one or more cytokines which stimulate dendritic cell induction, recruitment and/or maturation, as described herein can be administered together with one or more TLR agonists for therapeutic purposes.

Antibody Therapeutics

The mono- or di-F-CDN compounds as described herein can be used in combination with therapeutic antibodies. In some embodiments, the mechanism of action of the therapeutic antibody is Antibody-Dependent Cell-Mediated Cytotoxicity (ADCC). ADCC is a mechanism of cell-mediated immune defense whereby an effector cell of the immune system actively lyses a target cell, whose membrane-surface antigens have been bound by specific antibodies. It is one of the mechanisms through which antibodies, as part of the humoral immune response, can act to limit and contain infection. Classical ADCC is mediated by natural killer (NK) cells; macrophages, neutrophils and eosinophils can also mediate ADCC. ADCC is an important mechanism of action of therapeutic monoclonal antibodies, including trastuzumab and rituximab, against tumors. Compounds of the present invention may act to potentiate ADCC.

The following are an exemplary list of antibodies which may be used together with the mono- or di-F-CDN compounds of the present invention.

Muromonab-CD3: Used to prevent acute rejection of organ, e.g., kidney, transplants. The humanized versions show promise in inhibiting the autoimmune destruction of beta cells in Type 1 diabetes mellitus.

Infliximab (Remicade®) and adalimumab (Humira®): Bind to tumor necrosis factor-alpha (TNF-α). Used in some inflammatory diseases such as rheumatoid arthritis, psoriasis. Crohn's disease.

Omalizumab (Xolair®). Binds to IgE thus preventing IgE from binding to mast cells. Used against allergic asthma.

Daclizumab (Zenapax®). Binds to part of the IL-2 receptor exposed at the surface of activated T cells. Used to prevent acute rejection of transplanted kidneys.

Rituximab (trade name=Rituxan®). Binds to the CD20 molecule found on most B-cells and is used to treat B-cell lymphomas.

Ibritumomab (trade name=Zevalin®). This is a monoclonal antibody against the CD20 molecule on B cells (and lymphomas) conjugated to isotopes. Given to the lymphoma patient supplemented with Rituxan.

Tositumomab (Bexxar®). This is a conjugate of a monoclonal antibody against CD20 and the radioactive isotope iodine-131 (131I).

Cetuximab (Erbitux®). Blocks HER1, a receptor for epidermal growth factor (EGF) that is found on some tumor cells (some breast cancers, lymphomas).

Trastuzumab (Herceptin®). Blocks HER2, a growth factor receptor over-expressed in some 20% of breast cancers.

Adcetris®. A conjugate of a monoclonal antibody that binds CD30, a cell-surface molecule expressed by the cells of some lymphomas but not found on the normal stem cells needed to repopulate the bone marrow.

Alemtuzumab (Campath-1H®). Binds to CD52, a molecule found on lymphocytes and depletes both T cells and B cells. Has produced complete remission of chronic lymphocytic leukemia and shows promise in preventing rejection of kidney transplants.

Lym-1 (Oncolym®). Binds to the HLA-DR-encoded histocompatibility antigen that can be expressed at high levels on lymphoma cells.

Ipilimumab (Yervoy®) that acts to enhance the body's own immune response to tumors.

Vitaxin. Binds to a vascular integrin (alpha-v/beta-3) found on the blood vessels of tumors but not on the blood vessels supplying normal tissues. In Phase II clinical trials, Vitaxin has shown some promise in shrinking solid tumors without harmful side effects.

Bevacizumab (Avastin®). Binds to vascular endothelial growth factor (VEGF) preventing it from binding to its receptor. Used for the treatment of colorectal cancers.

Abeiximab (ReoPro®). Inhibits the clumping of platelets by binding the receptors on their surface that normally are linked by fibrinogen. Helpful in preventing reclogging of the coronary arteries in patients who have undergone angioplasty.

Additional therapeutic antibodies that may be used in combination with the mono- or di-F-CDN compounds as described herein include a prolactin receptor (PRLR) inhibitor, e.g. as disclosed in U.S. Pat. No. 7,867,493, a HER3 inhibitor, e.g. as disclosed in PCT Publication No. WO 2012/022814, an EGFR2 and/or EGFR4 inhibitor, e.g. as disclosed in PCT Publication No. WO 2014/160160, an M-CSF inhibitor, e.g. as disclosed in PCT Publication No. WO 2004/045532, an anti-APRIL antibody, e.g. as disclosed in U.S. Pat. No. 8,895,705, or an anti-SIRPα or anti-CD47 antibody, e.g. as disclosed in U.S. Pat. Nos. 8,728,476 and 8,562,997.

In one embodiment, the combination. e.g., a combination comprising a mono- or di-F-CDN compound as described herein, is used in combination a prolactin receptor (PRLR) inhibitor, a human monoclonal antibody molecule (Compound A26) as disclosed in U.S. Pat. No. 7,867,493), to treat a disorder. e.g., a disorder described herein. In one embodiment, the PRLR inhibitor is a human monoclonal antibody (Compound A26) disclosed in U.S. Pat. No. 7,867,493. In one embodiment, the mono- or di-F-CDN compound is used in combination with human monoclonal antibody molecule (Compound A26) described in U.S. Pat. No. 7,867,493 to treat a disorder such as, a cancer, a prostate cancer, or a breast cancer.

In another embodiment, the combination, e.g., a combination comprising a mono- or di-F-CDN compound as described herein, is used in combination with a HER3 inhibitor, Compound A31, or a compound disclosed in PCT Publication No. WO 2012/022814, to treat a disorder, e.g., a disorder described herein. In one embodiment, the HER3 inhibitor is Compound A31 or a compound disclosed in PCT Publication WO 2012/022814. In one embodiment, the mono- or di-F-CDN compound is used in combination with Compound A31, or a compound disclosed in PCT Publication WO 2012/022814, to treat a disorder such as a gastric cancer, an esophageal cancer, a head and neck cancer, a squamous cell carcinoma, a stomach cancer, a breast cancer (e.g., metastatic breast cancer), or a digestive/gastrointestinal cancer. In some embodiments. Compound A31 is a human monoclonal antibody molecule. In one embodiment, the HER3 inhibitor or Compound A31 is administered at a dose of about 3, 10, 20, or 40 mg/kg, e.g., once weekly (QW). In one embodiment, the compound is administered at a dose of about 3-10, 10-20, or 20-40 mg/kg.

In another embodiment, the combination, e.g., a combination comprising a mono- or di-F-CDN compound as described herein, is used in combination an FGFR2 and/or FGFR4 inhibitor. Compound A32, or a compound disclosed in a publication PCT Publication No. WO 2014/160160 (e.g., an antibody molecule drug conjugate against an FGFR2 and/or FGFR4. e.g., mAb 12425 as described therein), to treat a disorder, e.g., a disorder described herein. In one embodiment, the FGFR2 and/or FGFR4 inhibitor is Compound A32 or a compound disclosed in a publication PCT Publication No. WO 2014/160160. In one embodiment, the mono- or di-F-CDN compound is used in combination with Compound A32, or in further combination with a compound as described in Table 2, to treat a disorder such as a cancer, a gastric cancer, a breast cancer, a rhabdomyosarcoma, a liver cancer, an adrenal cancer, a lung cancer, an esophageal cancer, a colon cancer, or an endometrial cancer. In some embodiments, Compound A32 is an antibody molecule drug conjugate against an FGFR2 and/or FGFR4. e.g., mAb 12425.

In another embodiment, the combination, e.g., a combination comprising a mono- or di-F-CDN compound described herein, is used in combination an M-CSF inhibitor, Compound A33, or a compound disclosed in PCT Publication No. WO 2004/045532 (e.g., an antibody molecule or Fab fragment against M-CSF), to treat a disorder, e.g., a disorder described herein. In one embodiment, the M-CSF inhibitor is Compound A33 or a compound disclosed in PCT Publication No. WO 2004/045532. In one embodiment, the mono- or di-F-CDN compound is used in combination with Compound A33, or a compound as described in PCT Publication No. WO 2004/045532, to treat a disorder such as a cancer, a prostate cancer, a breast cancer, or pigmented villonodular synovitis (PVNS). In embodiments. Compound A33 is a monoclonal antibody molecule against M-CSF or a fragment (e.g., Fab fragment) thereof. In embodiments, the M-CSF inhibitor or Compound A33 is administered at an average dose of about 10 mg/kg.

Delivery Agents

Liposomes are vesicles formed from one ("unilamellar") or more ("multilamellar") layers of phospholipid. Because of the amphipathic character of the phospholipid building blocks, liposomes typically comprise a hydrophilic layer presenting a hydrophilic external face and enclosing a hydrophilic core. The versatility of liposomes in the incorporation of hydrophilic/hydrophobic components, their non-toxic nature, biodegradability, biocompatibility, adjuvanticity, induction of cellular immunity, property of sustained release and prompt uptake by macrophages, makes them attractive candidates for the delivery of antigens.

WO2010/104833, describes suitable liposomal preparations. Such liposomal formulations, referred to herein as VesiVax® (Molecular Express, Inc.), with our without the "immunogenic polypeptide(s) or carbohydrate(s)" referred to above, can contain one or more additional components such as peptidoglycan, lipopeptide, lipopolysaccharide, monophosphoryl lipid A, lipoteichoic acid, resiquimod, imiquimod, flagellin, oligonucleotides containing unmethylated CpG motifs, beta-galactosylceramide, muramyl dipeptide, all-trans retinoic acid, double-stranded viral RNA, heat shock proteins, dioctadecyldimethylammonium bromide, cationic surfactants, toll-like receptor agonists, dimyristoyltrimethylammoniumpropane, and nod-like receptor agonists. Advantageously, these liposomal formulations can be used to deliver one or more mono- or di-F-CDN compounds and compositions thereof described herein in accordance with the present invention.

Moreover, while the liposomal formulations discussed above employ a "steroid derivative" as an anchor for attaching an immunogenic polypeptide or carbohydrate to a liposome, the steroid may simply be provided as an unconjugated steroid such as cholesterol.

Suitable methods for preparing liposomes from lipid mixtures are well known in the art. See, e.g., Basu & Basu, *Liposome Methods and Protocols* (*Methods in Molecular Biology*), Humana Press, 2002; Gregoriadis, *Liposome Tech-*

*nology,* $3^{rd}$ *Edition*, Informa HealthCare, 2006. Preferred methods include extrusion, homogenization, and sonication methods described therein. An exemplary method for preparing liposomes for use in the present invention, which comprises drying a lipid mixture, followed by hydration in an aqueous vehicle and sonication to form liposomes, is described in WO2010/104833.

In certain embodiments, the liposomes are provided within a particular average size range. Liposome size can be selected, for example, by extrusion of an aqueous vehicle comprising liposomes through membranes having a preselected pore size and collecting the material flowing through the membrane. In preferred embodiments, the liposomes are selected to be substantially between 50 and 500 nm in diameter, more preferably substantially between 50 and 200 nm in diameter, and most preferably substantially between 50 and 150 nm in diameter. The term "substantially" as used herein in this context means that at least 75%, more preferably 80%, and most preferably at least 90% of the liposomes are within the designated range.

Other lipid and lipid-like adjuvants which may find use in the present invention include oil-in-water (o/w) emulsions (see, e.g., Muderhwa et al., J. Pharmaceut. Sci. 88: 1332-9, 1999)), VesiVax® TLR (Molecular Express. Inc.), digitonin (see, e.g., U.S. Pat. No. 5,698,432), and glucopyranosyl lipids (see. e.g., United States Patent Application 20100310602).

Nanoparticles also represent drug delivery systems suitable for most administration routes. Over the years, a variety of natural and synthetic polymers have been explored for the preparation of nanoparticles, of which Poly(lactic acid) (PLA), Poly(glycolic acid) (PGA), and their copolymers (PLGA) have been extensively investigated because of their biocompatibility and biodegradability. Nanoparticles and other nanocarriers act as potential carries for several classes of drugs such as anticancer agents, antihypertensive agents, immunomodulators, and hormones; and macromolecules such as nucleic acids, proteins, peptides, and antibodies. See. e.g., Crit. Rev. Ther. Drug Carrier Syst. 21:387-422, 2004; Nanomedicine: Nanotechnology, Biology and Medicine 1:22-30, 2005.

Chemotherapeutic Agents

In additional embodiments of the methods described herein, the mono- or di-F-CDN compounds as described herein are used in combination with chemotherapeutic agents (e.g. small molecule pharmaceutical compounds). Thus the methods further involve administering to the subject an effective amount of one or more chemotherapeutic agents as an additional treatment or a combination treatment. In certain embodiments the one or more chemotherapeutic agents is selected from the group consisting of abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvin-caleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), enzalutamide, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

In additional embodiments the methods described herein, the mono- or di-F-CDN compounds as described herein are used in combination with chemotherapeutic agents and/or additional agents for treating the indications as described in the methods herein. In some embodiments, the mono- or di-F-CDN compounds as described herein are used in combination with one or more agents selected from the group consisting of sotrastaurin, nilotinib, 5-(2,4-dihydroxy-5-isopropylphenyl)-N-ethyl-4-(4-(morpholinomethyl)phenyl) isoxazole-3-carboxamide, dactolisib, 8-(6-Methoxy-pyridin-3-yl)-3-methyl-1-(4-piperazin-1-yl-3-trifluoromethyl-phenyl)-1,3-dihydro-imidazo[4,5-c]quinolin-2-one, 3-(2,6-dichloro-3,5-dimethoxyphenyl)-1-(6-((4-(4-ethylpiperazin-1-yl)phenyl)amino)pyrimidin-4-yl)-1-methylurea, buparlisib, 8-(2,6-difluoro-3,5-dimethoxyphenyl)-N-(4-((dimethylamino)methyl)-1H-imidazol-2-yl)quinoxaline-5-carboxamide, (S)—N1-(4-methyl-5-(2-(1,1,1-trifluoro-2-methylpropan-2-yl)pyridin-4-yl)thiazol-2-yl)pyrrolidine-1,2-dicarboxamide, (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one, deferasirox, letrozole, (4S,5R)-3-(2'-amino-2-morpholino-4'-(trifluoromethyl)-[4,5'-bipyrimidin]-6-yl)-4-(hydroxymethyl)-5-methyloxazolidin-2-one, (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one, 4-((2-(((1R,2R)-2-hydroxycyclohexyl)amino)benzo[d]thiazol-6-yl)oxy)-N-methylpicolinamide, imatinib mesylate, 2-fluoro-N-methyl-4-(7-(quinolin-6-ylmethyl)imidazo[1,2-b][1,2,4]triazin-2-yl)benzamide, ruxolitinib, panobinostat, osilodrostat, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide, sonidegib phosphate, ceritinib, 7-cyclopentyl-N,N-dimethyl-2-((5-(piperazin-1-yl)pyridin-2-yl)amino)-7H-pyrrolo[2,3-d]pyrimidine-6-carboxamide, N-(4-((1R,3S,5S)-3-amino-5-methylcyclohexyl)pyridin-3-yl)-6-(2,6-difluorophenyl)-5-fluoropicolinamide, 2-(2',3-dimethyl-[2,4'-bipyridin]-5-yl)-N-(5-(pyrazin-2-yl)pyridin-2-yl)acetamide, encorafenib, 7-cyclopentyl-N,N-dimethyl-2-((5-((1R,6S)-9-methyl-4-oxo-3,9-diazabicyclo[4.2.1]nonan-3-yl)pyridin-2-yl) amino)-7H-pyrrolo[2,3-d]pyrimidine-6-carboxamide, binimetinib, midostaurin, everolimus, 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine, pasireotide diaspartate, dovitinib, (R,E)-N-(7-chloro-1-(1-(4-(dimethylamino)but-2-enoyl)azepan-3-yl)-1H-benzo[d]imidazol-2-yl)-2-methylisonicotinamide. $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine, 3-(4-(4-((5-chloro-4-((5-methyl-1H-pyrazol-3-yl)amino)pyrimidin-2-yl)amino)-5-fluoro-2-methylphenyl) piperidin-1-yl)thietane 1,1-dioxide, 5-chloro-$N^2$-(2-fluoro-5-methyl-4-(1-(tetrahydro-2H-pyran-4-yl)piperidin-4-yl) phenyl)-$N^4$-(5-methyl-1H-pyrazol-3-yl)pyrimidine-2,4-diamine, 5-chloro-N2-(4-(1-ethylpiperidin-4-yl)-2-fluoro-5-methylphenyl)-$N^4$-(5-methyl-1H-pyrazol-3-yl)pyrimidine-2,4-diamine, valspodar, and vatalanib succinate.

In one embodiment, the combination. e.g., a combination comprising a mono- or di-F-CDN compound as described herein, is used in combination with a PKC inhibitor, Sotrastaurin (Compound A1), or a compound disclosed in PCT Publication No. WO 2005/039549, to treat a disorder, e.g., a disorder described herein. In one embodiment, the PKC inhibitor is Sotrastaurin (Compound A1) or a compound disclosed in PCT Publication No. WO 2005/039549. In one embodiment, the mono- or di-F-CDN compound is used in combination with Sotrastaurin (Compound A1), or a compound as described in PCT Publication No. WO 2005/039549, to treat a disorder such as a cancer, a melanoma, a non-Hodgkin lymphoma, an inflammatory bowel disease, transplant rejection, an ophthalmic disorder, or psoriasis. In certain embodiments, Sotrastaurin (Compound A1) is administered at a dose of about 20 to 600 mg. e.g., about 200 to about 600 mg, about 50 mg to about 450 mg, about 100 mg to 400 mg, about 150 mg to 350 mg, or about 200 mg to 300 mg, e.g., about 50 mg, 100 mg, 150 mg, 200 mg, 300 mg, 400 mg, 500 mg, or 600 mg. The dosing schedule can vary from e.g., every other day to daily, twice or three times a day.

In one embodiment, the combination, e.g., a combination comprising a mono- or di-F-CDN compound as described herein, is used in combination with a BCR-ABL inhibitor. TASIGNA (Compound A2, nilotinib), or a compound disclosed in PCT Publication No. WO 2004/005281, to treat a disorder, e.g., a disorder described herein. In one embodiment, the BCR-ABL inhibitor is TASIGNA, or a compound disclosed in PCT Publication No. WO 2004/005281. In one embodiment, the mono- or di-F-CDN compound is used in combination with TASIGNA (Compound A2), or a compound as described in PCT Publication No. WO 2004/005281, to treat a disorder such as a lymphocytic leukemia, Parkinson's Disease, a neurologic cancer, a melanoma, a digestive/gastrointestinal cancer, a colorectal cancer, a myeloid leukemia, a head and neck cancer, or pulmonary hypertension. In one embodiment, the BCR-ABL inhibitor or TASIGNA is administered at a dose of about 300 mg (e.g., twice daily. e.g., for newly diagnosed Ph+ CML-CP), or about 400 mg, e.g., twice daily, e.g., for resistant or intolerant Ph+ CML-CP and CML-AP). BCR-ABL inhibitor or a Compound A2 is administered at a dose of about 300-400 mg.

In another embodiment, the combination, e.g., a combination comprising a mono- or di-F-CDN compound as described herein, is used in combination with an HSP90 inhibitor, such as 5-(2,4-dihydroxy-5-isopropylphenyl)-N-ethyl-4-(4-(morpholinomethyl)phenyl)isoxazole-3-carboxamide (Compound A3), or a compound disclosed in PCT Publication No. WO 2010/060937 or WO 2004/072051, to treat a disorder, e.g., a disorder described herein. In one embodiment, the HSP90 inhibitor is 5-(2,4-dihydroxy-5-isopropylphenyl)-N-ethyl-4-(4-(morpholinomethyl)phenyl) isoxazole-3-carboxamide (Compound A3), or a compound disclosed in PCT Publication No. WO 2010/060937 or WO 2004/072051. In one embodiment, the mono- or di-F-CDN compound is used in combination with 5-(2,4-dihydroxy-5-isopropylphenyl)-N-ethyl-4-(4-(morpholinomethyl)phenyl) isoxazole-3-carboxamide (Compound A3), or a compound as described in PCT Publication No. WO 2010/060937 or WO 2004/072051, to treat a disorder such as a cancer, a multiple myeloma, a non-small cell lung cancer, a lymphoma, a gastric cancer, a breast cancer, a digestive/gastrointestinal cancer, a pancreatic cancer, a colorectal cancer, a solid tumor, or a hematopoiesis disorder.

In another embodiment, the combination, e.g., a combination comprising a mono- or di-F-CDN compound as described herein, is used in combination with an inhibitor of PI3K and/or mTOR, Dactolisib (Compound A4) or 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806, to treat a disorder, e.g., a disorder described herein. In one embodiment, the PI3K and/or mTOR inhibitor is Dactolisib (Compound A4), 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806. In one embodiment, the mono- or di-F-CDN compound is used in combination with Dactolisib (Compound A4), 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound described in PCT Publication No. WO 2006/122806, to treat a disorder such as a cancer, a prostate cancer, a leukemia (e.g., lymphocytic leukemia), a breast cancer, a brain cancer, a bladder cancer, a pancreatic cancer, a renal cancer, a solid tumor, or a liver cancer.

In another embodiment, the combination, e.g., a combination comprising a mono- or di-F-CDN compound as described herein, is used in combination with an FGFR inhibitor, 3-(2,6-dichloro-3,5-dimethoxyphenyl)-1-(6-((4-(4-ethylpiperazin-1-yl)phenyl)amino)pyrimidin-4-yl)-1-methylurea (Compound A5) or a compound disclosed in U.S. Pat. No. 8,552,002, to treat a disorder, e.g., a disorder described herein. In one embodiment, the FGFR inhibitor is 3-(2,6-dichloro-3,5-dimethoxyphenyl)-1-(6-((4-(4-ethylpiperazin-1-yl)phenyl)amino)pyrimidin-4-yl)-1-methylurea (Compound A5) or a compound disclosed in U.S. Pat. No. 8,552,002. In one embodiment, the mono- or di-F-CDN compound is used in combination with Compound A5, or a compound as described in U.S. Pat. No. 8,552,002, to treat a disorder such as a digestive/gastrointestinal cancer, a hematological cancer, or a solid tumor. In one embodiment, the FGFR inhibitor or 3-(2,6-dichloro-3,5-dimethoxyphenyl)-1-(6-((4-(4-ethylpiperazin-1-yl)phenyl)amino)pyrimidin-4-yl)-1-methylurea (Compound A5) is administered at a dose of about 100-125 mg (e.g., per day). e.g., about 100 mg or about 125 mg.

In another embodiment, the combination, e.g., a combination comprising a mono- or di-F-CDN compound as described herein, is used in combination with a PI3K inhibitor, Buparlisib (Compound A6), or a compound disclosed in PCT Publication No. WO 2007/084786, to treat a disorder, e.g., a disorder described herein. In one embodiment, the PI3K inhibitor is Buparlisib (Compound A6) or a compound disclosed in PCT Publication No. WO 2007/084786. In one embodiment, the mono- or di-F-CDN compound is used in combination with Buparlisib (Compound A6), or a compound disclosed in PCT Publication No. WO 2007/084786, to treat a disorder such as, a prostate cancer, a non-small cell lung cancer, an endocrine cancer, a leukemia, an ovarian cancer, a melanoma, a bladder cancer, a breast cancer, a female reproductive system cancer, a digestive/gastrointestinal cancer, a colorectal cancer, a glioblastoma multiforme, a solid tumor, a non-Hodgkin lymphoma, a hematopoiesis disorder, or a head and neck cancer. In one embodiment, the PI3K inhibitor or Buparlisib (Compound A6) is administered at a dose of about 100 mg (e.g., per day).

In another embodiment, the combination, e.g., a combination comprising a mono- or di-F-CDN compound as described herein, is used in combination with an FGFR inhibitor, 8-(2,6-difluoro-3,5-dimethoxyphenyl)-N-(4-((dimethylamino)methyl)-1H-imidazol-2-yl)quinoxaline-5-carboxamide (Compound A7) or a compound disclosed in PCT Publication No. WO 2009/141386, to treat a disorder. e.g., a disorder described herein. In one embodiment, the FGFR inhibitor is 8-(2,6-difluoro-3,5-dimethoxyphenyl)-N-(4-((dimethylamino)methyl)-1H-imidazol-2-yl)quinoxaline-5-carboxamide (Compound A7) or a compound disclosed in PCT Publication No. WO 2009/141386. In one embodiment, the FGFR inhibitor is 8-(2,6-difluoro-3,5-dimethoxyphenyl)-N-(4-((dimethylamino)methyl)-1H-imidazol-2-yl)quinoxaline-5-carboxamide (Compound A7). In one embodiment, the mono- or di-F-CDN compound is used in combination with 8-(2,6-difluoro-3,5-dimethoxyphenyl)-N-(4-((dimethylamino)methyl)-1H-imidazol-2-yl)quinoxaline-5-carboxamide (Compound A7), or a compound disclosed in PCT Publication No. WO 2009/141386, to treat a disorder such as a cancer characterized by angiogenesis. In one embodiment, the FGFR inhibitor or 8-(2,6-difluoro-3,5-dimethoxyphenyl)-N-(4-((dimethylamino)methyl)-1H-imidazol-2-yl)quinoxaline-5-carboxamide (Compound A7) is administered at a dose of e.g., from approximately 3 mg to approximately 5 g. more preferably from approximately 10 mg to approximately 1.5 g per person per day, optionally divided into 1 to 3 single doses which may, for example, be of the same size.

In another embodiment the combination, e.g., a combination comprising a mono- or di-F-CDN compound as described herein, is used in combination with a PI3K inhibitor, (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) or a compound disclosed PCT Publication No. WO 2010/029082, to treat a disorder. e.g., a disorder described herein. In one embodiment, the PI3K inhibitor is (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) or a compound disclosed PCT Publication No. WO 2010/029082. In one embodiment, the mono- or di-F-CDN compound is used in combination with (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8), or a compound disclosed PCT Publication No. WO 2010/029082, to treat a disorder such as a gastric cancer, a breast cancer, a pancreatic cancer, a digestive/gastrointestinal cancer, a solid tumor, and a head and neck cancer. In one embodiment, the PI3K inhibitor or (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) is administered at a dose of about 150-300, 200-300, 200-400, or 300-400 mg (e.g., per day), e.g., about 200, 300, or 400 mg.

In another embodiment, the combination, e.g., a combination comprising a mono- or di-F-CDN compound as described herein, is used in combination with an inhibitor of cytochrome P450 (e.g., a CYP17 inhibitor) or a compound disclosed in PCT Publication No. WO 2010/149755, to treat a disorder. e.g., a disorder described herein. In one embodiment, the cytochrome P450 inhibitor (e.g., the CYP17 inhibitor) is a compound disclosed in PCT Publication No. WO 2010/149755. In one embodiment, the mono- or di-F-CDN compound is used in combination with a compound disclosed in PCT Publication No. WO 2010/149755, to treat prostate cancer.

In another embodiment, the combination. e.g., a combination comprising a mono- or di-F-CDN compound as described herein, is used in combination with an HDM2 inhibitor, (S)-1-(4-chlorophenyl)-7-isopropoxy-6-methoxy-2-(4-(methyl(((1 r,4S)-4-(4-methyl-3-oxopiperazin-1-yl)cyclohexyl)methyl)amino)phenyl)-1,2-dihydroisoquinolin-3(4H)-one (Compound A10) or a compound disclosed in PCT Publication No. WO 2011/076786, to treat a disorder, e.g., a disorder described herein). In one embodiment, the HDM2 inhibitor is (S)-1-(4-chlorophenyl)-7-isopropoxy-6-methoxy-2-(4-(methyl(((1 r,4S)-4-(4-methyl-3-oxopiperazin-1-yl)cyclohexyl)methyl)amino)phenyl)-1,2-dihydroisoquinolin-3(4H)-one (Compound A10) or a compound disclosed in PCT Publication No. WO 2011/076786. In one embodiment, the mono- or di-F-CDN compound is used in combination with (S)-1-(4-chlorophenyl)-7-isopropoxy-6-methoxy-2-(4-(methyl(((1 r,4S)-4-(4-methyl-3-oxopiperazin-1-yl)cyclohexyl)methyl)amino)phenyl)-1,2-dihydroisoquinolin-3(4H)-one (Compound A10), or a compound disclosed in PCT Publication No. WO 2011/076786, to treat a disorder such as a solid tumor. In one embodiment, the HDM2 inhibitor or (S)-1-(4-chlorophenyl)-7-isopropoxy-6-methoxy-2-(4-(methyl(((1 r,4S)-4-(4-methyl-3-oxopiperazin-1-yl)cyclohexyl)methyl)amino)phenyl)-1,2-dihydroisoquinolin-3(4H)-one (Compound A10) is administered at a dose of about 400 to 700 mg, e.g., administered three times weekly, 2 weeks on and one week off. In some embodiments, the dose is about 400, 500, 600, or 700 mg; about 400-500, 500-600, or 600-700 mg, e.g., administered three times weekly.

In another embodiment, the combination, e.g., a combination comprising a mono- or di-F-CDN compound as described herein, is used in combination with an iron chelating agent, Deferasirox (also known as EXJADE; Compound A11), or a compound disclosed in PCT Publication No. WO 1997/049395, to treat a disorder. e.g., a disorder described herein. In one embodiment, the iron chelating agent is Deferasirox or a compound disclosed in PCT Publication No. WO 1997/049395. In one embodiment, the iron chelating agent is Deferasirox (Compound A11). In one embodiment, the mono- or di-F-CDN compound is used in combination with Deferasirox (Compound A11), or a compound disclosed in PCT Publication No. WO 1997/049395, to treat iron overload, hemochromatosis, or myelodysplasia.

In another embodiment, the combination, e.g., a combination comprising a mono- or di-F-CDN compound as described herein, is used in combination with an aromatase inhibitor, Letrozole (also known as FEMARA; Compound A12), or a compound disclosed in U.S. Pat. No. 4,978,672, to treat a disorder, e.g., a disorder described herein. In one embodiment, the aromatase inhibitor is Letrozole (Compound A12) or a compound disclosed in U.S. Pat. No. 4,978,672. In one embodiment, the mono- or di-F-CDN compound is used in combination with Letrozole (Compound A12), or a compound disclosed in U.S. Pat. No. 4,978,672, to treat a disorder such as a cancer, a leiomyosarcoma, an endometrium cancer, a breast cancer, a female reproductive system cancer, or a hormone deficiency.

In another embodiment, the combination, e.g., a combination comprising a mono- or di-F-CDN compound as described herein, is used in combination with a PI3K inhibitor, e.g., a pan-PI3K inhibitor, (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826, to treat a disorder, e.g., a disorder described herein. In one embodiment, the PI3K inhibitor is (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826. In one embodiment, the mono- or di-F-CDN compound is used in combination with (4S,5R)-3-(2'-amino-2-morpholino-4'-(trifluoromethyl)-[4,5'-bipyrimidin]-6-yl)-4-(hydroxymethyl)-5-methyloxazolidin-2- one (Compound A13), or a compound disclosed in PCT Publication No. WO2013/124826, to treat a disorder such as a cancer or an advanced solid tumor.

In another embodiment, the combination, e.g., a combination comprising a mono- or di-F-CDN compound as described herein, is used in combination with an inhibitor of p53 and/or a p53/Mdm2 interaction, (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14), or a compound disclosed in PCT Publication No. WO2013/111105, to treat a disorder, e.g., a disorder described herein. In one embodiment, the p53 and/or a p53/Mdm2 interaction inhibitor is (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14) or a compound disclosed in PCT Publication No. WO2013/111105. In one embodiment, the mono- or di-F-CDN compound is used in combination with (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14), or a compound disclosed in PCT Publication No. WO2013/111105, to treat a disorder such as a cancer or a soft tissue sarcoma.

In another embodiment, the combination, e.g., a combination comprising a mono- or di-F-CDN compound as described herein, is used in combination with a CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, to treat a disorder. e.g., a disorder described herein. In one embodiment, the CSF-1R tyrosine kinase inhibitor is 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2005/073224. In one embodiment, the mono- or di-F-CDN compound is used in combination with 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2005/073224, to treat a disorder such as cancer.

In another embodiment, the combination, e.g., a combination comprising a mono- or di-F-CDN compound as described herein, is used in combination with an apoptosis inducer and/or an angiogenesis inhibitor, such as Imatinib mesylate (also known as GLEEVEC; Compound A16) or a compound disclosed in PCT Publication No. WO1999/003854, to treat a disorder, e.g., a disorder described. In one embodiment, the apoptosis inducer and/or an angiogenesis inhibitor is Imatinib mesylate (Compound A16) or a compound disclosed in PCT Publication No. WO1999/003854. In one embodiment, the mono- or di-F-CDN compound is used in combination with Imatinib mesylate (Compound A16), or a compound disclosed in PCT Publication No. WO1999/003854, to treat a disorder such as a cancer, a multiple myeloma, a prostate cancer, a non-small cell lung cancer, a lymphoma, a gastric cancer, a melanoma, a breast cancer, a pancreatic cancer, a digestive/gastrointestinal cancer, a colorectal cancer, a glioblastoma multiforme, a liver cancer, a head and neck cancer, asthma, multiple sclerosis, allergy, Alzheimer's dementia, amyotrophic lateral sclerosis, or rheumatoid arthritis. In certain embodiments, Imatinib mesylate (Compound A16) is administered at a dose of about 100 to 1000 mg, e.g., about 200 mg to 800 mg, about 300 mg to 700 mg, or about 400 mg to 600 mg. e.g., about 200 mg, 300 mg, 400 mg, 500 mg, 600 mg, or 700 mg. The dosing schedule can vary from e.g., every other day to daily, twice or three times a day. In one embodiment, Imatinib mesylate is administered at an oral dose from about 100 mg to 600 mg daily, e.g., about 100 mg, 200 mg, 260 mg, 300 mg, 400 mg, or 600 mg daily.

In another embodiment, the combination, e.g., a combination comprising a mono- or di-F-CDN compound as described herein, is used in combination with a JAK inhibitor, 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514, to treat a disorder. e.g., a disorder described herein. In one embodiment, the JAK inhibitor is 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514. In one embodiment, the mono- or di-F-CDN compound is used in combination with 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514, to treat a disorder such as colorectal cancer, myeloid leukemia, hematological cancer, autoimmune disease, non-Hodgkin lymphoma, or thrombocythemia. In one embodiment, the JAK inhibitor or a 2-fluoro-N-methyl-4-(7-(quinolin-6-ylmethyl)imidazo[1,2-b][1,2,4]triazin-2-yl)benzamide (Compound A17), or a dihydrochloric salt thereof is administered at a dose of about 400-600 mg (e.g., per day), e.g., about 400, 500, or 600 mg, or about 400-500 or 500-600 mg.

In another embodiment, the combination, e.g., a combination comprising a mono- or di-F-CDN compound as described herein, is used in combination with a JAK inhibitor, Ruxolitinib Phosphate (also known as JAKAFI; Compound A18) or a compound disclosed in PCT Publication No. WO 2007/070514 to treat a disorder, e.g., a disorder described herein. In one embodiment, the JAK inhibitor is Ruxolitinib Phosphate (Compound A18) or a compound disclosed in PCT Publication No. WO 2007/070514. In one embodiment, the mono- or di-F-CDN compound is used in combination with Ruxolitinib Phosphate (Compound A18), or a compound disclosed in PCT Publication No. WO 2007/070514, to treat a disorder such as a prostate cancer, a lymphocytic leukemia, a multiple myeloma, a lymphoma, a lung cancer, a leukemia, cachexia, a breast cancer, a pancreatic cancer, rheumatoid arthritis, psoriasis, a colorectal cancer, a myeloid leukemia, a hematological cancer, an autoimmune disease, a non-Hodgkin lymphoma, or thrombocythemia. In one embodiment, the JAK inhibitor or Ruxolitinib Phosphate (Compound A18) is administered at a dose of about 15-25 mg, e.g., twice daily. In some embodiments, the dose is about 15, 20, or 25 mg, or about 15-20 or 20-25 mg.

In another embodiment, the combination, e.g., a combination comprising a mono- or di-F-CDN compound as described herein, is used in combination with a histone deacetylase (HDAC) inhibitor. In some embodiments, the HDAC inhibitor is selected from the group consisting of panobinostat, vorinostat, romidepsin, chidamide, valproic acid, belinostat, pyroxamide, mocetinostat, abexinostat, entinostat, pracinostat, resminostat, givinostat, quisinostat, ricolinostat, CUDC-101, AR-42, CHR-2845, CHR-3996, 4SC-202, and CG200745. In some embodiments, the combination comprising a mono- or di-F-CDN compound as described herein, is used in combination with a histone deacetylase (HDAC) inhibitor, Panobinostat (Compound A19), or a compound disclosed in PCT Publication No. WO 2014/072493, to treat a disorder, e.g., a disorder described herein. In one embodiment, the HDAC inhibitor is Panobinostat (Compound A19) or a compound disclosed in PCT Publication No. WO 2014/072493. In one embodiment, the mono- or di-F-CDN compound is used in combination with Panobinostat (Compound A19), a compound disclosed in PCT Publication No. WO 2014/072493, to treat a disorder such as a small cell lung cancer, a respiratory/thoracic cancer, a prostate cancer, a multiple myeloma, myelodysplastic syndrome, a bone cancer, a non-small cell lung cancer, an endocrine cancer, a lymphoma, a neurologic cancer, a leukemia, HIV/AIDS, an immune disorder, transplant rejection, a gastric cancer, a melanoma, a breast cancer, a pancreatic cancer, a colorectal cancer, a glioblastoma multiforme, a myeloid leukemia, a hematological cancer, a renal cancer, a non-Hodgkin lymphoma, a head and neck cancer, a hematopoiesis disorders, or a liver cancer. In one embodiment, the HDAC inhibitor or Panobinostat (Compound A19) is administered at a dose of about 20 mg (e.g., per day).

In another embodiment, the combination, e.g., a combination comprising a mono- or di-F-CDN compound as described herein, is used in combination with an inhibitor of one or more of cytochrome P450 (e.g., 11B2), aldosterone or angiogenesis. Osilodrostat (Compound A20), or a compound disclosed in PCT Publication No. WO2007/024945, to treat a disorder, e.g., a disorder described herein. In one embodiment, the inhibitor of one or more of cytochrome P450 (e.g., 11B2), aldosterone or angiogenesis is Osilodrostat (Compound A20) or a compound disclosed in PCT Publication No. WO2007/024945. In one embodiment, the mono- or di-F-CDN compound is used in combination with Osilodrostat (Compound A20), or a compound disclosed in PCT Publication No. WO2007/024945, to treat a disorder such as Cushing's syndrome, hypertension, or heart failure therapy.

In another embodiment, the combination, e.g., a combination comprising a mono- or di-F-CDN compound as described herein, is used in combination with a IAP inhibitor, (S)—N—((S)-1-cyclohexyl-2-((S)-2-(4-(4-fluorobenzoyl)thiazol-2-yl)thiazol-2-yl)pyrrolidin-1-yl)-2-oxoethyl)-2-(methylamino)propanamide (Compound A21) or a compound disclosed in U.S. Pat. No. 8,552,003, to treat a disorder, e.g., a disorder described herein. In one embodiment, the IAP inhibitor is (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003. In one embodiment, the mono- or di-F-CDN compound is used in combination with (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, to treat a disorder such as a multiple myeloma, a breast cancer, an ovarian cancer, a pancreatic cancer, or a hematopoiesis disorder. In one embodiment, the IAP inhibitor or (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003 is administered at a dose of approximately 1800 mg, e.g., once weekly.

In another embodiment, the combination, e.g., a combination comprising a mono- or di-F-CDN compound as described herein, is used in combination a Smoothened (SMO) inhibitor, Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120, to treat a disorder, e.g., a disorder described herein. In one embodiment, the SMO inhibitor is Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120. In one embodiment, the mono- or di-F-CDN compound is used in combination with Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120 to treat a disorder such as a cancer, a medulloblastoma, a small cell lung cancer, a prostate cancer, a basal cell carcinoma, a pancreatic cancer, or an inflammation. In certain embodiments. Sonidegib phosphate (Compound A22) is administered at a dose of about 20 to 500 mg, e.g., about 40 mg to 400 mg, about 50 mg to 300 mg, or about 100 mg to 200 mg, e.g., about 50 mg, 100 mg, 150 mg, 200 mg, 250 mg, or 300 mg. The dosing schedule can vary from e.g., every other day to daily, twice or three times a day.

In another embodiment, the combination. e.g., a combination comprising a mono- or di-F-CDN compound as described herein, is used in combination with an Alk inhibitor, ceritinib (also known as ZYKADIA; Compound A23) or a compound disclosed in PCT Publication No. WO 2007/131201, to treat a disorder, e.g., a disorder described herein. In one embodiment, the Alk inhibitor is ceritinib (Compound A23) or a compound disclosed in PCT Publication No. WO 2007/131201. In one embodiment, the mono- or di-F-CDN compound is used in combination with ceritinib (Compound A23), or a compound disclosed in PCT Publication No. WO 2007/131201, to treat a disorder such as non-small cell lung cancer or solid tumors. In one embodiment, the Alk inhibitor or ceritinib (Compound A23) is administered at a dose of approximately 750 mg, e.g., once daily.

In another embodiment, the combination, e.g., a combination comprising a mono- or di-F-CDN compound as described herein, is used in combination with a JAK and/or CDK4/6 inhibitor, 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. Nos. 8,415,355 or 8,685,980, to treat a disorder. e.g., a disorder described herein. In one embodiment, the JAK and/or CDK4/6 inhibitor is 7-cyclopentyl-N,N-dimethyl-2-((5-(piperazin-1-yl)pyridin-2-yl)amino)-7H-pyrrolo[2,3-d]pyrimidine-6-carboxamide (Compound A24) or a compound disclosed in U.S. Pat. Nos. 8,415,355 or 8,685,980. In one embodiment, the mono- or di-F-CDN compound is used in combination with 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. Nos. 8,415,355 or 8,685,980, to treat a disorder such as a lymphoma, a neurologic cancer, a melanoma, a breast cancer, or a solid tumor. In one embodiment, the JAK and/or CDK4/6 inhibitor or 7-cyclopentyl-N,N-dimethyl-2-((5-(piperazin-1-yl)pyridin-2-yl)amino)-7H-pyrrolo[2,3-d]pyrimidine-6-carboxamide (Compound A24) is administered at a dose of approximately 200-600 mg. e.g., per day. In one embodiment, the compound is administered at a dose of about 200, 300, 400, 500, or 600 mg, or about 200-300, 300-400, 400-500, or 500-600 mg.

In another embodiment, the combination, e.g., a combination comprising a mono- or di-F-CDN compound as described herein, is used in combination with a PIM Kinase inhibitor. N-(4-((1R,3S,5S)-3-amino-5-methylcyclohexyl)pyridin-3-yl)-6-(2,6-difluorophenyl)-5-fluoropicolinamide (Compound A27) or a compound disclosed in PCT Publication No. WO 2010/026124, to treat a disorder, e.g., a disorder described herein. In one embodiment, the PIM Kinase inhibitor is N-(4-((1R,3S,5S)-3-amino-5-methylcyclohexyl)pyridin-3-yl)-6-(2,6-difluorophenyl)-5-fluoropicolinamide (Compound A27) or a compound disclosed in PCT Publication No. WO 2010/026124. In one embodiment, the mono- or di-F-CDN compound is used in combination with N-(4-((1R,3S,5S)-3-amino-5-methylcyclohexyl)pyridin-3-yl)-6-(2,6-difluorophenyl)-5-fluoropicolinamide (Compound A27), or a compound disclosed in PCT Publication No. WO 2010/026124, to treat a disorder such as a multiple myeloma, myelodysplastic syndrome, a myeloid leukemia, or a non-Hodgkin lymphoma.

In another embodiment, the combination, e.g., a combination comprising a mono- or di-F-CDN compound as described herein, is used in combination a Wnt signaling inhibitor, 2-(2',3-dimethyl-[2,4'-bipyridin]-5-yl)-N-(5-(pyrazin-2-yl)pyridin-2-yl)acetamide (Compound A28) or a compound disclosed in PCT publication No. WO 2010/101849, to treat a disorder, e.g., a disorder described herein. In one embodiment, the Wnt signaling inhibitor is 2-(2',3-dimethyl-[2,4'-bipyridin]-5-yl)-N-(5-(pyrazin-2-yl)pyridin-2-yl)acetamide (Compound A28) or a compound disclosed in PCT publication No. WO 2010/101849. In one embodiment, the Wnt signaling inhibitor is 2-(2',3-dimethyl-[2,4'-bipyridin]-5-yl)-N-(5-(pyrazin-2-yl)pyridin-2-yl)acetamide (Compound A28). In one embodiment, the mono- or di-F-CDN compound is used in combination with 2-(2',3-dimethyl-[2,4'-bipyridin]-5-yl)-N-(5-(pyrazin-2-yl)pyridin-2-yl)acetamide (Compound A28), or a compound disclosed in PCT publication No. WO 2010/101849, to treat a disorder such as a solid tumor (e.g., a head and neck cancer, a squamous cell carcinoma, a breast cancer, a pancreatic cancer, or a colon cancer). In certain embodiments, 2-(2',3-dimethyl-[2,4'-bipyridin]-5-yl)-N-(5-(pyrazin-2-yl)pyridin-2-yl)acetamide (Compound A28) is administered at a dose of about 1 to 50 mg, e.g., about 2 mg to 45 mg, about 3 mg to 40 mg, about 5 mg to 35 mg, 5 mg to 10 mg, or about 10 mg to 30 mg. e.g., about 2 mg, 5 mg, 10 mg, 20 mg, 30 mg, or 40 mg. The dosing schedule can vary from e.g., every other day to daily, twice or three times a day.

In another embodiment, the combination, e.g., a combination comprising a mono- or di-F-CDN compound as described herein, is used in combination with a BRAF inhibitor. Encorafenib (Compound A29), or a compound disclosed in PCT Publication No. WO 2011/025927, to treat a disorder, e.g., a disorder described herein. In one embodiment, the BRAF inhibitor is Encorafenib (Compound A29) or a compound disclosed in PCT Publication No. WO 2011/025927. In one embodiment, the mono- or di-F-CDN compound is used in combination with Encorafenib (Compound A29), or a compound disclosed in PCT Publication No. WO 2011/025927, to treat a disorder such as a non-small cell lung cancer, a melanoma, or a colorectal cancer. In one embodiment, the BRAF inhibitor or Encorafenib (Compound A29) is administered at a dose of about 200-300, 200-400, or 300-400 mg, e.g., per day. In one embodiment, the compound is administered at a dose of about 200, about 300 or about 400 mg.

In another embodiment, the combination, e.g., a combination comprising a mono- or di-F-CDN compound as described herein, is used in combination a CDK4/6 inhibitor, 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30), or a compound disclosed in PCT publication No. WO 2011/101409, to treat a disorder, e.g., a disorder described herein. In one embodiment, the CDK4/6 inhibitor is 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30) or a compound disclosed in PCT publication No. WO 2011/101409. In one embodiment, the mono- or di-F-CDN compound is used in combination with 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30), or a compound disclosed in PCT publication No. WO 2011/101409, to treat a disorder such as a cancer, a mantle cell lymphoma, a liposarcoma, a non-small cell lung cancer, a melanoma, a squamous cell esophageal cancer, or a breast cancer.

In another embodiment, the combination, e.g., a combination comprising a mono- or di-F-CDN compound as described herein, is used in combination with a MEK inhibitor, Binimetinib (Compound A34), or a compound disclosed in PCT Publication No. WO 2003/077914, to treat a disorder, e.g., a disorder described herein. In one embodiment, the MEK inhibitor is Binimetinib (Compound A34), or a compound disclosed in PCT Publication No. WO 2003/077914. In one embodiment, the mono- or di-F-CDN compound is used in combination with Binimetinib (Compound A34), or a compound disclosed in PCT Publication No. WO 2003/077914, to treat a disorder such as a non-small cell lung cancer, a multisystem genetic disorder, a melanoma, an ovarian cancer, a digestive/gastrointestinal cancer, a rheumatoid arthritis, or a colorectal cancer. In one embodiment, the MEK inhibitor or Binimetinib (Compound A34) is administered at a dose of about 45 mg, e.g., twice daily.

In another embodiment, the combination, e.g., a combination comprising a mono- or di-F-CDN compound as described herein, is used in combination an inhibitor of one or more of c-KIT, histamine release, Flt3 (e.g., FLK2/STK1) or PKC. Midostaurin (Compound A35) or a compound disclosed in PCT Publication No. WO 2003/037347, to treat a disorder, e.g., a disorder described herein. In one embodiment, the inhibitor is Midostaurin (Compound A35) or compound disclosed in PCT Publication No. WO 2003/037347. In one embodiment, the inhibitor of one or more of c-KIT, histamine release, Flt3 (e.g., FLK2/STK1) or PKC is Midostaurin. In one embodiment, the mono- or di-F-CDN compound is used in combination with Midostaurin (Compound A35), or compound disclosed in PCT Publication No. WO 2003/037347, to treat a disorder such as a cancer, a colorectal cancer, a myeloid leukemia, myelodysplastic syndrome, an age-related mascular degeneration, a diabetic complication, or a dermatologic disorder.

In another embodiment, the combination, e.g., a combination comprising a mono- or di-F-CDN compound as described herein, is used in combination with a TOR inhibitor (e.g., mTOR inhibitor), Everolimus (also known as AFINITOR; Compound A36) or a Compound disclosed in PCT Publication No. WO 2014/085318, to treat a disorder, e.g., a disorder described herein). In one embodiment, the TOR inhibitor is Everolimus (Compound A36) or a Compound disclosed in PCT Publication No. WO 2014/085318. In one embodiment, the mono- or di-F-CDN compound is used in combination with Everolimus (Compound A36) to treat a disorder such as an interstitial lung disease, a small cell lung cancer, a respiratory/thoracic cancer, a prostate cancer, a multiple myeloma, a sarcoma, an age-related macular degeneration, a bone cancer, tuberous sclerosis, a non-small cell lung cancer, an endocrine cancer, a lymphoma, a neurologic disorders, an astrocytoma, a cervical cancer, a neurologic cancer, a leukemia, an immune disorders, transplant rejection, a gastric cancer, a melanoma, epilepsy, a breast cancer, or a bladder cancer. In one embodiment, the TOR inhibitor or Everolimus is (Compound A36) administered at a dose of about 2.5-20 mg/day. In one embodiment, the compound is administered at a dose of about 2.5, 5, 10, or 20 mg/day, e.g., about 2.5-5, 5-10, or 10-20 mg/day.

In another embodiment, the combination, e.g., a combination comprising a mono- or di-F-CDN compound as described herein, is used in combination an inhibitor of one or more of VEGFR-2. PDGFRbeta, KIT or Raf kinase C, 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377, to treat a disorder, e.g., a disorder described herein. In one embodiment, the inhibitor of one or more of VEGFR-2, PDGFRbeta. KIT or Raf kinase C is 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377. In one embodiment, the mono- or di-F-CDN compound is used in combination with 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37), or a compound disclosed in PCT Publication No. WO 2007/030377, to treat a disorder such as a cancer, a melanoma, or a solid tumor.

In another embodiment, the combination, e.g., a combination comprising a mono- or di-F-CDN compound as described herein, is used in combination a somatostatin agonist and/or growth hormone release inhibitor, Pasireotide diaspartate (also known as SIGNIFOR; Compound A38) or a compound disclosed in PCT Publication No. WO2002/010192 or U.S. Pat. No. 7,473,761, to treat a disorder, e.g., a disorder described herein. In one embodiment, the somatostatin agonist and/or growth hormone release inhibitor is Pasireotide diaspartate (Compound A38) or a compound disclosed in PCT Publication No. WO2002/010192 or U.S. Pat. No. 7,473,761. In one embodiment, the mono- or di-F-CDN compound is used in combination with Pasireotide diaspartate (Compound A38), or a compound disclosed in PCT Publication No. WO2002/010192 or U.S. Pat. No. 7,473,761, to treat a disorder such as a prostate cancer, an endocrine cancer, a neurologic cancer, a skin cancer (e.g., a melanoma), a pancreatic cancer, a liver cancer. Cushing's syndrome, a gastrointestinal disorder, acromegaly, a liver and biliary tract disorder, or liver cirrhosis.

In another embodiment, the combination, e.g., a combination comprising a mono- or di-F-CDN compound as described herein, is used in combination a signal transduction modulator and/or angiogenesis inhibitor. Dovitinib (Compound A39) or a compound disclosed in PCT Publication No. WO 2009/115562, to treat a disorder. e.g., a disorder described herein. In one embodiment, the signal transduction modulator and/or angiogenesis inhibitor is Dovitinib (Compound A39) or a compound disclosed in PCT Publication No. WO 2009/115562. In one embodiment, the mono- or di-F-CDN compound is used in combination with Dovitinib (Compound A39), or a compound disclosed in PCT Publication No. WO 2009/115562, to treat a disorder such as a cancer, a respiratory/thoracic cancer, a multiple myeloma, a prostate cancer, a non-small cell lung cancer, an endocrine cancer, or a neurological genetic disorder.

In another embodiment, the combination, e.g., a combination comprising a mono- or di-F-CDN compound as described herein, is used in combination with an EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757, to treat a disorder. e.g., a disorder described herein. In one embodiment, the EGFR inhibitor is (R,E)-N-(7-chloro-1-(1-(4-(dimethylamino) but-2-enoyl)azepan-3-yl)-1H-benzo[d]imidazol-2-yl)-2-methylisonicotinamide (Compound A40) or a compound disclosed in PCT Publication No. WO 2013/184757. In one embodiment, the mono- or di-F-CDN compound is used in combination with (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, to treat a disorder such as a cancer, e.g., a solid tumor. In one embodiment, the EGFR inhibitor or (R,E)-N-(7-chloro-1-(1-(4-(dimethylamino)but-2-enoyl)azepan-3-yl)-1H-benzo[d]imidazol-2-yl)-2-methylisonicotinamide (Compound A40) is administered at a dose of 150-250 mg, e.g., per day. In one embodiment, the compound is administered at a dose of about 150, 200, or 250 mg, or about 150-200 or 200-250 mg.

In another embodiment, the combination, e.g., a combination comprising a mono- or di-F-CDN compound as described herein, is used in combination an ALK inhibitor, $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42) or a compound disclosed in PCT Publication No. WO 2008/073687, to treat a disorder, e.g., a disorder described herein. In one embodiment, the ALK inhibitor is $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42) or a compound disclosed in PCT Publication No. WO 2008/073687. In one embodiment, the mono- or di-F-CDN compound is used in combination with $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42), or a compound disclosed in PCT Publication No. WO 2008/073687, to treat a disorder such as a cancer, an anaplastic large-cell lymphoma (ALCL), a non-small cell lung carcinoma (NSCLC), or a neuroblastoma.

In another embodiment, the combination, e.g., a combination comprising a mono- or di-F-CDN compound as described herein, is used in combination an IGF-1R inhibitor, 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), or 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45) or a compound disclosed in PCT Publication No. WO 2010/002655, to treat a disorder, e.g., a disorder described. In one embodiment, the IGF-1R inhibitor is 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran- 4-yl)piperidin-4-yl)phenyl)-$N^4$-(5-methyl-1H-pyrazol-3-yl) pyrimidine-2,4-diamine (Compound A44), 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45), or a compound disclosed in PCT Publication No. WO 2010/002655. In one embodiment, the mono- or di-F-CDN compound is used in combination with 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), 5-chloro-N2-(4-(1-ethylpiperidin-4-yl)-2-fluoro-5-methylphenyl)-N4-(5-methyl-1H-pyrazol-3-yl)pyrimidine-2,4-diamine (Compound A45), or a compound disclosed in PCT Publication No. WO 2010/002655, to treat a disorder such as a cancer or a sarcoma.

In another embodiment, the combination, e.g., a combination comprising a mono- or di-F-CDN compound as described herein, is used in combination a P-Glycoprotein 1 inhibitor, Valspodar (also known as AMDRAY; Compound A46) or a compound disclosed in EP 296122, to treat a disorder. e.g., a disorder described herein. In one embodiment, the P-Glycoprotein 1 inhibitor is Valspodar (Compound A46) or a compound disclosed in EP 296122. In one embodiment, the mono- or di-F-CDN compound is used in combination with Valspodar (Compound A46), or a compound disclosed in EP 296122, to treat a disorder such as a cancer or a drug-resistant tumor.

In another embodiment, the combination, e.g., a combination comprising a mono- or di-F-CDN compound as described herein, is used in combination one or more of a VEGFR inhibitor, Vatalanib succinate (Compound A47) or a compound disclosed in WO 98/35958, to treat a disorder. e.g., a disorder described herein. In one embodiment, the VEGFR inhibitor is Vatalanib succinate (Compound A47) or a compound disclosed in WO 98/35958. In one embodiment, the mono- or di-F-CDN compound is used in combination with Vatalanib succinate (Compound A47), or a compound disclosed in EP 296122, to treat cancer.

In another embodiment, the combination. e.g., a combination comprising a mono- or di-F-CDN compound as described herein, is used in combination with an IDH inhibitor or a compound disclosed in WO2014/141104, to treat a disorder, e.g., a disorder described herein. In one embodiment, the IDH inhibitor is a compound disclosed in PCT Publication No. WO2014/141104. In one embodiment, the mono- or di-F-CDN compound is used in combination with a compound disclosed in WO2014/141104 to treat a disorder such as a cancer.

In another embodiment, the combination, e.g., a combination comprising a mono- or di-F-CDN compound as described herein, is used in combination with a BCL-ABL inhibitor or a compound disclosed in PCT Publication No. WO2013/171639, WO2013/171640, WO2013/171641, or WO2013/171642, to treat a disorder, e.g., a disorder described herein. In one embodiment, the BCL-ABL inhibitor is a compound disclosed in PCT Publication No. WO2013/171639, WO2013/171640, WO2013/171641, or WO2013/171642. In one embodiment, the mono- or di-F-CDN compound is used in combination with a compound disclosed in PCT Publication No. WO2013/171639, WO2013/171640, WO2013/171641, or WO2013/171642 to treat a disorder such as a cancer.

In another embodiment, the combination, e.g., a combination comprising a mono- or di-F-CDN compound as described herein, is used in combination with a c-RAF inhibitor or a compound disclosed in PCT Publication No. WO2014/151616, to treat a disorder, e.g., a disorder described herein. In one embodiment, the c-RAF inhibitor is Compound A50 or a compound disclosed in PCT Publication No. WO2014/151616. In one embodiment, the mono- or di-F-CDN compound is used in combination with a compound disclosed in PCT Publication No. WO2014/151616 to treat a disorder such as a cancer.

In another embodiment, the combination, e.g., a combination comprising a mono- or di-F-CDN compound as described herein, is used in combination with an ERK1/2 ATP competitive inhibitor or a compound disclosed in PCT Publication No. WO2015/066188, to treat a disorder, e.g., a disorder described herein. In one embodiment, the ERK1/2 ATP competitive inhibitor is a compound disclosed in PCT Publication No. WO2015/066188. In one embodiment, the mono- or di-F-CDN compound is used in combination with Compound A51 or a compound disclosed in PCT Publication No. WO2015/066188 to treat a disorder such as a cancer. In some embodiments, the combination. e.g., a combination comprising a mono- or di-F-CDN compound described herein, and Compound A51 or a compound disclosed in PCT Publication No. WO2015/066188, is administered in combination with one or more agents selected from, Compound A8, Compound A17, Compound A23, Compound A24, Compound A27, Compound A29, and Compound A33.

In some embodiments, the combination, e.g., a combination comprising a mono- or di-F-CDN compound as described herein, is administered in combination with an anti-cancer agent having a known activity in an immune cell assay, e.g., in one or more of a huMLR assay, a T cell proliferation assay, and a B-cell proliferation assay, where such assays are known in the art, and can be used to demonstrate the compounds will not inhibit an immune response (i.e. demonstrate little or no inhibition in such assays). An IC50 in such assays can be determined for the compounds to be used in combination with the mono- or di-F-CDN compound. In embodiments, the anti-cancer agent has an IC50 of, e.g., >1 μM, 1-4 μM, or greater than 4 μM, e.g., 4-10 μM or 4-20 μM, or greater than 20 μM. In embodiments, the second therapeutic agent is chosen from one or more of: Compound A9, Compound A16, Compound A17, Compound A21, Compound A22, Compound A25, Compound A28, Compound A48, and Compound A49.

In some embodiments, the Compound A28 (or a compound related to Compound A28) is administered at a dose of approximately 5-10 or 10-30 mg. In some embodiments, the Compound A22 (or compound related to Compound A22) is administered at a dose of about 200 mg. In some embodiments, the Compound A17 (or compound related to Compound A17) is administered at a dose of approximately 400-600 mg. In some embodiments, the Compound A16 (or compound related to Compound A16) is administered at a dose of approximately 400-600 mg PO qDay. In some embodiments, the Compound A29 (or compound related to Compound A29) is administered at a dose of approximately 200-400 or 300-400 mg. In some embodiments, the Compound A24 (or compound related to Compound A24) is administered at a dose of approximately 200-600 mg. In some embodiments, the Compound A23 (ceritinib) (or compound related to ceritinib) is administered at a dose of approximately 750 mg once daily. In some embodiments, the Compound A8 (or compound related to Compound A8) is administered at a dose of approximately 200-400 or 300-400 mg. In some embodiments, the Compound A5 (or compound related to Compound A5) is administered at a dose of approximately 100-125 mg. In some embodiments, the Compound A6 (or compound related to Compound A6) is administered at a dose of about 100 mg. In some embodiments, the Compound A1 (or compound related to Compound A1) is administered at a dose of approximately 200-300 or 200-600 mg. In some embodiments, the Compound A40 (or compound related to Compound A40) is administered at a dose of approximately 150-250 mg. In embodiments, the Compound A10 (or compound related to Compound A10) is administered at a dose of approximately 400 to 700 mg, e.g., administered three times weekly, 2 weeks on and one week off. In embodiments, the BCR-ABL inhibitor is administered at a dose of approximately 20 mg bid-80 mg bid.

TABLE 2

Therapeutic agents that can be administered in combination with the mono- or di-F-CDN compounds as described herein.

| Compound designation/generic name | Patent/Reference | Compound Structure |
|---|---|---|
| A1<br>Sotrastaurin | EP 1682103<br>US 2007/142401<br>WO 2005/039549 | 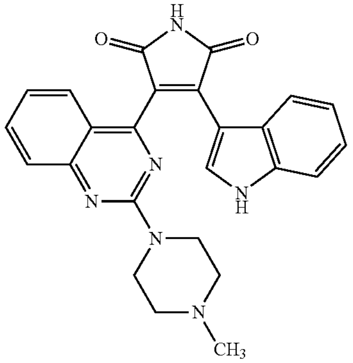 [SMILES: CN1CCN(c2nc(C3=C(c4c[nH]c5ccccc45)C(=O)NC3=O)c3ccccc3n2)CC1] |
| A2<br>Nilotinib HCl monohydrate<br>TASIGNA ® | WO 2004/005281<br>U.S. Pat. No. 7,169,791 | 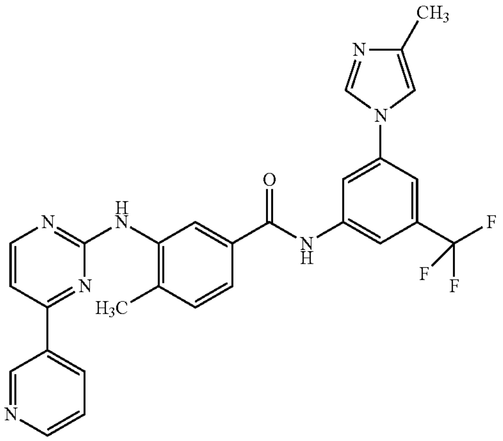<br>HCl•$H_2O$ |
| A3 | WO 2010/060937<br>WO 2004/072051<br>EP 1611112<br>U.S. Pat. No. 8,450,310 | 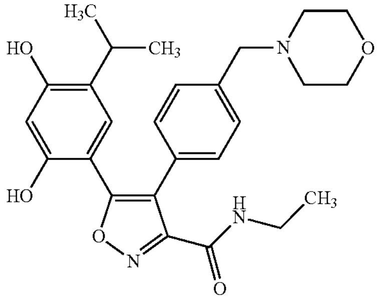 [SMILES: CCNC(=O)c1noc(-c2cc(C(C)C)c(O)cc2O)c1-c1ccc(CN2CCOCC2)cc1] |

TABLE 2-continued
| Therapeutic agents that can be administered in combination with the mono- or di-F-CDN compounds as described herein. | | |
|---|---|---|
| Compound designation/generic name | Patent/Reference | Compound Structure |
| A4 Dactolisib | WO 2006/122806 | 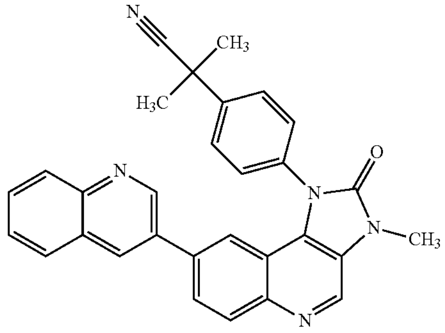 [SMILES: Cn1c(=O)n(-c2ccc(C(C)(C)C#N)cc2)c2c3cc(-c4cnc5ccccc5c4)ccc3ncc21] |
| A5 | U.S. Pat. No. 8,552,002 | 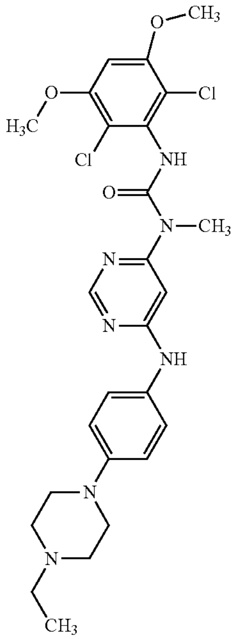 |
| A6 Buparlisib | WO 2007/084786 | 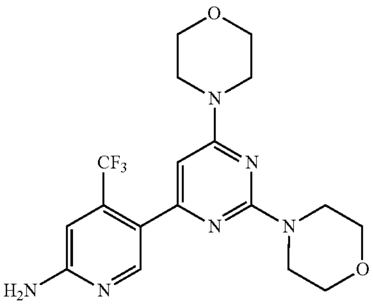 [SMILES: Nc1cc(C(F)(F)F)c(-c2cc(N3CCOCC3)nc(N3CCOCC3)n2)cn1] |

TABLE 2-continued
Therapeutic agents that can be administered in combination with the mono- or di-F-CDN compounds as described herein.
| Compound designation/generic name | Patent/Reference | Compound Structure |
| --- | --- | --- |
| A7 | WO 2009/141386<br>US 2010/0105667 | 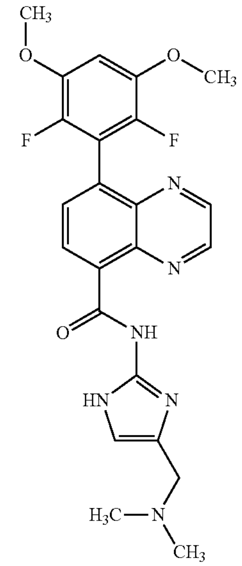 [SMILES: COc1cc(OC)c(F)c(-c2ccc(C(=O)Nc3nc(CN(C)C)c[nH]3)c3nccnc23)c1F] |
| A8 | WO 2010/029082 | 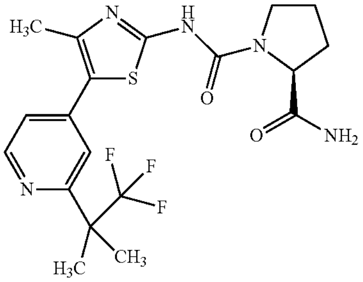 [SMILES: Cc1nc(NC(=O)N2CCC[C@H]2C(N)=O)sc1-c1ccnc(C(C)(C)C(F)(F)F)c1] |
| A9<br>CYP17 inhibitor | WO 2010/149755<br>U.S. Pat. No. 8,263,635 B2<br>EP 2445903 B1 | |
| A10 | WO 2011/076786 | 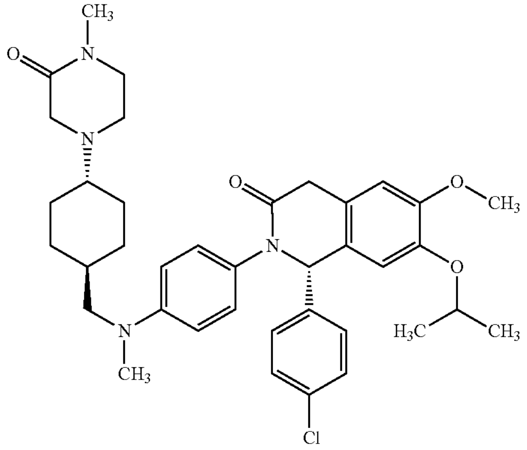 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)cc1)C(=O)C2] |

TABLE 2-continued
| Compound designation/generic name | Patent/Reference | Compound Structure |
|---|---|---|
| Therapeutic agents that can be administered in combination with the mono- or di-F-CDN compounds as described herein. | | |
| A11 Deferasirox EXJADE ® | WO 1997/049395 | 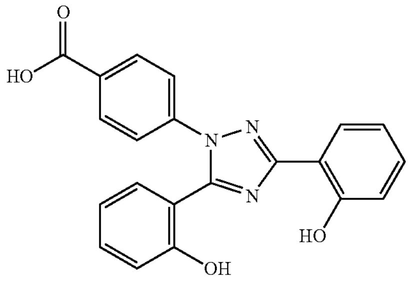 [SMILES: O=C(O)c1ccc(-n2nc(-c3ccccc3O)nc2-c2ccccc2O)cc1] |
| A12 Letrozoie FEMARA ® | U.S. Pat. No. 4,978,672 | 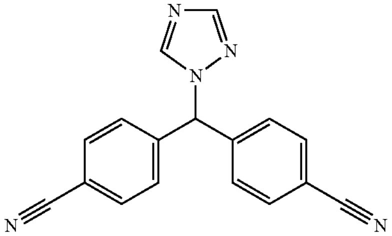 [SMILES: N#Cc1ccc(C(c2ccc(C#N)cc2)n2cncn2)cc1] |
| A13 | WO 2013/124826 US 2013/0225574 | 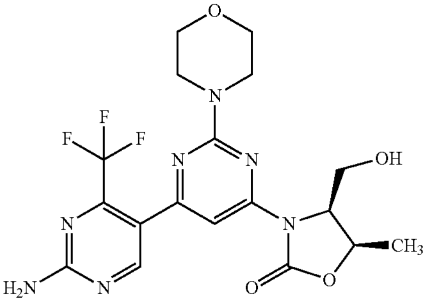 [SMILES: C[C@H]1OC(=O)N(c2cc(-c3cnc(N)nc3C(F)(F)F)nc(N3CCOCC3)n2)[C@H]1CO] |
| A14 | WO 2013/111105 | 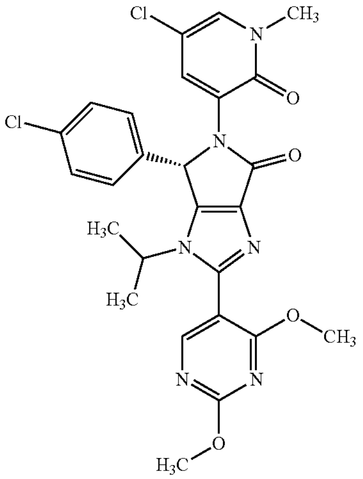 [SMILES: COc1ncc(-c2nc3c(n2C(C)C)[C@H](c2ccc(Cl)cc2)N(c2cc(Cl)cn(C)c2=O)C3=O)c(OC)n1] |

TABLE 2-continued
| Therapeutic agents that can be administered in combination with the mono- or di-F-CDN compounds as described herein. | | |
|---|---|---|
| Compound designation/generic name | Patent/Reference | Compound Structure |
| A15 | WO 2005/073224 | 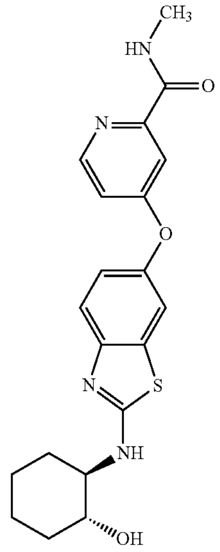 [SMILES: CNC(=O)c1cc(Oc2ccc3nc(N[C@@H]4CCCC[C@H]4O)sc3c2)ccn1] |
| A16<br>Imatinib mesylate<br>GLEEVEC ® | WO 1999/003854 | 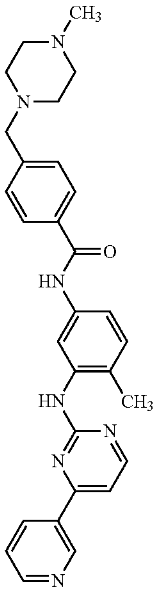<br>mesylate |

TABLE 2-continued

Therapeutic agents that can be administered in combination with the mono- or di-F-CDN compounds as described herein.

| Compound designation/generic name | Patent/Reference | Compound Structure |
|---|---|---|
| A17 | EP 2099447<br>U.S. Pat. No. 7,767,675<br>U.S. Pat. No. 8,420,645 | 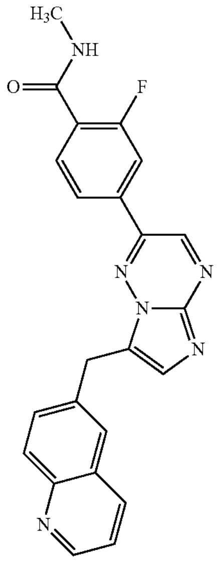<br>dihydrochloride salt |
| A18<br>Ruxotitinib phosphate<br>JAKAFI ® | WO 2007/070514<br>EP 2474545<br>U.S. Pat. No. 7,598,257<br>WO 20141018632 | 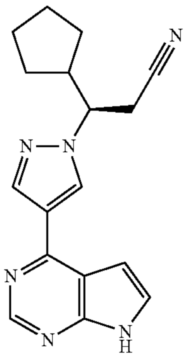<br>$H_3PO_4$ |
| A19<br>Panobinostat | WO 2014/072493<br>WO 2002/022577<br>EP 1870399 | 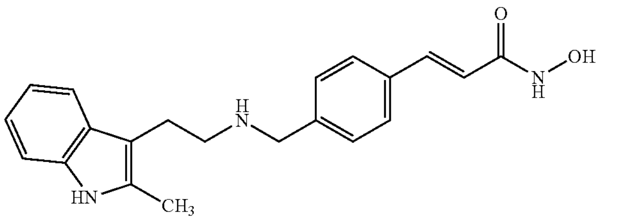 [SMILES: Cc1[nH]c2ccccc2c1CCNCc1ccc(/C=C/C(=O)NO)cc1] |
| A20<br>Osilodrostat | WO 2007/024945 | 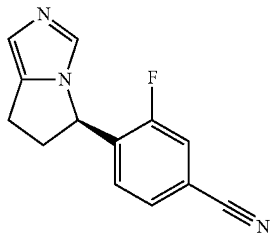 [SMILES: N#Cc1ccc([C@H]2CCc3cncn32)c(F)c1] |

TABLE 2-continued
| Compound designation/generic name | Patent/Reference | Compound Structure |
|---|---|---|
| Therapeutic agents that can be administered in combination with the mono- or di-F-CDN compounds as described herein. | | |
| A21 | WO 2008/016893<br>EP 2051990<br>U.S. Pat. No. 8,546,336 | 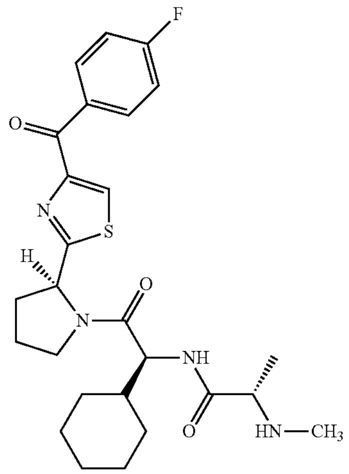 [SMILES: CN[C@@H](C)C(=O)N[C@H](C(=O)N1CCC[C@H]1c1nc(C(=O)c2ccc(F)cc2)cs1)C1CCCCC1] |
| A22<br>Sonidegib phosphate | WO 2007/131201<br>EP 2021328<br>U.S. Pat. No. 8,178,563 | 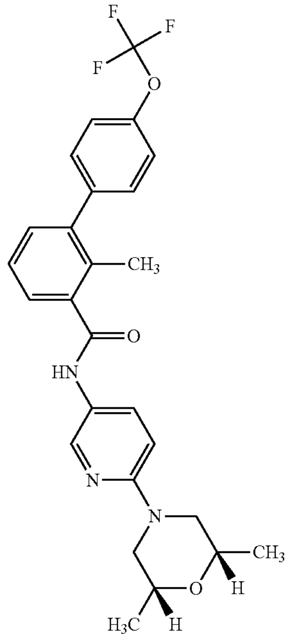 [SMILES: Cc1c(C(=O)Nc2ccc(N3C[C@@H](C)O[C@@H](C)C3)nc2)cccc1-c1ccc(OC(F)(F)F)cc1] |
| A23<br>Ceritinib<br>ZYKADIA ™ | WO 2008/073687<br>U.S. Pat. No. 8,039,479 | 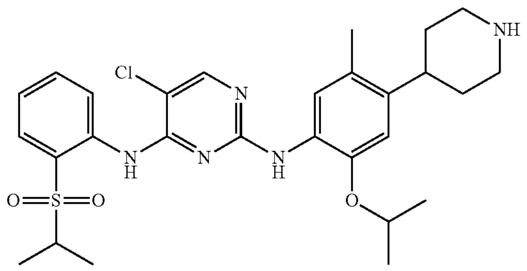 [SMILES: Cc1cc(Nc2ncc(Cl)c(Nc3ccccc3S(=O)(=O)C(C)C)n2)c(OC(C)C)cc1C1CCNCC1] |

TABLE 2-continued
| Therapeutic agents that can be administered in combination with the mono- or di-F-CDN compounds as described herein. | | |
|---|---|---|
| Compound designation/generic name | Patent/Reference | Compound Structure |
| A24 | U.S. Pat. No. 8,415,355<br>U.S. Pat. No. 8,685,980 | 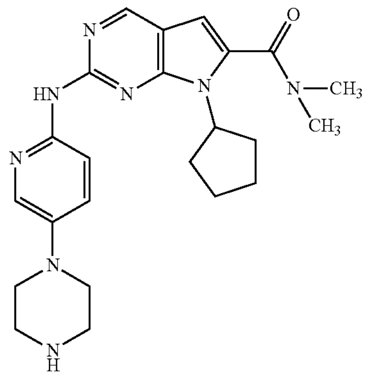 [SMILES: CN(C)C(=O)c1cc2cnc(Nc3ccc(N4CCNCC4)cn3)nc2n1C1CCCC1] |
| A25 | WO 2010/007120 | 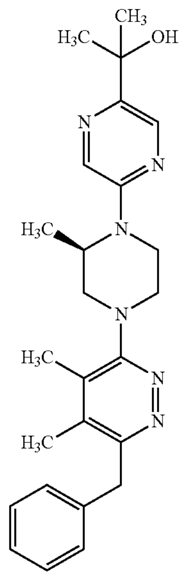 [SMILES: Cc1c(Cc2ccccc2)nnc(N2CCN(c3cnc(C(C)(C)O)cn3)[C@H](C)C2)c1C] |
| A26 | U.S. Pat. No. 7,867,493 | Human monoclonal antibody to PRLR |
| A27 | WO 2010/026124<br>EP 2344474<br>US 2010/0056576<br>WO 2008/106692 | 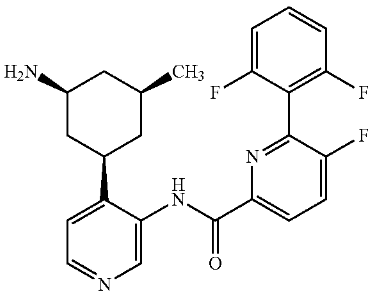 [SMILES: C[C@@H]1C[C@H](N)C[C@H](c2ccncc2NC(=O)c2ccc(F)c(-c3c(F)cccc3F)n2)C1] |

TABLE 2-continued
Therapeutic agents that can be administered in combination with the mono- or di-F-CDN compounds as described herein.
| Compound designation/generic name | Patent/Reference | Compound Structure |
| --- | --- | --- |
| A28 | WO 2010/101849 | 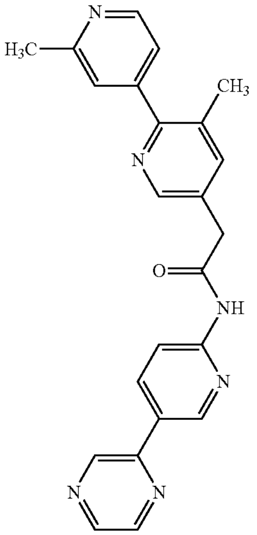 [SMILES: Cc1cc(-c2ncc(CC(=O)Nc3ccc(-c4cnccn4)cn3)cc2C)ccn1] |
| A29<br>Encorafenib | WO 2011/025927 | 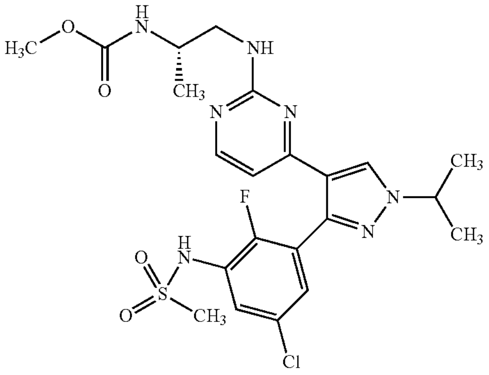 [SMILES: COC(=O)N[C@@H](C)CNc1nccc(-c2cn(C(C)C)nc2-c2cc(Cl)cc(NS(C)(=O)=O)c2F)n1] |
| A30 | WO 2011/101409 | 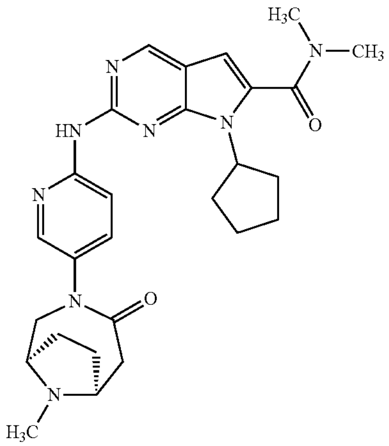 [SMILES: CN(C)C(=O)c1cc2cnc(Nc3ccc(N4C[C@H]5CC[C@@H](CC4=O)N5C)cn3)nc2n1C1CCCC1] |
| A31 | WO 2012/022814<br>EP 2606070<br>U.S. Pat. No. 8,735,551 | Human monoclonal antibody to HER3 |

TABLE 2-continued

Therapeutic agents that can be administered in combination with the mono- or di-F-CDN compounds as described herein.

| Compound designation/generic name | Patent/Reference | Compound Structure |
|---|---|---|
| A32 | WO 2014/160160<br>Ab: 12425 (see Table 1, paragraph [00191])<br>Linker: SMCC (see paragraph [00117]<br>Payload: DM1 (see paragraph [00111]<br>See also Claim 29 | Antibody Drug Conjugate (ADC) |
| A33 | WO 2004/045532 | Monoclonal antibody or Fab to M-CSF |
| A34<br>Binimetinib | WO 2003/077914 | 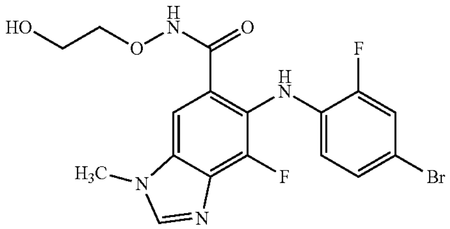 [SMILES: Cn1cnc2c(F)c(Nc3ccc(Br)cc3F)c(C(=O)NOCCO)cc21] |
| A35<br>Midostaurin | WO 2003/037347<br>EP 1441737<br>US 2012/252785 | 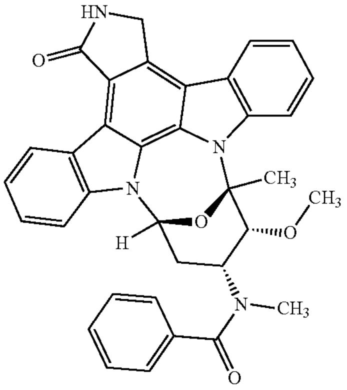 [SMILES: CO[C@@H]1[C@H](N(C)C(=O)c2ccccc2)C[C@H]2O[C@]1(C)n1c3ccccc3c3c4c(c5c6ccccc6n2c5c31)C(=O)NC4] |
| A36<br>Everolimus<br>AFINITOR ® | WO 2014/085318 | 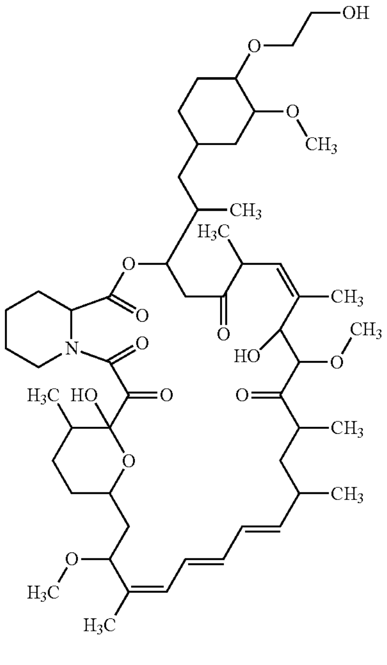 [SMILES: COC1CC2CCC(C)C(O)(O2)C(=O)C(=O)N2CCCCC2C(=O)OC(C(C)CC2CCC(OCCO)C(OC)C2)CC(=O)C(C)/C=C(/C)C(O)C(OC)C(=O)C(C)CC(C)/C=C/C=C/C=C\1C] |

TABLE 2-continued
| Compound designation/generic name | Patent/Reference | Compound Structure |
|---|---|---|
| Therapeutic agents that can be administered in combination with the mono- or di-F-CDN compounds as described herein. | | |
| A37 | WO 2007/030377<br>U.S. Pat. No. 7,482,367 | 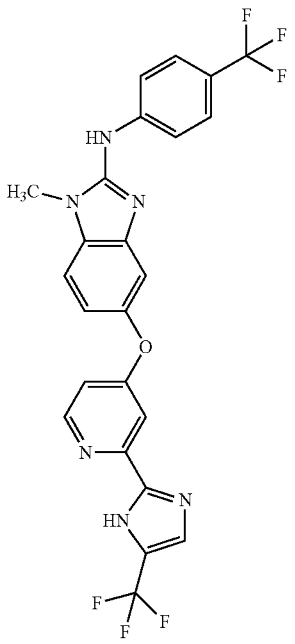 [SMILES: Cn1c(Nc2ccc(C(F)(F)F)cc2)nc2cc(Oc3ccnc(-c4ncc(C(F)(F)F)[nH]4)c3)ccc21] |
| A38<br>Pasireotide<br>diaspartate<br>SIGNIFOR ® | WO 2002/010192<br>U.S. Pat. No. 7,473,761 | 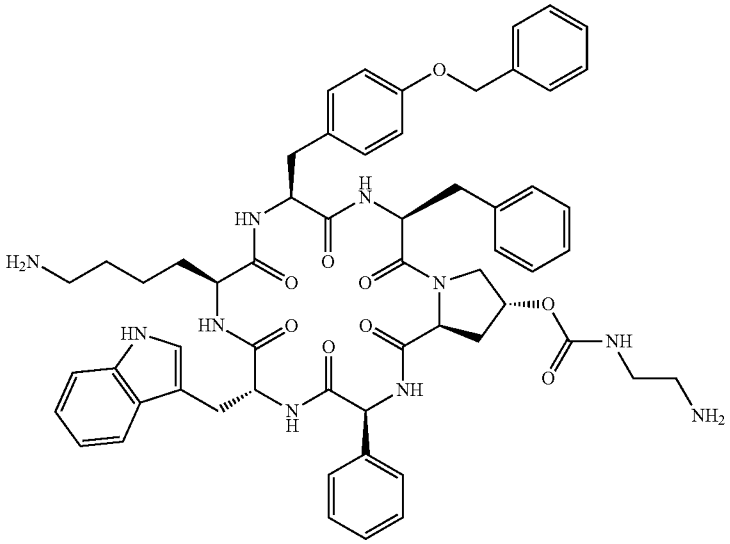 [SMILES: NCCCC[C@@H]1NC(=O)[C@@H](Cc2c[nH]c3ccccc23)NC(=O)[C@H](c2ccccc2)NC(=O)[C@@H]2C[C@@H](OC(=O)NCCN)CN2C(=O)[C@H](Cc2ccccc2)NC(=O)[C@H](Cc2ccc(OCc3ccccc3)cc2)NC1=O] |

TABLE 2-continued
| Therapeutic agents that can be administered in combination with the mono- or di-F-CDN compounds as described herein. | | |
|---|---|---|
| Compound designation/generic name | Patent/Reference | Compound Structure |
| A39 Dovitinib | WO 2009/115562 U.S. Pat. No. 8,563,556 | 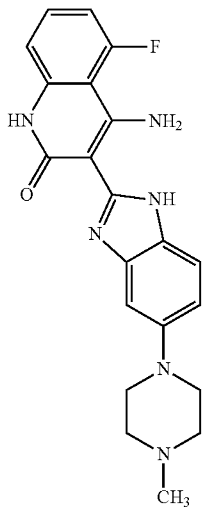 [SMILES: CN1CCN(c2ccc3[nH]c(-c4c(N)c5c(F)cccc5[nH]c4=O)nc3c2)CC1] |
| A40 | WO 2013/184757 | 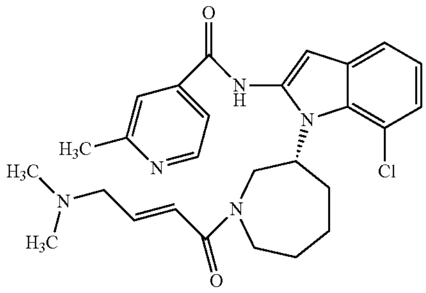 [SMILES: Cc1cc(C(=O)Nc2cc3cccc(Cl)c3n2[C@@H]2CCCCN(C(=O)/C=C/CN(C)C)C2)ccn1] |
| A41 | WO 2006/122806 | 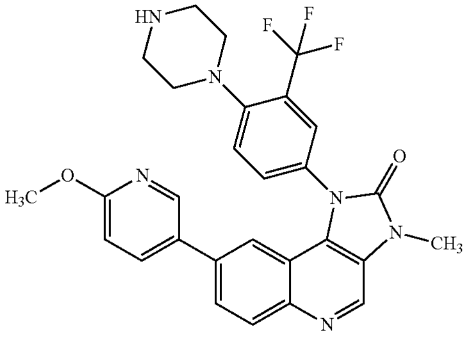 |

TABLE 2-continued
| Therapeutic agents that can be administered in combination with the mono- or di-F-CDN compounds as described herein. | | |
|---|---|---|
| Compound designation/generic name | Patent/Reference | Compound Structure |
| A42 | WO 2008/073687<br>U.S. Pat. No. 8,372,858 | 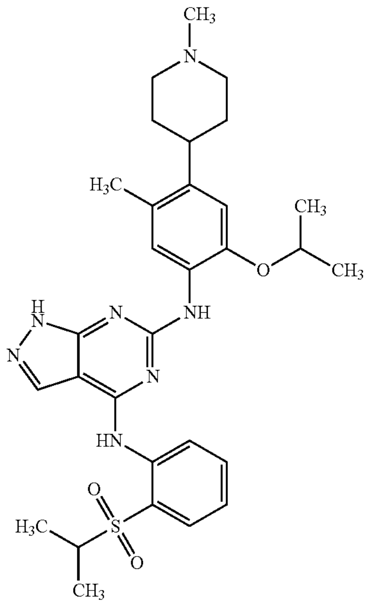 [SMILES: Cc1cc(Nc2nc(Nc3ccccc3S(=O)(=O)C(C)C)c3cn[nH]c3n2)c(OC(C)C)cc1C1CCN(C)CC1] |
| A43 | WO 2010/002655<br>U.S. Pat. No. 8,519,129 | 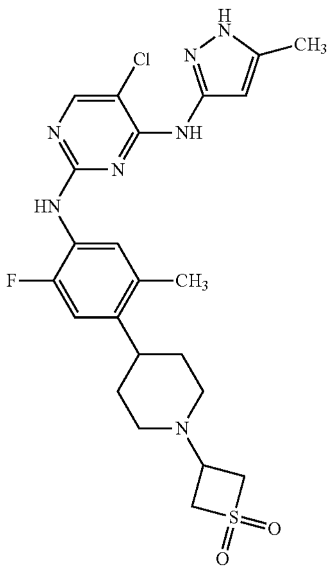 [SMILES: Cc1cc(Nc2nc(Nc3cc(C)c(C4CCN(C5CS(=O)(=O)C5)CC4)cc3F)ncc2Cl)n[nH]1] |

TABLE 2-continued
| Therapeutic agents that can be administered in combination with the mono- or di-F-CDN compounds as described herein. | | |
|---|---|---|
| Compound designation/generic name | Patent/Reference | Compound Structure |
| A44 | WO 2010/002655<br>U.S. Pat. No. 8,519,129 | 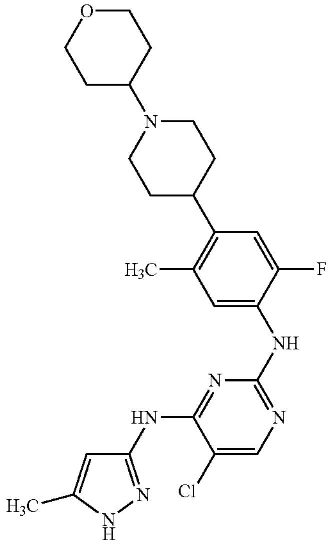 [SMILES: Cc1cc(Nc2nc(Nc3cc(C)c(C4CCN(C5CCOCC5)CC4)cc3F)ncc2Cl)n[nH]1] |
| A45 | WO 2010/002655 | 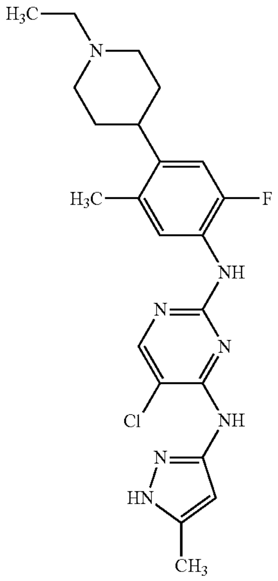 [SMILES: CCN1CCC(c2cc(F)c(Nc3ncc(Cl)c(Nc4cc(C)[nH]n4)n3)cc2C)CC1] |

TABLE 2-continued

| Compound designation/generic name | Patent/Reference | Compound Structure |
| --- | --- | --- |
| | | Therapeutic agents that can be administered in combination with the mono- or di-F-CDN compounds as described herein. |
| A46 Valspodar AMDRAY ™ | EP 296122 | 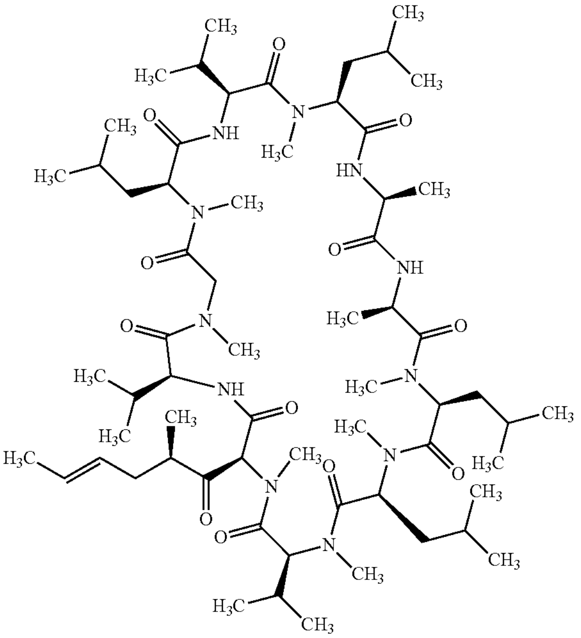 [SMILES: C/C=C/C[C@@H](C)C(=O)[C@H]1C(=O)N[C@@H](C(C)C)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] |
| A47 Vatalanib succinate | WO 98/35958 | 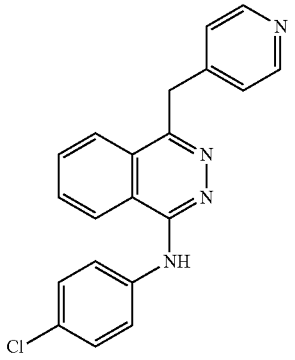 succinate |
| A48 | WO 2014/141104 | IDH inhibitor |
| A49 | WO 2013/171639 WO 2013/171640 WO 2013/171641 WO 2013/171642 | BCR-ABL inhibitor |
| A50 | WO 2014/151616 | cRAF inhibitor |
| A51 | WO 2015/066188 | ERK1/2 ATP competitive inhibitor |

Immunomodulatory Cell Lines

By "inactivated tumor cell" is meant a tumor cell (either "autologous" or "allogeneic" to the patient) which has been treated to prevent division of the cells. For purposes of the present invention, such cells preserve their immunogenicity and their metabolic activity. Such tumor cells are genetically modified to express a transgene which is expressed within a patient as part of cancer therapy. Thus, a composition or vaccine of the invention comprises neoplastic (e.g., tumor) cells that are autologous or allogeneic to the patient undergoing treatment and is most preferably the same general type of tumor cell as is afflicting the patient. For example, a patient suffering from melanoma will typically be administered a genetically modified cell derived from a melanoma. Methods for inactivating tumor cells for use in the present invention, such as the use of irradiation, are well known in the art.

In some embodiments, the inactivated tumor cells of the present invention are modified to express and secrete one or more heat shock proteins. For example, gp96-Ig fusion proteins can be expressed and secreted to stimulate an immune response (Yamazaki et al., The Journal of Immunology, 1999, 163:5178-5182; Strbo et al., Immunol Res.

2013 December; 57(1-3):311-25). In some embodiments the inactivated tumor cells are modified to express and secrete a gp96-Ig fusion protein.

The inactivated tumor cells of the present invention are administered to the patient together with one or more costimulatory molecules or agents. A preferred costimulatory agent comprises one or more cytokines which stimulate dendritic cell induction, recruitment, and/or maturation. Methods for assessing such costimulatory agents are well known in the literature. Induction and maturation of DCs is typically assessed by increased expression of certain membrane molecules such as CD80 and CD86, and/or secretion of pro-inflammatory cytokines, such as IL-12 and type I interferons following stimulation.

In preferred embodiments, the inactivated tumor cells themselves are modified to express and secrete one or more cytokines which stimulate dendritic cell induction, recruitment, and/or maturation. The present invention is described in exemplary terms with regard to the use of GM-CSF. Thus, by way of example, the tumor cell may express a transgene encoding GM-CSF as described in U.S. Pat. Nos. 5,637,483, 5,904,920, 6,277,368 and 6,350,445, as well as in US Patent Publication No. 20100150946. A form of GM-CSF-expressing genetically modified cancer cells or a "cytokine-expressing cellular vaccine" for the treatment of pancreatic cancer is described in U.S. Pat. Nos. 6,033,674 and 5,985,290.

Other suitable cytokines which may be expressed by such inactivated tumor cells and/or bystander cells instead of, or together with, GM-CSF include, but are not limited to, one or more of CD40 ligand, FLT-3 ligand, IL-12, CCL3, CCL20, and CCL21. This list is not meant to be limiting.

While it is preferred that the inactivated tumor cells administered to the subject express one or more cytokines of interest, the tumor cell line may be accompanied by an inactivated bystander cell line which expresses and secretes one or more cytokines which stimulate dendritic cell induction, recruitment, and/or maturation. The bystander cell line may provide all of the cytokines which stimulate dendritic cell induction, recruitment, and/or maturation, or may supplement cytokines which stimulate dendritic cell induction, recruitment, and/or maturation expressed and secreted by the inactivated tumor cells. By way of example, immunomodulatory cytokine-expressing bystander cell lines are disclosed in U.S. Pat. Nos. 6,464,973, and 8,012,469. Dessureault et al., Ann. Surg. Oncol. 14: 869-84, 2007, and Eager and Nemunaitis, Mol. Ther. 12: 18-27, 2005.

By "Granulocyte-macrophage colony stimulating factor (GM-CSF) polypeptide" is meant a cytokine or fragment thereof having immunomodulatory activity and having at least about 85% amino acid sequence identity to GenBank Accession No. AAA52122.1.

Vaccines

In certain embodiments, the CDN compositions are administered in conjunction with one or more vaccines intended to stimulate an immune response to one or more predetermined antigens. Examples of target antigens that may find use in the invention are listed in the following table. The target antigen may also be a fragment or fusion polypeptide comprising an immunologically active portion of the antigens listed in the table. This list is not meant to be limiting.

TABLE 1

| Antigens. | |
|---|---|
| Antigen | Reference |
| Tumor antigens | |
| Mesothelin | GenBank Acc. No. NM_005823; U40434; NM_013404; BC003512 (see also, e.g., Hassan, et al. (2004) Clin. Cancer Res. 10: 3937-3942; Muminova, et al. (2004) BMC Cancer 4: 19; Iacobuzio-Donahue, et al. (2003) Cancer Res. 63: 8614-8622). |
| Wilms' tumor-1 associated protein (Wt-1), including isoform A; isoform B; isoform C; isoform D. | WT-1 isoform A (GenBank Acc. Nos. NM_000378; NP_000369). WT-1 isoform B (GenBank Acc. Nos. NM_024424; NP_077742). WT-1 isoform C (GenBank Acc. Nos. NM_024425; NP_077743). WT-1 isoform D (GenBank Acc. Nos. NM_024426; NP_077744). |
| Stratum corneum chymotryptic enzyme (SCCE), and variants thereof. | GenBank Acc. No. NM_005046; NM_139277; AF332583. See also, e.g., Bondurant, et al. (2005) Clin. Cancer Res. 11: 3446-3454; Santin, et al. (2004) Gynecol. Oncol. 94: 283-288; Shigemasa, et al. (2001) Int. J. Gynecol. Cancer 11: 454-461; Sepehr, et al. (2001) Oncogene 20: 7368-7374. |
| MHC class I chain-related protein A (MICA); MHC class I chain-related protein B (MICB). | See, e.g., Groh, et al. (2005) Proc. Natl. Acad. Sci. USA 102: 6461-6466; GenBank Acc. Nos. NM_000247; BC_016929; AY750850; NM_005931. |
| Gastrin and peptides derived from gastrin; gastrin/CCK-2 receptor (also known as CCK-B). | Harris, et al. (2004) Cancer Res. 64: 5624-5631; Gilliam, et al. (2004) Eur. J. Surg. Oncol. 30: 536-543; Laheru and Jaffee (2005) Nature Reviews Cancer 5: 459-467. |
| Glypican-3 (an antigen of, e.g., hepatocellular carcinoma and melanoma). | GenBank Acc. No. NM_004484. Nakatsura, et al. (2003) Biochem. Biophys. Res. Commun. 306: 16-25; Capurro, et al. (2003) Gasteroenterol. 125: 89-97; Nakatsura, et al. (2004) Clin. Cancer Res. 10: 6612-6621). |
| Coactosin-like protein. | Nakatsura, et al. (2002) Eur. J. Immunol. 32: 826-836; Laheru and Jaffee (2005) Nature Reviews Cancer 5: 459-467. |
| Prostate stem cell antigen (PSCA). | GenBank Acc. No. AF043498; AR026974; AR302232 (see also, e.g., Argani, et al. (2001) Cancer Res. 61: 4320-4324; Christiansen, et al. (2003) Prostate 55: 9-19; Fuessel, et al. (2003) 23: 221-228). |

TABLE 1-continued

Antigens.

| Antigen | Reference |
|---|---|
| Prostate acid phosphatase (PAP); prostate-specific antigen (PSA); PSM; PSMA. | Small, et al. (2000) J. Clin. Oncol. 18: 3894-3903; Altwein and Luboldt (1999) Urol. Int. 63: 62-71; Chan, et al. (1999) Prostate 41: 99-109; Ito, et al. (2005) Cancer 103: 242-250; Schmittgen, et al. (2003) Int. J. Cancer 107: 323-329; Millon, et al. (1999) Eur. Urol. 36: 278-285. |
| Six-transmembrane epithelial antigen of prostate (STEAP). | See, e.g., Machlenkin, et al. (2005) Cancer Res. 65: 6435-6442; GenBank Acc. No. NM_018234; NM_001008410; NM_182915; NM_024636; NM_012449; BC011802. |
| Prostate carcinoma tumor antigen-1 (PCTA-1). | See, e.g., Machlenkin, et al. (2005) Cancer Res. 65: 6435-6442; GenBank Acc. No. L78132. |
| Prostate tumor-inducing gene-1 (PTI-1). | See, e.g., Machlenkin, et al. (2005) Cancer Res. 65: 6435-6442). |
| Prostate-specific gene with homology to G protein-coupled receptor. | See, e.g., Machlenkin, et al. (2005) Cancer Res. 65: 6435-6442). |
| Prostase (an antrogen regulated serine protease). | See, e.g., Machlenkin, et al. (2005) Cancer Res. 65: 6435-6442; GenBank Acc. No. BC096178; BC096176; BC096175. |
| Proteinase 3. | GenBank Acc. No. X55668. |
| Cancer-testis antigens, e.g., NY-ESO-1; SCP-1; SSX-1; SSX-2; SSX-4; GAGE, CT7; CT8; CT10; MAGE-1; MAGE-2; MAGE-3; MAGE-4; MAGE-6; LAGE-1. | GenBank Acc. No. NM_001327 (NY-ESO-1) (see also, e.g., Li, et al. (2005) Clin. Cancer Res. 11: 1809-1814; Chen, et al. (2004) Proc. Natl. Acad. Sci. USA. 101(25): 9363-9368; Kubuschok, et al. (2004) Int. J. Cancer. 109: 568-575; Scanlan, et al. (2004) Cancer Immun. 4: 1; Scanlan, et al. (2002) Cancer Res. 62: 4041-4047; Scanlan, et al. (2000) Cancer Lett. 150: 155-164; Dalerba, et al. (2001) Int. J. Cancer 93: 85-90; Ries, et al. (2005) Int. J. Oncol. 26: 817-824. |
| MAGE-A1, MAGE-A2; MAGE-A3; MAGE-A4; MAGE-A6; MAGE-A9; MAGE-A10; MAGE-A12; GAGE-3/6; NT-SAR-35; BAGE; CA125. | Otte, et al. (2001) Cancer Res. 61: 6682-6687; Lee, et al. (2003) Proc. Natl. Acad. Sci. USA 100: 2651-2656; Sarcevic, et al. (2003) Oncology 64: 443-449; Lin, et al. (2004) Clin. Cancer Res. 10: 5708-5716. |
| GAGE-1; GAGE-2; GAGE-3; GAGE-4; GAGE-5; GAGE-6; GAGE-7; GAGE-8; GAGE-65; GAGE-11; GAGE-13; GAGE-7B. | De Backer, et al. (1999) Cancer Res. 59: 3157-3165; Scarcella, et al. (1999) Clin. Cancer Res. 5: 335-341. |
| HIP1R; LMNA; KIAA1416; Seb4D; KNSL6; TRIP4; MBD2; HCAC5; MAGEA3. | Scanlan, et al. (2002) Cancer Res. 62: 4041-4047. |
| DAM family of genes, e.g., DAM-1; DAM-6. | Fleishhauer, et al. (1998) Cancer Res. 58: 2969-2972. |
| RCAS1. | Enjoji, et al. (2004) Dig. Dis. Sci. 49: 1654-1656. |
| RU2. | Van Den Eynde, et al. (1999) J. Exp. Med. 190: 1793-1800. |
| CAMEL. | Slager, et al. (2004) J. Immunol. 172: 5095-5102; Slager, et al. (2004) Cancer Gene Ther. 11: 227-236. |
| Colon cancer associated antigens, e.g., NY-CO-8; NY-CO-9; NY-CO-13; NY-CO-16; NY-CO-20; NY-CO-38; NY-CO-45; NY-CO-9/HDAC5; NY-CO-41/MBD2; NY-CO-42/TRIP4; NY-CO-95/KIAA1416; KNSL6; seb4D. | Scanlan, et al. (2002) Cancer Res. 62: 4041-4047. |
| N-Acetylglucosaminyl-tranferase V (GnT-V). | Dosaka-Akita, et al. (2004) Clin. Cancer Res. 10: 1773-1779. |
| Elongation factor 2 mutated (ELF2M). | Renkvist, et al. (2001) Cancer Immunol Immunother. 50: 3-15. |
| HOM-MEL-40/SSX2 | Neumann, et al. (2004) Int. J. Cancer 112: 661-668; Scanlan, et al. (2000) Cancer Lett. 150: 155-164. |
| BRDT. | Scanlan, et al. (2000) Cancer Lett. 150: 155-164. |
| SAGE; HAGE. | Sasaki, et al. (2003) Eur. J. Surg. Oncol. 29: 900-903. |
| RAGE. | See, e.g., Li, et al. (2004) Am. J. Pathol. 164: 1389-1397; Shirasawa, et al. (2004) Genes to Cells 9: 165-174. |
| MUM-1 (melanoma ubiquitous mutated); MUM-2; MUM-2 Arg-Gly mutation; MUM-3. | Gueguen, et al. (1998) J. Immunol. 160: 6188-6194; Hirose, et al. (2005) Int. J. Hematol. 81: 48-57; Baurain, et al. (2000) J. Immunol. 164: 6057-6066; Chiari, et al. (1999) Cancer Res. 59: 5785-5792. |
| LDLR/FUT fusion protein antigen of melanoma. | Wang, et al. (1999) J. Exp. Med. 189: 1659-1667. |

TABLE 1-continued

Antigens.

| Antigen | Reference |
|---|---|
| NY-REN series of renal cancer antigens. | Scanlan, et al. (2002) Cancer Res. 62: 4041-4047; Scanlan, et al. (1999) Cancer Res. 83: 456-464. |
| NY-BR series of breast cancer antigens, e.g., NY-BR-62; NY-BR-75; NY-BR-85; NY-BR-62; NY-BR-85. | Scanlan, et al. (2002) Cancer Res. 62: 4041-4047; Scanlan, et al. (2001) Cancer Immunity 1: 4. |
| BRCA-1; BRCA-2. | Stolier, et al. (2004) Breast J. 10: 475-480; Nicoletto, et al. (2001) Cancer Treat Rev. 27: 295-304. |
| DEK/CAN fusion protein. | Von Lindern, et al. (1992) Mol. Cell. Biol. 12: 1687-1697. |
| Ras, e.g., wild type ras, ras with mutations at codon 12, 13, 59, or 61, e.g., mutations G12C; G12D; G12R; G12S; G12V; G13D; A59T; Q61H. K-RAS; H-RAS; N-RAS. | GenBank Acc. Nos. P01112; P01116; M54969; M54968; P01111; P01112; K00654. See also, e.g., GenBank Acc. Nos. M26261; M34904; K01519; K01520; BC006499; NM_006270; NM_002890; NM_004985; NM_033360; NM_176795; NM_005343. |
| BRAF (an isoform of RAF). | Tannapfel, et al. (2005) Am. J. Clin. Pathol. 123: 256-2601; Tsao and Sober (2005) Dermatol. Clin. 23: 323-333. |
| Melanoma antigens, including HST-2 melanoma cell antigens. | GenBank Acc. No. NM_206956; NM_206955; NM_206954; NM_206953; NM_006115; NM_005367; NM_004988; AY148486; U10340; U10339; M77481. See, eg., Suzuki, et al. (1999) J. Immunol. 163: 2783-2791. |
| Survivin | GenBank Acc. No. AB028869; U75285 (see also, e.g., Tsuruma, et al. (2004) J. Translational Med. 2: 19 (11 pages); Pisarev, et al. (2003) Clin. Cancer Res. 9: 6523-6533; Siegel, et al. (2003) Br. J. Haematol. 122: 911-914; Andersen, et al. (2002) Histol. Histopathol. 17: 669-675). |
| MDM-2 | NM_002392; NM_006878 (see also, e.g., Mayo, et al. (1997) Cancer Res. 57: 5013-5016; Demidenko and Blagosklonny (2004) Cancer Res. 64: 3653-3660). |
| Methyl-CpG-binding proteins (MeCP2; MBD2). | Muller, et al. (2003) Br. J. Cancer 89: 1934-1939; Fang, et al. (2004) World J. Gastreenterol. 10: 3394-3398. |
| NA88-A. | Moreau-Aubry, et al. (2000) J. Exp. Med. 191: 1617-1624. |
| Histone deacetylases (HDAC), e.g., HDAC5. | Waltregny, et al. (2004) Eur. J. Histochem. 48: 273-290; Scanlan, et al. (2002) Cancer Res. 62: 4041-4047. |
| Cyclophilin B (Cyp-B). | Tamura, et al. (2001) Jpn. J. Cancer Res. 92: 762-767. |
| CA 15-3; CA 27.29. | Clinton, et al. (2003) Biomed. Sci. Instrum. 39: 408-414. |
| Heat shock protein Hsp70. | Faure, et al. (2004) Int. J. Cancer 108: 863-870. |
| GAGE/PAGE family, e.g., PAGE-1; PAGE-2; PAGE-3; PAGE-4; XAGE-1; XAGE-2; XAGE-3. | Brinkmann, et al. (1999) Cancer Res. 59: 1445-1448. |
| MAGE-A, B, C, and D families. MAGE-B5; MAGE-B6; MAGE-C2; MAGE-C3; MAGE-3; MAGE-6. | Lucas, et al. (2000) Int. J. Cancer 87: 55-60; Scanlan, et al. (2001) Cancer Immun. 1: 4. |
| Kinesin 2; TATA element modulatory factor 1; tumor protein D53; NY | Scanlan, et al. (2001) Cancer Immun. 30: 1-4. |
| Alpha-fetoprotein (AFP) | Grimm, et al. (2000) Gastroenterol. 119: 1104-1112. |
| SART1; SART2; SART3; ART4. | Kumamuru, et al. (2004) Int. J. Cancer 108: 686-695; Sasatomi, et al. (2002) Cancer 94: 1636-1641; Matsumoto, et al. (1998) Jpn. J. Cancer Res. 89: 1292-1295; Tanaka, et al. (2000) Jpn. J. Cancer Res. 91: 1177-1184. |
| Preferentially expressed antigen of melanoma (PRAME). | Matsushita, et al. (2003) Leuk. Lymphoma 44: 439-444; Oberthuer, et al. (2004) Clin. Cancer Res. 10: 4307-4313. |
| Carcinoembryonic antigen (CEA), CAP1-6D enhancer agonist peptide. | GenBank Acc. No. M29540; E03352; X98311; M17303 (see also, e.g., Zaremba (1997) Cancer Res. 57: 4570-4577; Sarobe, et al. (2004) Curr. Cancer Drug Targets 4: 443-454; Tsang, et al. (1997) Clin. Cancer Res. 3: 2439-2449; Fong, et al. (2001) Proc. Natl. Acad. Sci. USA 98: 8809-8814). |
| HER-2/neu. | Disis, et al. (2004) J. Clin. Immunol. 24: 571-578; Disis and Cheever (1997) Adv. Cancer Res. 71: 343-371. |
| Cdk4; cdk6; p16 (INK4); Rb protein. | Ghazizadeh, et al. (2005) Respiration 72: 68-73; Ericson, et al. (2003) Mol. Cancer Res. 1: 654-664. |
| TEL; AML1; TEL/AML1. | Stams, et al. (2005) Clin. Cancer Res. 11: 2974-2980. |

TABLE 1-continued

| Antigens. | |
|---|---|
| Antigen | Reference |
| Telomerase (TERT). | Nair, et al. (2000) Nat. Med. 6: 1011-1017. |
| 707-AP. | Takahashi, et al. (1997) Clin. Cancer Res. 3: 1363-1370. |
| Annexin, e.g., Annexin II. | Zimmerman, et al. (2004) Virchows Arch. 445: 368-374. |
| BCR/ABL; BCR/ABL p210; BCR/ABL p190; CML-66; CML-28. | Cobaldda, et al. (2000) Blood 95: 1007-1013; Hakansson, et al. (2004) Leukemia 18: 538-547; Schwartz, et al. (2003) Semin. Hematol. 40: 87-96; Lim, et al. (1999) Int. J. Mol. Med. 4: 665-667. |
| BCL2; BLC6; CD10 protein. | Iqbal, et al. (2004) Am. J. Pathol. 165: 159-166. |
| CDC27 (this is a melanoma antigen). | Wang, et al. (1999) Science 284: 1351-1354. |
| Sperm protein 17 (SP17); 14-3-3-zeta; MEMD; KIAA0471; TC21. | Arora, et al. (2005) Mol. Carcinog. 42: 97-108. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Gp100/pmel-17. | GenBank Acc. Nos. AH003567; U31798; U31799; U31807; U31799 (see also, e.g., Bronte, et al. (2000) Cancer Res. 60: 253-258). |
| TARP. | See, e.g., Clifton, et al. (2004) Proc. Natl. Acad. Sci. USA 101: 10166-10171; Virok, et al. (2005) Infection Immunity 73: 1939-1946. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Melanocortin 1 receptor (MC1R); MAGE-3; gp100; tyrosinase; dopachrome tautomerase (TRP-2); MART-1. | Salazar-Onfray, et al. (1997) Cancer Res. 57: 4348-4355; Reynolds, et al. (1998) J. Immunol. 161: 6970-6976; Chang, et al. (2002) Clin. Cancer Res. 8: 1021-1032. |
| MUC-1; MUC-2. | See, e.g., Davies, et al. (1994) Cancer Lett. 82: 179-184; Gambus, et al. (1995) Int. J. Cancer 60: 146-148; McCool, et al. (1999) Biochem. J. 341: 593-600. |
| Spas-1. | U.S. Published patent application No. 20020150588 of Allison, et al. |
| CASP-8; FLICE; MACH. | Mandruzzato, et al. (1997) J. Exp. Med. 186: 785-793. |
| CEACAM6; CAP-1. | Duxbury, et al. (2004) Biochem. Biophys. Res. Commun. 317: 837-843; Morse, et al. (1999) Clin. Cancer Res. 5: 1331-1338. |
| HMGB1 (a DNA binding protein and cytokine). | Brezniceanu, et al. (2003) FASEB J. 17: 1295-1297. |
| ETV6/AML1. | Codrington, et al. (2000) Br. J. Haematol. 111: 1071-1079. |
| Mutant and wild type forms of adenomatous polyposis coli (APC); beta-catenin; c-met; p53; E-cadherin; cyclooxygenase-2 (COX-2). | Clements, et al. (2003) Clin. Colorectal Cancer 3: 113-120; Gulmann, et al. (2003) Appl. Immunohistochem. Mol. Morphol. 11: 230-237; Jungck, et al. (2004) Int. J. Colorectal. Dis. 19: 438-445; Wang, et al. (2004) J. Surg. Res. 120: 242-248; Abutaily, et al. (2003) J. Pathol. 201: 355-362; Liang, et al. (2004) Br. J. Surg. 91: 355-361; Shirakawa, et al. (2004) Clin. Cancer Res. 10: 4342-4348. |
| Renal cell carcinoma antigen bound by mAB G250. | Mulders, et al. (2003) Urol. Clin. North Am. 30: 455-465; Steffens, et al. (1999) Anticancer Res. 19: 1197-1200. |
| EphA2 | See. e.g., U.S. Patent Publication No. 2005/0281783 A1; Genbank Accession No. NM_004431 (human); Genbank Accession No. NM_010139 (Mouse); Genbank Accession No. AB038986 (Chicken, partial sequence); GenBank Accession Nos. NP_004422, AAH37166, and AAA53375 (human); GenBank Accession Nos. NP_034269 (mouse), AAH06954 (mouse), XP_345597 (rat), and BAB63910 (chicken). |
| EGFRvIII | See, e.g., WO/2012/068360 |
| *Francisella tularensis* antigens | |
| *Francisella tularensis* A and B. | Complete genome of subspecies Schu S4 (GenBank Acc. No. AJ749949); of subspecies Schu 4 (GenBank Acc. No. NC_006570). Outer membrane protein (43 kDa) Bevanger, et al. (1988) J. Clin. Microbiol. 27: 922-926; Porsch-Ozcurumez, et al. (2004) Clin. Diagnostic. Lab. Immunol. 11: 1008-1015). Antigenic components of *F. tularensis* include, e.g., 80 antigens, including 10 kDa and 60 kDa chaperonins (Havlasova, et al. (2002) Proteomics 2: 857-86), nucleoside diphosphate kinase, isocitrate dehydrogenase, RNA-binding protein Hfq, the chaperone ClpB (Havlasova, et al. (2005) Proteomics 5: 2090-2103). See also, e.g., Oyston and Quarry (2005) Antonie Van Leeuwenhoek 87: 277-281; Isherwood, et al. (2005) Adv. Drug Deliv. Rev. 57: 1403-1414; Biagini, et al. (2005) Anal. Bioanal. Chem. 382: 1027-1034. |

TABLE 1-continued

| Antigens. | |
|---|---|
| Antigen | Reference |
| Malarial antigens | |
| Circumsporozoite protein (CSP); SSP2; HEP17; Exp-1 orthologs found in *P. falciparum*; and LSA-1. | See, e.g., Haddad, et al. (2004) Infection Immunity 72: 1594-1602; Hoffman, et al. (1997) Vaccine 15: 842-845; Oliveira-Ferreira and Daniel-Ribeiro (2001) Mem. Inst. Oswaldo Cruz, Rio de Janeiro 96: 221-227. CSP (see, e.g., GenBank Acc. No. AB121024). SSP2 (see, e.g., GenBank Acc. No. AF249739). LSA-1 (see, e.g., GenBank Acc. No. Z30319). |
| Ring-infected erythrocyte survace protein (RESA); merozoite surface protein 2 (MSP2); Spf66; merozoite surface protein 1(MSP1); 195A; BVp42. | See, e.g., Stirnadel, et al. (2000) Int. J. Epidemiol. 29: 579-586; Krzych, et al. (1995) J. Immunol. 155: 4072-4077. See also, Good, et al. (2004) Immunol. Rev. 201: 254-267; Good, et al. (2004) Ann. Rev. Immunol. 23: 69-99. MSP2 (see, e.g., GenBank Acc. No. X96399; X96397). MSP1 (see, e.g., GenBank Acc. No. X03371). RESA (see, e.g., GenBank Acc. No. X05181; X05182). |
| Apical membrane antigen 1 (AMA1). | See, e.g., Gupta, et al. (2005) Protein Expr. Purif. 41: 186-198. AMA1 (see, e.g., GenBank Acc. No. A`13; AJ494905; AJ490565). |
| Viruses and viral antigens | |
| Hepatitis A | GenBank Acc. Nos., e.g., NC_001489; AY644670; X83302; K02990; M14707. |
| Hepatitis B | Complete genome (see, e.g., GenBank Acc. Nos. AB214516; NC_003977; AB205192; AB205191; AB205190; AJ748098; AB198079; AB198078; AB198076; AB074756). |
| Hepatitis C | Complete genome (see, e.g., GenBank Acc. Nos. NC_004102; AJ238800; AJ238799; AJ132997; AJ132996; AJ000009; D84263). |
| Hepatitis D | GenBank Acc. Nos, e.g. NC_001653; AB118847; AY261457. |
| Human papillomavirus, including all 200+ subtypes (classed in 16 groups), such as the high risk subtypes 16, 18, 30, 31, 33, 45. | See, e.g., Trimble, et al. (2003) Vaccine 21: 4036-4042; Kim, et al. (2004) Gene Ther. 11: 1011-1018; Simon, et al. (2003) Eur. J. Obstet. Gynecol. Reprod. Biol. 109: 219-223; Jung, et al. (2004) J. Microbiol. 42: 255-266; Damasus-Awatai and Freeman-Wang (2003) Curr. Opin. Obstet. Gynecol. 15: 473-477; Jansen and Shaw (2004) Annu. Rev. Med. 55: 319-331; Roden and Wu (2003) Expert Rev. Vaccines 2: 495-516; de Villiers, et al. (2004) Virology 324: 17-24; Hussain and Paterson (2005) Cancer Immunol. Immunother. 54: 577-586; Molijn, et al. (2005) J. Clin. Virol. 32 (Suppl. 1) S43-S51. GenBank Acc. Nos. AY686584; AY686583; AY686582; NC_006169; NC_006168; NC_006164; NC_001355; NC_001349; NC_005351; NC_001596). |
| Human T-cell lymphotropic virus (HTLV) types I and II, including the HTLV type I subtypes Cosmopolitan, Central African, and Austro-Melanesian, and the HTLV type II subtypes Iia, Iib, Iic, and Iid. | See, e.g., Capdepont, et al. (2005) AIDS Res. Hum. Retrovirus 21: 28-42; Bhigjee, et al. (1999) AIDS Res. Hum. Restrovirus 15: 1229-1233; Vandamme, et al. (1998) J. Virol. 72: 4327-4340; Vallejo, et al. (1996) J. Acquir. Immune Defic. Syndr. Hum. Retrovirol. 13: 384-391. HTLV type I (see, e.g., GenBank Acc. Nos. AY563954; AY563953. HTLV type II (see, e.g., GenBank Acc. Nos. L03561; Y13051; AF139382). |
| Coronaviridae, including Coronaviruses, such as SARS-coronavirus (SARS-CoV), and Toroviruses. | See, e.g., Brian and Baric (2005) Curr. Top. Microbiol. Immunol. 287: 1-30; Gonzalez, et al. (2003) Arch. Virol. 148: 2207-2235; Smits, et al. (2003) J. Virol. 77: 9567-9577; Jamieson, et al. (1998) J. Infect. Dis. 178: 1263-1269 (GenBank Acc. Nos. AY348314; NC_004718; AY394850). |
| Rubella virus. | GenBank Acc. Nos. NC_001545; AF435866. |
| Mumps virus, including the genotypes A, C, D, G, H, and I. | See, e.g., Orvell, eta 1. (2002) J. Gen. Virol. 83: 2489-2496. See, e.g., GenBank Acc. Nos. AY681495; NC_002200; AY685921; AF201473. |
| Coxsackie virus A including the serotypes 1, 11, 13, 15, 17, 18, 19, 20, 21, 22, and 24 (also known as Human enterovirus C; HEV-C). | See, e.g., Brown, et al. (2003) J. Virol. 77: 8973-8984. GenBank Acc. Nos. AY421768; AY790926: X67706. |
| Coxsackie virus B, including subtypes 1-6. | See, e.g., Ahn, et al. (2005) J. Med. Virol. 75: 290-294; Patel, et al. (2004) J. Virol. Methods 120: 167-172; Rezig, et al. (2004) J. Med. Virol. 72: 268-274. GenBank Acc. No. X05690. |
| Human enteroviruses including, e.g., human enterovirus A (HEV-A, CAV2 to CAV8, CAV10, CAV12, CAV14, CAV16, and EV71) and also | See, e.g., Oberste, et al. (2004) J. Virol. 78: 855-867. Human enterovirus A (GenBank Acc. Nos. NC_001612); human enterovirus B (NC_001472); human enterovirus C (NC_001428); human enterovirus D (NC_001430). Simian enterovirus A (GenBank Acc. No. NC_003988). |

TABLE 1-continued

| Antigens. | |
|---|---|
| Antigen | Reference |
| including HEV-B (CAV9, CBV1 to CBV6, E1 to E7, E9, E11 to E21, E24 to E27, E29 to E33, and EV69 and E73), as well as HEV. | |
| Polioviruses including PV1, PV2, and PV3. | See, e.g., He, et al. (2003) J. Virol. 77: 4827-4835; Hahsido, et al. (1999) Microbiol. Immunol. 43: 73-77. GenBank Acc. No. AJ132961 (type 1); AY278550 (type 2); X04468 (type 3). |
| Viral encephalitides viruses, including equine encephalitis, Venezuelan equine encephalitis (VEE) (including subtypes IA, IB, IC, ID, IIIC, IIID), Eastern equine encephalitis (EEE), Western equine encephalitis (WEE), St. Louis encephalitis, Murray Valley (Australian) encephalitis, Japanese encephalitis, and tick-born encephalitis. | See, e.g., Hoke (2005) Mil. Med. 170: 92-105; Estrada-Franco, et al. (2004) Emerg. Infect. Dis. 10: 2113-2121; Das, et al. (2004) Antiviral Res. 64: 85-92; Aguilar, et al. (2004) Emerg. Infect. Dis. 10: 880-888; Weaver, et al. (2004) Arch. Virol. Suppl. 18: 43-64; Weaver, et al. (2004) Annu. Rev. Entomol. 49: 141-174. Eastern equine encephalitis (GenBank Acc. No. NC__003899; AY722102); Western equine encephalitis (NC__003908). |
| Human herpesviruses, including cytomegalovirus (CMV), Epstein-Barr virus (EBV), human herpesvirus-1 (HHV-1), HHV-2, HHV-3, HHV-4, HHV-5, HHV-6, HHV-7, HHV-8, herpes B virus, herpes simplex virus types 1 and 2 (HSV-1, HSV-2), and varicella zoster virus (VZV). | See, e.g., Studahl, et al. (2000) Scand. J. Infect. Dis. 32: 237-248; Padilla, et al. (2003) J. Med. Virol. 70 (Suppl. 1) S103-S110; Jainkittivong and Langlais (1998) Oral Surg. Oral Med. 85: 399-403. GenBank Nos. NC__001806 (herpesvirus 1); NC__001798 (herpesvirus 2); X04370 and NC__001348 (herpesvirus 3); NC__001345 (herpesvirus 4); NC__001347 (herpesvirus 5); X83413 and NC__000898 (herpesvirus 6); NC__001716 (herpesvirus 7). Human herpesviruses types 6 and 7 (HHV-6; HHV-7) are disclosed by, e.g., Padilla, et al. (2003) J. Med. Virol. 70 (Suppl. 1)S103-S110. Human herpesvirus 8 (HHV-8), including subtypes A-E, are disclosed in, e.g., Treurnicht, et al. (2002) J. Med. Virul. 66: 235-240. |
| HIV-1 including group M (including subtypes A to J) and group O (including any distinguishable subtypes) (HIV-2, including subtypes A-E. | See, e.g., Smith, et al. (1998) J. Med. Virol. 56: 264-268. See also, e.g., GenBank Acc. Nos. DQ054367; NC__001802; AY968312; DQ011180; DQ011179; DQ011178; DQ011177; AY588971; AY588970; AY781127; AY781126; AY970950; AY970949; AY970948; X61240; AJ006287; AJ508597; and AJ508596. |
| Epstein-Barr virus (EBV), including subtypes A and B. | See, e.g., Peh, et al. (2002) Pathology 34: 446-450. Epstein-Barr virus strain B95-8 (GenBank Acc. No. V01555). |
| Reovirus, including serotypes and strains 1, 2, and 3, type 1 Lang, type 2 Jones, and type 3 Dearing. | See, e.g., Barthold, et al. (1993) Lab. Anim. Sci. 43: 425-430; Roner, et al. (1995) Proc. Natl. Acad. Sci. USA 92: 12362-12366; Kedl, et al. (1995) J. Virol. 69: 552-559. GenBank Acc. No. K02739 (sigma-3 gene surface protein). |
| Cytomegalovirus (CMV) subtypes include CMV subtypes I-VII. | See, e.g., Chern, et al. (1998) J. Infect. Dis. 178: 1149-1153; Vilas Boas, et al. (2003) J. Med. Virol. 71: 404-407; Trincado, et al. (2000) J. Med. Virol. 61: 481-487. GenBank Acc. No. X17403. |
| Rhinovirus, including all serotypes. | Human rhinovirus 2 (GenBank Acc. No. X02316); Human rhinovirus B (GenBank Acc. No. NC__001490); Human rhinovirus 89 (GenBank Acc. No. NC__001617); Human rhinovirus 39 (GenBank Acc. No. AY751783). |
| Adenovirus, including all serotypes. | AY803294; NC__004001; AC__000019; AC__000018; AC__000017; AC__000015; AC__000008; AC__000007; AC__000006; AC__000005; AY737798; AY737797; NC__003266; NC__002067; AY594256; AY594254; AY875648; AJ854486; AY163756; AY594255; AY594253; NC__001460; NC__001405; AY598970; AY458656; AY487947; NC__001454; AF534906; AY45969; AY128640; L19443; AY339865; AF532578. |
| Filoviruses, including Marburg virus and Ebola virus, and strains such as Ebola-Sudan | See, e.g., Geisbert and Jahrling (1995) Virus Res. 39: 129-150; Hutchinson, et al. (2001) J. Med. Virol. 65: 561-566. Marburg virus (see, e.g., GenBank Acc. No. NC__001608). Ebola virus (see, e.g., GenBank Acc. Nos. NC__006432; AY769362; NC__002549; |

TABLE 1-continued

| Antigens. | |
|---|---|
| Antigen | Reference |
| (EBO-S), Ebola-Zaire (EBO-Z), and Ebola-Reston (EBO-R). | AF272001; AF086833). |
| Arenaviruses, including lymphocytic choriomeningitis (LCM) virus, Lassa virus, Junin virus, and Machupo virus. | Junin virus, segment S (GenBank Acc. No. NC_005081); Junin virus, segment L (GenBank Acc. No. NC_005080). |
| Rabies virus. | See, e.g., GenBank Acc. Nos. NC_001542; AY956319; AY705373; AF499686; AB128149; AB085828; AB009663. |
| Arboviruses, including West Nile virus, Dengue viruses 1 to 4, Colorado tick fever virus, Sindbis virus, Togaviraidae, Flaviviridae, Bunyaviridae, Reoviridae, Rhabdoviridae, Orthomyxoviridae, and the like. | Dengue virus type 1 (see, e.g., GenBank Acc. Nos. AB195673; AY762084). Dengue virus type 2 (see, e.g., GenBank Acc. Nos. NC_001474; AY702040; AY702039; AY702037). Dengue virus type 3 (see, e.g., GenBank Acc. Nos. AY923865; AT858043). Dengue virus type 4 (see, e.g., GenBank Acc. Nos. AY947539; AY947539; AF326573). Sindbis virus (see, e.g., GenBank Acc. Nos. NC_001547; AF429428; J02363; AF103728). West Nile virus (see, e.g., GenBank Acc. Nos. NC_001563; AY603654). |
| Poxvirus including orthopoxvirus (variola virus, monkeypox virus, vaccinia virus, cowpox virus), yatapoxvirus (tanapox virus, Yaba monkey tumor virus), parapoxvirus, and molluscipoxvirus. | Viriola virus (see, e.g., GenBank Acc. Nos. NC_001611; Y16780; X72086; X69198). |
| Yellow fever. | See, e.g., GenBank Acc. No. NC_002031; AY640589; X03700. |
| Hantaviruses, including serotypes Hantaan (HTN), Seoul (SEO), Dobrava (DOB), Sin Nombre (SN), Puumala (PUU), and Dobrava-like Saaremaa (SAAV). | See, e.g., Elgh, et al. (1997) J. Clin. Microbiol. 35: 1122-1130; Sjolander, et al. (2002) Epidemiol. Infect. 128: 99-103; Zeier, et al. (2005) Virus Genes 30: 157-180. GenBank Acc. No. NC_005222 and NC_005219 (Hantavirus). See also, e.g., GenBank Acc. Nos. NC_005218; NC_005222; NC_005219. |
| Flaviviruses, including Dengue virus, Japanese encephalitis virus, West Nile virus, and yellow fever virus. | See, e.g., Mukhopadhyay, et al. (2005) Nature Rev. Microbiol. 3: 13-22. GenBank Acc. Nos NC_001474 and AY702040 (Dengue). GenBank Acc. Nos. NC_001563 and AY603654. |
| Measles virus. | See, e.g., GenBank Acc. Nos. AB040874 and AY486084. |
| Human parainfluenzaviruses (HPV), including HPV types 1-56. | Human parainfluenza virus 2 (see, e.g., GenBank Acc. Nos. AB176531; NC003443). Human parainfluenza virus 3 (see, e.g., GenBank Acc. No. NC_001796). |
| Influenza virus, including influenza virus types A, B, and C. | Influenza nucleocapsid (see, e.g., GenBank Acc. No. AY626145). Influenza hemagglutinin (see, e.g., GenBank Acc. Nos. AY627885; AY555153). Influenza neuraminidase (see, e.g., GenBank Acc. Nos. AY555151; AY577316). Influenza matrix protein 2 (see, e.g., GenBank Acc. Nos. AY626144(.Influenza basic protein 1 (see, e.g., GenBank Acc. No. AY627897). Influenza polymerase acid protein (see, e.g., GenBank Acc. No. AY627896). Influenza nucleoprotein (see, e.g., GenBank Acc. Nno. AY627895). |
| Influenza A virus subtypes, e.g., swine viruses (SIV): H1N1 influenzaA and swine influenza virus. | Hemagglutinin of H1N1 (GenBank Acc. No. S67220). Influenza A virus matrix protein (GenBank Acc. No. AY700216). Influenza virus A H5H1 nucleoprotein (GenBank Acc. No. AY646426). H1N1 haemagglutinin (GenBank Acc. No. D00837). See also, GenBank Acc. Nos. BD006058; BD006055; BD006052. See also, e.g., Wentworth, et al. (1994) J. Virol. 68: 2051-2058; Wells, et al. (1991) J.A.M.A. 265: 478-481. |
| Respiratory syncytial virus (RSV), including subgroup A and subgroup B. | Respiratory syncytial virus (RSV) (see, e.g., GenBank Acc. Nos. AY353550; NC_001803; NC001781). |
| Rotaviruses, including human rotaviruses A to E, bovine rotavirus, rhesus monkey rotavirus, and human-RVV | Human rotavirus C segment 8 (GenBank Acc. No. AJ549087); Human rotavirus G9 strain outer capsid protein (see, e.g., GenBank Acc. No. DQ056300); Human rotavirus B strain non-structural protein 4 (see, e.g., GenBank Acc. No. AY548957); human rotavirus A strain major inner capsid protein (see, e.g., GenBank Acc. No. AY601554). |

TABLE 1-continued

| Antigens. | |
|---|---|
| Antigen | Reference |
| reassortments. | |
| Polyomavirus, including simian virus 40 (SV40), JC virus (JCV) and BK virus (BKV). | See, e.g., Engels, et al. (2004) J. Infect. Dis. 190: 2065-2069; Vilchez and Butel (2004) Clin. Microbiol. Rev. 17: 495-508; Shivapurkar, et al. (2004) Cancer Res. 64: 3757-3760; Carbone, et al. (2003) Oncogene 2: 5173-5180; Barbanti-Brodano, et al. (2004) Virology 318: 1-9) (SV40 complete genome in, e.g., GenBank Acc. Nos. NC_001669; AF168994; AY271817; AY271816; AY120890; AF345344; AF332562). |
| Coltiviruses, including Colorado tick fever virus, Eyach virus. | Attoui, et al. (1998) J. Gen. Virol. 79: 2481-2489. Segments of Eyach virus (see, e.g., GenBank Acc. Nos. AF282475; AF282472; AF282473; AF282478; AF282476; NC_003707; NC_003702; NC_003703; NC_003704; NC_003705; NC_003696; NC_003697; NC_003698; NC_003699; NC_003701; NC_003706; NC_003700; AF282471; AF282477). |
| Calciviruses, including the genogroups Norwalk, Snow Mountain group (SMA), and Saaporo. | Snow Mountain virus (see, e.g., GenBank Acc. No. AY134748). |
| Parvoviridae, including dependovirus, parvovirus (including parvovirus B19), and erythrovirus. | See, e.g., Brown (2004) Dev. Biol. (Basel) 118: 71-77; Alvarez-Lafuente, et al. (2005) Ann. Rheum. Dis. 64: 780-782; Ziyaeyan, et al. (2005) Jpn. J. Infect. Dis. 58: 95-97; Kaufman, et al. (2005) Virology 332: 189-198. |

Other organisms for which suitable antigens are known in the art include, but are not limited to, *Chlamydia trachomatis, Streptococcus pyogenes* (Group A Strep), *Streptococcus agalactia* (Group B Strep), *Streptococcus pneumonia, Staphylococcus aureus, Escherichia coli, Haemophilus influenzae, Neisseria meningitidis, Neisseria gonorrheae, Vibrio cholerae, Salmonella* species (including *typhi, typhimurium*), *enterica* (including *Helicobactor pylori Shigella flexneri* and other Group D *shigella* species), *Burkholderia mallei, Burkholderia pseudomallei, Klebsiella pneumonia, Clostridium* species (including *C. difficile*). *Vibrio parahaemolyticus* and *V. vulnificus*. This list is not meant to be limiting.

Pharmaceutical Compositions

The term "pharmaceutical" as used herein refers to a chemical substance intended for use in the cure, treatment, or prevention of disease and which is subject to an approval process by the U.S. Food and Drug Administration (or a non-U.S. equivalent thereof) as a prescription or over-the-counter drug product. Details on techniques for formulation and administration of such compositions may be found in Remington, The Science and Practice of Pharmacy 21$^{st}$ Edition (Mack Publishing Co., Easton, Pa.) and Nielloud and Marti-Mestres, Pharmaceutical Emulsions and Suspensions: 2$^{nd}$ Edition (Marcel Dekker, Inc, New York).

For the purposes of this disclosure, the pharmaceutical compositions may be administered by a variety of means including non-parenterally, parenterally, by inhalation spray, topically, or rectally in formulations containing pharmaceutically acceptable carriers, adjuvants and vehicles. "Non-parenteral administration" encompasses oral, buccal, sublingual, topical, transdermal, ophthalmic, otic, nasal, rectal, cervical, pulmonary, mucosal, and vaginal routes. The term parenteral as used here includes but is not limited to subcutaneous, intravenous, intramuscular, intraarterial, intradermal, intrathecal and epidural injections with a variety of infusion techniques. Intraarterial and intravenous injection as used herein includes administration through catheters. Administration via intracoronary stents and intracoronary reservoirs is also contemplated. Intra-tumoral (directly into the tumor mass) or peri-tumoral (around the tumor mass) administration of the compounds of the present invention may directly activate locally infiltrating DC, directly promote tumor cell apoptosis or sensitize tumor cells to cytotoxic agents. The term oral as used herein includes, but is not limited to oral ingestion, or delivery by a sublingual or buccal route. Oral administration includes fluid drinks, energy bars, as well as pill formulations.

Pharmaceutical compositions may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing a drug compound in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents; such as magnesium stearate, stearic acid or talc. Tablets may be uncoated, or may be coated by known techniques including enteric coating, colonic coating, or microencapsulation to delay disintegration and adsorption in the gastrointestinal tract and/or provide a sustained action over a longer period. For example, a time delay material such as glyceryl monostearate or glyceryl distearate alone or with a wax may be employed.

Formulations for oral use may be also presented as hard gelatin capsules where the drug compound is mixed with an inert solid diluent, for example calcium phosphate or kaolin, or as soft gelatin capsules wherein the active ingredient is mixed with water or an oil medium, such as peanut oil, liquid paraffin or olive oil.

Pharmaceutical compositions may be formulated as aqueous suspensions in admixture with excipients suitable for the manufacture of aqueous-suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as *arachis* oil, olive oil, sesame oil or coconut oil, or a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the disclosure may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 20 to 500 mg of active material compounded with an appropriate and convenient amount of carrier material which may vary from about 5 to about 95% of the total compositions. It is preferred that the pharmaceutical composition be prepared which provides easily measurable amounts for administration. Typically, an effective amount to be administered systemically is about 0.1 mg/kg to about 100 mg/kg and depends upon a number of factors including, for example, the age and weight of the subject (e.g., a mammal such as a human), the precise condition requiring treatment and its severity, the route of administration, and will ultimately be at the discretion of the attendant physician or veterinarian. It will be understood, however, that the specific dose level for any particular patient will depend on a variety of factors including the activity of the specific compound employed, the age, body weight, general health, sex and diet of the individual being treated; the time and route of administration; the rate of excretion; other drugs which have previously been administered; and the severity of the particular condition undergoing therapy, as is well understood by those skilled in the art.

As noted above, formulations of the disclosure suitable for oral administration may be presented as discrete units such as capsules, cachets or tablets each containing a predetermined amount of the active ingredient, as a powder or granules; as a solution or a suspension in an aqueous or non-aqueous liquid, or as an oil-in-water liquid emulsion or a water-in-oil liquid emulsion. The pharmaceutical compositions may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropyl ethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made in a suitable machine using a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric or colonic coating to provide release in parts of the gut other than the stomach. This is particularly advantageous with the mono- or di-F-CDN compounds as described herein when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

When a disclosed compound or its salt is named or depicted by structure, it is to be understood that the compound or salt, including solvates (particularly, hydrates) thereof, may exist in crystalline forms, non-crystalline forms or a mixture thereof. The compound or salt, or solvates (particularly, hydrates) thereof, may also exhibit polymorphism (i.e. the capacity to occur in different crystalline forms). These different crystalline forms are typically known as "polymorphs." It is to be understood that when named or depicted by structure, the disclosed compound, or solvates (particularly, hydrates) thereof, also include all polymorphs thereof. Polymorphs have the same chemical composition but differ in packing, geometrical arrangement, and other descriptive properties of the crystalline solid state. Polymorphs may have different physical properties such as density, shape, hardness, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjust the conditions used during the crystallization or recrystallization of the compound.

For solvates of compounds of this invention, or salts thereof, that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, dimethyl sulfoxide, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

Because of their potential use in medicine, the salts of the compounds of this invention are preferably pharmaceutically acceptable. Suitable pharmaceutically acceptable salts include those described by P. Heinrich Stahl and Camille G. Wermuth in Handbook of Pharmaceutical Salts: Properties. Selection, and Use, 2nd ed. (Wiley-VCH: 2011) and also Remington's Pharmaceutical Sciences, 18th ed. (Mack Publishing. Easton Pa.: 1990) and also Remington: The Science and Practice of Pharmacy, 19th ed. (Mack Publishing, Easton Pa.: 1995). Salt encompassed within the term "pharmaceutically acceptable salts" refer to non-toxic salts of the compounds in this invention.

Salts of the compounds of this invention containing a basic amine or other basic functional group may be prepared by any suitable method known in the art, including treatment of the free bases with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, formic acid, alginic acid, pyruvic acid, oxalic acid, glycolic acid, salicylic acid, pyranosildyl acid, such as glucuronic acid or galacturonic acid, alphahydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, glycolate, resinate, lactates, camsylates, tartrates, mandelates, and sulfonates, such as xylenesulfonates, methanesulfonates, propanesulfonates, naphthalene-1-sulfonates and naphthalene-2-sulfonates.

Salts of the compounds of this invention containing a phosphate diester, phosphorothioate diester or other acidic functional group can be prepared by reacting with a suitable base. Pharmaceutically acceptable salts include, but are not limited to: acetate, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydoxymethyl)aminomethane. Additional pharmaceutically acceptable salts are known to those skilled in the art.

Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, zinc, as well as salts made from physiologically acceptable organic bases such as diethylamine, isopropylamine, olamine, benzathine, benethamine, tromethamine (2-amino-2-(hydroxymethyl)propane-1,3-diol), morpholine, epolamine, piperidine, piperazine, picoline, dicyclohexylamine, N,N'-dibenzylethylenediamine, 2-hydroxyethylamine, tri-(2-hydroxyethyl)amine, chloroprocaine, choline, deanol, imidazole, diethanolamine, ethylenediamine, meglumine (N-methylglucamine), procaine, dibenzylpiperidine, dehydroabietylamine, glucamine, collidine, quinine, quinolone, erbumine and basic amino acids such as lysine and arginine.

The mono- or di-F-CDN compounds as described herein that include salts thereof can be described by structures wherein the —SH or —OH in the phosphate or thiophosphate bond (e.g. R5 or R6 of the compound of Formula I as described herein) are represented as $—S^-$ or $—O^-$ with a corresponding cation to form salts of the compounds as described herein. For example, a salt of the compound of Formula II of the third aspect as described herein can be represented by the following structures:

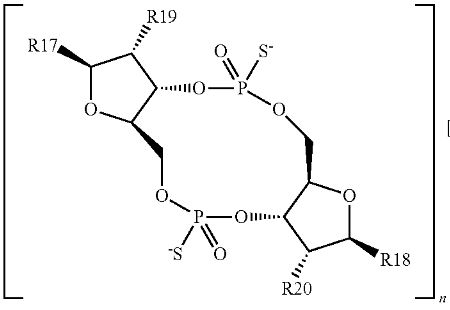

$[A^{y+}]_m$ wherein $A^{y+}$ represents a mono or polyvalent salt cation, and n and m are the lowest possible whole number for a given y. For example when $A^{y+}$ is monovalent, i.e. when y is 1, such as $Na^+$, $K^+$, $NH_4^+$, $TEAH^+$ or the like, n is 1 and m is 2; when y is 2, such as $Ca^{2+}$, $Mg^{2+}$ and the like, n is 1 and m is 1; when y is 3, e.g. $Al^{3+}$ or the like, n is 3 and m is 2. For example, salts of a monovalent or divalent salt cation can be represented as

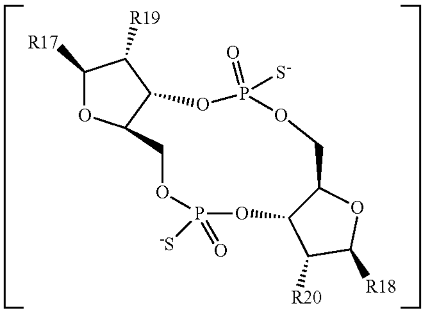

$[A^+]_2$ or

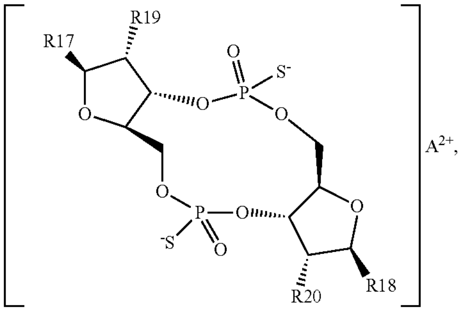

$A^{2+}$, respectively, or in cases where n=1, these can be represented without brackets, e.g. as

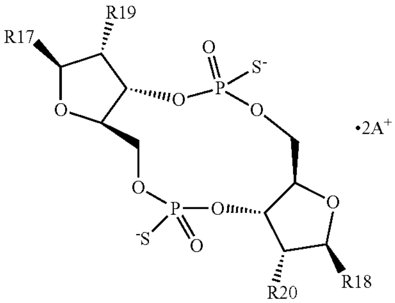

•$2A^+$ or

-continued

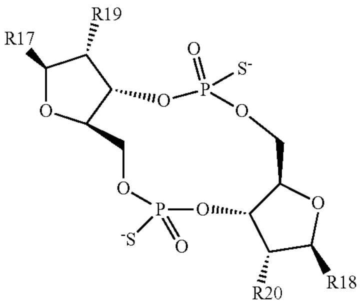

•$A^{2+}$.

Alternatively, monovalent salts can be depicted with $A^+$ adjacent each of the —$S^-$ or —$O^-$. For example, the sodium salt of a mono- or di-F-RR-CDN compounds of Formula II as described herein can be depicted as

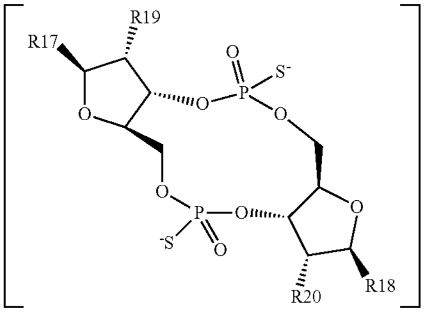

$[Na^+]_2$,

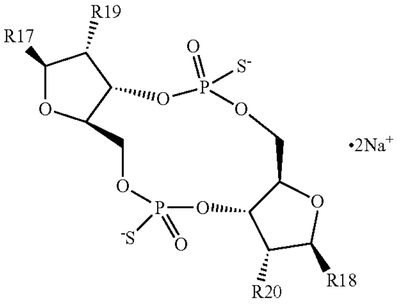

•$2Na^+$ or

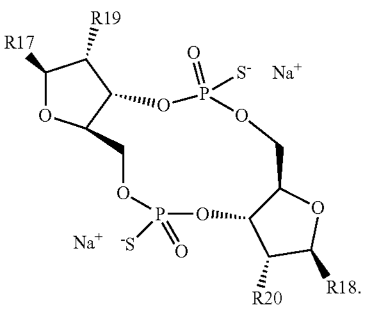

In some instances, the compounds may include salts of the 2'OH group as well, for example, tris-triethylammonium salts of a compound of Formula II, e.g. wherein R19 is F and R20 is OH may have the structure represented as

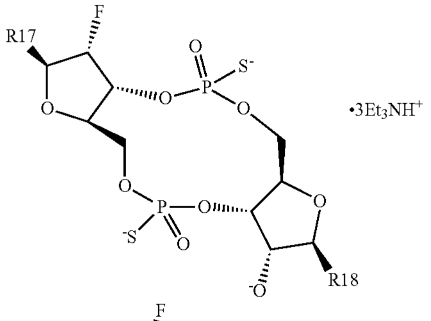

or

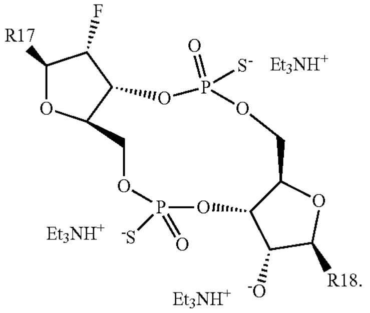

Other non-pharmaceutically acceptable salts, e.g. trifluoroacetate or triethylammonium may be used, for example in the isolation of compounds of the invention, and are included within the scope of this invention.

The invention includes within its scope all possible stoichiometric and non-stoichiometric forms of the salts of the compounds of this invention.

If a compound of this invention containing a basic amine or other basic functional group is isolated as a salt, the corresponding free base form of that compound may be prepared by any suitable method known to the art, including treatment of the salt with an inorganic or organic base, suitably an inorganic or organic base having a higher $pK_a$ than the free base form of the compound. Similarly, if a compound of this invention containing a phosphate diester, phosphorothioate diester or other acidic functional group is isolated as a salt, the corresponding free acid form of that compound may be prepared by any suitable method known to the art, including treatment of the salt with an inorganic or organic acid, suitably an inorganic or organic acid having a lower $pK_a$ than the free acid form of the compound.

An effective amount of a mono- or di-F-CDN compound, or a pharmaceutically acceptable salt, pharmaceutically acceptable solvate or pharmaceutically acceptable hydrate thereof as described herein, for a particular patient may vary depending on factors such as the condition being treated, the overall health of the patient, the route and dose of administration and the severity of side effects. Guidance for methods of treatment and diagnosis is available (see, e.g., Maynard, et al. (1996) A Handbook of SOPs for Good Clinical Practice, Interpharm Press. Boca Raton, Fla.; Dent (2001) Good Laboratory and Good Clinical Practice, Urch Publ., London, UK).

An effective amount may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of a pharmaceutical composition comprising the mono- or di-F-CDN compound, or a pharmaceutically acceptable salt, pharmaceutically acceptable solvate or pharmaceutically acceptable hydrate thereof as described herein. Where there is more than one administration of a pharmaceutical composition in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach. Lippincott. Williams & Wilkins, Phila., Pa.; Chabner and Longo (eds.) (2001) Cancer Chemotherapy and Biotherapy, Lippincott, Williams & Wilkins, Phila., Pa.). Generally, co-administration or administration together indicates treating a subject with two or more agents, where the agents can be administered simultaneously or at different times. For example, such agents may be delivered to a single subject as separate administrations, which may be at essentially the same time or different times, and which may be by the same route or different routes of administration. Such agents may be delivered to a single subject in the same administration (e.g. same formulation) such that they are administered at the same time by the same route of administration.

As noted, the compositions of the present invention are preferably formulated as pharmaceutical compositions for parenteral or enteral delivery. A typical pharmaceutical composition for administration to an animal subject comprises a pharmaceutically acceptable vehicle such as aqueous solutions, non-toxic excipients, including salts, preservatives, buffers and the like. See, e.g., *Remington's Pharmaceutical Sciences, 15th Ed*., Easton ed., Mack Publishing Co., pp 1405-1412 and 1461-1487 (1975); *The*

*National Formulary XIV,* 14*th Ed*., American Pharmaceutical Association, Washington, D.C. (1975). Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to routine skills in the art.

Repeated administrations of a particular vaccine (homologous boosting) have proven effective for boosting humoral responses. Such an approach may not be effective at boosting cellular immunity because prior immunity to the vector tends to impair robust antigen presentation and the generation of appropriate inflammatory signals. One approach to circumvent this problem has been the sequential administration of vaccines that use different antigen-delivery systems (heterologous boosting). In a heterologous boosting regimen, at least one prime or boost delivery comprises delivery of the inactivated tumor cell/mono- or di-F-CDN compound or compositions thereof described herein. The heterologous arm of the regimen may comprise delivery of antigen using one or more of the following strategies:

- inactivated or attenuated bacteria or viruses comprising the antigen of interest, which are particles that have been treated with some denaturing condition to render them ineffective or inefficient in mounting a pathogenic invasion;
- purified antigens, which are typically naturally-produced antigens purified from a cell culture of the pathogen or a tissue sample containing the pathogen, or a recombinant version thereof;
- live viral or bacterial delivery vectors recombinantly engineered to express and/or secrete antigens in the host cells of the subject. These strategies rely on attenuating (e.g., via genetic engineering) the viral or bacterial vectors to be non-pathogenic and non-toxic;
- antigen presenting cell (APC) vectors, such as a dendritic cell (DC) vector, which comprise cells that are loaded with an antigen, or transfected with a composition comprising a nucleic acid encoding the antigen (e.g., Provenge® (Dendreon Corporation) for the treatment of castration-resistant metastatic prostate cancer);
- liposomal antigen delivery vehicles; and
- naked DNA vectors and naked RNA vectors which may be administered by a gene gun, electroporation, bacterial ghosts, microspheres, microparticles, liposomes, polycationic nanoparticles, and the like.

A prime vaccine and a boost vaccine can be administered by any one or combination of the following routes. In one aspect, the prime vaccine and boost vaccine are administered by the same route. In another aspect, the prime vaccine and boost vaccine are administered by different routes. The term "different routes" encompasses, but is not limited to, different sites on the body, for example, a site that is oral, non-oral, enteral, parenteral, rectal, intranode (lymph node), intravenous, arterial, subcutaneous, intramuscular, peritumor, intratumor, infusion, mucosal, nasal, in the cerebrospinal space or cerebrospinal fluid, and so on, as well as by different modes, for example, oral, intravenous, and intramuscular.

An effective amount of a prime or boost vaccine may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the vaccine. Where there is more than one administration of a vaccine the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals, such as a priming schedule consisting of administration at 1 day, 4 days, 7 days, and 25 days, just to provide a non-limiting example.

EXAMPLES

The following examples serve to illustrate the present invention. These examples are in no way intended to limit the scope of the invention.

General Methods

Anhydrous solvents and reagents suitable for solution phase oligonucleotide synthesis were purchased from commercial suppliers (Aldrich, ChemGenes Corporation. Wilmington, Mass., USA) and handled under dry argon or nitrogen using anhydrous technique. Phosphoramidite coupling reactions and H-phosphonate cyclizations were carried out in anhydrous acetonitrile or pyridine under dry argon or nitrogen. The starting materials for all reactions in dry pyridine were dried by concentration (three times) from pyridine, unless indicated otherwise. Chromatography conditions were as follows unless indicated otherwise in the example below. Preparative silica gel flash chromatography was carried out under medium pressure chromatography (MPLC) using RediSep Rf silica columns (Teledyne Isco, Lincoln, Nebr.) on a Combiflash Rf+ UV-Vis (Teledyne Isco) using gradients of methanol in dichloromethane. Reverse phase preparative chromatography was executed under MPLC conditions using RediSep Rf C18 Aq columns (Teledyne Isco) on a Combiflash Rf+ UV-Vis using gradients of acetonitrile in aqueous 10 mM TEAA solution. Analytical high pressure liquid chromatography (HPLC) was performed on a Shimadzu Prominence HPLC system with two LC-20AD pumps and a SPD-M30A photodiode array detector monitoring at 254 nm. Gradients of 10 mM TEAA in acetonitrile or 20 mM $NH_4OAc$ in acetonitrile were used with either a 5 micron (Thermo Scientific Acclaim 120) C-18 column (4.6×250 mm) or a 10 micron (Thermo Scientific Hypersil) C-18 column (4.0×250 mm) at room temperature. Preparative HPLC was carried out on a Shimadzu preparative LC20-AP HPLC system, equipped with a SPD-20A UV/Vis detector monitoring at 254 nm on a Varian Microsorb 60-8 C-18 41.6×250 mm column using gradients of 10 mM TEAA and acetonitrile at a flow rate of 50 ml/min. Solid phase extractions using C-18 Sep-Pak (Waters) were carried out at loadings of 3% (wt/wt). Analytical LCMS were recorded using a Shimadzu LCMS system featuring a Prominence HPLC coupled to a Shimadzu LCMS-2020 single quadrupole mass spectrometer, using an electrospray ionization source (ESI).

$^1H$ NMR. $^{19}F$ NMR, $^{31}P$ NMR and $^{13}C$ NMR spectra were recorded in $CDCl_3$, d6-DMSO, $CD_3OD$ or $D_2O$ as solvent. The operating frequency for 1H was 400 MHz, $^{19}F$ was 376 MHz, $^{31}P$ was 162 MHz, and $^{13}C$ was 100 MHz. All spectra were recorded at ambient temperature (20-25° C.) unless otherwise noted. The temperature for variable-temperature experiments was calibrated monthly or bimonthly using the ethylene glycol method described in C. Amman. P. Meier and A. E. Merbach, *J. Magn. Reson.* 1982, 46, 319-321.

The final compounds may exist as the triethylammonium ($TEAH^+$ or $Et_3N^+$) salt, which can be converted to other salt forms (including but not limited to sodium ($Na^+$) or ammonium ($NH_4^+$)) using standard ion exchange techniques or other well known methods.

Assignments of Stereochemistry at the phosphorus were made in analogy to literature methods (Zhao et al. Nucleosides, Nucleotides, and Nucleic Acid 289:352-378, 2009) or as discussed in the examples below.

Compound names were generated using the software program ChemBioDraw Ultra V 14.0 available from CambridgeSoft Corporation, 100 CambridgePark Drive, Cambridge, Mass. 02140 USA (http://www.cambridgesoft.com). Abridged names of compounds, or reference compounds used in the examples, are also provided in the following Table 3. Reference compounds 3',3'-RR-(G)(A), 3',3'-RR-(G)(G) and 3',3'-RR-(A)(A) were prepared according to methods as described in PCT Publication No. WO2014/093936, incorporated by reference with respect to such syntheses. Structures in the examples may also be represented as salts, e.g. —$O^-$ $A^+$ or —$S^-$ $A^+$, where $A^+$ is the salt cation.

TABLE 3

Abridged compound names and structures.

| Example number and abridged Compound names | Structure |
|---|---|
| Example 1 Compound 6<br>3'3'-RR-(2'F-A)(2'F-A);<br>dithio-(Rp,Rp)-cyclic-<br>[2'F-A(3',5')p-2'-F-A(3',5')p]<br>(2R,3R,3aR,5R,7aR,9R,10R,10aR,12R,14aR)-2,9-bis(6-amino-9H-purin-9-yl)-3,10-difluoro-5,12-dimercaptooctahydro-2H,7H-difuro[3,2-d:3',2'-j][1,3,7,9]tetraoxa[2,8]diphosphacyclododecine 5,12-dioxide | 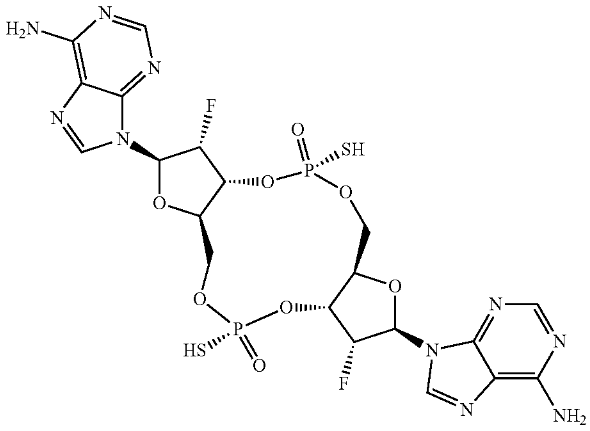 [SMILES: Nc1ncnc2c1ncn2[C@@H]1O[C@@H]2CO[P@@](=O)(S)O[C@H]3[C@@H](F)[C@H](n4cnc5c(N)ncnc54)O[C@@H]3CO[P@@](=O)(S)O[C@H]2[C@H]1F] |
| Example 1 Compound 6a<br>3'3'-RS-(2'F-A)(2'F-A);<br>dithio-(Rp,Sp)-cyclic-[2'F-A(3',5')p-2'F-A(3',5')p]<br>(2R,3R,3aR,5R,7aR,9R,10R,10aR,12S,14aR)-2,9-bis(6-amino-9H-purin-9-yl)-3,10-difluoro-5,12-dimercaptooctahydro-2H,7H-difuro[3,2-d:3',2'-j][1,3,7,9]tetraoxa[2,8]diphosphaeyclododecine 5,12-dioxide | 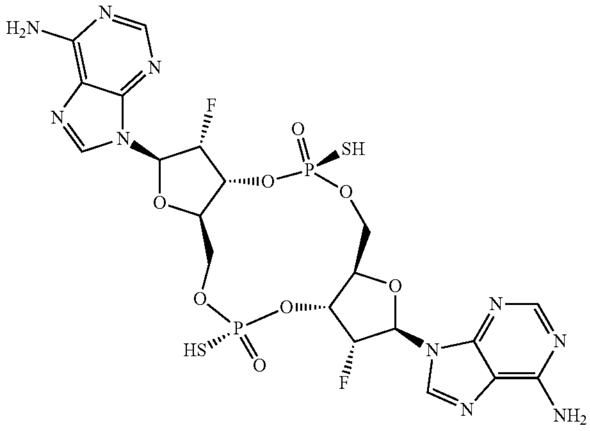 [SMILES: Nc1ncnc2c1ncn2[C@@H]1O[C@@H]2CO[P@@](=O)(S)O[C@H]3[C@@H](F)[C@H](n4cnc5c(N)ncnc54)O[C@@H]3CO[P@](=O)(S)O[C@H]2[C@H]1F] |

TABLE 3-continued

| Abridged compound names and structures. | |
|---|---|
| Example number and abridged Compound names | Structure |
| Example 2 Compound 14<br>3'3'-RR-(2'F-G)(2'F-A);<br>dithio-(Rp,Rp)-cyclic-<br>[2'F-G(3',5')p-2'F-A(.3',5')p]<br>2-amino-9-<br>((2R,3R,3aR,5R,7aR,9R,10R,10aR,12R,14aR)-9-<br>(6-amino-9H-purin-9-yl)-3,10-difluoro-5,12-<br>dimercapto-5,12-dioxidooctahydro-2H,7H-<br>difuro[3,2-d:3',2'-<br>j][1,3,'7,9]tetraoxa[2,8]diphosphacyclododecin-2-<br>yl)-1,9-dihydro-6H-purin-6-one | 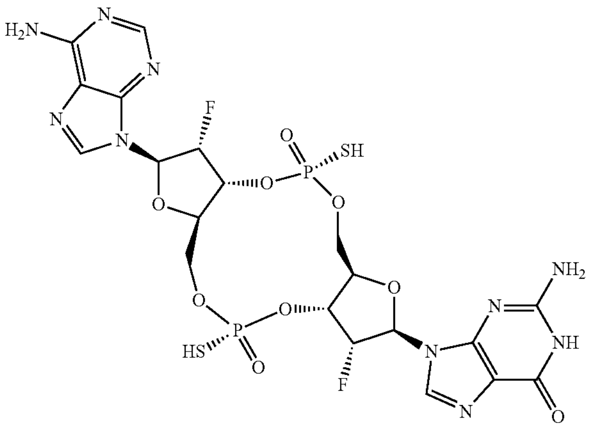 [SMILES: Nc1nc2c(ncn2[C@@H]2O[C@@H]3CO[P@@](=O)(S)O[C@H]4[C@@H](F)[C@H](n5cnc6c(N)ncnc65)O[C@@H]4CO[P@@](=O)(S)O[C@H]3[C@H]2F)c(=O)[nH]1] |
| Example 2 Compound 14a<br>3'3'-RS-(2'F-G)(2'F-A);<br>dithio-(Rp,Sp)-cyclic-<br>[2'F-G(3',5')p-2'F-A(3',5')p]<br>2-amino-9-<br>((2R,3R,3aR,5R,7aR,9R,10R,10aR,12S,14aR)-9-<br>(6-amino-9H-purin-9-yl)-3,10-difluoro-5,12-<br>dimercapto-5,12-dioxidooctahydro-2H,7H-<br>difuro[3,2-d:3',2'-<br>j][1,3,7,9]tetraoxa[2,8]diphosphacyclododecin-2-<br>yl)-1,9-dihydro-6H-purin-6-one | 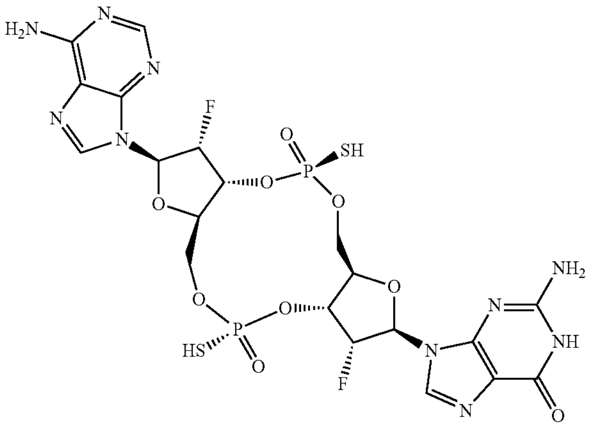 [SMILES: Nc1nc2c(ncn2[C@@H]2O[C@@H]3CO[P@](=O)(S)O[C@H]4[C@@H](F)[C@H](n5cnc6c(N)ncnc65)O[C@@H]4CO[P@@](=O)(S)O[C@H]3[C@H]2F)c(=O)[nH]1] |
| Example 3 Compound 17<br>3'3'-RR-(2'F-G)(2'F-G);<br>dithio-(Rp,Rp)-cyclic-<br>[2'F-G(3',5')p-2'F-G(3',5')p]<br>9,9'-<br>((2R,3R,3aR,5R,7aR,9R,10R,10aR,12R,14aR)-<br>3,10-difluoro-5,12-dimercapto-5,12-<br>dioxidooctahydro-2H,7H-difuro[3,2-d:3',2'-<br>j][1,3,7,9]tetraoxa[2,8]diphosphacyclododecine-<br>2,9-diyl)bis(2-amino-1,9-dihydro-6H-purin-6-one) | 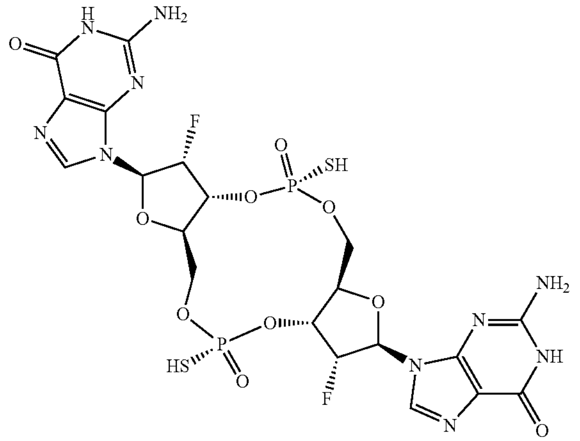 [SMILES: Nc1nc2c(ncn2[C@@H]2O[C@@H]3CO[P@@](=O)(S)O[C@H]4[C@@H](F)[C@H](n5cnc6c(=O)[nH]c(N)nc65)O[C@@H]4CO[P@@](=O)(S)O[C@H]3[C@H]2F)c(=O)[nH]1] |

TABLE 3-continued

| Abridged compound names and structures. | |
|---|---|
| Example number and abridged Compound names | Structure |
| Example 3 Compound 17a 3'3'-RS-(2'F-G)(2'F-G); dithio-(Rp,Sp)-cyclic-[2'F-G(3',5')p-2'F-G(3',5')p] 9,9'-((2R,3R,3aR,5R,7aR,9R,10R,10aR,12S,14aR)-3,10-difluoro-5,12-dimercapto-5,12-dioxidooctahydro-2H,7H-difuro[3,2-d:3',2'-j][1,3,7,9]tetraoxa[2,8]diphosphacyclododecine-2,9-diyl)bis(2-amino-1,9-dihydro-6H-purin-6-one) | 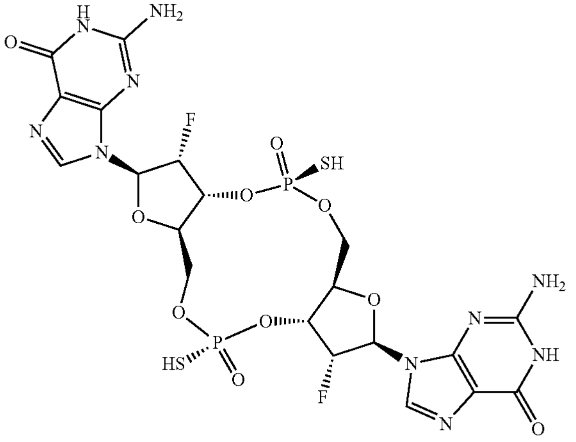 [SMILES: Nc1nc2c(ncn2[C@@H]2O[C@@H]3CO[P@@](=O)(S)O[C@H]4[C@@H](F)[C@H](n5cnc6c(=O)[nH]c(N)nc65)O[C@@H]4CO[P@](=O)(S)O[C@H]3[C@H]2F)c(=O)[nH]1] |
| Example 7 Compound 25 3'3'-RR-(2'F-iBuG)(2'F-BzA); dithio-(Rp,Rp)-cyclic-[2'F-iBuG(3',5')p-2'F-BzA(3',5')p] N-(9-((2R,3R,3aR,5R,7aR,9R,10R,10aR,12R,14aR)-3,10-difluoro-9-(2-isobutyramido-6-oxo-1,6-dihydro-9H-purin-9-yl)-5,12-dimercapto-5,12-dioxidooctahydro-2H,7H-difuro[3,2-d:3',2'-j][1,3,7,9]tetraoxa[2,8]diphosphacyclododecin-2-yl)-9H-purin-6-yl)benzamide | 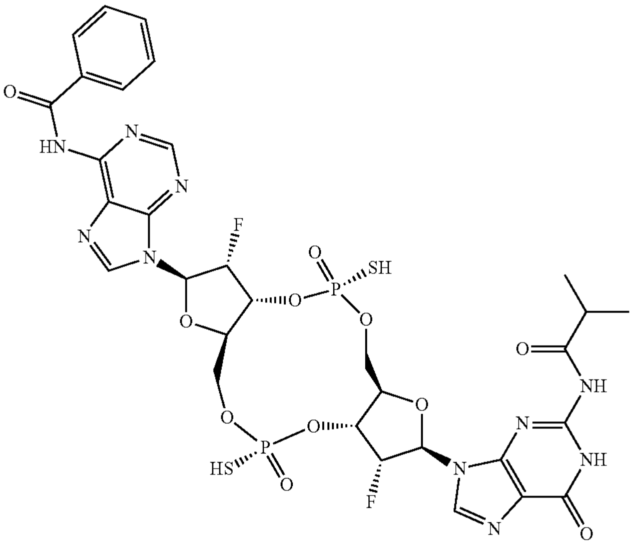 [SMILES: CC(C)C(=O)Nc1nc2c(ncn2[C@@H]2O[C@@H]3CO[P@@](=O)(S)O[C@H]4[C@@H](F)[C@H](n5cnc6c(NC(=O)c7ccccc7)ncnc65)O[C@@H]4CO[P@@](=O)(S)O[C@H]3[C@H]2F)c(=O)[nH]1] |
| Example 7 Compound 25a 3'3'-RS-(2'F-iBuG)(2'F-BzA); dithio-(Rp,Sp)-cyclic-[2'F-iBuG(3',5')p-2'F-BzA(3',5')p] N-(9-((2R,3R,3aR,5S,7aR,9R,10R,10aR,12R,14aR)-3,10-difluoro-9-(2-isobutyramido-6-oxo-1,6-dihydro-9H-purin-9-yl)-5,12-dimercapto-5,12-dioxidooctahydro-2H,7H-difuro[3,2-d:3',2'-j][1,3,7,9]tetraoxa[2,8]diphosphacyclododecin-2-yl)-9H-purin-6-yl)benzamide | 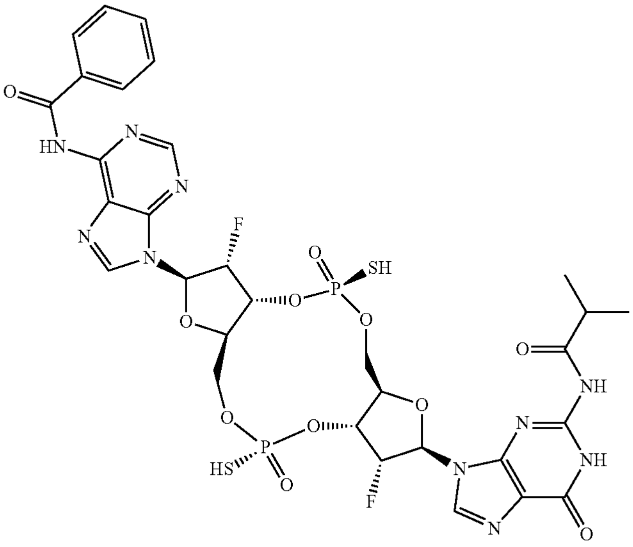 [SMILES: CC(C)C(=O)Nc1nc2c(ncn2[C@@H]2O[C@@H]3CO[P@](=O)(S)O[C@H]4[C@@H](F)[C@H](n5cnc6c(NC(=O)c7ccccc7)ncnc65)O[C@@H]4CO[P@@](=O)(S)O[C@H]3[C@H]2F)c(=O)[nH]1] |

TABLE 3-continued

Abridged compound names and structures.

| Example number and abridged Compound names | Structure |
|---|---|
| Example 8 Compound 26<br>3'3'-RR-(2'F-iBuG)(2'F-A);<br>dithio-(Rp,Rp)-cyclic-<br>[2'F-iBuG(3',5')p-2'F-A(3',5')p]<br>N-(9-<br>((2R,3R,3aR,5R,7aR,9R,10R,10aR,12R,14aR)-9-<br>(6-amino-9H-purin-9-yl)-3,10-difluoro-5,12-<br>dimercapto-5,12-dioxidooctahydro-2H,7H-<br>difuro[3,2-d:3',2'-<br>j][1,3,7,9]tetraoxa[2,8]diphosphacyclododecin-2-<br>yl)-6-oxo-6,9-dihydro-1H-purin-2-<br>yl)isobutyramide | 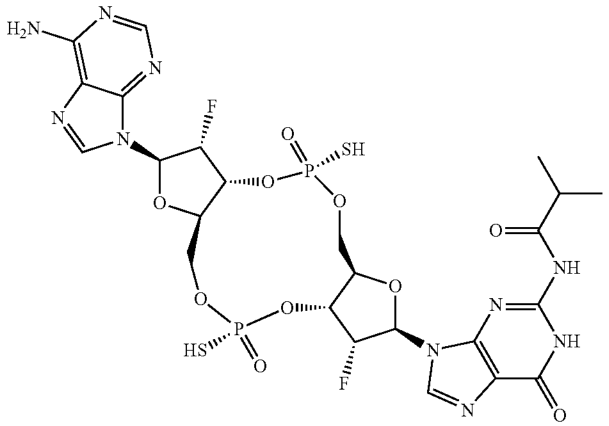 [SMILES: CC(C)C(=O)Nc1nc2c(ncn2[C@@H]2O[C@@H]3CO[P@@](=O)(S)O[C@H]4[C@@H](F)[C@H](n5cnc6c(N)ncnc65)O[C@@H]4CO[P@@](=O)(S)O[C@H]3[C@H]2F)c(=O)[nH]1] |
| Example 9 Compound 27<br>3'3'-RR-(2'F-BzA)(2'F-BzA);<br>dithio-(Rp,Rp)-cyclic-<br>[2'F-BzA(3',5')p-2'F-BzA(3',5')p]<br>N,N'-<br>(((2R,3R,3aR,5R,7aR,9R,10R,10aR,12R,14aR)-<br>3,10-difluoro-5,12-dimercapto-5,12-<br>dioxidooctahydro-2H,7H-difuro[3,2-d:3',2'-<br>j][1,3,7,9]tetraoxa[2,8]diphosphacyclododecine-<br>2,9-diyl)bis(9H-purine-9,6-diyl))dibenzamide | 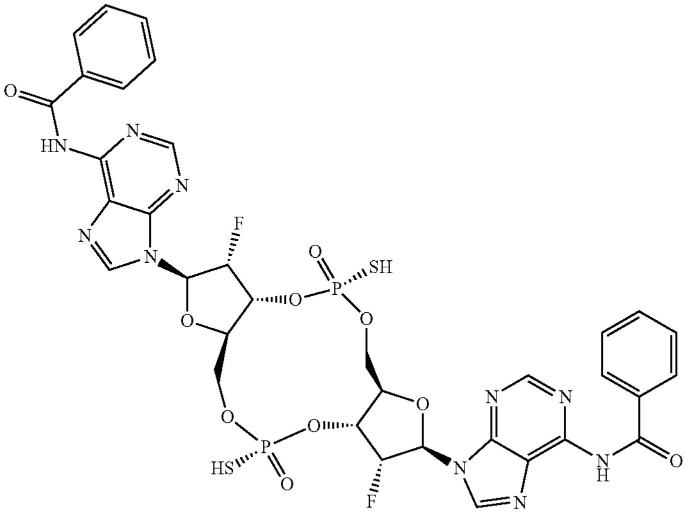 [SMILES: O=C(Nc1ncnc2c1ncn2[C@@H]1O[C@@H]2CO[P@@](=O)(S)O[C@H]3[C@@H](F)[C@H](n4cnc5c(NC(=O)c6ccccc6)ncnc54)O[C@@H]3CO[P@@](=O)(S)O[C@H]2[C@H]1F)c1ccccc1] |
| Example 4 Compound 22<br>3'3'-RR-(A)(2'F-A);<br>dithio-(Rp,Rp)-cyclic-[A(3',5')p-2'F-A(3',5')p]<br>(2R,3R,3aR,5R,7aR,9R,10R,10aS,12R,14aR)-2,9-<br>bis(6-amino-9H-purin-9-yl)-3-fluoro-10-hydroxy-<br>5,12-dimercaptooctahydro-2H,7H-difuro[3,2-<br>d:3',2'-<br>j][1,3,7,9]tetraoxa[2,8]diphosphacyclododecine-<br>5,12-dioxide | 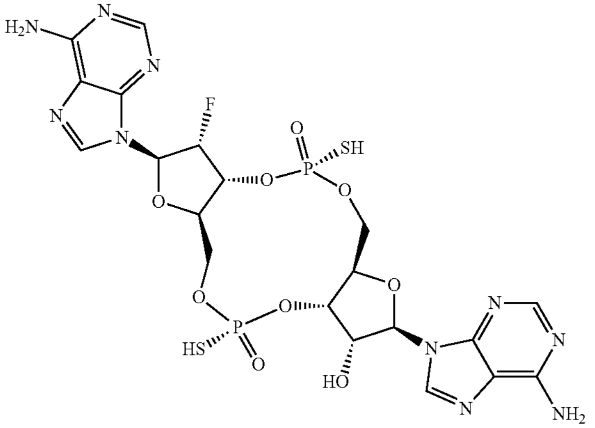 [SMILES: Nc1ncnc2c1ncn2[C@@H]1O[C@@H]2CO[P@@](=O)(S)O[C@H]3[C@@H](F)[C@H](n4cnc5c(N)ncnc54)O[C@@H]3CO[P@@](=O)(S)O[C@H]2[C@H]1O] |

TABLE 3-continued

| Abridged compound names and structures. | |
|---|---|
| Example number and abridged Compound names | Structure |
| Example 4 Compound 22a<br>3'3'-RS-(A)(2'F-A);<br>dithio-(Rp,Rp),-cyclic-[A(3',5')p-2'F-A(3',5')p]<br>(2R,3R,3aR,5S,7aR,9R,10R,10aS,12R,14aR)-2,9-bis(6-amino-9H-purin-9-yl)-3-fluoro-10-hydroxy-5,12-dimercaptooctahydro-2H,7H-difuro[3,2-d:3',2'-j][1,3,7,9]tetraoxa[2,8]diphosphacyclododecine 5,12-dioxide | 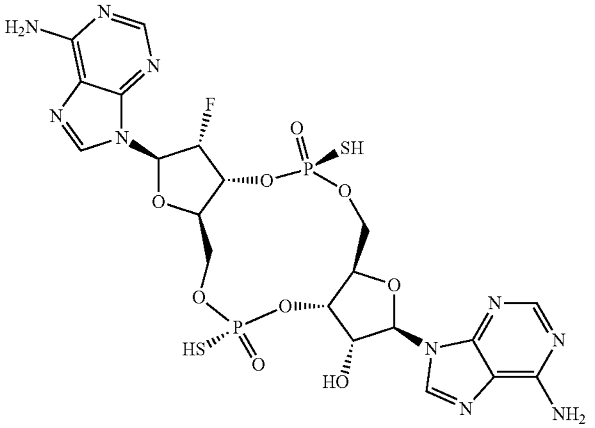 |
| Example 5 Compound 23<br>3'3'-RR-(2'F-G)(A)<br>dithio-(Rp,Rp)-cyclic-<br>[2'F-G(3',5')p-A(3',5')p]<br>2-amino-9-((2R,3R,3aR,5R,7aR,9R,10R,10aS,12R,14aR)-9-(6-amino-9H-purin-9-yl)-3-fluoro-10-hydroxy-5,12-dimercapto-5,12-dioxidooctahydro-2H,7H-difuro[3,2-d:3',2'-j][1,3,7,9]tetraoxa[2,8]diphosphacycloclodecin-2-yl)-1,9-dihydro-6H-purin-6-one | 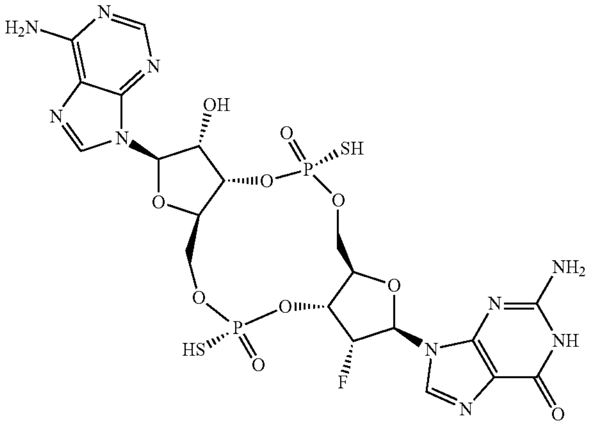 [SMILES: Nc1nc2c(ncn2[C@@H]2O[C@@H]3CO[P@@](=O)(S)O[C@H]4[C@@H](O)[C@H](n5cnc6c(N)ncnc65)O[C@@H]4CO[P@@](=O)(S)O[C@H]3[C@H]2F)c(=O)[nH]1] |
| Example 5 Compound 23a<br>3'3'-SR-(2'F-G)(A)<br>dithio-(Sp,Rp)-cyclic-[2'F-G(3',5')p-A(3',5')p]<br>2-amino-9-((2R,3R,3aR,5S,7aR,9R,10R,10aS,12R,14aR)-9-(6-amino-9H-purin-9-yl)-3-fluora-10-hydroxy-5,12-dimercapto-5,12-dioxidooctahydro-2H,7H-difuro[3,2-d:3',2'-j][1,3,7,9]tetraoxa[2,8]diphosphaeyclododecin-2-yl)-1,9-dihydro-6H-purin-6-one | 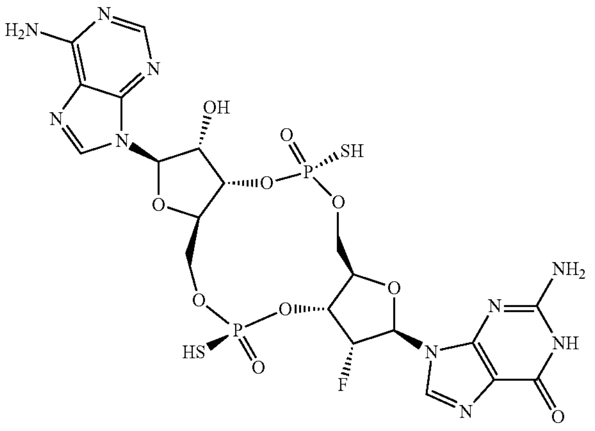 [SMILES: Nc1nc2c(ncn2[C@@H]2O[C@@H]3CO[P@@](=O)(S)O[C@H]4[C@@H](O)[C@H](n5cnc6c(N)ncnc65)O[C@@H]4CO[P@](=O)(S)O[C@H]3[C@H]2F)c(=O)[nH]1] |

TABLE 3-continued

| Abridged compound names and structures. | |
|---|---|
| Example number and abridged Compound names | Structure |
| Example 6 Compound 24<br>3'3'-RR-(G)(2'F-A)<br>dithio-(Rp,Rp)-cyclic-[G(3',5')p-2'F-A(3',5')p]<br>2-amino-9-<br>((2R,3R,3aS,5R,7aR,9R,10R,10aR,12R,14aR)-9-<br>(6-amino-9H-purin-9-yl)-10-fluoro-3-hydroxy-<br>5,12-dimercapto-5,12-dioxidooctahydro-2H,7H-<br>difuro[3,2-d:3',2'-<br>j][1,3,7,9]tetraoxa[2,8]diphosphacyclododecin-2-<br>yl)-1,9-dihydro-6H-purin-6-one | 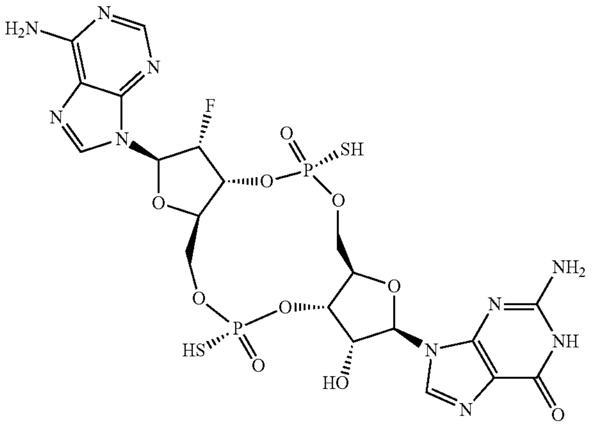 [SMILES: Nc1nc2c(ncn2[C@@H]2O[C@@H]3CO[P@@](=O)(S)O[C@H]4[C@@H](F)[C@H](n5cnc6c(N)ncnc65)O[C@@H]4CO[P@@](=O)(S)O[C@H]3[C@H]2O)c(=O)[nH]1] |
| Example 6 Compound 24a<br>3'3'-RS-(G)(2'F-A)<br>dithio-(Rp,Sp)-cyclic-[G(3',5')p-2'F-A(3',5')p]<br>2-amino-9-<br>((2R,3R,3aS,5R,7aR,9R,10R,10aR,12S,14aR)-9-<br>(6-amino-9H-purin-9-yl)-10-fluoro-3-hydroxy-<br>5,12-dimercapto-5,12-dioxidooctahydro-2H,7H-<br>difuro[3,2-d:3',2'-<br>j][1,3,7,9]tetraoxa[2,8]diphosphacyclododecin-2-<br>yl)-1,9-dihydro-6H-purin-6-one | 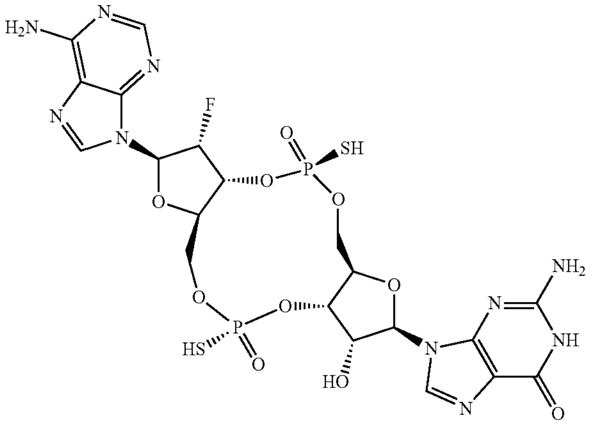 [SMILES: Nc1nc2c(ncn2[C@@H]2O[C@@H]3CO[P@](=O)(S)O[C@H]4[C@@H](F)[C@H](n5cnc6c(N)ncnc65)O[C@@H]4CO[P@@](=O)(S)O[C@H]3[C@H]2O)c(=O)[nH]1] |
| Example 10 Compound 30<br>3'3'-(2'F-G)(2'F-A);<br>cyclic-[2'F-G(3',5')p-2'F-A(3',5')p]<br>2-amino-9-((2R,3R,3aR,7aR,9R,10R,10aR,14aR)-<br>9-(6-amino-9H-purin-9-yl)-3,10-difluoro-5,12-<br>dihydroxy-5,12-dioxidooctahydro-2H,7H-<br>difuro[3,2-d:3',2'-<br>j][1,3,7,9]tetraoxa[2,8]diphosphacyclododecin-2-<br>yl)-1,9-dihydro-6H-purin-6-one | 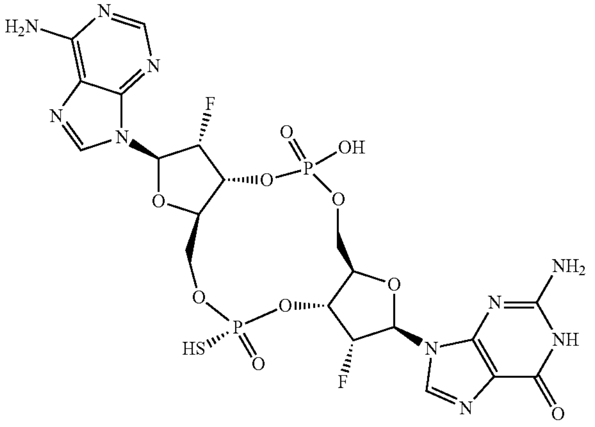 [SMILES: Nc1nc2c(ncn2[C@@H]2O[C@@H]3COP(=O)(O)O[C@H]4[C@@H](F)[C@H](n5cnc6c(N)ncnc65)O[C@@H]4CO[P@@](=O)(S)O[C@H]3[C@H]2F)c(=O)[nH]1] |

TABLE 3-continued

| Abridged compound names and structures. | |
|---|---|
| Example number and abridged Compound names | Structure |
| Example 1 Compound 7<br>3'3'-RR-(2'βF-A)(2'βF-A)<br>dithio-(Rp,Rp)-cyclic-<br>[2'βF-A(3',5')p-2'βF-A(3',5')p]<br>(2R,3S,3aR,5R,7aR,9R,10S,10aR,12R,14aR)-2,9-bis(6-amino-9H-purin-9-yl)-3,10-difluoro-5,12-dimercaptooctahydro-2H,7H-difuro[3,2-d:3',2'-j][1,3,7,9]tetraoxa[2,8]diphosphacyclododecine 5,12-dioxide | 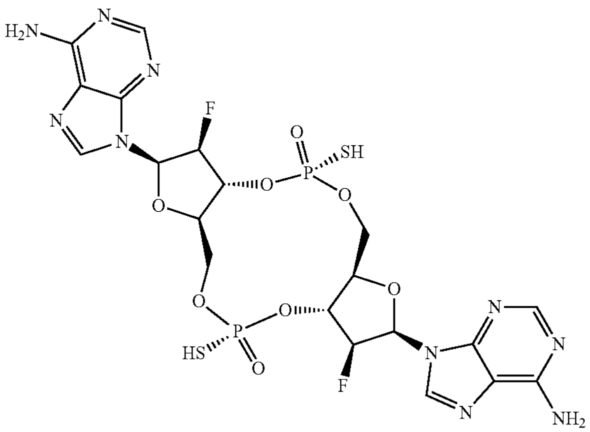 [SMILES: Nc1ncnc2c1ncn2[C@@H]1O[C@@H]2CO[P@@](=O)(S)O[C@H]3[C@H](F)[C@H](n4cnc5c(N)ncnc54)O[C@@H]3CO[P@@](=O)(S)O[C@H]2[C@@H]1F] |
| Example 1 Compound 7a<br>3'3'-RS-(2'βF-A)(2'βF-A)<br>dithio-(Rp,Sp)-cyclic-<br>[2'βF-A(3',5')p-2'βF-A(3',5')p]<br>(2R,3S,3aR,5R,7aR,9R,10S,10aR,12S,14aR)-2,9-bis(6-amino-9H-purin-9-yl)-3,10-difluoro-5,12-dimercaptooctahydro-2H,7H-difuro[3,2-d:3',2'-j][1,3,7,9]tetraoxa[2,8]diphosphacyclododecine 5,12-dioxide | 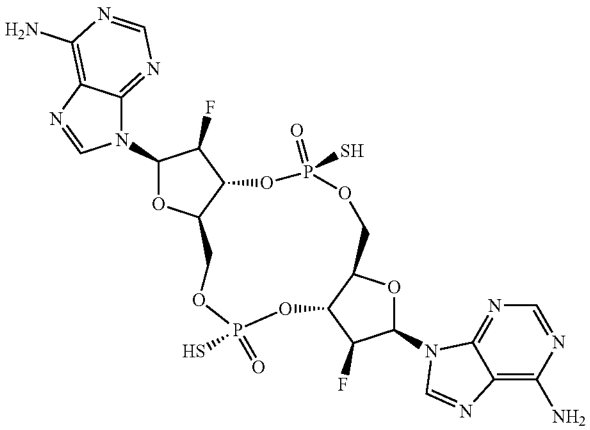 |
| CDA<br>3'3'-(A)(A)<br>cyclic-[A(3',5')p-A(3',5')p] | 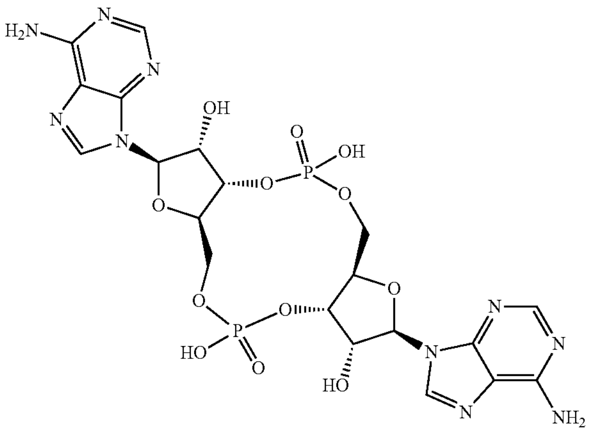 [SMILES: Nc1ncnc2c1ncn2[C@@H]1O[C@@H]2COP(=O)(O)O[C@H]3[C@@H](O)[C@H](n4cnc5c(N)ncnc54)O[C@@H]3COP(=O)(O)O[C@H]2[C@H]1O] |

TABLE 3-continued
| Abridged compound names and structures. | |
|---|---|
| Example number and abridged Compound names | Structure |
| cGAMP<br>3'3'-(G)(A)<br>cyclic-[G(3',5')p-A(3',5')p] | 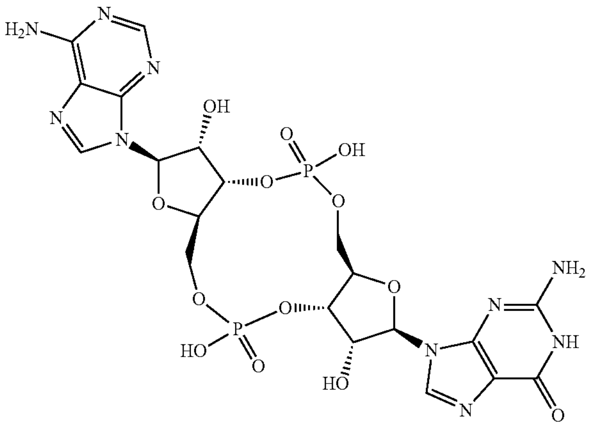 [SMILES: Nc1nc2c(ncn2[C@@H]2O[C@@H]3COP(=O)(O)O[C@H]4[C@@H](O)[C@H](n5cnc6c(N)ncnc65)O[C@@H]4COP(=O)(O)O[C@H]3[C@H]2O)c(=O)[nH]1] |
| RR-CDA<br>3'3'-RR-(A)(A)<br>dithio-(Rp,Rp)-cyclic-[A(3',5')p-A(3',5')p] | 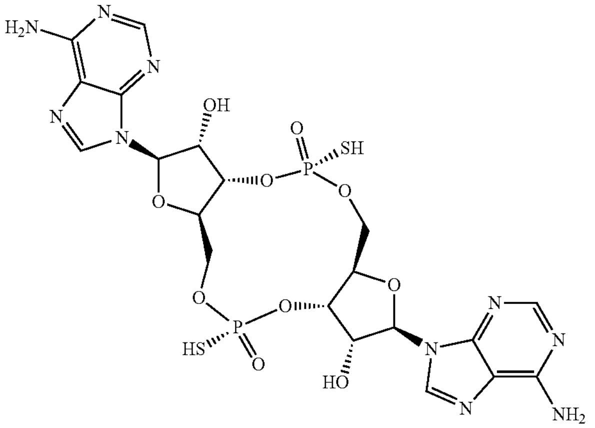 |
| RR-CDG<br>3'3'-RR-(G)(G)<br>dithio-(RpRp)-cyclic-[G(3',5')p-G(3',5')p] | 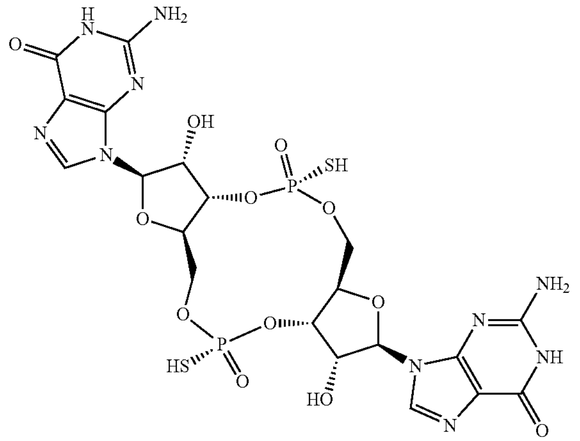 [SMILES: Nc1nc2c(ncn2[C@@H]2O[C@@H]3CO[P@@](=O)(S)O[C@H]4[C@@H](O)[C@H](n5cnc6c(=O)[nH]c(N)nc65)O[C@@H]4CO[P@@](=O)(S)O[C@H]3[C@H]2O)c(=O)[nH]1] |

TABLE 3-continued

| Abridged compound names and structures. | |
|---|---|
| Example number and abridged Compound names | Structure |
| RR-cGAMP 3'3'-RR-(G)(A) dithio-(Rp,Rp)-cyclic-[G(3',5')p-A(3',5')p] | 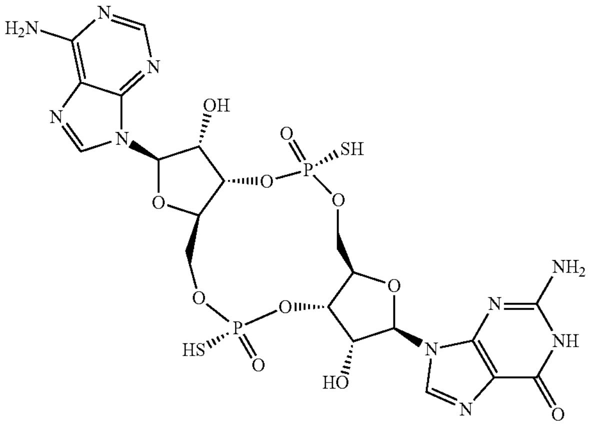 |
| ML-cGAMP 2'3'-(G)(A); cyclic-[G(2',5')pA(3',5')p] | 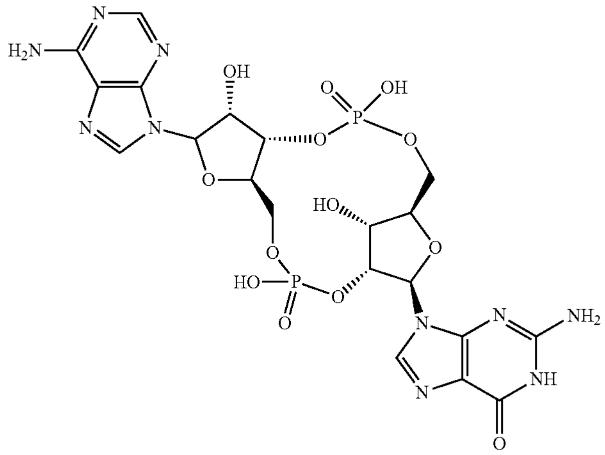 [SMILES: Nc1nc2c(ncn2[C@@H]2O[C@@H]3COP(=O)(O)O[C@@H]4[C@@H](COP(=O)(O)O[C@@H]2[C@@H]3O)OC(n2cnc3c(N)ncnc32)[C@@H]4O)c(=O)[nH]1] |

Abbreviations and Acronyms. SalPCl=Salicyl chlorophosphite (2-chloro-4H-benzo[d][1,3,2]dioxaphosphinin-4-one). DCA=dichloroacetic acid. DDTT=3-((N,N-dimethylaminomethylidene)amino)-3H-1,2,4-dithiazole-5-thione. DAST=diethylaminosulfur trifluoride. $NaHCO_3$=sodium bicarbonate. DCM=$CH_2Cl_2$=dichloromethane. EtOH=ethanol. EtOAc=ethyl acetate. KOAc=potassium acetate. MeCN=acetonitrile. MeOH=methanol. $NH_4OAc$=ammonium acetate. DMAP=N,N-dimethylpyridin-4-amine. DMOCP=2-chloro-5,5-dimethyl-1,3,2-dioxaphosphorinane-2-oxide. DMTCl=4,4'-dimethoxytrityl chloride. DMT=4,4-dimethoxytrityl. N-phenyltriflamide=1,1,1-trifluoro-N-phenyl-N-((trifluoromethyl)sulfonyl) methanesulfonamide. TBAF=tetrabutylammonium fluoride. TBS=tert-butyldimethylsilyl. TEAA=Triethylammonium acetate. TEA=trimethylamine. $TEAH^+$=triethylammonium. TEAB=treithylammonium bicarbonate. TFA=trifluoroacetic acid. TMSCl=trimethylsilyl chloride. HF=hydrofluoric acid. THF=tetrahydrofuran. G=Guanine. $G^{ib}$=isobutyryl guanine. A=adenine. $A^{Bz}$=benzoyl adenine. AMA=ammonium hydroxide/40% methylamine solution in water.

Example 1: Synthesis of 3',3'-RR-(2'F-A)(2'F-A) (6) and 3',3'-RS-(2'F-A)(2'F-A) (6a)

(2R,3R,3aR,5R,7aR,9R,10R,10aR,12R,14aR)-2,9-bis(6-amino-9H-purin-9-yl)-3,10-difluoro-5,12-dimercaptooctahydro-2H,7H-difuro[3,2-d:3',2'-j][1,3,7,9]tetraoxa[2,8]diphosphacyclododecine 5,12-dioxide (6), also referred to as 3',3'-RR-(2'F-A)(2'F-A) or dithio-(Rp,Rp)-cyclic-[2'F-A(3',5')p-2'F-A(3',5')p], and (2R,3R,3aR,5R,7aR,9R,10R,10aR,12S,14aR)-2,9-bis(6-amino-9H-purin-9-yl)-3,10-difluoro-5,12-dimercaptooctahydro-2H,7H-difuro[3,2-d:3',2'-j][1,3,7,9]tetraoxa[2,8]diphosphacyclododecine 5,12-dioxide (6a), 3',3'-RS-(2'F-A)(2'F-A) or dithio-(Rp,Sp)-cyclic-[2'F-A(3',5')p-2'F-A(3',5')p], were prepared according to the following scheme 1.

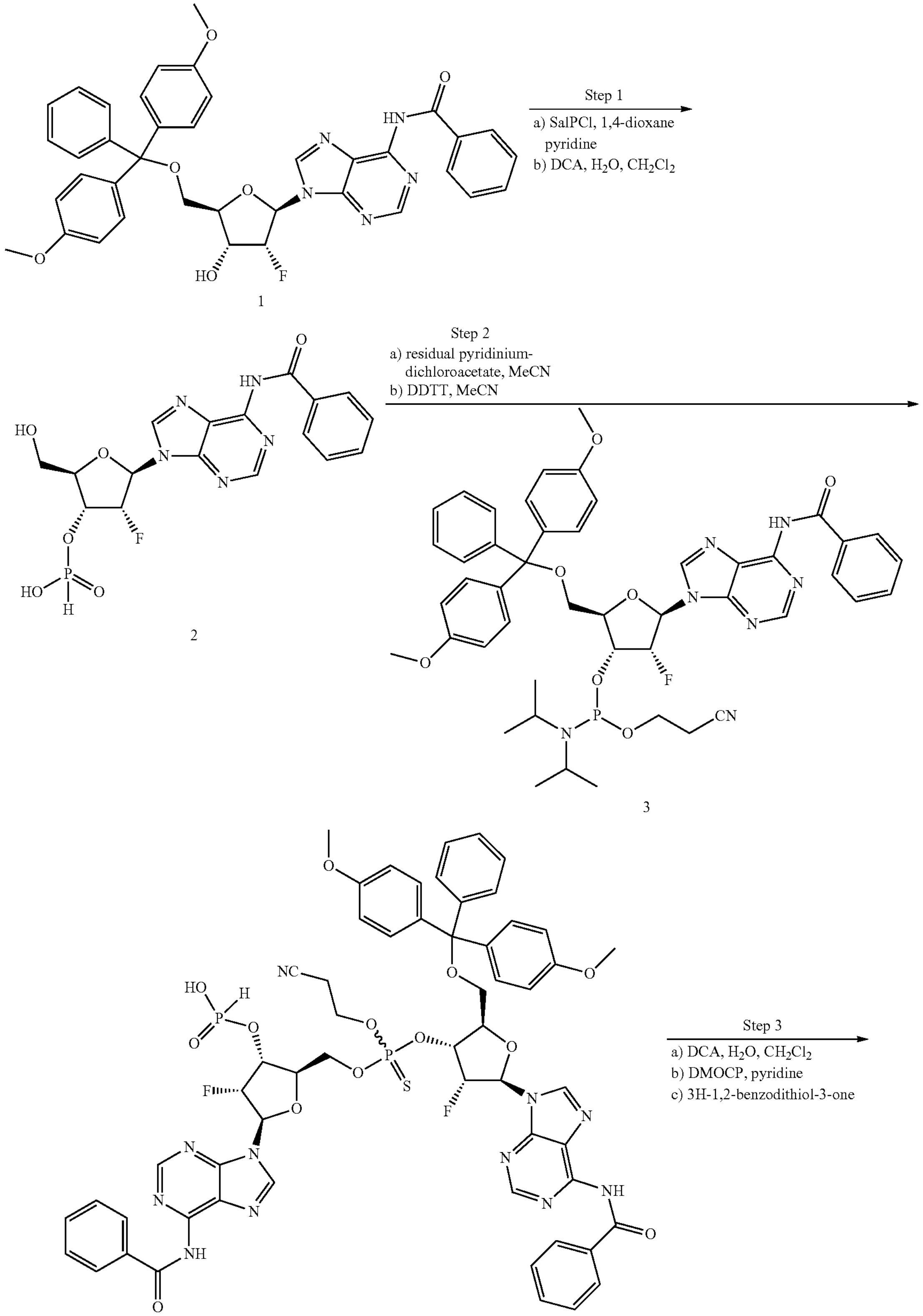
1
2
3
4

-continued

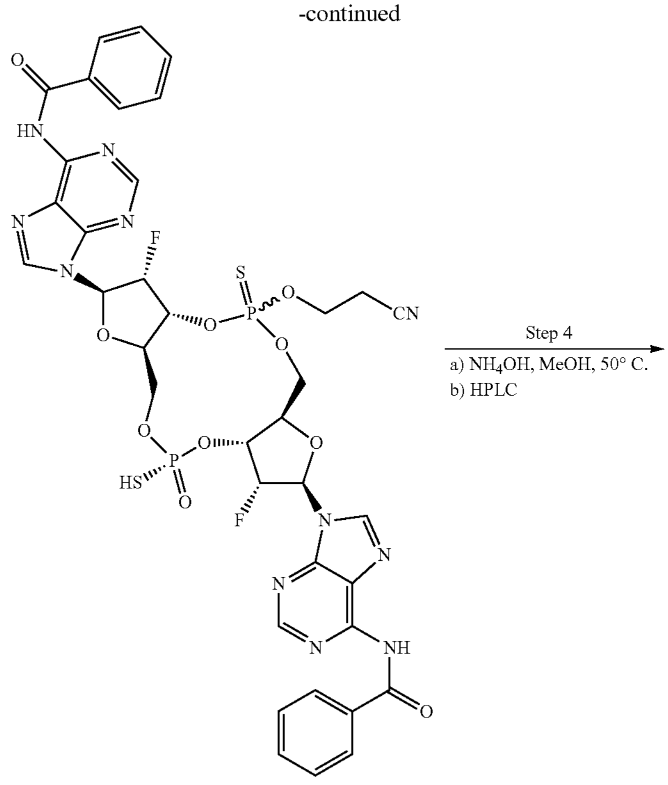

5

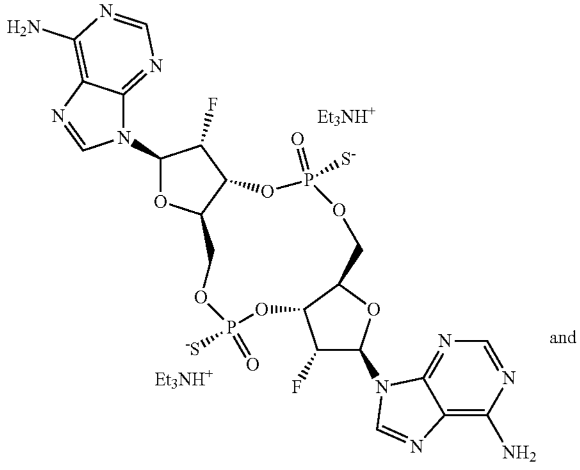

6 and

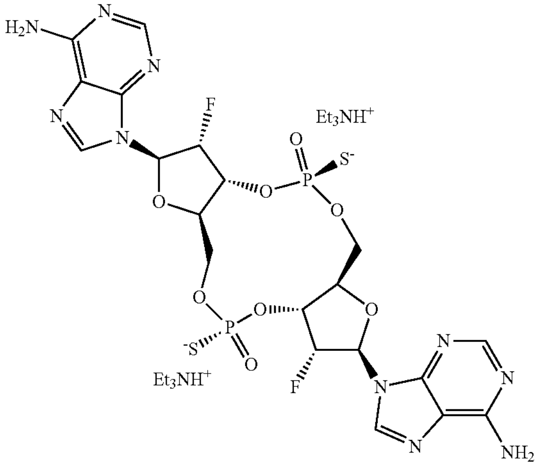

6a

Step 1:

Preparation of (2R,3R,4R,5R)-5-(6-benzamido-9H-purin-9-yl)-4-fluoro-2-(hydroxymethyl)tetrahydrofuran-3-yl hydrogen phosphonate (2): To a solution of N-(9-((2R,3R,4R,5R)-5-((bis(4-methoxyphenyl)(phenyl)methoxy)methyl)-3-fluoro-4-hydroxytetrahydrofuran-2-yl)-9H-purin-6-yl)benzamide (1, 2.0 g, 3.0 mmol, ChemGenes) in 1,4-dioxane (25 mL) and pyridine (8 mL) was added a solution of SalPCl (0.84 g, 4.1 mmol) in 1,4-dioxane (12 mL). After 30 min. to the stirred reaction mixture at room temperature was introduced water (4 mL), and the resulting mixture was poured into a 1N aqueous $NaHCO_3$ solution (100 mL). This aqueous mixture was extracted with EtOAc (3×100 mL) and the layers were partitioned. The EtOAc extracts were combined and concentrated to dryness in vacuo as a colorless foam. The colorless foam was dissolved in $CH_2Cl_2$ (30 mL) to give a colorless solution. To this solution was added water (0.5 mL) and a 6% (v/v) solution of DCA in $CH_2Cl_2$ (30 mL). After ten min of stirring at room temperature, to the red solution was charged pyridine (3.5 mL). The resulting white mixture was concentrated in vacuo and water was removed as an azeotrope after concentration with MeCN (30 mL). This azeotrope process was repeated two more times with MeCN (30 mL). On the last evaporation, the resulting white slurry of compound 2 was left in MeCN (15 mL).

Step 2:

Preparation of (2R,3R,4R,5R)-5-(6-benzamido-9H-purin-9-yl)-2-((((((2R,3R,4R,5R)-5-(6-benzamido-9H-purin-9-yl)-2-((bis(4-methoxyphenyl)(phenyl)methoxy)methyl)-4- fluorotetrahydrofuran-3-yl)oxy)(2-cyanoethoxy) phosphorothioyl)oxy)methyl)-4-fluorotetrahydrofuran-3-yl hydrogen phosphonate (4): To a solution of (2R,3R,4R,5R)-5-(6-benzamido-9H-purin-9-yl)-2-((bis(4-methoxyphenyl) (phenyl)methoxy)methyl)-4-fluorotetrahydrofuran-3-yl (2-cyanoethyl) diisopropylphosphoramidite (3, 2.5 g, 2.9 mmol, ChemGenes) in MeCN (20 mL) was dried through concentration in vacuo. This process was repeated two more times to remove water as an azeotrope. On the last azeotrope, to the solution of compound 3 in MeCN (7 mL) was introduced ten 3 Å molecular sieves and the solution was stored under an atmosphere of nitrogen. To a stirred mixture of compound 2 with residual pyridin-1-ium dichloroacetate in MeCN (15 mL) was added the solution of compound 3 in MeCN (7 mL). After five min. to the stirred mixture was added DDTT (650 mg, 3.2 mmol). After 30 min, the yellow mixture was concentrated in vacuo to give compound 4 as a yellow oil.

Step 3:

Preparation of N,N'-(((2R,3R,3aR,7aR,9R,10R,10aR,12R,14aR)-5-(2-cyanoethoxy)-3,10-difluoro-12-mercapto-12-oxido-5-sulfidooctahydro-2H,7H-difuro[3,2-d:3',2'-j][1,3,7,9]tetraoxa[2,8]diphosphacyclododecine-2,9-diyl)bis(9H-purine-9,6-diyl))dibenzamide (5): To a solution of compound 4 in $CH_2Cl_2$ (60 mL) was added water (0.35 mL) and a 6% (v/v) solution of DCA in $CH_2Cl_2$ (60 mL). After ten min at room temperature, to the red solution was introduced pyridine (20 mL). The resulting yellow mixture was concentrated in vacuo until approximately 20 mL of the yellow mixture remained. To the yellow mixture was introduced pyridine (20 mL) and the mixture was concentrated in vacuo until approximately 20 mL of the yellow mixture remained. To the yellow mixture was added pyridine (30 mL) and the mixture was concentrated in vacuo until approximately 30 mL of the yellow mixture remained. To the stirred yellow mixture in pyridine (30 mL) was added DMOCP (1.6 g, 8.4 mmol). After seven min. to the dark orange solution was added water (1.4 mL), followed immediately by the introduction of 3H-1,2-benzodithiol-3-one (0.71 mg, 4.2 mmol). After five min, the dark orange solution was poured into a 1N aqueous $NaHCO_3$ solution (400 mL). After ten min, the biphasic mixture was extracted with EtOAc (200 mL) and diethyl ether (200 mL). After separation, the aqueous layer was back extracted with EtOAc (200 mL) and diethyl ether (200 mL). The organic extracts were combined and concentrated in vacuo. To the concentrated yellow oil was added toluene (75 mL) and the mixture was evaporated in vacuo to remove residual pyridine. This procedure was repeated twice with toluene (75 mL). The resulting oil was purified by silica gel chromatography (0% to 10% MeOH in $CH_2Cl_2$) to provide compound 5 (67 mg, 2.5% yield) as an orange oil.

Step 4:

Preparation of 3',3'-RR-(2'F-A)(2'F-A) (6) and 3',3'-RS-(2'F-A)(2'F-A) (6a): To a stirred solution of compound 5 (65 mg, 0.07 mmol) in MeOH (0.9 mL) was added aqueous ammonium hydroxide (0.9 mL) and the orange slurry was heated at 50° C. After two hours, the orange solution was allowed to cool and concentrated in vacuo. The orange residue was purified by reverse phase silica gel chromatography (0% to 30% MeCN in 10 mM aqueous TEAA) to obtain compound 6 (18 mg, 38% yield) as a white mono-triethylammonium salt after lyophilization. LCMS-ESI: 693.25 $[M-H]^-$ (calculated for $C_{20}H_{22}F_2N_{10}O_8P_2S_2$: 694.305); $R_t$: 16.698' min by HPLC conditions (10 mM TEAA, 2% to 20%); $R_t$: 20.026'. min by LCMS conditions (20 mM $NH_4OAc$, 2% to 20%). $^1H$ NMR (400 MHz, 45° C., $D_2O$) δ 8.44 (s, 2H), 8.24 (s, 2H), 6.52 (d, J=16.4 Hz, 2H), 5.80 (d, J=3.6 Hz, 1H), 5.67 (d, J=4.0 Hz, 1H), 5.37-5.26 (m, 2H), 4.77-4.65 (m, 4H), 4.22 (dd, J=11.4 Hz, 6.0 Hz, 2H), 3.34 (q, J=7.0 Hz, 6H), 1.43 (t, J=7.0 Hz, 9H). $^{19}F$ NMR (400 MHz, 45° C., $D_2O$) δ −200.74 to −200.98 (m). $^{31}P$ NMR (45° C., $D_2O$) δ 54.46. The stereochemistry of this compound, as depicted in Scheme 1, was confirmed by the co-crystal structure bound to wild type STING protein.

The sodium salt of compound 6 was also prepared. On a small micro column (1 mL capacity) from Bio-Rad (Bio-Spin, Cat #732-6008) was loaded Bio-Rad's AG® 50W-X2 Resin (catalog 143-5241, biotech grade, 100-200 mesh, Hydrogen form, CAS 69011-20-7) up to the 0.2 marker on the micro column. The resin was soaked five times with millipore filtered water (0.5 mL) and the resulting water washes were allowed to flow through under gravity. The washes were discarded. The resin was treated with 2 mL of 1 N aqueous sodium hydroxide solution. Afterwards, the condensed resin was washed six times with 2 mL of millipore filtered water. The $TEAH^+$ salt of compound 6 (5 mg) was dissolved in 2 mL of millipore filtered water and loaded onto the resin. The resin was washed six times with 2 mL of millipore filtered water and the desired product was collected from the eluting fractions and lyophilized overnight to provide the sodium salt of compound 6 (3 mg).

The Rp,Sp isomer was also isolated after purification in the reverse phase chromatography step, to provide compound 6a (9.0 mg, 99%) as the bis-triethylammonium salt after lyophilization. LCMS-ESI: 693.30 $[M-H]^-$ (calculated for $C_{20}H_{22}F_2N_{10}O_8P_2S_2$: 694.05); $R_t$ 13.830' min by HPLC conditions (10 mM TEAA, 2% to 20%). $R_t$ 15.032' min by LCMS conditions (20 mM $NH_4OAc$, 2% to 20%). $^1H$ NMR. (400 MHz, 45° C., $D_2O$) δ 8.65 (s, 1H), 8.50 (s, 1H), 8.34 (s, 1H), 8.26 (s, 1H), 6.58 (dd, J=16.4, 2.8 Hz, 2H), 6.00 (dd, J=51.2, 3.6 Hz, 1H), 5.69 (dd, J=51.2, 3.8 Hz, 1H), 5.32-5.15 (m, 2H), 4.77-4.67 (m, 3H), 4.61 (d, J=12.4 Hz, 1H), 4.25 (dd, J=11.8, 4.2 Hz, 2H), 3.33 (q, J=7.2 Hz, 12H), 1.43 (t, J=7.2 Hz, 18H). $^{19}F$ NMR (400 MHz, 45° C., $D_2O$) δ −200.75 to −201.31 (m). $^{31}P$ NMR (45° C., $D_2O$) δ 54.69, 54.64.

The compounds (2R,3S,3aR,5R,7aR,9R,10S,10aR,12R,14aR)-2,9-bis(6-amino-9H-purin-9-yl)-3,10-difluoro-5,12-dimercaptooctahydro-2H,7H-difuro[3,2-d:3',2'-j][1,3,7,9]tetraoxa[2.8]diphosphacyclododecine 5,12-dioxide (7), also referred to as 3',3'-RR-(2'βF-A)(2'αF-A) or dithio-(Rp,Rp)-cyclic-[2',βF-A(3',5')p-2'βF-A(3',5')p] and (2R,3S,3aR,5R,7aR,9R,10S,10aR,12S,14aR)-2,9-bis(6-amino-9H-purin-9-yl)-3,10-difluoro-5,12-dimercaptooctahydro-2H,7H-difuro[3,2-d:3',2'-j][1,3,7,9]tetraoxa[2,8]diphosphacyclododecine 5,12-dioxide (7a), also referred to as 3',3'-RS-(2'βF-A)(2'βF-A) or dithio-(Rp,Sp)-cyclic-[2'βF-A(3',5')p-2'βF-A(3',5')p].

7

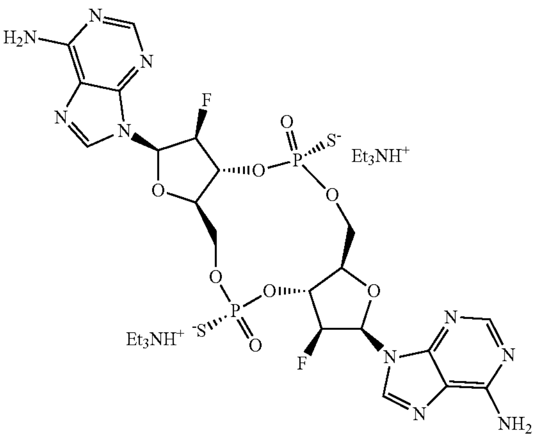

and

7a

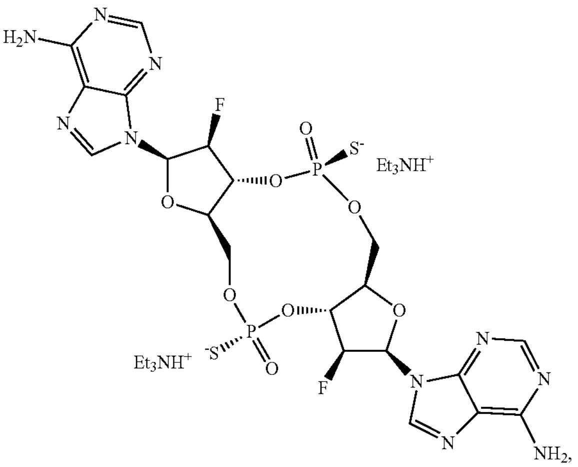

were prepared similarly to the method of Scheme 1, where N-(9-((2R,3S,4R,5R)-5-((bis(4-methoxyphenyl)(phenyl)methoxy)methyl)-3-fluoro-4-hydroxytetrahydrofuran-2-yl)-9H-purin-6-yl)benzamide (0.4 g, 0.6 mmol, Glen Research, Sterling, Va.) was used in place of compound 1 in Step 1, and (2R,3R,4S,5R)-5-(6-benzamido-9H-purin-9-yl)-2-((bis(4-methoxyphenyl)(phenyl)methoxy)methyl)-4-fluorotetrahydrofuran-3-yl (2-cyanoethyl) diisopropylphosphoramidite (0.5 g, 0.6 mmol. Glen Research) was used in place of compound 3 in Step 2. Compound 7 (6.4 mg, 97% purity) and compound 7a (5.0 mg, 93% purity) were obtained as the bis-triethylammonium salts after purification by reverse phase HPLC and lyophilization.

Compound 7: LCMS-ESI: 695.75 $[M+H]^+$ (calculated for $C_{20}H_{22}F_2N_{10}O_8P_2S_2$: 694.05); $R_t$ 16.779' min by HPLC conditions (10 mM TEAA, 2% to 20%). $R_t$ 7.616' min by LCMS conditions (20 mM $NH_4OAc$, 2% to 50%). $^1H$ NMR. (400 MHz, 45 OC, $D_2O$) δ 8.65 (s, 2H), 8.49 (s, 2H), 6.79 (dd, J=14.4, 4.2 Hz, 2H), 5.86 (br s, 1H), 5.74 (br s, 1H), 5.52-5.44 (m, 2H), 4.59 (br s, 2H), 4.51-4.40 (m, 4H), 3.39 (q, J=7.2 Hz, 12H), 1.48 (t, J=7.2 Hz, 18H). $^{19}F$ NMR (400 MHz, 45° C., $D_2O$) δ −196.47 to −196.70 (m).

Compound 7a: LCMS-ESI: 695.75 $[M+H]^+$ (calculated for $C_{20}H_{22}F_2N_{10}O_8P_2S_2$: 694.05); $R_t$ 14.216' min by HPLC conditions (10 mM TEAA, 2% to 20%). $R_t$ 8.106' min by LCMS conditions (20 mM $NH_4OAc$, 2% to 50%). $^1H$ NMR. (400 MHz, 45° C., $D_2O$) δ 8.65 (s, 1H), 8.61 (s, 1H), 8.44 (s, 2H), 6.73 (d, J=14.8 Hz, 2H), 5.88-5.64 (m, 2H), 5.48-5.41 (m, 2H), 4.57 (br s, 2H), 4.46-4.35 (m, 4H), 3.34 (q, J=7.2 Hz, 12H), 1.43 (t, J=7.2 Hz, 18H). $^{19}F$ NMR (400 MHz, 45° C., $D_2O$) δ −196.98 to −197.61 (m). $^{31}P$ NMR (45° C., $D_2O$) δ 57.28, 55.16, 55.09.

Example 2: Synthesis of 3',3'-RR-(2'F-G)(2'F-A) (14) and 3',3'-RS-(2'F-G)(2'F-A) (14a)

2-Amino-9-((2R,3R,3aR,5R,7aR,9R,10R,10aR,12R,14aR)-9-(6-amino-9H-purin-9-yl)-3,10-difluoro-5,12-dimercapto-5,12-dioxidooctahydro-2H,7H-difuro[3,2-d:3',2'-j][1,3,7,9]tetraoxa[2,8]diphosphacyclododecin-2-yl)-1,9-dihydro-6H-purin-6-one (14), also referred to as 3',3'-RR-(2'F-G)(2'F-A) or dithio-(Rp,Rp)-cyclic-[2'F-G(3',5')p-2'F-A(3',5')p], and 2-amino-9-((2R,3R,3aR,5R,7aR,9R,10R,10aR,12S,14aR)-9-(6-amino-9H-purin-9-yl)-3,10-difluoro-5,12-dimercapto-5,12-dioxidooctahydro-2H,7H-difuro[3,2-d:3',2'-j][1,3,7,9]tetraoxa[2,8]diphosphacyclododecin-2-yl)-1,9-dihydro-6H-purin-6-one (14a), also referred to as 3',3'-RS-(2'F-G)(2'F-A) or dithio-(Rp,Sp)-cyclic-[2'F-G(3',5')p-2'F-A(3',5')p], were prepared according to the following scheme 2.

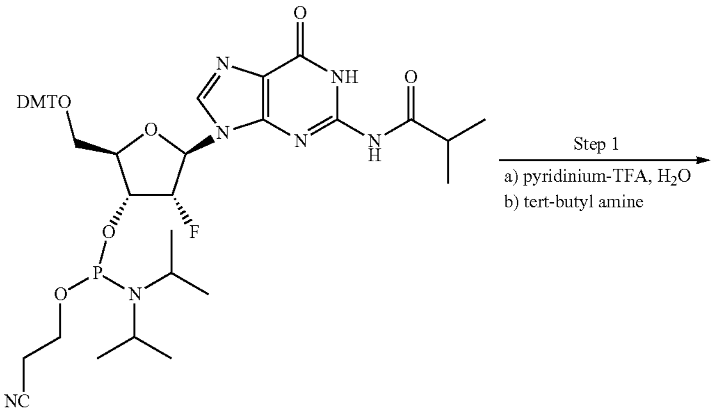

8

-continued
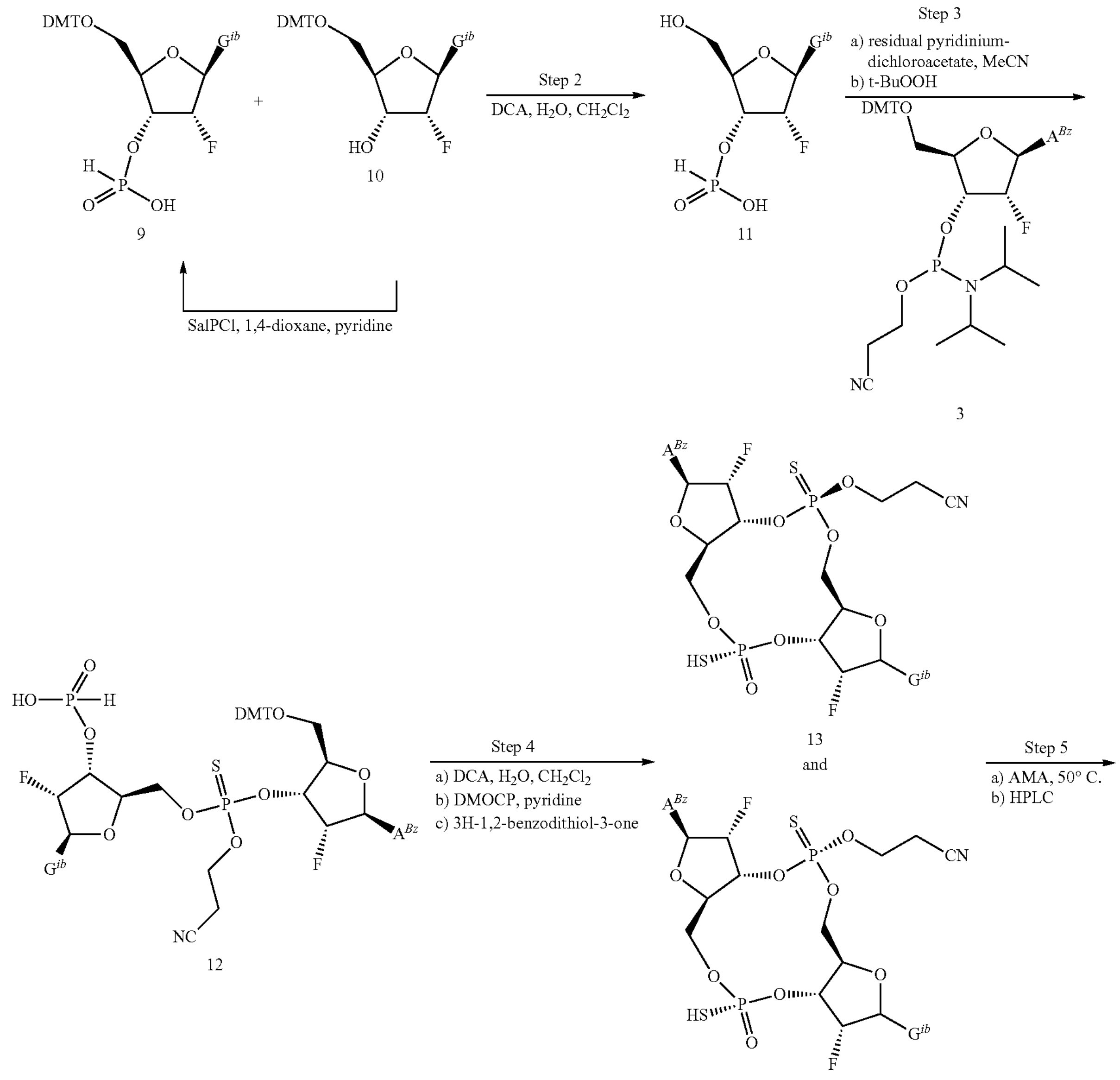
9 + 10 → 11; 3; 12; 13 and 13a
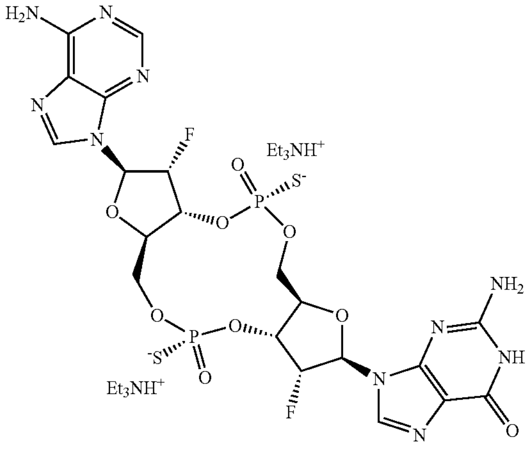
14
or
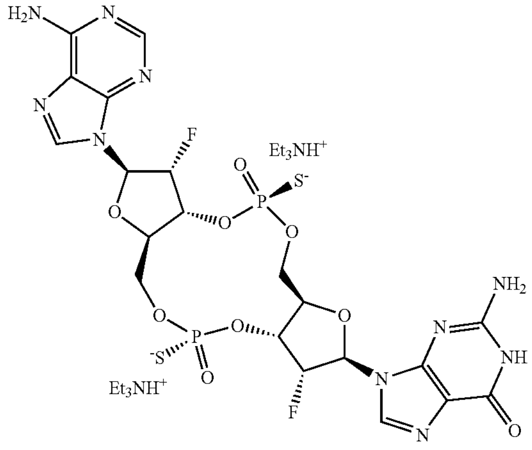
14a Step 1:

Preparation of (2R,3R,4R,5R)-2-((bis(4-methoxyphenyl)(phenyl)methoxy)methyl)-4-fluoro-5-(2-isobutyramido-6-oxo-1,6-dihydro-9H-purin-9-yl)tetrahydrofuran-3-yl hydrogen phosphonate (9): To a solution of (2R,3R,4R,5R)-2-((bis(4-methoxyphenyl)(phenyl)methoxy)methyl)-4-fluoro-5-(2-isobutyramido-6-oxo-1,6-dihydro-9H-purin-9-yl) tetrahydrofuran-3-yl (2-cyanoethyl) diisopropylphosphoramidite (8, 1 g. ChemGenes) in acetonitrile (5 mL) and water (36 μL) was added pyridinium trifluoroacetate (232 mg). The reaction was stirred for 1 min followed by the addition of tert-butylamine (5 mL). The reaction proceeded for 10 min and was concentrated in vacuo, and co-evaporated in vacuo with acetonitrile (2×10 mL) to give a mixture of compounds 9 and 10 ~(4:1). The mixture was taken up in anhydrous 1,4-dioxane (9 mL) followed by addition of anhydrous pyridine (3 mL) and a solution of SalPCl (210 mg) in 1,4-dioxane (4.5 mL). After stirring for 15 min the reaction mixture was quenched with water (1.5 mL) followed by the addition of saturated $NaHCO_3$ solution (60 mL). The mixture was extracted 3×60 mL with EtOAc and the combined organic layers were concentrated in vacuo to give a 1.7 g crude mixture of mostly compound 9 (6:1).

Step 2:

Preparation of (2R,3R,4R,5R)-4-fluoro-2-(hydroxymethyl)-5-(2-isobutyramido-6-oxo-1,6-dihydro-9H-purin-9-yl)tetrahydrofuran-3-yl hydrogen phosphonate (11): To a solution of compound 9 (1.7 g) and DCM (12 mL) was added water (0.18 mL) followed by a solution of 6% solution of DCA in DCM (12 mL). After 10 min the reaction mixture was quenched with pyridine (1.4 mL) and then concentrated in vacuo. The crude material was co-evaporated in vacuo with 3×6.6 mL anhydrous acetonitrile leaving 1.4 mL of compound 11.

Step 3:

Preparation of (2R,3R,4R,5R)-2-((((((2R,3R,4R,5R)-5-(6-benzamido-9H-purin-9-yl)-2-((bis(4-methoxyphenyl)(phenyl)methoxy)methyl)-4-fluorotetrahydrofuran-3-yl)oxy)(2-cyanoethoxy)phosphorothioyl)oxy)methyl)-4-fluoro-5-(2-isobutyramido-6-oxo-1,6-dihydro-9H-purin-9-yl)tetrahydrofuran-3-yl hydrogen phosphonate (12): A solution of compound 3 (co-evaporated in vacuo 3×6.6 mL with anhydrous acetonitrile, leaving 4 mL) in 4 mL of anhydrous acetonitrile was added and the 1.4 mL solution of compound 11 and the reaction was stirred for 2 min. DDTT (0.226 g) was added and the reaction proceeded for 30 min. then was concentrated in vacuo to dryness to give 3.6 g of compound 12.

Step 4:

Preparation of N-(9-((2R,3R,3aR,5R,7aR,9R,10R,10aR,12R,14aR)-5-(2-cyanoethoxy)-3,10-difluoro-9-(2-isobutyramido-6-oxo-1,6-dihydro-9H-purin-9-yl)-12-mercapto-12-oxido-5-sulfidooctahydro-2H,7H-difuro[3,2-d:3',2'-j][1,3,7,9]tetraoxa[2.8]diphosphacyclododecin-2-yl)-9H-purin-6-yl)benzamide (13): To a solution of compound 12 (1.8 g) in DCM (12 mL) was added water (60 μL) followed by a 6% solution of DCA in DCM (12 mL). After 10 min the reaction mixture was quenched with pyridine (5 mL) and concentrated in vacuo to remove the DCM. An additional amount of pyridine (15 mL) was added and the mixture was concentrated in vacuo to 10 mL. DMOCP (292 mg) was added and the reaction was stirred for 3 min followed by the addition of water (266 μL) and then 3-H-1,3-benzodithiol-3-one (130 mg). After 5 min the reaction was quenched with a saturated solution of $NaHCO_3$ (75 mL) and extracted with a 1:1 mixture of ethyl ether and EtOAc. The aqueous layer was further extracted with an additional 25 mL of 1:1 mixture of ethyl ether and EtOAc. The combined organic layers were concentrated in vacuo to give 1.2 g of crude compound 13. Normal phase silica gel purification (100% DCM to 90 DCM:10 MeOH) gave 50 mg of compound 13 as a white solid (enriched in the $R_pR_p$ diastereomer) and 20 mg of N-(9-((2R,3R,3aR,5S,7aR,9R,10R,10aR,12R,14aR)-5-(2-cyanoethoxy)-3,10-difluoro-9-(2-isobutyramido-6-oxo-1,6-dihydro-9H-purin-9-yl)-12-mercapto-12-oxido-5-sulfidooctahydro-2H,7H-difuro[3,2-d:3',2'-j][1,3,7,9]tetraoxa[2,8]diphosphacyclododecin-2-yl)-9H-purin-6-yl)benzamide (13a) enriched in the $R_pS_p$ diastereomer.

Step 5:

Preparation of RR-(2'F-G)(2'F-A) (14) and 3',3'-RS-(2'F-G)(2'F-A) (14a): A solution of $R_pR_p$ enriched compound 13 (50 mg) in AMA (0.84 mL) and EtOH (0.3 6 mL) was heated to 50° C. for 4 h. The reaction mixture was cooled to room temperature and sparged with argon for 10 min. then concentrated in vacuo. Purification by reverse phase C18 MPLC and preparative HPLC gave 9 mg of compound 14 as the tris-triethylammonium salt. LCMS-ESI: 711.30 $[M+H]^+$ (calculated for $C_{20}H_{22}F_2N_{10}O_9P_2S_2$: 710.05); $R_t$: 12.7 min (2-50% MeCN/$NH_4OAc$ (20 mM) buffer, 20 min, 1 mL/min. 5 μm Acclaim 120). $^1H$ NMR (400 MHz, 45° C., $D_2O$) δ 8.53 (s, 1H), 8.35 (s, 1H), 8.10 (s, 1H), 5.72 (dd, J=14.0, 4.4 Hz, 1H), 5.58 (dd, J=14.0, 4.0 Hz, 1H), 5.31-5.22 (m, 2H), 4.70-4.59 (m, 2H), 4.24-4.19 (m), 3.26 (q, J=7.2 Hz, 21H), 2.05 (s, 1.7H), 1.40 (t, J=7.2 Hz, 32H). $^{19}F$ NMR (400 MHz, 45° C., $D_2O$) δ −199.2 (td, J=56, 24 Hz), 200.1 (td, J=56, 24, 20 Hz). $^{31}P$ NMR (45° C., $D_2O$) δ 54.91; 54.65. See FIG. 1.

RS-(2'F-G)(2'F-A) (14a) was similarly prepared and purified from the compound 13a enriched in the $R_pS_p$ diastereomer. A solution of compound 13a (20 mg) in AMA (0.42 mL) and EtOH (0.18 mL) was heated to 50° C. for 4 h. The reaction mixture was cooled to room temperature and sparged with argon for 10 min. then concentrated in vacuo. Purification by reverse phase C18 MPLC and preparative HPLC gave 6.9 mg of compound 14a as the tetra-triethylammonium salt. LCMS-ESI: 711.25 $[M+H]^+$ (calculated for $C_{20}H_{22}F_2N_{10}O_9P2S_2$: 710.05); $R_t$: 8.7 min (2-50% MeCN/$NH_4OAc$ (20 mM) buffer, 20 min, 1 mL/min. 5 μm Acclaim 120). $^1H$ NMR (400 MHz, 45° C., $D_2O$) δ 8.53 (s, 1H), 8.37 (s, 1H), 8.23 (s, 1H), 6.62 (d, J=17.6 Hz, 1H), 6.42 (d, J=17.6 Hz, 1H), 5.97 (dd, J=51.6, 4 Hz, 1H), 5.64 (dd, J=51.6, 4 Hz, 1H), 5.27-5.25 (m, 2H), 4.64-4.52 (m, 2H), 4.24 (td, J=10.8 Hz, 3.2 Hz, 2H), 3.27 (q, J=7.2 Hz, 24H), 2.05 (s, 2H), 1.40 (t, J=7.2 Hz, 36H). $^{19}F$ NMR (400 MHz, 45° C., $D_2O$) δ −199.8 (td, J=53, 18 Hz), −200.9-201.1 (m), $^{31}P$ NMR (45° C., $D_2O$) δ 55.3; 54.62.

Example 3: Synthesis of 3',3'-RR-(2'F-G)(2'F-G) (17) and 3',3'-RS-(2'F-G)(2'F-G) (17a)

9,9'-((2R,3R,3aR,5R,7aR,9R,10R,10aR,12R,14aR)-3,10-difluoro-5,12-dimercapto-5,12-dioxidooctahydro-2H,7H-difuro[3,2-d:3',2'-j][1,3,7,9]tetraoxa[2,8]diphosphacyclododecine-2,9-diyl)bis(2-amino-1,9-dihydro-6H-purin-6-one) (17), also referred to as 3',3'-RR-(2'F-G)(2'F-G) or dithio-(Rp,Rp)-cyclic-[2'F-G(3',5')p-2' F-G(3',5')p], and 9,9'-((2R,3R,3aR,5R,7aR,9R,10R,10aR,12S,14aR)-3,10-difluoro-5,12-dimercapto-5,12-dioxidooctahydro-2H,7H-difuro[3,2-d:3',2'-j][1,3,7,9]tetraoxa[2,8]diphosphacyclododecine-2,9-diyl)bis(2-amino-1,9-dihydro-6H-purin-6-one) (17a), also referred to as 3',3'-RS-(2'F-G)(2'F-G) or dithio-(Rp,Sp)-cyclic-[2'F-G(3',5')p-2'F-G(3',5')p], were prepared according to the following scheme 3.

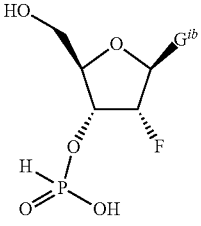

11

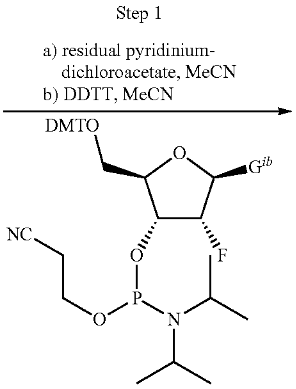

8

-continued

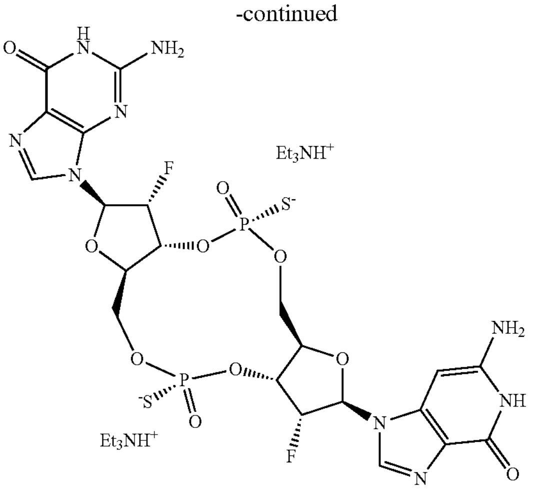

17 or

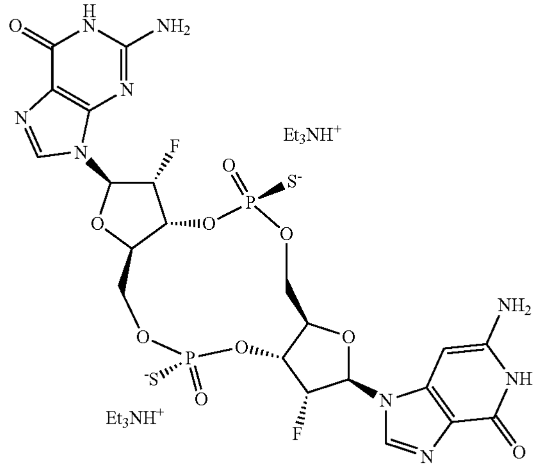

17a

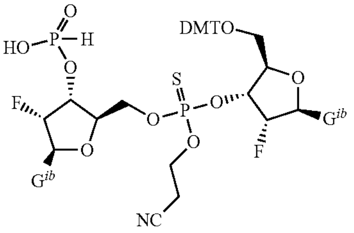

15

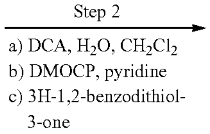

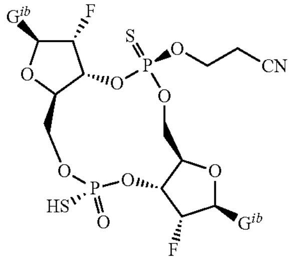

16 and

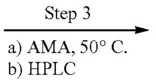

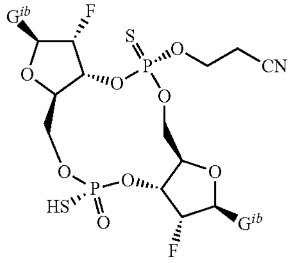

16a

Step 1:

Preparation of (2R,3R,4R,5R)-2-((((((2R,3R,4R,5R)-2-((bis(4-methoxyphenyl)(phenyl)methoxy)methyl)-4-fluoro-5-(2-isobutyramido-6-oxo-16-dihydro-9H-purin-9-yl)tetrahydrofuran-3-yl)oxy)(2-cyanoethoxy)phosphorothioyl)oxy)methyl)-4-fluoro-5-(2-isobutyramido-6-oxo-16-dihydro-9H-purin-9-yl)tetrahydrofuran-3-yl hydrogen phosphonate (15): A solution of compound 8 (ChemGenes, coevapped 3×13 mL with anhydrous MeCN) in 8 mL of anhydrous MeCN was added to compound 11 (in 3 mL of MeCN, prepared according to Scheme 2 from 3.4 g of compound 9) and the reaction was stirred for 2 min. DDTT (0.452 g) was added and the reaction proceeded for 30 min. then was concentrated to dryness in vacuo to give 8.14 g of compound 15.

Step 2:

Preparation of N,N'-(((2R,3R,3aR,5R,7aR,9R,10R,10aR,12R,14aR)-5-(2-cyanoethoxy)-3,10-difluoro-12-mercapto-12-oxido-5-sulfidooctahydro-2H,7H-difuro[3,2-d:3',2'-j][1,3,7,9]tetraoxa[2,8]diphosphacyclododecine-2,9-diyl)bis(6-oxo-6,9-dihydro-1H-purine-9,2-diyl))bis(2-methylpropanamide) (16): To a solution of crude compound 15 (8.4 g) in DCM (48 mL) was added water (240 μL) followed by a 6% solution of DCA in DCM (48 mL). After 10 min the reaction mixture was quenched with pyridine (20 mL) and concentrated in vacuo to remove the DCM. An additional amount of pyridine (60 mL) was added and the mixture was concentrated in vacuo to 20 mL. DMOCP (1.2 g) was added and the reaction was stirred for 3 min followed by the addition of water (1 mL) and then 3-H-1,3-benzodithiol-3-one (520 mg). After 5 min the reaction was quenched with a saturated solution of $NaHCO_3$ (300 mL) and extracted with a 1:1 mixture of ethyl ether and EtOAc. The aqueous layer was further extracted with DCM. The combined organic layers were concentrated in vacuo to give crude compound 16. Normal phase silica gel purification (100% DCM to 90 DCM:10 MeOH) gave 150 mg of 16 as a white solid (enriched in the $R_pR_p$ diastereomer) and 260 mg of N,N'-(((2R,3R,3aR,5S,7aR,9R,10R,10aR,12R,14aR)-5-(2-cyanoethoxy)-3,10-difluoro-12-mercapto-12-oxido-5-sulfidooctahydro-2H,7H-difuro[3,2-d:3',2'-j][1,3,7,9]tetraoxa[2,8]diphosphacyclododecine-2,9-diyl)bis(6-oxo-6,9-dihydro-1H-purine-9,2-diyl))bis(2-methylpropanamide) (16a) enriched in the $R_pS_p$ diastereomer.

Step 3:

Preparation of 3',3'-RR-(2'F-G)(2'F-G) (17): A solution of compound 16 (75 mg) in AMA (1.3 mL) and EtOH (0.54 mL) was heated to 50° C. for 4 h. The reaction mixture was cooled to room temperature and sparged with argon for 10 min, then concentrated in vacuo. Purification by reverse phase C18 MPLC and preparative HPLC gave 19 mg of compound 17 as the bis-triethylammonium salt. LCMS-ESI: 725.25 $[M-H]^-$ (calculated for $C_{20}H_{22}F_2N_{10}O_{10}P_2S_2$: 726.04); $R_t$: 10.44 min (2-50% MeCN/$NH_4$OAc (20 mM) buffer, 20 min. 1 mL/min. 5 μm Acclaim 120). $^1$H NMR (400 MHz, 45 OC, $D_2O$) δ 8.15 (s, 2H), 6.40 (d, J=18.8 Hz, 2H), 5.67 (d, J=52.0 Hz, 2H), 5.34-5.26 (m, 2H), 4.66-4.61 (m, 4H), 4.22-4.18 (m, 2H), 3.36 (q, J=7.2 Hz, 10H), 1.43 (t, J=7.2 Hz, 15H). $^{19}$F NMR (400 MHz, 45° C., $D_2O$) δ −199.2--199.4 (m), $^{31}$P NMR (45° C., $D_2O$) δ 54.7.

3',3'-RS-(2'F-G)(2'F-G) (17a) was similarly prepared. A solution of compound 16a (160 mg) in AMA (1.3 mL) and EtOH (0.54 mL) was heated to 50° C. for 4 h. The reaction mixture was cooled to room temperature and sparged with argon for 10 min, then concentrated in vacuo. Purification by reverse phase C18 MPLC and preparative HPLC gave 6.5 mg of compound 17a as the ammonium salt. LCMS-ESI: 725.25 $[M-H]^-$ (calculated for $C_{20}H_{22}F_2N_{10}O_{10}P_2S_2$: 726.04); $R_t$: 9.17 min (2-50% MeCN/$NH_4$OAc (20 mM) buffer, 20 min, 1 mL/min, 5 μm Acclaim 120). $^1$H NMR (400 MHz, 45° C., $D_2O$) δ 8.33 (s, 1H), 8.15 (s, 1H), 6.40 (dd, J=17.6, 7.6 Hz, 2H), 6.02 (dd, J=51.6, 3.2 Hz, 1H), 5.72 (dd, J=51.2, 3.2 Hz, 1H), 5.39-5.29 (m, 2H), 4.66-4.52 (m, 4H), 4.25-4.17 (m, 2H), 2.15 (s, 1.4H).

Example 4: Synthesis of 3',3'-RR-(A)(2'F-A) (22) and 3',3'-RS-(A)(2'F-A) (22a)

(2R,3R,3aR,5R,7aR,9R,10R,10aS,12R,14aR)-2,9-bis(6-amino-9H-purin-9-yl)-3-fluoro-10-hydroxy-5,12-dimercaptooctahydro-2H,7H-difuro[3,2-d:3',2'-j][1,3,7,9]tetraoxa[2,8]diphosphacyclododecine 5,12-dioxide (22), also referred to as 3',3'-RR-(A)(2'F-A) or dithio-(Rp,Rp)-cyclic-[A(3',5')p-2'F-A(3',5')p], and (2R,3R,3aR,5S,7aR,9R,10R,10aS,12R,14aR)-2,9-bis(6-amino-9H-purin-9-yl)-3-fluoro-10-hydroxy-5,12-dimercaptooctahydro-2H,7H-difuro[3,2-d:3',2'-j][1,3,7,9]tetraoxa[2,8]diphosphacyclododecine 5,12-dioxide (22a), also referred to as 3',3'-RS-(A)(2'F-A) or dithio-(Rp,Rp)-cyclic-[A(3',5')p-2'F-A(3',5')p], were prepared according to the following scheme 4.

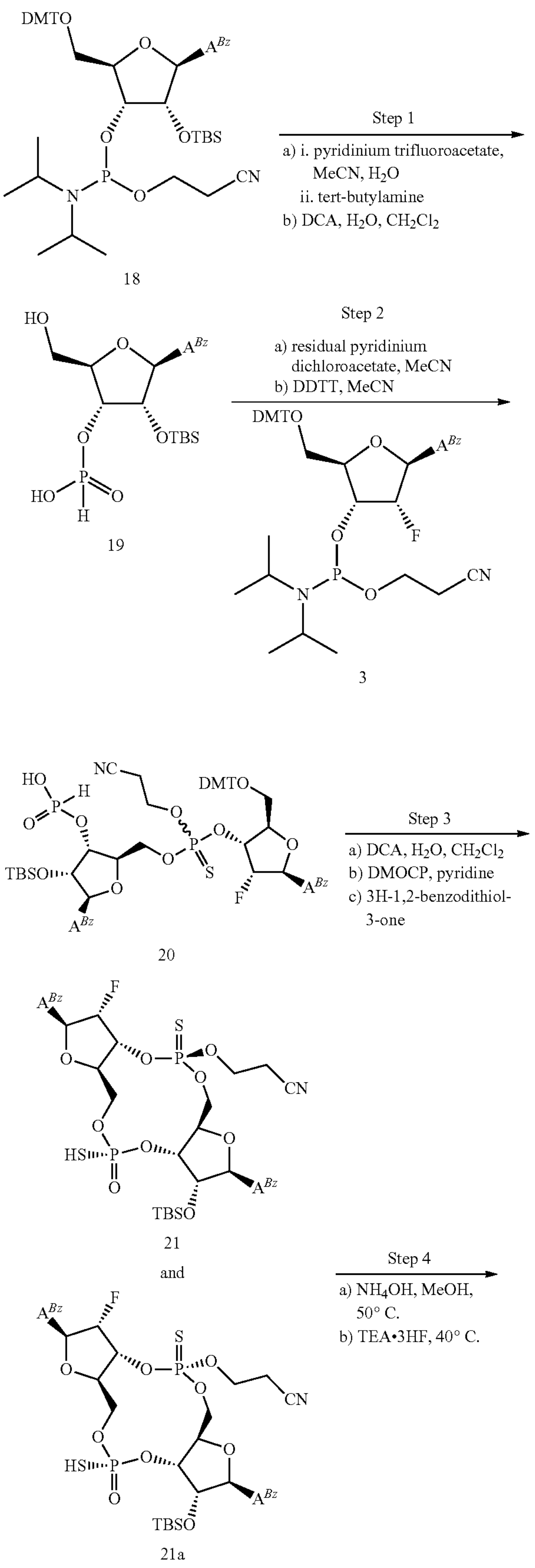

18
19
3
20
21
and
21a

-continued

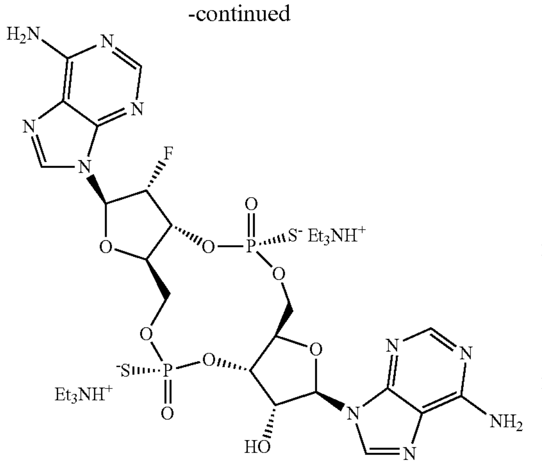

22 or

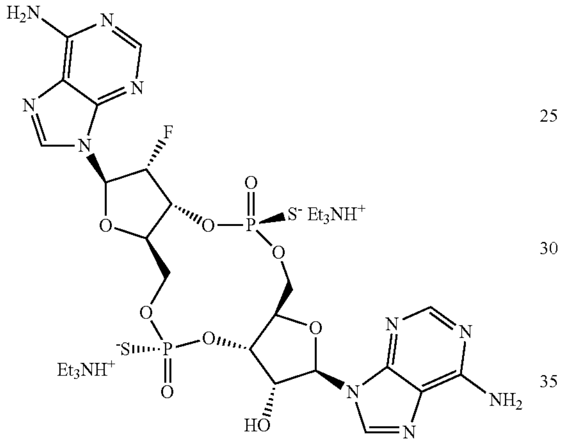

22a

Step 1:

Preparation of (2R,3R,4R,5R)-5-(6-benzamido-9H-purin-9-yl)-4-((tert-butyldimethylsilyl)oxy)-2-(hydroxymethyl)tetrahydrofuran-3-yl hydrogen phosphonate (19): To a solution of (2R,3R,4R,5R)-5-(6-benzamido-9H-purin-9-yl)-2-((bis(4-methoxyphenyl)(phenyl)methoxy)methyl)-4-((tert-butyldimethylsilyl)oxy)tetrahydrofuran-3-yl (2-cyanoethyl) diisopropylphosphoramidite (18, 2.0 g, 2.0 mmol, ChemGenes) in MeCN (10 mL) was added water (0.07 mL) followed by pyridinium trifluoroacetate (0.47 g, 2.4 mmol, 1.2 equiv, Aldrich). After stirring for eight minutes, to the colorless reaction was introduced tert-butylamine (10 mL, 95 mmol, 47 equiv, Aldrich). After ten minutes, the colorless solution was concentrated in vacuo and water was removed as an azeotrope after concentration three more times with MeCN (30 mL) to give a colorless foam. The colorless foam was dissolved in $CH_2Cl_2$ (25 mL), which resulted in a colorless solution. To this colorless solution was added water (0.36 mL) and a 6% (v/v) solution of DCA in $CH_2Cl_2$ (24 mL), which turned the colorless solution into a bright red solution. After ten minutes of stirring at room temperature, to the red solution was introduced pyridine (3 mL). The resulting white mixture was concentrated in vacuo and water was removed as an azeotrope after concentration with MeCN (30 mL). This azeotrope process was repeated three more times with MeCN (30 mL). On the last evaporation, the resulting white slurry of compound 19 was kept in MeCN (15 mL).

Step 2:

Preparation of (2R,3R,4R,5R)-5-(6-benzamido-9H-purin-9-yl)-2-((((((2R,3R,4R,5R)-5-(6-benzamido-9H-purin-9-yl)-2-((bis(4-methoxyphenyl)(phenyl)methoxy)methyl)-4-fluorotetrahydrofuran-3-yl)oxy)(2-cyanoethoxy)phosphorothioyl)oxy)methyl)-4-((tert-butyldimethylsilyl)oxy)tetrahydrofuran-3-yl hydrogen phosphonate (20): To a solution of compound 3 (0.1.8 g, 2.0 mmol, ChemGenes) in MeCN (20 mL) was dried through concentration in vacuo. This process was repeated two more times with MeCN (20 mL) to remove water as an azeotrope. On the last azeotrope, to the solution of compound 3 in MeCN (6 mL) was added six 3 Å molecular sieves and the solution was stored under an atmosphere of nitrogen. To a stirred mixture of compound 19 with residual pyridin-1-ium dichloroacetate in MeCN (15 mL) was introduced the solution of compound 3 in MeCN (6 mL). After ten minutes, to the stirred mixture was added DDTT (460 mg, 2.2 mmol). After 30 minutes, the yellow mixture was concentrated in vacuo to provide compound 20 as a yellow oil.

Step 3:

Preparation of N,N'-(((2R,3R,3aR,5R,7aR,9R,10R,10aR,12R,14aR)-3-((tert-butyldimethylsilyl)oxy)-12-(2-cyanoethoxy)-10-fluoro-5-mercapto-5-oxido-12-sulfidooctahydro-2H,7H-difuro[3,2-d:3',2'-j][1,3,7,9]tetraoxa[2,8]diphosphacyclododecine-2,9-diyl)bis(9H-purine-9,6-diyl))dibenzamide (21) and N,N'-(((2R,3R,3aR,5R,7aR,9R,10R,10aR,12S,14aR)-3-((tert-butyldimethylsilyl)oxy)-12-(2-cyanoethoxy)-10-fluoro-5-mercapto-5-oxido-12-sulfidooctahydro-2H,7H-difuro[3,2-d:3',2'-j][1,3,7,9]tetraoxa[2,8]diphosphacyclododecine-2,9-diyl)bis(9H-purine-9,6-diyl))dibenzamide (21a): To a light yellow solution of compound 20 in $CH_2Cl_2$ (50 mL) was introduced water (0.24 mL) and a 6% (v/v) solution of DCA in $CH_2Cl_2$ (50 mL), resulting in a red solution. After stirring for ten minutes at room temperature, to the red solution was added pyridine (15 mL). The resulting yellow mixture was concentrated in vacuo until approximately 25 mL of the yellow mixture remained. To the yellow mixture was added more pyridine (50 mL) and the mixture was concentrated in vacuo until approximately 30 mL of the yellow mixture remained. This process was repeated one more time with pyridine (50 mL) until 30 mL of the yellow mixture remained. To the stirred yellow mixture in pyridine (30 mL) was introduced DMOCP (1.1 g, 6.0 mmol, 3 equiv, Aldrich). After five minutes of stirring, to the dark orange solution was added water (1.0 mL), followed immediately by the addition of 3H-1,2-benzodithiol-3-one (0.5 g, 3.0 mmol, 1.5 equiv, Aldrich). After five minutes of stirring, the dark orange solution was poured into a 1N aqueous solution of $NaHCO_3$ (400 mL). After ten minutes of stirring, the biphasic mixture was extracted with EtOAc (200 mL) and $CH_2Cl_2$ (200 mL). After separation of the layers, the aqueous layer was back extracted two more times with $CH_2Cl_2$ (400 mL). The organic extracts were combined and concentrated in vacuo. To the concentrated yellow oil was introduced toluene (100 mL) and residual pyridine was removed in vacuo. This procedure was repeated one more time with toluene (100 mL). The resulting yellow oil was purified by silica gel chromatography (0% to 10% MeOH in $CH_2Cl_2$) to provide compound 21 (270 mg, 13%) as a yellow solid and compound 21a (120 mg).

Step 4:

Preparation of 3',3'-RR-(A)(2'F-A) (22) and 3',3'-RS-(A)(2'F-A) (22a): To a stirred solution of compound 21 (150 mg), enriched in the Rp,Rp diastereomer, in MeOH (2.0 mL) was introduced 30% aqueous ammonium hydroxide (2.0 mL) and the yellow slurry was heated at 50° C. After two hours, the yellow solution was allowed to cool to room temperature and the yellow solution was concentrated in vacuo. To the residual solid was added triethylamine trihydrofluoride (1.2 mL, Aldrich) and the yellow solution was heated to 40° C. After two hours, the yellow solution was allowed to cool to room temperature. This yellow solution was slowly introduced to a cooled solution of 1M TEAB (6 mL) and TEA (1.0 mL) in an ice-water bath. The resulting yellow mixture was allowed to stir for 30 minutes. The yellow mixture was purified by reverse phase chromatography on a C18 column (0% to 20% MeCN in 10 mM aqueous TEAA) to obtain compound 22 (24 mg, 23%) in 96% purity as a white tris-triethylammonium salt after lyophilization. LCMS-ESI: 693.25 $[M+H]^+$ (calculated for $C_{20}H_{23}FN_{10}O_9P_2S_2$: 692.06); $R_t$ 12.339' min by HPLC conditions (10 mM TEAA, 2% to 20%). $R_t$ 7.625' min by LCMS conditions (20 mM $NH_4OAc$, 2% to 20%). $^1H$ NMR. (400 MHz, 45° C., $D_2O$) δ 8.65 (s, 1H), 8.56 (s, 1H), 8.37 (s, 1H), 8.27 (s, 1H), 6.58 (d, J=16.8 Hz, 1H), 6.33 (s, 1H), 5.69 (dd, J=51.6, 3.6 Hz, 1H), 5.36-5.27 (m, 1H), 5.21 (d, J=4.4 Hz, 1H), 5.11-5.05 (m, 1H), 4.76-4.65 (m, 3H), 4.60 (d, J=12.4 Hz, 1H), 4.25 (dd, J=11.8, 4.4 Hz, 2H), 3.24 (q, J=7.2 Hz, 18H), 1.37 (t, J=7.2 Hz, 27H). $^{19}F$ NMR (400 MHz, 45° C., $D_2O$) δ −200.73 to −200.93 (m). $^{31}P$ NMR (45° C., $D_2O$) δ 54.79.

Compound 21a enriched in the $R_pS_p$ diastereomer was similarly reacted to provide compound 22a (29 mg, 34%) in 95% purity as a white pentakis-triethylammonium salt after purification by reverse phase chromatography and lyophilization. LCMS-ESI: 691.25 $[M-H]^-$ (calculated for $C_{20}H_{23}FN_{10}O_9P_2S_2$: 692.06); $R_t$ 10.399' min by HPLC conditions (10 mM TEAA, 2% to 20%). $R_t$ 10.236' min by LCMS conditions (20 mM $NH_4OAc$, 2% to 20%). $^1H$ NMR. (400 MHz, 45° C., $D_2O$) δ 8.74 (s, 1H), 8.69 (s, 1H), 8.37 (s, 1H), 8.33 (s, 1H), 6.62 (d, J=16.4 Hz, 1H), 6.36 (s, 1H), 5.93 (dd, J=51.6, 2.8 Hz, 1H), 5.31-5.23 (m, 1H), 5.19 (d, J=4.4 Hz, 1H), 5.13-5.07 (m, 1H), 4.77-4.65 (m, H), 4.62-4.59 (m, 2H), 4.29-4.25 (m, 2H), 3.34 (q, J=7.2 Hz, 30H), 1.43 (t, J=7.2 Hz, 45H). $^{19}F$ NMR (400 MHz, 45° C., $D_2O$) δ −201.58 to −201.78 (m). $^{31}P$ NMR (45° C., $D_2O$) δ 55.00.

Example 5: Synthesis of 3',3'-RR-(2'F-G)(A) (23) and 3',3'-SR-(2'F-G)(A) (23a)

2-amino-9-((2R,3R,3aR,5R,7aR,9R,10R,10aS,12R,14aR)-9-(6-amino-9H-purin-9-yl)-3-fluoro-10-hydroxy-5,12-dimercapto-5,12-dioxidooctahydro-2H,7H-difuro[3,2-d:3',2'-j][1,3,7,9]tetraoxa[2.8]diphosphacyclododecin-2-yl)-1,9-dihydro-6H-purin-6-one (23), also referred to as 3',3'-RR-(2'F-G)(A) or dithio-(Rp,Rp)-cyclic-[2'F-G(3',5')p-A(3',5')p], and 2-amino-9-((2R,3R,3aR,5S,7aR,9R,10R,10aS,12R,14aR)-9-(6-amino-9H-purin-9-yl)-3-fluoro-10-hydroxy-5,12-dimercapto-5,12-dioxidooctahydro-2H,7H-difuro[3,2-d:3',2'-j][1,3,7,9]tetraoxa[2.8]diphosphacyclododecin-2-yl)-1,9-dihydro-6H-purin-6-one (23a), also referred to as 3',3'-SR-(2'F-G)(A) or dithio-(Sp,Rp)-cyclic-[2'F-G(3',5')p-A(3',5')p]

23

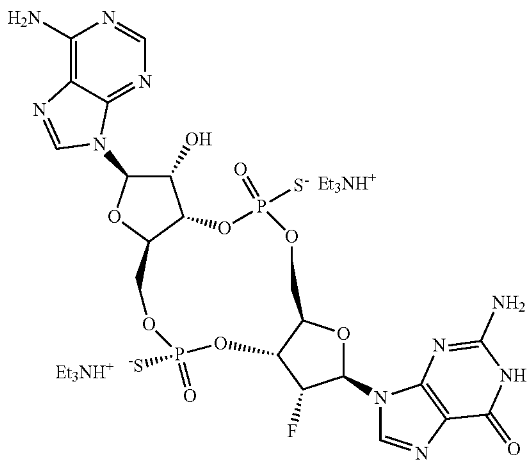

and

23a

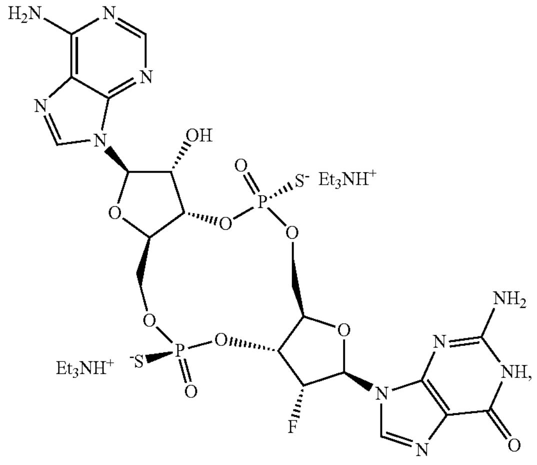

were prepared according to the methods of Example 4, Scheme 4. Compound 18 (2.0 g, 2.0 mmol. ChemGenes) was used in Step 1, compound 8 (2.0 g, 2.3 mmol. ChemGenes) was used in place of compound 3 in Step 2, and in Step 4, aqueous ammonium hydroxide was replaced with the same proportion of AMA, to obtain compound 23 (33 mg, 99% purity) as the bis-triethyloammonium salt and compound 23a (50 mg, 98% purity) as the tris-triethylammonium salt after purification by reverse phase preparatory HPLC and lyophilization.

Compound 23: LCMS-ESI: 707.80 $[M-H]^+$ (calculated for $C_{20}H_{23}FN_{10}O_{10}P_2S_2$: 708.05); $R_t$ 14.310' min by HPLC conditions (10 mM TEAA, 2% to 20%). $R_t$ 7.274' min by LCMS conditions (20 mM $NH_4OAc$, 2% to 50%). $^1H$ NMR. (400 MHz, 45° C., $D_2O$) δ 8.56 (s, 1H), 8.35 (s, 1H), 8.12 (s, 1H), 6.39 (d, J=18.4 Hz, 1H), 6.31 (s, 1H), 5.69 (dd, J=51.6, 4.2 Hz, 1H), 5.38-5.30 (m, 1H), 5.19-5.14 (m, 1H), 4.91 (d, J=4.4 Hz, 1H), 4.65-4.63 (m, 4H), 4.23-4.18 (m, 2H), 3.34 (q, J=7.2 Hz, 12H), 1.41 (t, J=7.2 Hz, 18H). $^{19}F$ NMR (400 MHz, 45 OC, $D_2O$) δ −199.47 to −199.72 (m). $^{31}P$ NMR (45° C., $D_2O$) δ 54.70, 54.52.

Compound 23a: LCMS-ESI: 709.80 $[M+H]^+$ (calculated for $C_{20}H_{23}FN_{10}O_{10}P_2S_2$: 708.05); $R_t$ 17.348' min by HPLC conditions (10 mM TEAA, 2% to 20%). $R_t$ 6.354' min by LCMS conditions (20 mM $NH_4OAc$, 2% to 50%). $^1H$ NMR. (400 MHz, 45° C., $D_2O$) δ 8.74 (s, 1H), 8.36 (s, 1H), 8.12

(s, 1H), 6.41 (d, J=19.2 Hz, 1H), 6.33 (s, 1H), 5.98 (dd, J=51.6, 4.4 Hz, 1H), 5.41-5.29 (m, 1H), 5.19-5.13 (m, 1H), 4.89 (d, J=4.4 Hz, 1H), 4.63 (d, J=9.2 Hz, 3H), 4.57 (d, J=12.0 Hz, 1H), 4.28-4.18 (m, 2H), 3.34 (q, J=7.2 Hz, 18H), 1.42 (t, J=7.2 Hz, 27H). $^{19}F$ NMR (400 MHz, 45° C., $D_2O$) δ −200.11 to −200.36 (m). $^{31}P$ NMR (45° C., $D_2O$) δ 55.32, 55.25, 54.66.

Example 6: Synthesis of 3',3'-RR-(G)(2'F-A) (24) and 3',3'-RS-(G)(2'F-A) (24a)

2-amino-9-((2R,3R,3aS,5R,7aR,9R,10R,10aR,12R,14aR)-9-(6-amino-9H-purin-9-yl)-10-fluoro-3-hydroxy-5,12-dimercapto-5,12-dioxidooctahydro-2H,7H-difuro[3,2-d:3',2'-j][1,3,7,9]tetraoxa[2,8]diphosphacyclododecin-2-yl)-1,9-dihydro-6H-purin-6-one (24), also referred to as 3',3'-RR-(G)(2'F-A) or dithio-(Rp,Rp)-cyclic-[G(3',5')p-2'F-A(3',5')p], and 2-amino-9-((2R,3R,3aS,5R,7aR,9R,10R,10aR,12S,14aR)-9-(6-amino-9H-purin-9-yl)-10-fluoro-3-hydroxy-5,12-dimercapto-5,12-dioxidooctahydro-2H,7H-difuro[3,2-d:3',2'-j][1,3,7,9]tetraoxa[2.8]diphosphacyclododecin-2-yl)-1,9-dihydro-6H-purin-6-one (24a), also referred to as 3',3'-RS-G)(2'F-A) or dithio-(Rp,Sp)-cyclic-[G(3',5')p-2'F-A(3',5')p]

24

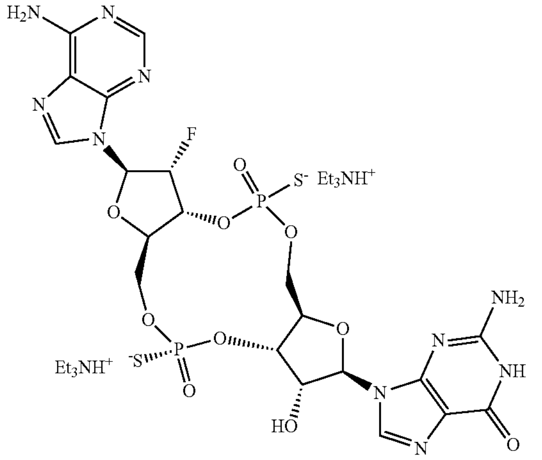

and

24a

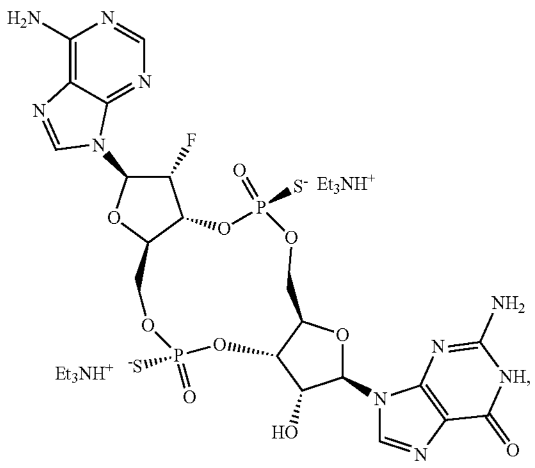

were prepared according to the methods of Example 4, Scheme 4. Compound 3 (2.1 g, 2.4 mmol, ChemGenes) was used in place of compound 18 in Step 1, and (2R,3R,4R,5R)-2-((bis(4-methoxyphenyl)(phenyl)methoxy)methyl)-4-((tert-butyldimethylsilyl)oxy)-5-(2-isobutyramido-6-oxo-1,6-dihydro-9H-purin-9-yl)tetrahydrofuran-3-yl (2-cyanoethyl) diisopropylphosphoramidite (1.6 g, 1.6 mmol, ChemGenes) was used in place of compound 3 in Step 2, to obtain compound 24 (10 mg, 94% purity) and compound 24a (50 mg, 96% purity) as the pentakis-triethylammonium salts after purification by reverse phase preparatory HPLC and lyophilization.

Compound 24: LCMS-ESI: 708.00 [M−H]+ (calculated for $C_{20}H_{23}FN_{10}O_{10}P_2S_2$: 708.05); $R_t$ 14.878' min by HPLC conditions (10 mM TEAA, 2% to 20%). $R_t$ 7.381' min by LCMS conditions (20 mM $NH_4OAc$, 2% to 50%). $^1H$ NMR. (400 MHz, 45° C., $D_2O$) δ 8.52 (s, 1H), 8.34 (s, 1H), 8.12 (s, 1H), 6.60 (d, J=16.8 Hz, 1H), 6.13 (d, J=1.2 Hz, 1H), 5.68 (dd, J=51.6, 4.2 Hz, 1H), 5.39-5.25 (m, 1H), 5.21-5.15 (m, 1H), 4.90 (d, J=2.8 Hz, 1H), 4.70-4.63 (m, 2H), 4.61-4.57 (m, 2H), 4.23-4.20 (m, 2H), 3.34 (q, J=7.2 Hz, 30H), 1.43 (t, J=7.2 Hz, 45H). $^{19}F$ NMR (400 MHz, 45° C., $D_2O$) δ −200.12 to −200.31 (m). $^{31}P$ NMR (45° C., $D_2O$) δ 54.9, 54.4.

Compound 24a: LCMS-ESI: 710.10 [M+H]+ (calculated for $C_{20}H_{23}FN_{10}O_{10}P_2S_2$: 708.05); $R_t$ 12.633' min by HPLC conditions (10 mM TEAA, 2% to 20%). $R_t$ 8.662' min by LCMS conditions (20 mM $NH_4OAc$, 2% to 50%). $^1H$ NMR. (400 MHz, 45° C., $D_2O$) δ 8.63 (s, 1H), 8.47 (s, 1H), 8.34 (s, 1H), 6.72 (d, J=17.2 Hz, 1H), 6.23 (d, J=2.0 Hz, 1H), 6.05 (dd, J=51.6, 4.4 Hz, 1H), 5.47-5.32 (m, 1H), 5.31-5.24 (m, 1H), 4.98-4.90 (m, 1H), 4.87-4.85 (m, 1H), 4.84-4.78 (m, 1H), 4.69-4.65 (m, 1H), 4.63-4.56 (m, 1H), 4.38-4.28 (m, 2H), 3.34 (q, J=7.2 Hz, 30H), 1.47 (t, J=7.2 Hz, 45H). $^{19}F$ NMR (400 MHz, 45° C., $D_2O$) δ −200.91 to −201.11 (m). $^{31}P$ NMR (45° C., $D_2O$) δ 55.6, 55.5, 54.5.

Example 7: Synthesis of 3',3'-RR-(2'F-iBuG)(2'F-BzA) (25) and 3',3'-RS-(2'F-iBuG)(2'F-BzA) (25a)

N-(9-((2R,3R,3aR,5R,7aR,9R,10R,10aR,12R,14aR)-3,10-difluoro-9-(2-isobutyramido-6-oxo-1,6-dihydro-9H-purin-9-yl)-5,12-dimercapto-5,12-dioxidooctahydro-2H,7H-difuro[3,2-d:3',2'-j][1,3,7,9]tetraoxa[2,8]diphosphacyclododecin-2-yl)-9H-purin-6-yl)benzamide (25), also referred to as 3',3'-RR-(2'F-iBuG)(2'F-BzA), or dithio-(Rp,Rp)-cyclic-[2'F-iBuG(3',5')p-2' F-BzA(3',5')p], and N-(9-((2R,3R,3aR,5S,7aR,9R,10R,10aR,12R,14aR)-3,10-difluoro-9-(2-isobutyramido-6-oxo-1,6-dihydro-9H-purin-9-yl)-5,12-dimercapto-5,12-dioxidooctahydro-2H,7H-difuro[3,2-d:3',2'-j][1,3,7,9]tetraoxa[2,8]diphosphacyclododecin-2-yl)-9H-purin-6-yl)benzamide (25a), also referred to as 3',3'-RS-(2'F-iBuG)(2'F-BzA), or dithio-(Rp,Sp)-cyclic-[2'F-iBuG(3',5')p-2'F-BzA(3',5')p], were prepared according to the following Scheme 5.

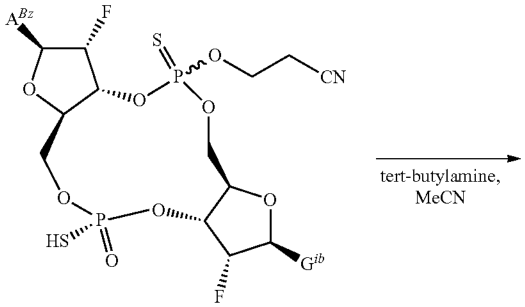

13'

-continued

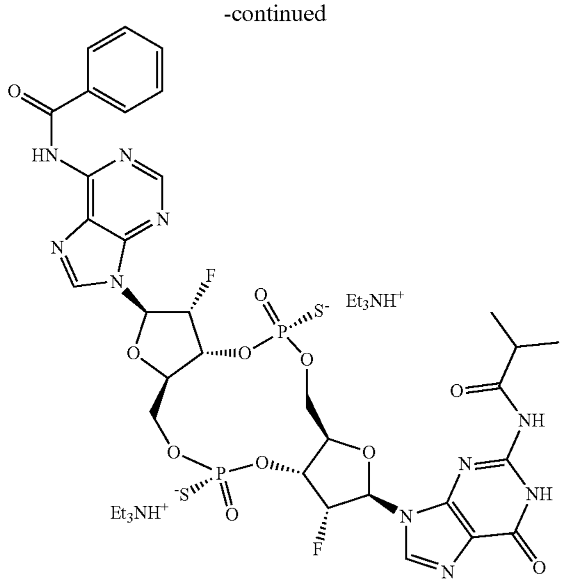

25 and

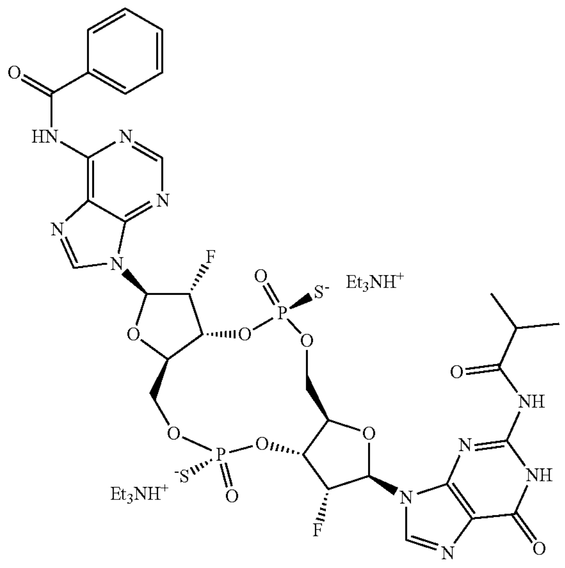

25a

To a solution of compound 13' (155 mg, 0.17 mmole, 1 eq, a mixture of diastereomers 13 and 13a, see Example 2) in MeCN (0.83 mL) was added tert-butylamine (0.82 mL, 7.8 mmol, 47 eq). The reaction proceeded for 10 mins and was concentrated in vacuo. Purification by reverse phase C18 MPLC gave 57 mg of compound 25a as the triethylammonium salt and 41 mg of compound 25 as the triethylammonium salt.

Compound 25: LCMS-ESI: 883.35 [M−H]$^-$ (calculated for $C_{31}H_{32}F_2N_{10}O_{11}P_2S_2$: 884.11); $R_t$: 5.42 min (20-100% MeCN/$NH_4$OAc (20 mM) buffer, 10 min, 1 mL/min. 5 μm Acclaim 120). $^1$H NMR (400 MHz, 45° C., $D_2O$) δ 8.85 (s, 1H), 8.80 (s, 1H), 8.31 (s, 1H), 8.13 (d, J=7.6 Hz, 2H), 7.82 (t, J=7.2 Hz, 1H), 7.73 (t, J=7.6 Hz, 2H), 6.74 (d, J=16.8 Hz, 1H), 6.50 (s, J=19.2 Hz, 1H), 5.84 (dd, J=6.4.4.8 Hz, 1H), 5.7 (dd, J=7.6, 4.0 Hz, 1H), 5.36-5.21 (m, 2H), 4.64-4.62 (m, 2H), 4.23 (td, J=12, 4.8 Hz, 2H), 3.35 (q, J=7.2 Hz, 12H), 2.78-2.72 (m, 1H), 2.05 (s, 0.2H), 1.40 (t, J=7.2 Hz, 18H), 1.19 (dd, J=6.8 Hz, 2.4 Hz, 6H).

Compound 25a: LCMS-ESI: 883.30 [M−H]$^-$ (calculated for $C_{31}H_{32}F_2N_{10}O_{11}P_2S_2$: 884.11); $R_t$: 5.16 min (20-100% MeCN/$NH_4$OAc (20 mM) buffer, 10 min, 1 mL/min, 5 μm Acclaim 120). $^1$H NMR (400 MHz, 45° C., $D_2O$) δ 8.91 (s, 1H), 8.85 (s, 1H), 8.36 (s, 1H), 8.14 (d, J=7.6 Hz, 2H), 7.83 (t, J=7.6 Hz, 1H), 7.72 (t, J=8.0 Hz, 2H), 6.75 (d, J=16.8 Hz, 1H), 6.50 (d, J=20.4 Hz, 1H), 6.05 (dd, J=50.8 Hz, 3.6 Hz, 1H), 5.9 (dd, J=52.0 Hz, 4.4 Hz, 1H), 5.41-5.20 (m, 2H), 4.81-4.76 (m, 2H), 4.63-4.42 (m, 2H), 4.30-4.22 (m, 2H), 3.35 (q, J=7.2 Hz, 9H), 2.52-2.43 (m, 1H), 2.05 (s, 0.5H), 1.40 (t, J=7.2 Hz, 12H), 1.19 (dd, J=59.2 Hz, 6.8 Hz, 6H).

Example 8: Synthesis of 3',3'-RR-(2'F-iBuG)(2'F-A) (26)

N-(9-((2R,3R,3aR,5R,7aR,9R,10R,10aR,12R,14aR)-9-(6-amino-9H-purin-9-yl)-3,10-difluoro-5,12-dimercapto-5,12-dioxidooctahydro-2H,7H-difuro[3,2-d:3',2'-j][1,3,7,9]tetraoxa[2,8]diphosphacyclododecin-2-yl)-6-oxo-6,9-dihydro-1H-purin-2-yl)isobutyramide (26), also referred to as RR-(2'F-iBuG)(2'F-A) or dithio-(Rp,Rp)-cyclic-[2'F-iBuG(3',5')p-2'F-A(3',5')p], was prepared according to the following Scheme 6.

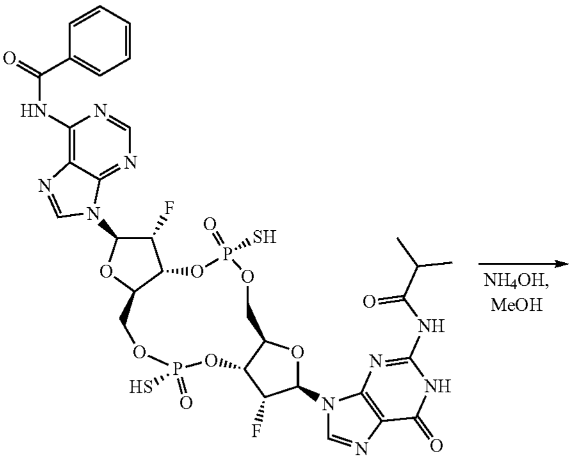

25

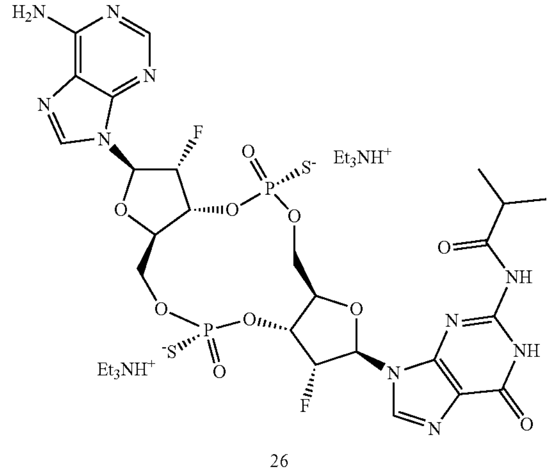

26

To a solution of 25 (20 mg, per Example 7, Scheme 5) in MeCN (0.83 mL) was added concentrated $NH_4OH$ (0.35 mL) and MeOH (0.35 mL). The reaction proceeded for 3 h at room temperature and was concentrated in vacuo. Purification by reverse phase C18 MPLC gave 6.1 mg of compound 26. LCMS-ESI: 779.90 $[M-H]^-$ (calculated for $C_{24}H_{28}F_2N_{10}O_{10}P_2S_2$: 780.09); $R_t$: 9.01 min (2-50% MeCN/$NH_4$OAc (20 mM) buffer, 10 min, 1 mL/min, 5 μm Acclaim 120). $^1$H NMR (400 MHz, 45° C., $D_2O$) δ 8.48 (s, 1H), 8.24 (s, 1H), 8.19 (s, 1H), 6.36 (d, 16.4 Hz, 1H), 6.23 (d, J=17.6 Hz, 1H) 5.60 (d, J=51.6 Hz, 1H), 5.20 (d, J=52.0 Hz, 1H), 5.18-5.08 (m, 2H), 4.61-4.30 (m, 4H), 4.00 (s, 3H), 3.17 (q, J=6.0 Hz, 16H), 2.74-2.73 (m, 1H), 2.05 (s, 0.3H), 1.30 (t, J=6.8 Hz, 24H), 1.18 (t, J=7.6 Hz, 6H).

Example 9: Synthesis of 3',3'-RR-(2'F-BzA)(2'F-BzA) (27)

N,N'-(((2R,3R,3aR,5R,7aR,9R,10R,10aR,12R,14aR)-3,10-difluoro-5,12-dimercapto-5,12-dioxidooctahydro-2H,7H-difuro[3,2-d:3',2'-j][1,3,7,9]tetraoxa[2.8]diphosphacyclododecine-2,9-diyl)bis(9H-purine-9,6-diyl))dibenzamide (27), also referred to as 3',3'-RR-(2'F-BzA)(2'F-BzA) or dithio-(Rp,Rp)-cyclic-[2'F-BzA(3',5')p-2'F-BzA(3',5')p] was prepared according to the following Scheme 7.

-continued

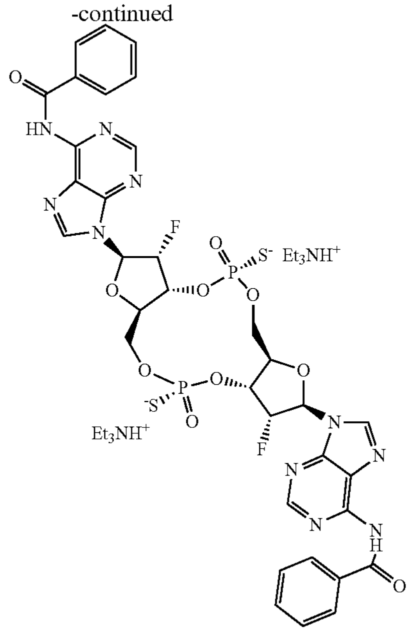

27

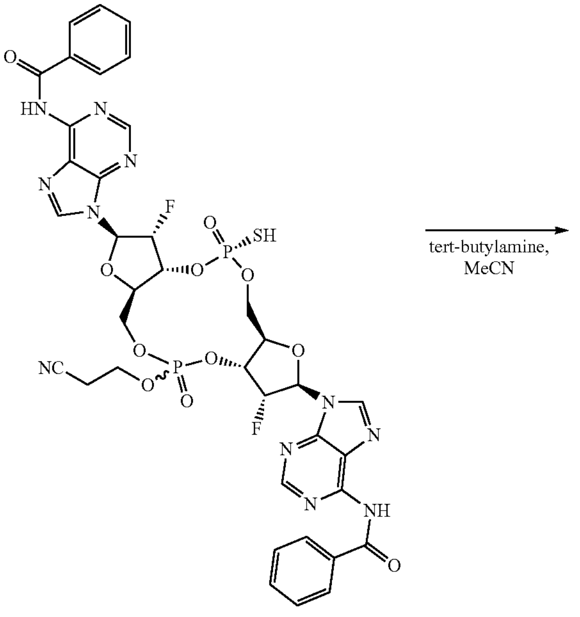

5

To a solution of compound 5 (400 mg, 0.418 mmole, 1 eq. see e.g. Example 1 Scheme 1, isolated after Step 3) in MeCN (2.5 mL) was added tert-butylamine (2.18 mL, 50 eq). The mixture was capped and stirred for 45 minutes. The mixture was concentrated in vacuo to give 282.1 mg of crude compound 27. The reaction was purified using a prep-HPLC-C18 (75% 10 mM TEAA to 55% acetonitrile/10 mM TEAA) to give 4.9 mg of compound 27 (>95% pure) as the triethylammonium salt. LCMS-ESI: 903.9 $[M+H]^+$ (Calculated for $C_{34}H_{30}F_2N_{10}O_{10}P_2S_2$: 902.10); $R_t$: 6.79 min (2-80% MeCN/$NH_4$OAc (20 mM) buffer, 10 min, 1 mL/min, 5 μm Acclaim 120). $^1$H NMR (400 MHz, 45° C., MeOD) δ 8.76 (s, 2H), 8.70 (d, J=12 Hz, 2H), 8.03 (t, J=10 Hz, 4H), 7.60 (d, J=6.8 Hz, 2H), 7.52 (d, J=6.4 Hz, 4H), 6.53 (t, J=8.8 Hz, 2H), 5.59-5.46 (d, J=52.4 Hz, 1H), 5.17-5.11 (m, 1H), 4.51-4.36 (m, 2H), 4.03 (d, J=9.2 Hz, 2H). $^{19}$F NMR (400 MHz, 45° C., MeOD) δ -201.54--201.74, $^{31}$P NMR (45° C., MeOD) δ 55.68.

Example 10: Synthesis of 3',3'-(2'F-G)(2'F-A) (30)

2-amino-9-((2R,3R,3aR,7aR,9R,10R,10aR,14aR)-9-(6-amino-9H-purin-9-yl)-3,10-difluoro-5,12-dihydroxy-5,12-dioxidooctahydro-2H,7H-difuro[3,2-d:3',2'-j][1,3,7,9]tetraoxa[2.8]diphosphacyclododecin-2-yl)-1,9-dihydro-6H-purin-6-one, also referred to as 3',3'-(2'F-G)(2'F-A) or cyclic-[2'F-G(3',5')p-2'F-A(3',5')p] was prepared according to the following Scheme 8.

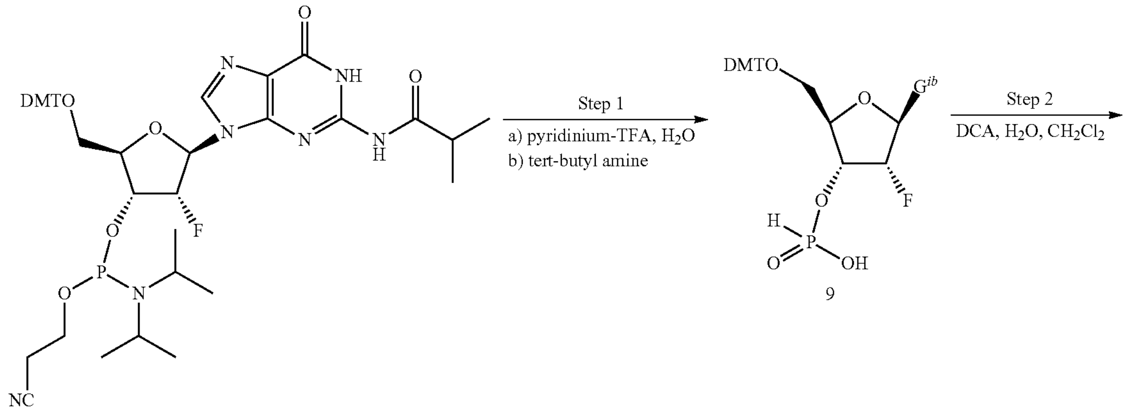

8 9

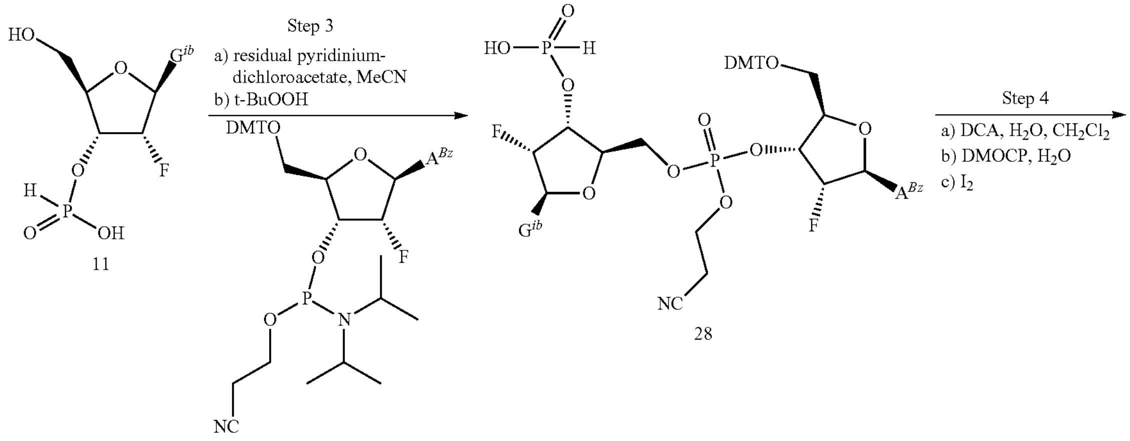

11 3 28

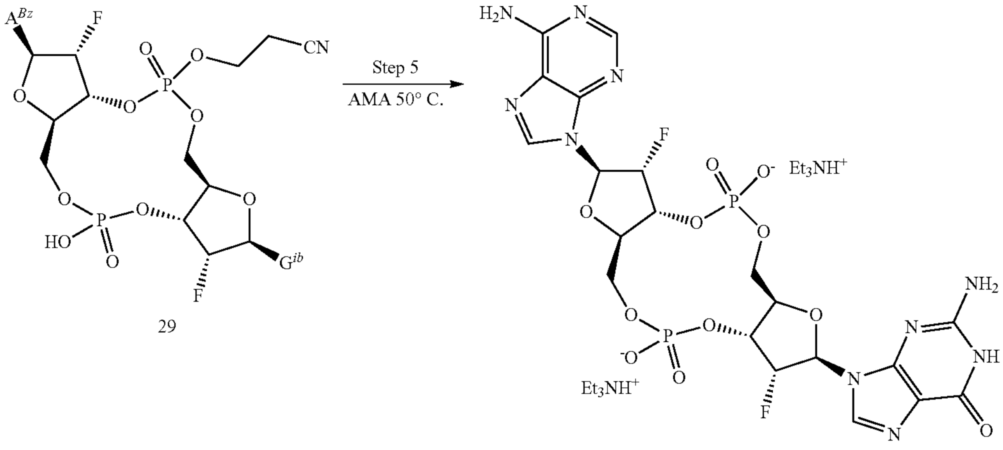

29 30

Step 1:

Preparation of (2R,3R,4R,5R)-2-((bis(4-methoxyphenyl)(phenyl)methoxy)methyl)-4-fluoro-5-(2-isobutyramido-6-oxo-1,6-dihydro-9H-purin-9-yl)tetrahydrofuran-3-yl hydrogen phosphonate (9): To a solution of compound 8 (10 g, 10 mmole, ChemGenes, see Example 2) in MeCN (50 mL) and water (360 μL) was added pyridinium trifluoroacetate (2.32 mg). The reaction was stirred for 1 min followed by the addition of tert-butylamine (50 mL). The reaction proceeded for 10 min and was concentrated in vacuo and coevapped with acetonitrile (2×100 mL) in vacuo to give a mixture of compound 9 and 10 ~(4:1, see Example 1).

Step 2:

Preparation of (2R,3R,4R,5R)-4-fluoro-2-(hydroxymethyl)-5-(2-isobutyramido-6-oxo-1,6-dihydro-9H-purin-9-yl)tetrahydrofuran-3-yl hydrogen phosphonate (11): To a solution of the crude mixture of compound 9 and 10 (~8.5 g, 5 mmole) and DCM (60 mL) was added water (0.09 mL) followed by a solution of 6% solution of DCA in DCM (60 mL). After 10 min the reaction mixture was quenched with pyridine (7.0 mL) and then concentrated in vacuo. The crude mixture was coevapped with 3×35 mL anhydrous MeCN leaving 7.0 mL of crude compound 11.

Step 3:

Preparation of (2R,3R,4R,5R)-2-((((((2R,3R,4R,5R)-5-(6-benzamido-9H-purin-9-yl)-2-((bis(4-methoxyphenyl)(phenyl)methoxy)methyl)-4-fluorotetrahydrofuran-3-yl)oxy)(2-cyanoethoxy)phosphoryl)oxy)methyl)-4-fluoro-5-(2-isobutyramido-6-oxo-1,6-dihydro-9H-purin-9-yl)tetrahydrofuran-3-yl hydrogen phosphonate (28): A solution of compound 3 was coevapped 3×35 mL with anhydrous MeCN, leaving 20 mL anhydrous MeCN, and was added to the crude solution of compound 11 and the reaction was stirred for 2 min. t-BuOOH (2.73 mL of a 5.5 M solution in decane) was added and the reaction proceeded for 30 min. An aqueous solution of sodium bisulfite (1.25 g in 2.5 mL water) was added and the mixture was stirred for 5 min. It was then concentrated to dryness in vacuo to give 22 g of compound 28.

Step 4:

Preparation of N-(9-((2R,3R,3aR,7aR,9R,10R,10aR,14aR)-5-(2-cyanoethoxy)-3,10-difluoro-12-hydroxy-9-(2-isobutyramido-6-oxo-1,6-dihydro-9R-purin-9-yl)-5,12-di-oxidooctahydro-2R,7H-difuro[3,2-d:3',2'-j][1,3,7,9]tetraoxa[2,8]diphosphacyclododecin-2-yl)-9H-purin-6-yl)benzamide (29): To a solution of compound 28 (22 g) in DCM (120 mL) was added water (600 μL) followed by a 6% solution of DCA in DCM (120 mL). After 10 min the reaction mixture was quenched with pyridine (50 mL) and concentrated in vacuo to remove the DCM. An additional amount of pyridine (150 mL) was added and the mixture was concentrated in vacuo to 100 mL. DMOCP (2.92 g) was added and the reaction was stirred for 3 min followed by the addition of water (3.2 mL) and then iodine (1.65 g). After 5 min the reaction was quenched with a solution of sodium bisulfite (0.1 g $NaHSO_3$ in 700 mL water) and extracted with a 1:1 mixture of ethyl ether and EtOAc (800 mL). The aqueous layer was further extracted with an additional 200 mL of DCM. The combined organic layers were concentrated in vacuo to give 7 g of crude compound 29.

Step 5:

Preparation of 3',3'-(2'F-G)(2'F-A) (30): A solution of compound 30 (3.15 g) in AMA (22 mL) and EtOH (9.45 mL) was heated to 50° C. for 4 h. The reaction mixture was cooled to room temperature and sparged with argon for 10 min. Purification by reverse phase C18 MPLC and preparative HPLC gave 22 mg of compound 30. LCMS-ESI: 677.30 $[M-H]^-$ (calculated for $C_{20}H_{22}F_2N_{10}O_{10}P_2$: 678.09); $R_t$: 8.73 min (2-50% MeCN/$NH_4OAc$ (20 mM) buffer, 20 min. 1 mL/min, 5 μm Acclaim 120). $^1H$ NMR (400 MHz, 45° C., $D_2O$) δ 8.52 (s, 1H), 8.33 (s, 1H), 8.13 (s, 1H), 6.60 (d, J=17.2 Hz, 1H), 6.40 (d, J=18.4 Hz, 1H), 5.75 (d, J=4.0 Hz, 1H), 5.62 (d, J=3.6 Hz, 1H), 5.18-5.10 (m, 2H), 4.66-4.52 (m, 3H), 4.31-4.25 (m, 2H), 3.35 (q, J=7.2 Hz, 26H), 2.05 (s, 6.45H), 1.43 (t, J=7.2 Hz, 39H).

Example 11: In Vitro Binding Analysis of Mono- or Di-F-CDNs with Purified STING Protein DNA encoding amino acids 140-379 (amino acid numbering corresponding to Swiss Prot Q86WV6) was amplified from plasmids containing the full length sequence of human STING alleles via polymerase chain reaction with the following primers: forward TACTTCCAATCCAATGCAGC-CCCAGCTGAGATCTCTG (SEQ ID NO: 8) and reverse TTATCCACTTCCAATGTTATTATTATCAAGA-GAAATCCGTGCGGAG (SEQ ID NO: 9). STING variant alleles were assigned according to Yi, et al. (2013), PLoS One, 8(10), e77846 (DOI: 10.1371/journal.pone.0077846. PCR products were cloned into bacterial expression vector encoding a N-terminal hexa-histidine affinity tag (6xHIS) followed by a small ubiquitin-like modifier (SUMO) solubility sequence (Butt, et al, (2005) Protein expression and purification 43.1, 1-9) and tobacco etch virus protease cleavage site (TEV) using ligation independent cloning (Aslanidis, et al. (1990) Nucleic acids research, 18.20, 6069-6074).

Plasmids encoding 6xHIS-SUMO-TEV-STING amino acids 140-379 were transformed into Rosetta2 (DE3) *E. coli* cells (EMD Millipore) for protein expression. Cells were grown in lysogeny broth at 37° C. until a 600 nM absorbance of 0.6 was reached. Cells were then transferred to 18° C., and protein expression was induced overnight by the addition of isopropyl β-D-1-thiogalactopyranoside to the media at a concentration of 0.25 mM. Cells were harvested by centrifugation at 6.000 times gravity for 10 minutes. Cell pellets were re-suspended on ice in a buffer containing 50 mM Tris hydrochloride (Tris-HCl) pH 7.5, 500 mM sodium chloride (NaCl), 20 mM imidazole, 10% glycerol, 1 mM tris(2-carboxyethyl)phosphine hydrochloride (TCEP) and protease inhibitor tablet (Pierce) (Buffer A). Cells were lysed using an S-450D sonifier (Emmerson industrial) on ice. Cell lysate was centrifuged at 15,000 times gravity for 30 minutes at 4° C. Soluble material was applied to nickel-nitrilotriacetic acid (Ni-NTA) coupled Sepharose CL-6B (Qiagen) for 1 hour with gentle rocking at 4° C. After transfer to a gravity flow poly-prep column (Bio-Rad), resin was washed extensively in buffer A. Protein was eluted from the column in a buffer containing 20 mM Tris-HCl pH 7.5, 150 mM NaCl, 300 mM imidazole, 10% glycerol and 0.5 mM TCEP. To remove the 6xHIS-SUMO tag eluted protein was mixed with TEV protease (Sigma) at a ratio of 1:250 (w:w) and dialyzed overnight against a buffer containing 20 mM Tris-HCl pH 7.5. 150 mM NaCl, 5 mM imidazole, 10% glycerol and 0.5 mM TCEP. TEV protease and 6xHIS-SUMO tags were depleted by the addition of Ni-NTA resin (Qiagen) to the sample, purified STING amino acids 140-379 was collected by removal of the resin using a poly-prep column. STING AA140-379 was concentrated with a 10,000 Dalton molecular weight cutoff centrifuge concentrator (EMD Millipore) to a final concentration of approximately 10 mg/ml. Protein was aliquoted, flash frozen in liquid nitrogen and stored at −80° C. until use.

Differential scanning fluorometry (DSF) is a technique that measures the ability of ligands to bind to and stabilize purified proteins (Niesen, et al, (2007) Nature protocols 2.9, 2212-2221). The protein is heated in the presence of a dye that binds to and fluoresces in hydrophobic environments. The protein is thermally denatured by heating resulting in increased dye binding to the unfolded protein and fluorescence. The temperature midpoint ($T_m$) of a proteins denaturation is established by calculating the half maximal value of the denaturation curve. The temperature midpoint of the protein in the presence of a ligand is directly related to the affinity of the ligand for the protein and therefore its ability to stabilize the protein at higher temperatures.

DSF was performed in a 20 μL reaction comprising 20 mM Tris-HCl pH 7.5, 150 mM NaCl, 1:500 dilution of SYPRO Orange (Life Technologies), 1 mg/ml purified STING AA140-379 protein and ligand at a concentration of 1 mM. Samples were placed in hard shell PCR plate (Bio-Rad). The fluorescence as a function of temperature was recorded in a CFX 96 real time PCR machine (Bio-Rad) reading on the HEX channel, excitation 450-490, emission 560-580 nm. The temperature gradient was from 15-80° C.

ramping 0.5° C. per 15 seconds and recording every 0.5° C. After subtraction of the background signal from a sample lacking protein and ligand. The midpoint temperature ($T_m$) was calculated by fitting the curves of the fluorescence as a function of temperature to a Boltzmann sigmoidal function (Graph Pad Prism). The change in thermal stability of STING AA140-379 in the presence of ligand ($T_m$ Shift) was calculated by subtracting the $T_m$ (Protein and Ligand) from $T_m$ (Protein alone).

CDN compounds cyclic-[A(3',5')p-A(3',5')p] (CDA, 3',3'-(A)(A)), dithio-(Rp,Rp)-cyclic-[A(3',5')p-A(3',5')p] (3',3'-RR-(A)(A)), dithio-(Rp,Rp)-cyclic-[2'F-A(3',5')p-2'F-A(3',5')p] (3',3'-RR-(2'F-A)(2'F-A)), cyclic-[G(3',5')p-A(3',5')p] (cGAMP, 3',3'-(G)(A)), cyclic-[G(2',5')pA(3',5')p](ML-cGAMP, 2',3'-(G)(A)) and dithio-(Rp,Rp)-cyclic-[2'F-G(3',5')p-2'F-A(3',5')p](3',3'-RR-(2'F-G)(2'F-A)) were evaluated for their ability to bind to purified STING proteins by DSF.

Figure 3:
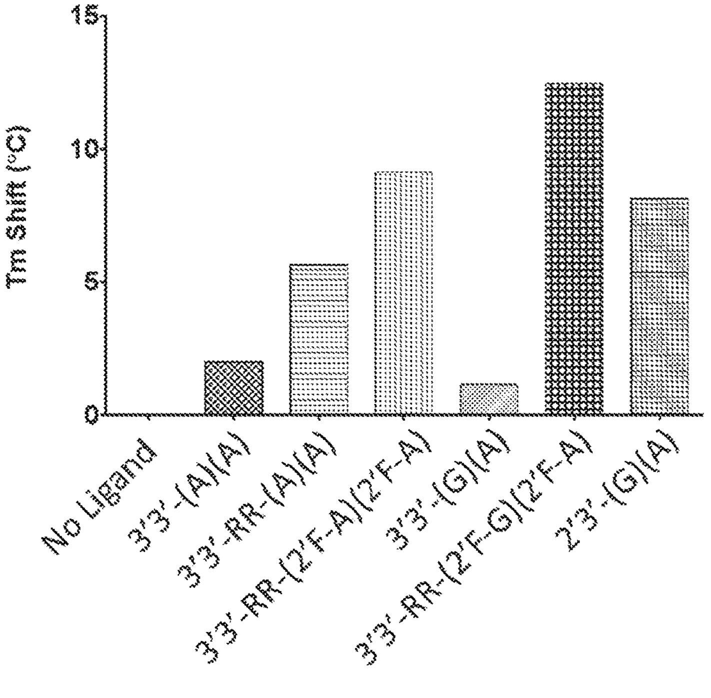
FIG. 3 depicts binding of mono- or di-F CDNs to human STING WT protein.

FIGS. 2 and 3 show that fluorine substituted CDN compounds 3',3'-RR-(2'F-A)(2'F-A) and 3',3'-RR-(2'F-G)(2'F-A) showed an increased $T_m$ shift over non fluorine substituted compounds 3',3'-(A)A), 3',3'-RR-(A)(A), 3',3'-(G)(A) and the endogenous cellular ligand 2',3'-(G)(A). The increased $T_m$ shift of the fluorine substituted compounds 3',3'-RR-(2'F-A)(2'F-A) and 3',3'-RR-(2'F-G)(2'F-A) demonstrated they increase the thermal stability of both hSTING (REF) (FIG. 2) and hSTING (WT) proteins (FIG. 3) indicating a strengthened binding interaction between hSTING (WT), hSTING (REF) and fluorine substituted CDN compounds. FIG. 2 additionally demonstrated that CDNs containing (3',5')p (3',5')p intra-nucleotide phosphate linkages with 2',2"-difluoro-dithio-(Rp,Rp) substitutions could bind strongly to a variant that is weekly bound by unmodified CDNs containing (3',5')p (3',5')p intra-nucleotide phosphate linkages.

Each of wild type hSTING. HAQ allele hSTING and REF allele hSTING were also used with each of the reference compounds and compounds of the invention as listed in the following Table 4. These results demonstrate improved binding for 3',3'-RR-(2'F-A)(2'F-A), 3',3'-RR-(2'F-G)(2'F-G) and 3',3'-RR-(2'F-G)(2'F-A) relative to each of their OH reference, i.e. 3',3'-RR-(A)(A), 3',3'-RR-(G)(G), and 3',3'-RR-(G)(A), respectively in all three hSTING, with the 3',3'-RR-(2'F-A)(2'F-A) and 3',3'-RR-(2'F-G)(2'F-A) showing improved binding over the naturally produced 2',3'-(G)(A). The compounds 3',3'-RR-(2'F-BzA)(2'F-BzA), 3',3'-RR-(2'F-iBuG)(2'F-BzA), and 3',3'-RR-(2'F-iBuG)(2'F-A), having a protecting group on one both of the base amino groups, also showed improved binding relative to 3',3'-RR-(A)(A) or 3',3'-RR-(G)(A) when measured with the REF allele. The mono-F derivatives 3',3'-RR-(2'F-G)(A) and 3',3'-RR-(G)(2'F-A) also showed improved binding relative to the OH reference 3',3'-RR-(G)(A) in all three hSTING.

TABLE 4

$T_m$ shifts in hSTING WT, HAQ allele and REF allele.

| Example/Compound | Compound name | hSTING $T_m$ Shift (° C.) WT | HAQ | REF |
|---|---|---|---|---|
| Reference | 3'3'-(A)(A) | 4.5 | 10.2 | 2.0 |
| Reference | 3'3'-(2'F-A)(2'F-A) | 12.6 | 20.6 | 6.4 |
| Reference | 3'3'-RR-(A)(A) | 9.6 | 15.5 | 5.7 |
| Example 1 Compound 6 | 3'3'-RR-(2'F-A)(2'F-A) | 19.3 | 32.4 | 9.1 |
| Example 1 Compound 6a | 3'3'-RS-(2'F-A)(2'F-A) | * | * | * |
| Example 4 Compound 22 | 3'3'-RR-(A)(2'F-A) | 9.4 | 16.0 | 5.4 |
| Example 4 Compound 22a | 3'3'-RS-(A)(2'F-A) | 6.4 | 11.4 | 4.3 |
| Example 9 Compound 27 | 3'3'-RR-(2'F-BzA) (2'F-BzA) | 8.9 | 10.1 | 8.7 |
| Example 1 Compound 7 | 3'3'-RR-(2'βF-A) (2'βF-A) | 3.1 | 11.2 | 0.3 |
| Example 1 Compound 7a | 3'3'-RS-(2'βF-A) (2'βF-A) | 0.1 | 3.1 | 0 |
| Reference | 3'3'-(G)(G) | 6.1 | 9.97 | 6.1 |
| Reference | 3'3'-RR-(G)(G) | 9.5 | 15.3 | 10.3 |
| Example 3 Compound 17 | 3'3'-RR-(2'F-G)(2'F-G) | 12.6 | 22.6 | 11.4 |
| Example 3 Compound 17a | 3'3'-RS-(2'F-G)(2'F-G) | * | * | * |
| Reference | 2'3'-(G)(A) | 16.1 | 26.8 | 7.0 |
| Reference | 3'3'-(G)(A) | 2 | 10.5 | 2.5 |
| Reference | 3'3'-RR-(G)(A) | 11.1 | 21.0 | 7.2 |
| Example 2 Compound 14 | 3'3'-RR-(2'F-G)(2'F-A) | 19.3 | 34.2 | 12.5 |
| Example 2 Compound 14a | 3'3'-RS-(2'F-G)(2'F-A) | * | * | * |
| Example 5 Compound 23 | 3'3'-RR-(2'F-G)(A) | 14.7 | 25.9 | 9.5 |
| Example 5 Compound 23a | 3'3'-SR-(2'F-G)(A) | 10.6 | 16.5 | 7.8 |
| Example 6 Compound 24 | 3'3'-RR-(G)(2'F-A) | 15.9 | 28.8 | 9.7 |
| Example 6 Compound 24a | 3'3'-RS-(G)(2'F-A) | 9.3 | 15.3 | 7.0 |
| Example 10 Compound 30 | 3'3'-(2'F-G)(2'F-A) | 14.3 | 27.7 | 7.8 |
| Example 7 Compound 25 | 3'3'-RR-(2'F-iBuG) (2'F-BzA) | 10.6 | 14.7 | 8.6 |
| Example 7 Compound 25a | 3'3'-RS-(2'F-iBuG) (2'F-BzA) | 6.8 | 89 | 5.4 |
| Example 8 Compound 26 | 3'3'-RR-(2'F-iBuG) (2'F-A) | 13.3 | 18.4 | 10.5 |

* Compound was not compatible with the assay.

Figure 6A:
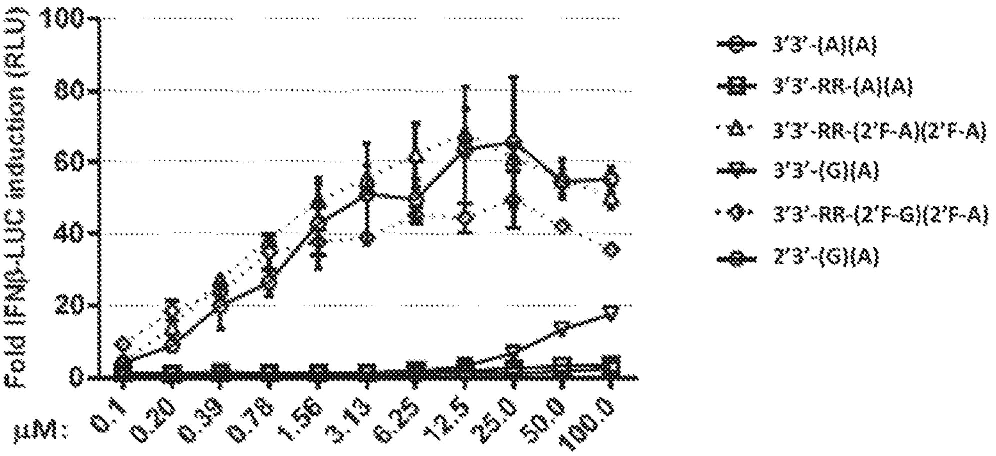
FIG. 6A-B depicts the fold IFNβ luciferase reporter induction by hSTING(REF) in HEK293T cells over a dose range (6A) and at 6.25 μM CDN (6B).
Figure 6B:
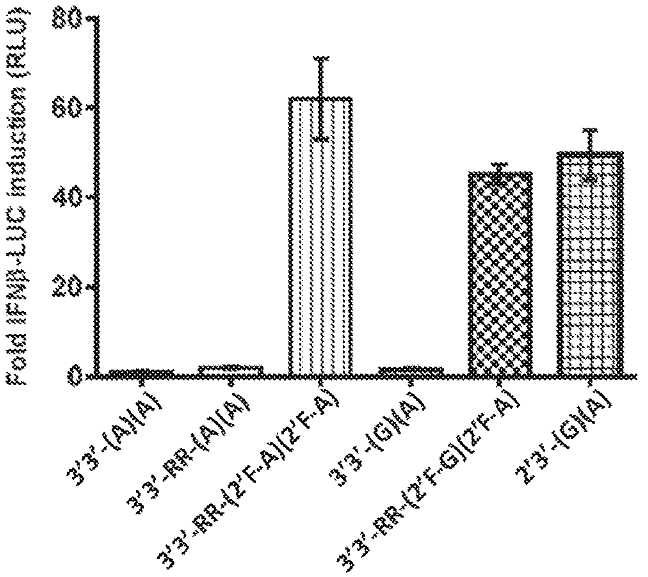

Example 12: 3',3'-Di-F-CDN Derivative Molecules Activation of Human STING Signaling in HEK293T Cells To evaluate the signaling capacity of two known natural human STING variants, hSTING(WT) and hSTING (REF), in response to native and fluorine substituted CDN compounds, we measured the activity of an IFN-β-reporter in human embryonic kidney (HEK) 293T cell lines that stably expressing hSTING(WT) or hSTING(REF). The sequence of the hSTING(REF) allele has been described (Ishikawa, H., and Barber, G. N. (2008). *Nature* 455, 674-678), and has the NCBI Reference Sequence NP_938023 (FIG. 6). The sequences of the hSTING(WT) and hSTING(REF) variant alleles were are also described in Yi, et al., 2013, *PLoS One,* 8(10), e77846 (DOI: 10.1371/journal.pone.0077846.

The parental HEK293T cell line does not express endogenous functional STING, so the responsiveness of exogenously expressed STING alleles to various CDN compounds can be evaluated using stable HEK293T STING-expressing cell lines. These lines were generated with MSCV2.2 retroviral plasmids which contain full length STING cDNA with a c-terminal HA epitope tag cloned upstream of an IRES in frame with green fluorescent protein (GFP). Retroviral vectors were transfected into the amphotropic Phoenix packaging cell line using Lipofectamine (Invitrogen). After two days viral supernatants were harvested and used for transduction of HEK293T cells.

GFP positive cells were sorted using a Mo Flo cell sorter at the Cancer Research Laboratory Flow Cytometry Facility at UC Berkeley. $10^4$ HEK293T STING cells were seeded in 96-well plates and transiently transfected (using Lipofectamine 2000) with 50 ng of a human IFN-β reporter plasmid (pLuc-IFN-β) expressing the human IFN-β promoter upstream of a firefly luciferase reporter gene (Fitzgerald et al., 2003, *Nature Immunology,* 4(5): 491-496) and 10 ng of plasmid expressing a constitutively active thymidine kinase (TK) *Renilla reniformis* luciferase reporter gene (Promega) for normalization. 24 hours later, cells were stimulated with native and synthetic CDN derivative molecules using digitonin permeabalization to ensure uniform uptake. Each STING cell line was stimulated in 25 ul digitonin buffer (50 mM HEPES, 100 mM KCL, 3 mM MgCl2, 0.1 mM DTT, 85 mM Sucrose, 0.2% BSA, 1 mM ATP, 0.1 mM GTP, 10 ug/ml digitonin) with 2-fold dilutions from 0.1 μM to 100 μM of each of the following CDN compounds: cyclic-[A(3',5')p-A(3',5')p] (CDA, 3',3'-(A)(A)), dithio-(Rp,Rp)-cyclic-[A(3',5')p-A(3',5')p] (3',3'-RR-(A)(A)), dithio-(Rp,Rp)-cyclic-[2'F-A(3',5')p-2'F-A(3',5')p] (3',3'-RR-(2'F-A)(2'F-A)), cyclic-[G(3',5')p-A(3',5')p] (3',3'-(G)(A)), cyclic-[G(2',5')p-A(3',5')p] (2',3'-(G)(A)) and dithio-(Rp,Rp)-cyclic-[2'F-G(3',5')p-2'F-A(3',5')p] (3',3'-RR-(2'F-G)(2'F-A)).

After 20 min, the stimulation mixtures were removed and 200 ul of DMEM media supplemented with 10% (vol/vol) fetal bovine serum, 1% L-Glutamine, and 1% Penicillin/Streptomycin was added. Cells were incubated an additional 6 hours (37° C. 5% $CO_2$) and then cell lysates were prepared and reporter gene activity measured on a Spectramax M3 luminometer using the Dual-Glo Luciferase Assay System (Promega, catalog #E2920) as described by the manufacturer. IFNβ firefly luciferase reporter gene activity was normalized to TK *renilla* luciferase gene activity and plotted as fold induction over activity in unstimulated cells (mean+/−s.e.m.).

Figure 5A:
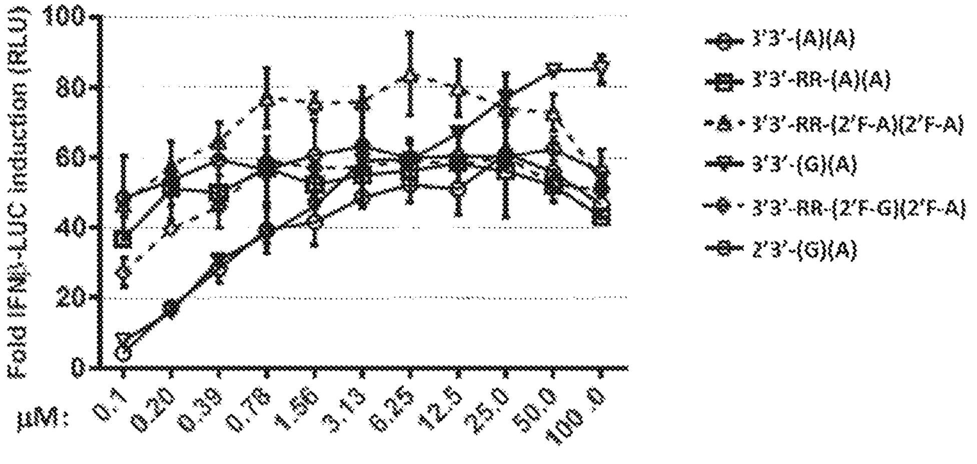
FIG. 5A-B depicts the fold IFN 3 luciferase reporter induction by hSTING(WT) in HEK293T cells over a dose range (5A) and at 6.25 μM CDN (5B).
Figure 5B:
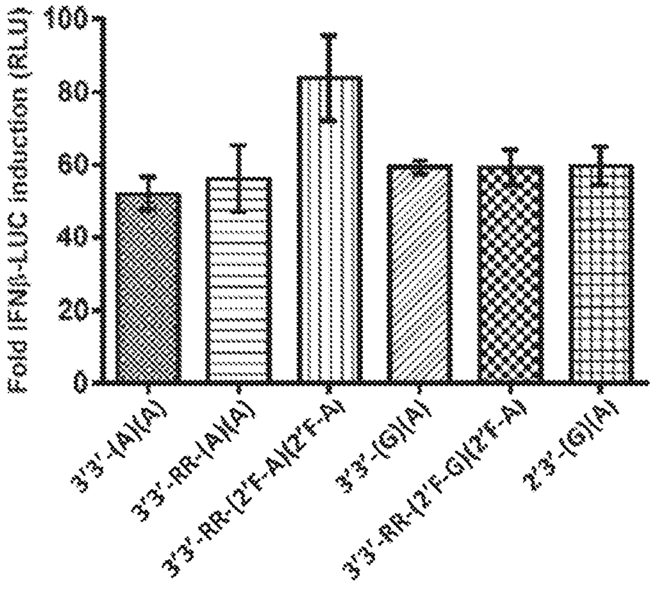

As shown in FIGS. 5A (dose course) and 5B (6.25 μM CDN), the fluorine substituted CDN compound 3',3'-RR-(2'F-A)(2'F-A) induced higher levels of IFNβ reporter activity by hSTING(WT) than the non-fluorine substituted compounds 3',3'-(A)(A) and the dithio-(Rp,Rp) derivative OH reference compound, 3',3'-RR-(A)(A), at the doses tested. 3',3'-RR-(2'F-A)(2'F-A) also stimulated higher levels of IFNβ reporter activity by hSTING(WT) when compared to the endogenous cellular ligand 2',3'-(G)(A). The fluorine substituted CDN compound 3',3'-RR-(2'F-G)(2'F-A) also strongly induced IFNβ reporter activity by hSTING(WT), and at lower doses, 3',3'-RR-(2'F-G)(2'F-A) more potently induced IFNβ reporter activity by hSTING(WT) than the compound 3',3'-(G)(A). As shown in 6A (dose course) and 6B (6.25 μM CDN), HEK 293T cells expressing hSTING (REF) responded poorly to stimulation with 3',3'-(A)(A), 3',3'-RR-(A)(A) and 3',3'-(G)(A), all of which contain canonical (3',5')p (3',5')p intra-nucleotide phosphate linkages. In contrast, the fluorine substituted CDN compounds 3',3'-RR-(2'F-A)(2'F-A) and 3',3'-RR-(2'F-G)(2'F-A) strongly induced IFNβ reporter activity, to a level similar to the endogenous cellular ligand 2',3'-(G)(A) that has a (2',5')p-(3',5')p intra-nucleotide phosphate linkage. These results indicated that CDN compounds containing canonical (3',5')p-(3',5')p intra-nucleotide phosphate linkages with 2',2"-difluoro-dithio-(Rp,Rp) substitutions potently activated hSTING(REF), an allele that is typically refractory to stimulation by CDNs containing canonical (3',5')p (3',5')p intra-nucleotide phosphate linkages.

Taken together, the data in FIGS. 5A,B and 6A,B demonstrate that fluorine substituted CDNs, 3',3'-RR-(2'F-A)(2'F-A) and 3',3'-RR-(2'F-G)(2'F-A), are capable of strongly activating hSTING(REF) and hSTING(WT), and therefore enable human STING signaling across a broad range of the human population that express different variants of STING.

Example 13: Induction of Type I Interferon by CDNs

The induction of type I interferon was measured in human primary blood mononuclear cells (hPBMCs) to evaluate the potency of mono- or di-F-CDN compounds as described herein. hPBMCs from two unique donors were used: one donor was homozygous for the wild type (WT) STING allele ($STING^{WT/WT}$) and the other donor was homozygous for the so-called reference (REF) STING allele ($STING^{REF/REF}$). The STING genotype of these donors was determined by PCR amplification and sequencing: genomic DNA was isolated from $10^4$ hPBMCs using Quick Extract DNA Extraction Solution (Epicentre) and was used to amplify regions of exon 3, 6, and 7 of the human STING gene. Primers for amplification and sequencing were: hSTING exon3F GCTGAGACAGGAGCTTTGG (SEQ ID NO: 10), hSTING exon3R AGCCAGAGAGGTTCAAGGA (SEQ ID NO: 11), hSTING exon6F GGCCAATGAC-CTGGGTCTCA (SEQ ID NO: 12), hSTING exon6R CAC-CCAGAATAGCATCCAGC (SEQ ID NO: 13), hSTING exon7F TCAGAGTTGGGTATCAGAGGC (SEQ ID NO: 14), hSTING exon7R ATCTGGTGTGCTGGGAAGAGG (SEQ ID NO: 15), STING variant alleles were assigned according to Yi, et al., 2013, PLoS One, 8(10), e77846 (DOI: 10.1371/journal.pone.0077846).

Cryopreserved hPBMCs were thawed and $10^6$ cells were either left untreated or treated with reference compounds 3',3'-RR-(A)(A), 3',3'-RR-(G)(G), 2',3'-(G)(A), 3',3'-(G)(A) or 3',3'-RR-(G)(A), or mono- or di-F compounds 3',3'-RR-(2'F-A)(2'F-A), 3',3'-RR-(2'F-A)(A), 3',3'-RR-(2'F-G)(2'F-G), 3',3'-RR-(2'F-G)(2'F-A), 3',3'-RR-(2'F-G)(A), and 3',3'-RR-(G)(2'F-A), in RPMI media supplemented with 10% fetal bovine serum, 1% L-Glutamine, and 1% Penicillin/Streptomycin. Cells were incubated at 37° C., 5% $CO_2$ with concentrations ranging from 100 μM to 0.1 μM of each CDN. After 2 hours (FIGS. 7 and 8) or 2 hours and 6 hours (FIGS. 9-13) stimulation, cells were harvested by centrifugation and washed once with phosphate-buffered saline. Cellular RNA was isolated using the *Aurum* Total RNA 96 Kit and cDNA was synthesized using the iScript cDNA Synthesis Kit. Target and reference gene expression was assessed by real-time qRT-PCR using PrimePCR probe assays and the CFX96 gene cycler (all reagents and equipment from BioRad). Normalized IFNβ expression was expressed relative to untreated cells. Target genes included type I interferon (IFNβ), Th1-associated cytokines (IFNγ, IL-12p40) and NF-kB dependent inflammatory cytokines (TNFα, IL-6). Reference genes included GUSB alone (FIGS. 7 and 8) or GUSB and HSP90AB1 (FIGS. 9-13).

Figure 7A:
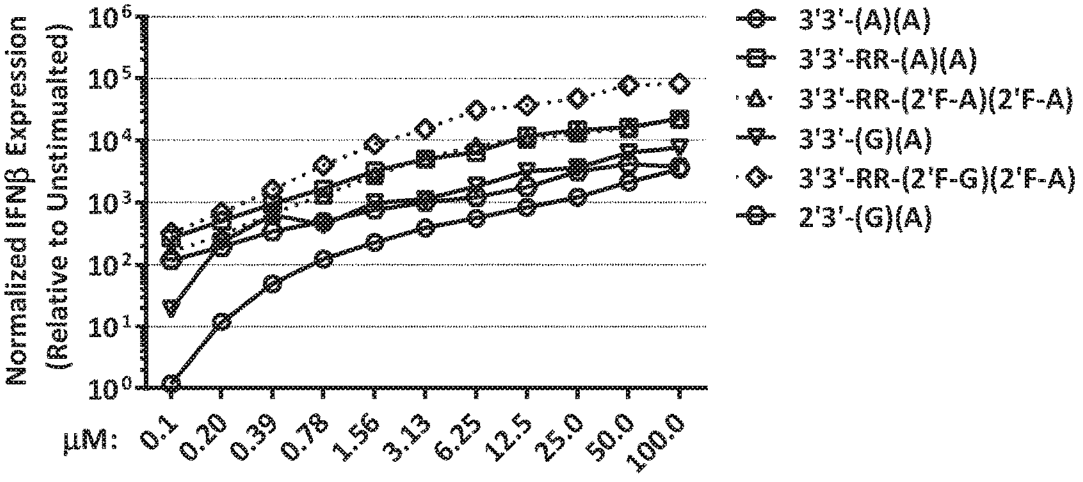
FIG. 7A-B depicts relative IFNβ expression by $STING^{WT/WT}$ hPBMCs over at dose range (7A) and at 6.25 μM CDN (7B).
Figure 7B:
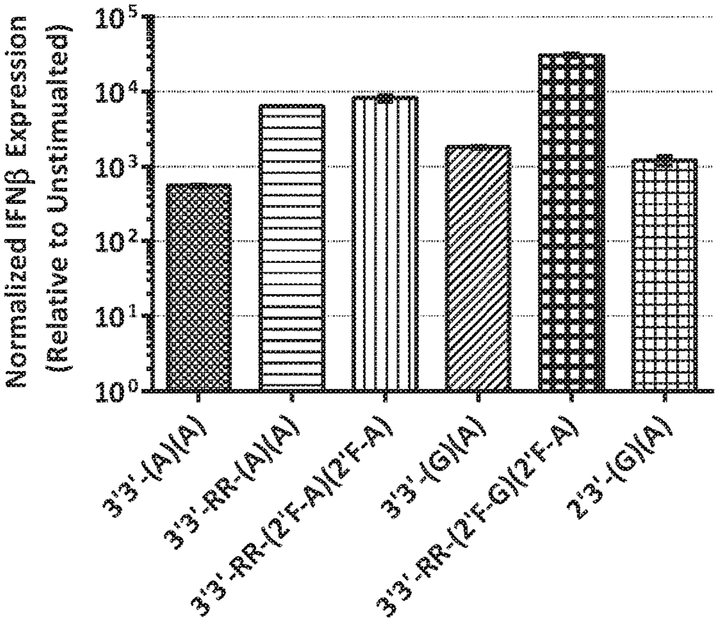
Figure 8A:
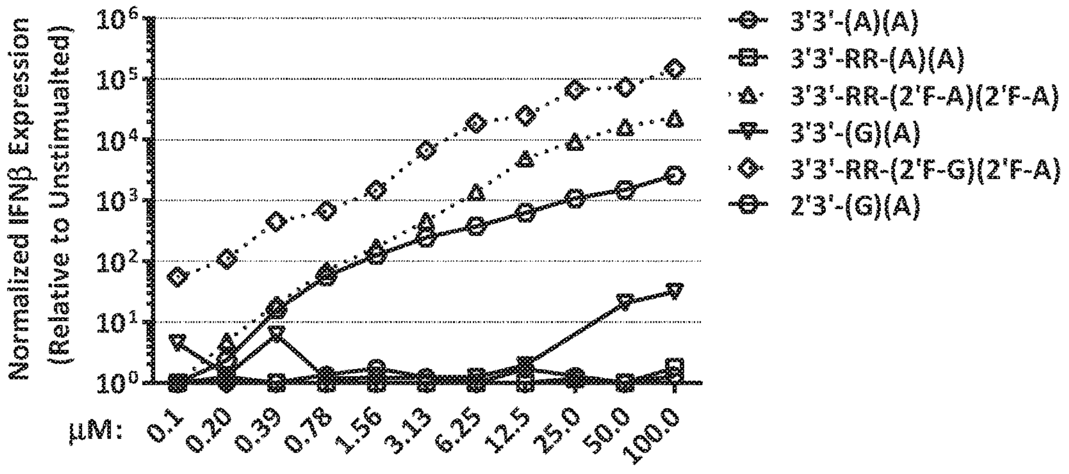
FIG. 8A-B depicts relative IFNβ expression by $STING^{REF/REF}$ hPBMCs over at dose range (8A) and at 6.25 μM CDN (8B).
Figure 8B:
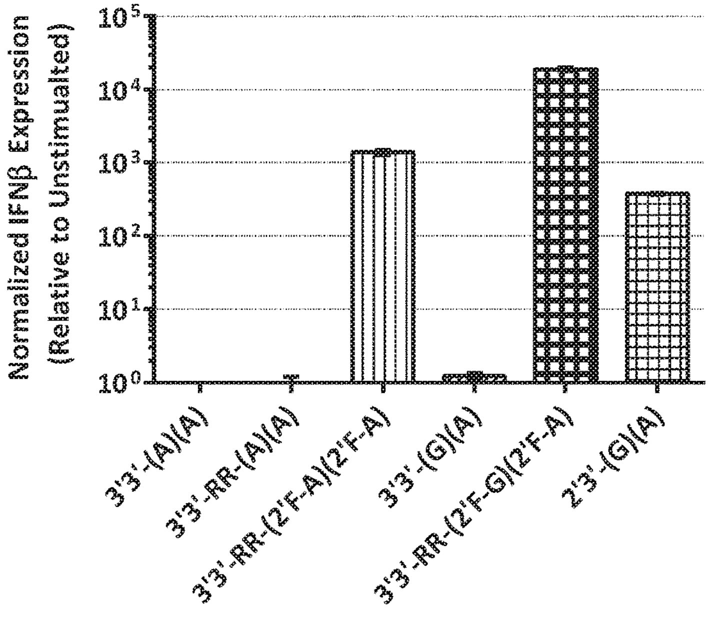

FIGS. 7A and 8A (dose course) and 7B and 8B (6.25 μM CDN) show the relative normalized IFNβ expression by hPBMC homozygous for the WT STING allele (FIG. 7A, 7B) or for the REF STING allele (FIG. 8A, 8B). Regarding $STING^{WT/WT}$ hPBMCs, both the 3',3'-RR-(A)(A) and 3',3'-RR-(2'F-A)(2'F-A) induced similar levels of IFNβ; however, both of these derivatives induced higher levels of IFNβ transcript when compared to the 3',3'-(A)(A) compound, which was the least potent WT STING agonist in this example. At all doses, 3',3'-RR-(2'F-A)(2'F-A) stimulated higher levels of IFNβ transcript by $STING^{WT/WT}$ hPBMCs when compared to non-canonical 2',3'-(G)(A) naturally produced by mammalian cells. Additionally, 3',3'-RR-(2'F-G)(2'F-A) was the most potent inducer of type I interferon in $STING^{WT/WT}$ hPBMCs, eliciting ~10-100-fold higher levels of IFNβ when compared to the parent cGAMP compound in the dose range tested. Regarding $STING^{REF/REF}$ hPBMCs, 3',3'-(A)(A), 3',3'-RR-(A)(A) and 3',3'-(G)(A) did not stimulate production of appreciable IFNβ transcript levels at the doses tested. In contrast, 2',3'-(G)(A), 3',3'-RR-(2'F-A)(2'F-A), and 3',3'-RR-(2'F-G)(2'F-A) stimulated dose-dependent production of IFNβ transcript by $STING^{REF/REF}$ hPBMCs.

In the dose range tested in FIGS. 7 and 8, both 3',3'-RR-(2'F-A)(2'F-A) and 3',3'-RR-(2'F-G)(2'F-A) were more potent inducers of IFNβ transcript $STING^{REF/REF}$ hPBMCs than 2',3'-(G)(A), 3',3'-RR-(2'F-G)(2'F-A) was an extremely potent stimulator of the REF STING allele, as IFNβ transcript levels were 12- to 70-fold higher when cells were stimulated with 3',3'-RR-(2'F-G)(2'F-A) compared to cells similarly dosed with 2',3'-(G)(A). These results demonstrated that 2',2"-diF-RR derivatives of CDA and cGAMP were more potent stimulators of human cells homozygous for WT or REF STING than their corresponding parent compounds or naturally-produced non-canonical 2',3'-(G)(A). These results also demonstrated that compounds containing canonical R(3',5')pR(3',5')p intra-nucleotide phosphate linkages with 2',2"-difluoro-dithio-(Rp,Rp) modifications could stimulate IFN production by human cells homozygous for the REF STING allele that is typically refractory to stimulation by CDNs containing canonical linkages.

Figure 9A:
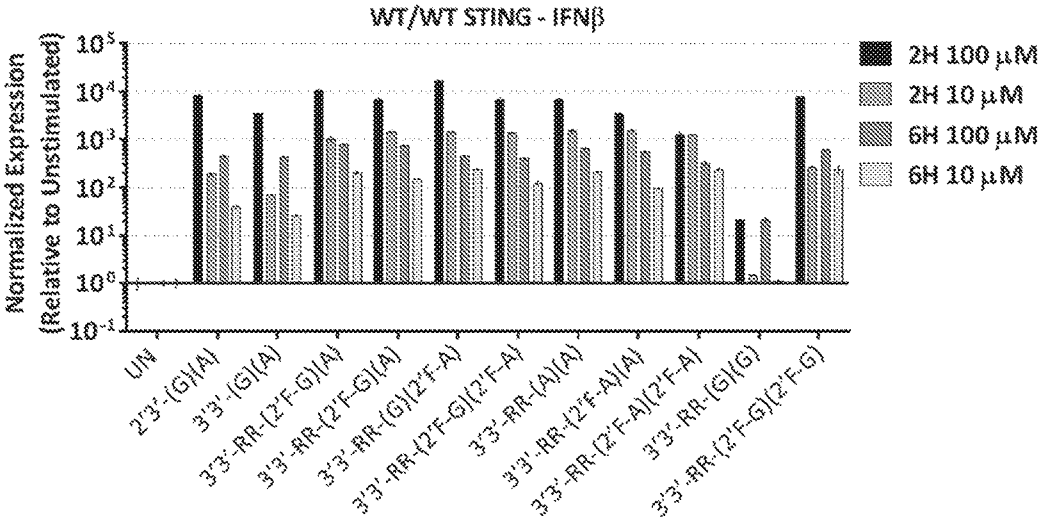
FIG. 9A-B depicts the normalized IFNβ expression in hPBMCs with hSTING(WT) (9A) or REF hSTING(REF) (9B) treated with CDNs.
Figure 9B:
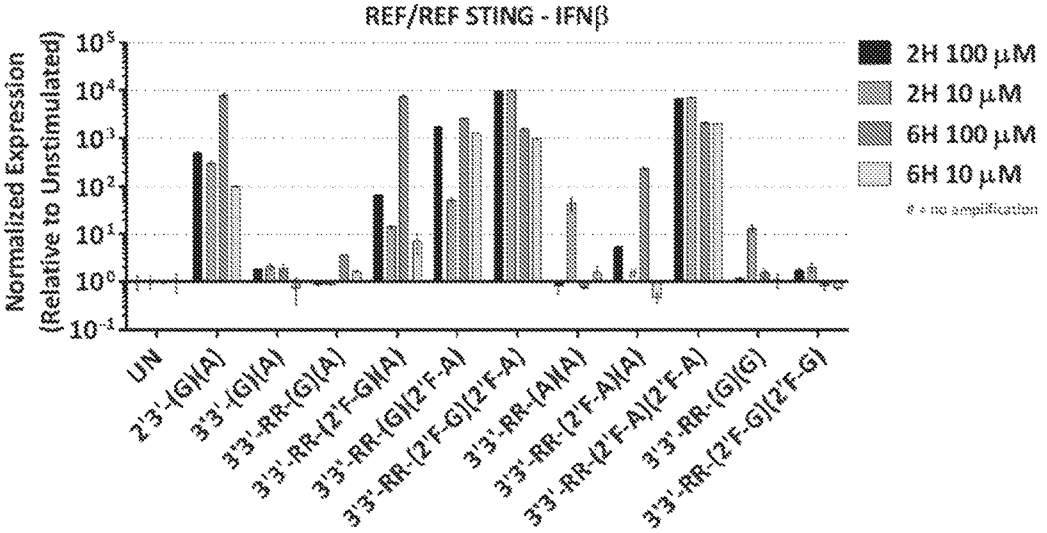
Figure 10A:
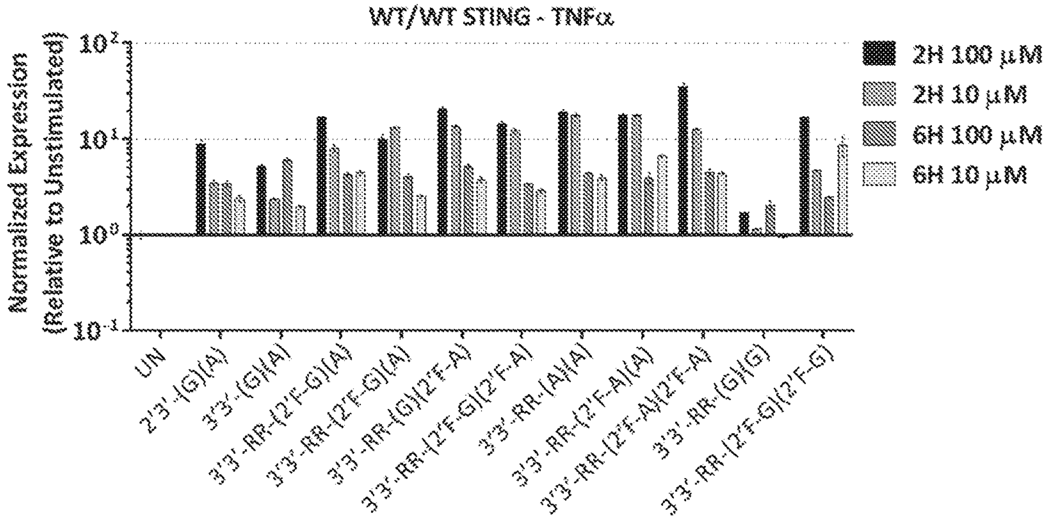
FIG. 10A-B depicts the normalized TNFα expression in hPBMCs with hSTING(WT) (10A) or REF hSTING(REF) (10B) treated with CDNs.
Figure 10B:
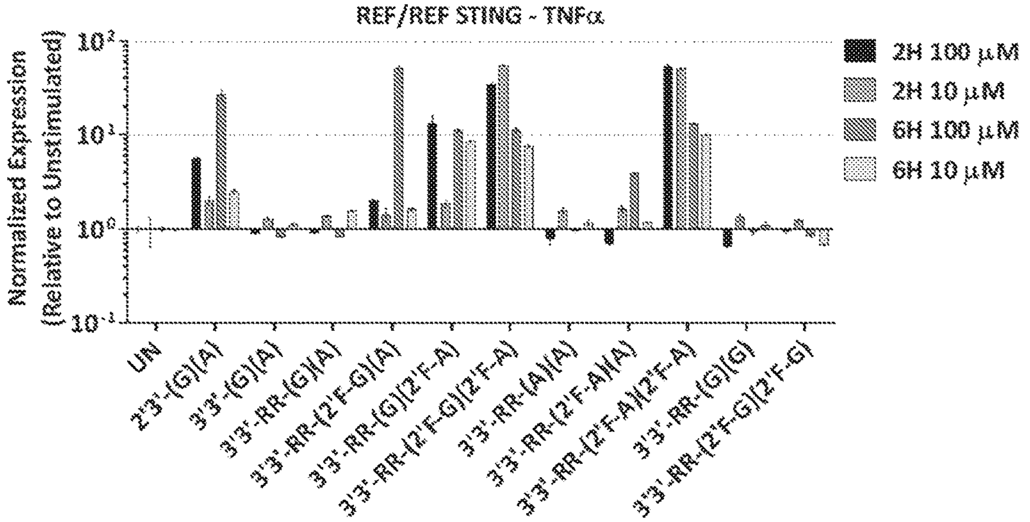
Figure 11A:
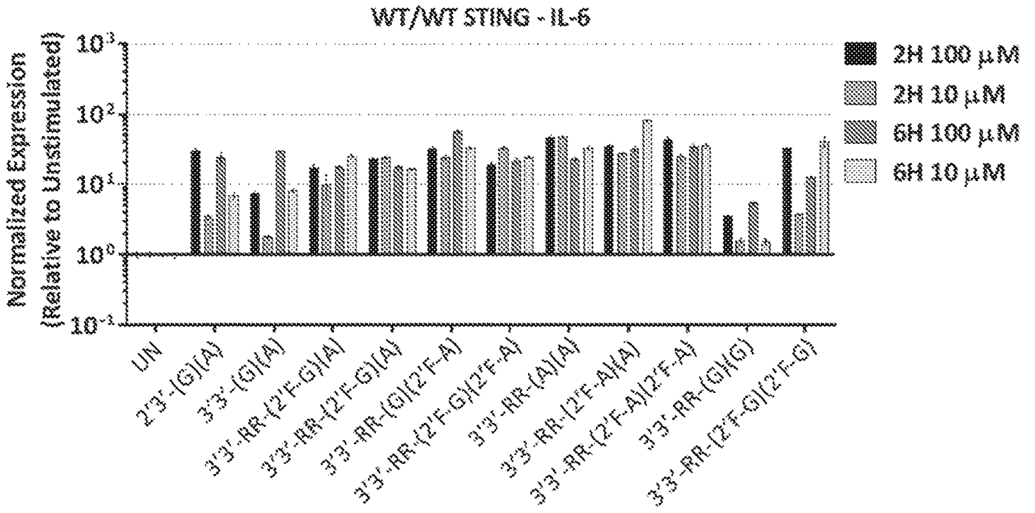
FIG. 11A-B depicts the normalized IL-6 expression in hPBMCs with hSTING(WT) (11A) or REF hSTING(REF) (11B) treated with CDNs.
Figure 11B:
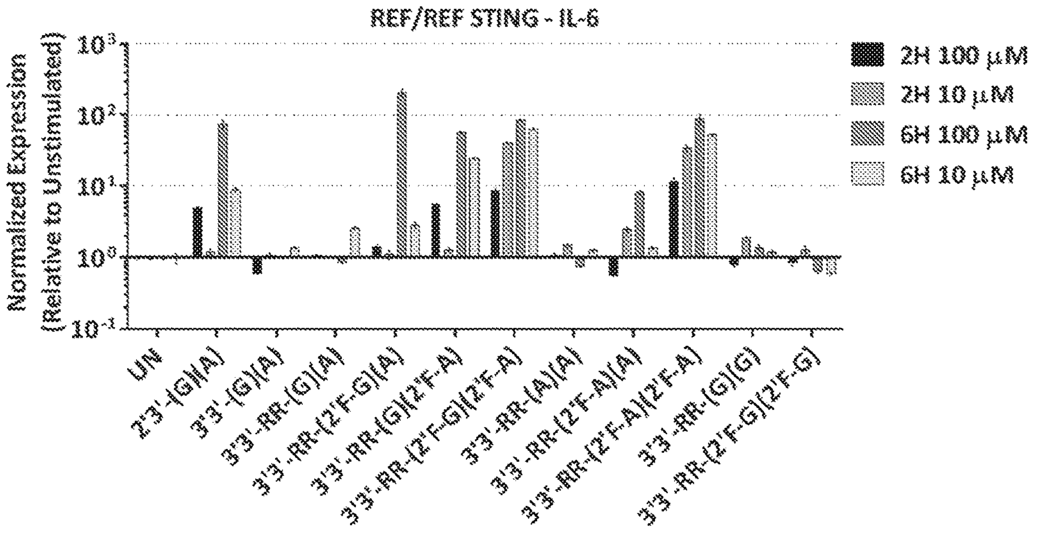
Figure 12A:
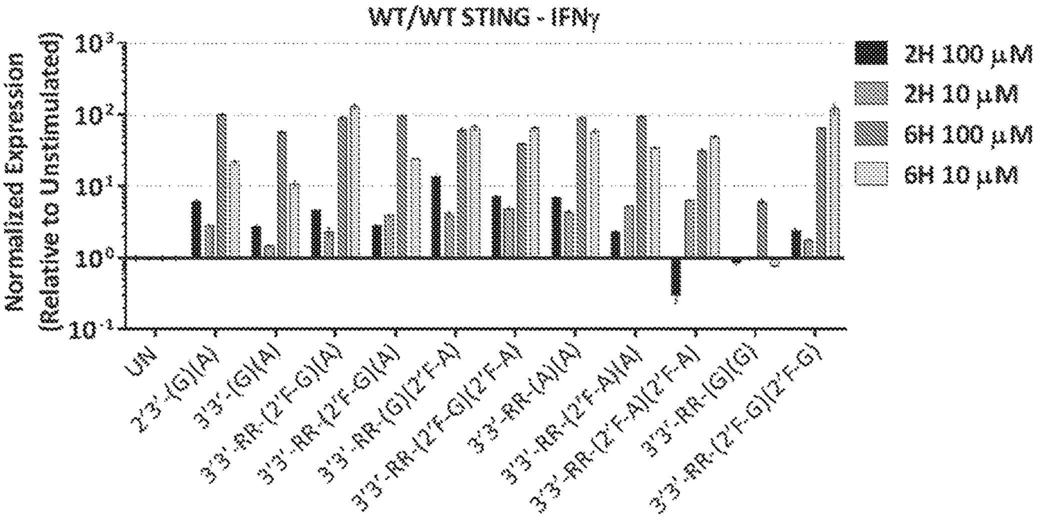
FIG. 12A-B depicts the normalized IFNγ expression in hPBMCs with hSTING(WT) (12A) or REF hSTING(REF) (12B) treated with CDNs.
Figure 12B:
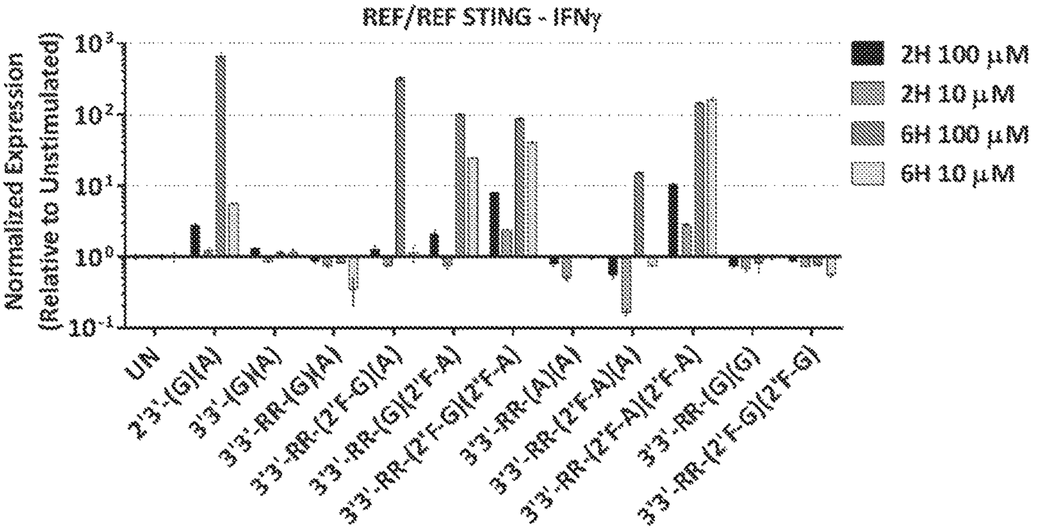
Figure 13A:
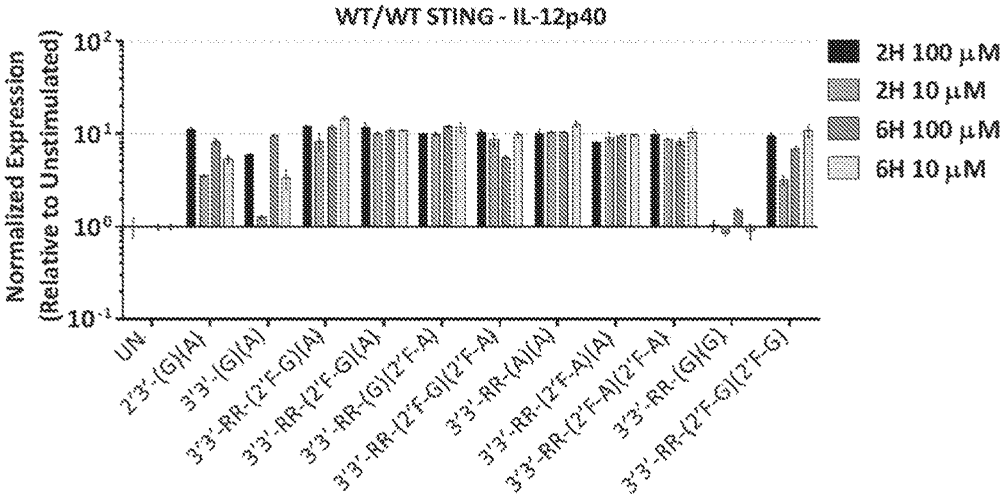
FIG. 13A-B depicts the normalized IL-12p40 expression in hPBMCs with hSTING(WT) (13A) or REF hSTING (REF) (13B) treated with CDNs.
Figure 13B:
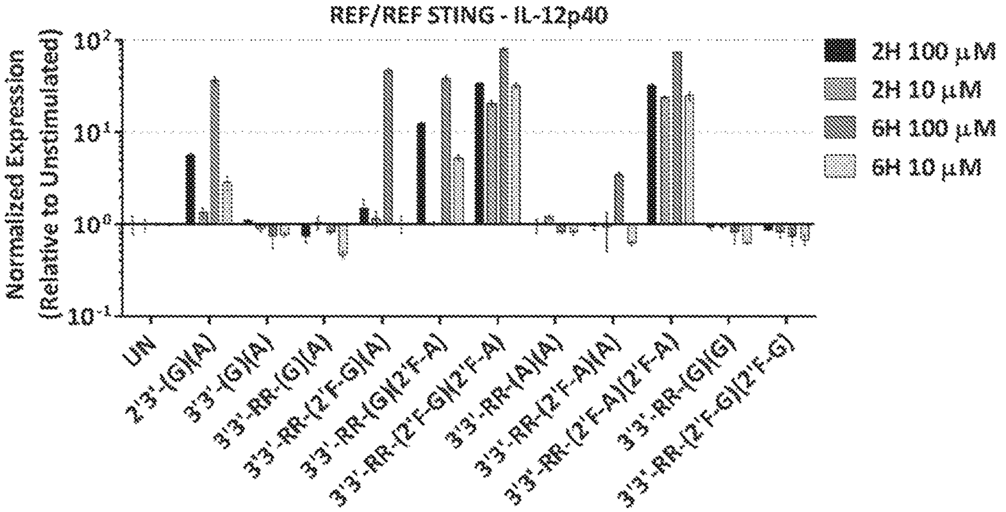

Results for mono- or di-F CDNs 3',3'-RR-(2'F-G)(A), 3',3'-RR-(G)(2'F-A) and 3',3'-RR-(2'F-G)(2'F-A) with 3',3'-(G)(A) and 3',3'-RR-(G)(A) as reference; 3',3'-RR-(2'F-A)(A) and 3',3'-RR-(2'F-A)(2'F-A) with 3',3'-RR-(A)(A) as reference; and 3',3'-RR-(2'F-G)(2'F-G) with 3',3'-RR-(G)(G) as reference are shown in FIG. 9A (IFNβ, WT/WT), FIG. 9B (IFNβ, REF/REF), FIG. 10A (TNFα, WT/WT), FIG. 10B (TNFα, REF/REF), FIG. 11A (IL-6, WT/WT), FIG. 11B (IL-6, REF/REF), FIG. 12A (IFNγ, WT/WT). FIG. 12B (IFNγ, REF/REF). FIG. 13A (IL-12p40, WT/WT) and FIG. 13B (IL-12p40. REF/REF). Regarding $STING^{WT/WT}$ hPBMCs, with the exception of 3',3'-RR-(G)(G), all of the compounds tested elicited potent, dose-dependent cytokine responses. Depending on the cytokines, responses in $STING^{WT/WT}$ hPBMCs were highest at 2 hours (IFNβ, TNFα) or 6 hours (IFNγ) stimulation. IL-6 and IL-12p40 responses were similar in $STING^{WT/WT}$ hPBMCs at both time points. Regarding $STING^{REF/REF}$ hPBMCs, the naturally-produced mammalian compound 2',3'-(G)(A) induced robust, dose-dependent responses for all of the cytokines that peaked at 6 hours of stimulation. Compared to 3',3'-(G)(A) and 3',3'-RR-(G)(A) reference compounds, 3',3'-RR-(2'F-G)(A), 3',3'-RR-(G)(2'F-A), and 3',3'-RR-(2'F-G)(2'F-A) induced more robust dose-dependent responses of each of the cytokines tested. The presence of 2'F substitutions on both the adenine and guanine gave the most robust responses, and a mono 2'F substitution on the adenine base elicited more potent responses than a mono 2'F substitution on the guanine base. Compared to 3',3'-RR-(A)(A) reference compound, di-F substituted 3',3'-RR-(2'F-A)(2'F-A) induced more robust responses of all of the cytokines tested, with IFNβ and TNFα responses peaking after 2 hours stimulation. Although less robust than the di-F compound, the mono-F substituted 3',3'-RR-(2'F-A)(A) compound was also able to elicit cytokine responses at 6 hours stimulation with 100 μM of compound. The mono- and di-F-CDN compounds generally show a robust cytokine response in hPBMC, in particular the 3',3'-RR-(2'F-A)(2'F-A) and 3',3'-RR-(2'F-G)(2'F-A), demonstrating a more robust response than their OH reference compound in $STING^{REF/REF}$, with responses similar to, or in some instances more robust than the naturally produced 2',3'-(G)(A).

Example 14: Mono- and Di-F-CDN Compound Activation of Human STING Signaling in THP1 Cells To determine the relative level of type I interferon induced in human cells by each of the mono- or di-F-CDN as a signature of adjuvant potency, 100,000 THP1-Dual cells (a human monocyte cell line containing the hSTING HAQ allele transfected with an IRF-3 inducible secreted luciferase reporter gene (Invivogen) which express secreted luciferase under the control of a promoter comprised of five IFN-stimulated response elements) were activated with 30 ng/ml phorbol 12-myristate 13-acetate overnight in a 96-well dish. Cells were washed with fresh media and incubated for 30 min at 37° C. with 5% $CO_2$ with compounds in 3 fold titration steps from 2,000 to 0.0338 μM in PB buffer (50 mM 4-(2-hydroxyethyl)-1-piperazineethanesulfonic acid, 100 mM KCl, 3 mM $MgCl_2$, 0.1 mM dithiothreitol, 85 mM sucrose, 1 mM ATP, 0.1 mM GTP and 0.2% bovine serum albumin). After 30 minutes, cells were washed and fresh RPMI media containing 10% FBS was added, and cells were incubated at 37° C. with 5% $CO_2$. Cell culture supernatants from each sample were collected after overnight incubation, and 10 μL of the cell culture supernatants was added to 50 μL QUANTI-Luc reagent (Invivogen). Type I interferon activation was determined by measuring secreted luciferase levels on a SpectraMax M3 spectrophotometer (Molecular Devices). The EC50 value was determined from the dose-response curve for the 10 concentrations from the serial dilution of the reference compounds and compounds of the invention tested in this assay as listed in Table 5. These results demonstrate improved activity for diF compounds 3',3'-RR-(2'F-A)(2'F-A), 3',3'-RS-(2'F-A)(2'F-A), 3',3'-RR-(2'F-G)(2'F-G), 3',3'-RR-(2'F-G)(2'F-A), 3',3'-RS-(2'F-G)(2'F-A) and 3',3'-RR-(2'F-iBuG)(2'F-A) relative to each of their OH reference compounds. The mono-F derivatives 3',3'-RR-(2'F-G)(A) and 3',3'-RR-(G)(2'F-A) also showed improved activity relative to the OH reference 3',3'-RR-(G)(A).

TABLE 5

EC50 without digitonin in THP1 cells (HAQ allele).

| Example/Compound | Compound name | EC50 (μM) |
|---|---|---|
| Reference | 3'3'-RR-(A)(A) | 25 |
| Example 1 Compound 6 | 3'3'-RR-(2'F-A)(2'F-A) | 19 |
| Example 1 Compound 6a | 3'3'-RS-(2'F-A)(2'F-A) | 8 |
| Example 4 Compound 22 | 3'3'-RR-(A)(2'F-A) | 59 |
| Example 4 Compound 22a | 3'3'-RS-(A)(2'F-A) | 99 |
| Example 9 Compound 27 | 3'3'-RR-(2'F-BzA)(2'F-BzA) | >150 |
| Example 1 Compound 7 | 3'3'-RR-(2'βF-A)(2'βF-A) | 284 |
| Example 1 Compound 7a | 3'3'-RS-(2'βF-A)(2'βF-A) | >150 |
| Reference | 3'3'-RR-(G)(G) | 75 |
| Example 3 Compound 17 | 3'3'-RR-(2'F-G)(2'F-G) | 8 |
| Example 3 Compound 17a | 3'3'-RS-(2'F-G)(2'F-G) | >150 |
| Reference | 2'3'-(G)(A) | 242 |
| Reference | 3'3'-RR-(G)(A) | 28 |
| Example 2 Compound 14 | 3'3'-RR-(2'F-G)(2'F-A) | 3 |
| Example 2 Compound 14a | 3'3'-RS-(2'F-G)(2'F-A) | 18 |
| Example 5 Compound 23 | 3'3'-RR-(2'F-G)(A) | 15 |
| Example 5 Compound 23a | 3'3'-SR-(2'F-G)(A) | 25 |
| Example 6 Compound 24 | 3'3'-RR-(G)(2'F-A) | 13 |
| Example 6 Compound 24a | 3'3'-RS-(G)(2'F-A) | 89 |
| Example 10 Compound 30 | 3'3'-(2'F-G)(2'F-A) | 10 |
| Example 7 Compound 25 | 3'3'-RR-(2'F-iBuG)(2'F-BzA) | 78 |
| Example 7 Compound 25a | 3'3'-RS-(2'F-iBuG)(2'F-BzA) | >150 |
| Example 8 Compound 26 | 3'3'-RR-(2'F-iBuG)(2'F-A) | 23 |

Example 15: Di-F-CDN Derivatives Induce T Cell-Mediated Anti-Tumor Immunity

To determine whether the derivative molecules elicit anti-tumor immunity, 6-8 week old female C57BL/6 mice (8 mice per group) were implanted with B16.SIY cells (5×$10^5$ cells in 100 μL PBS). Mice were treated with reference compound 3',3'-RR-(A)(A) and di-F compound 3',3'-RR-(2'F-A)(2'F-A) (5, 50, 100 μg in a total volume of 40 μL HBSS), or HBSS vehicle control. Treatments began when tumors reached a volume of approximately 100 $mm^3$, on day 9 post tumor implantation. The CDN compounds were administered by subcutaneous injection into the center of the tumor (IT) using a 27 gauge needle. Mice were bled on day 16 post tumor implantation and PBMCs were isolated by Ficoll gradient (Miltenyi Biotech). $1\times10^5$ PBMCs were pre-incubated with anti-CD16/32 monoclonal antibody to block potential nonspecific binding, and labeled with PE-MHC class I pentamer (Proimmune) consisting of murine H-2Kb complexed to SIYRYYGL (SIY. SEQ ID NO: 16) peptide, anti-TCRβ-AF700 (H57-597), anti-CD8-Pacific Blue (53-6.7), anti-CD4-Pacific Orange (RM4-5) (all antibodies from BioLegend) and the Fixable Viability Dye eFluor 450 (eBioscience). Stained cells were analyzed using FACS Versa cytometer with FACSDiva software (BD). Data analysis was conducted with FlowJo software (Tree Star).

Figure 14A:
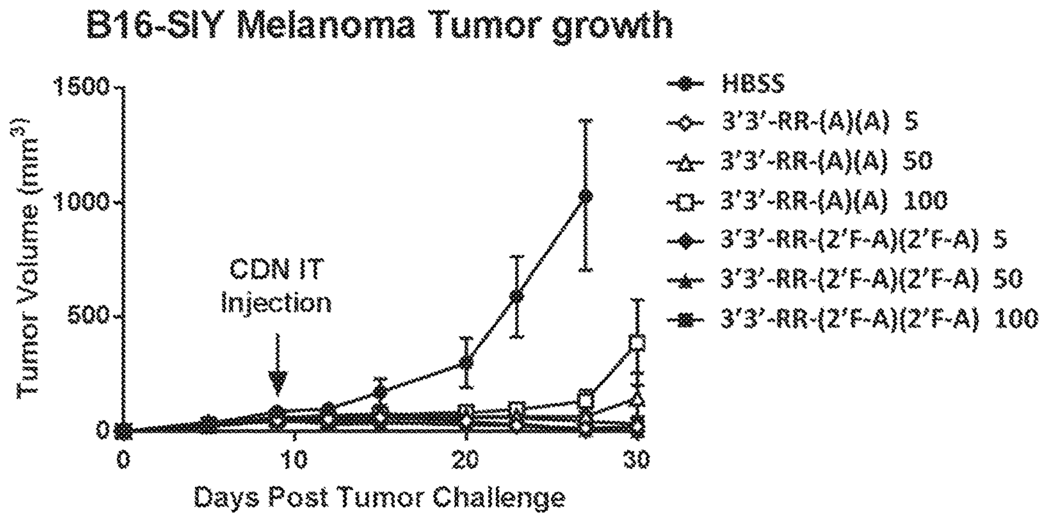
FIG. 14A-B depicts the tumor volume (14A) and percent of $SIY^+$ $CD8^+$ T-cells (14B) in a B16-SIY melanoma mouse model, following intra-tumoral injection of CDNs.
Figure 14B:
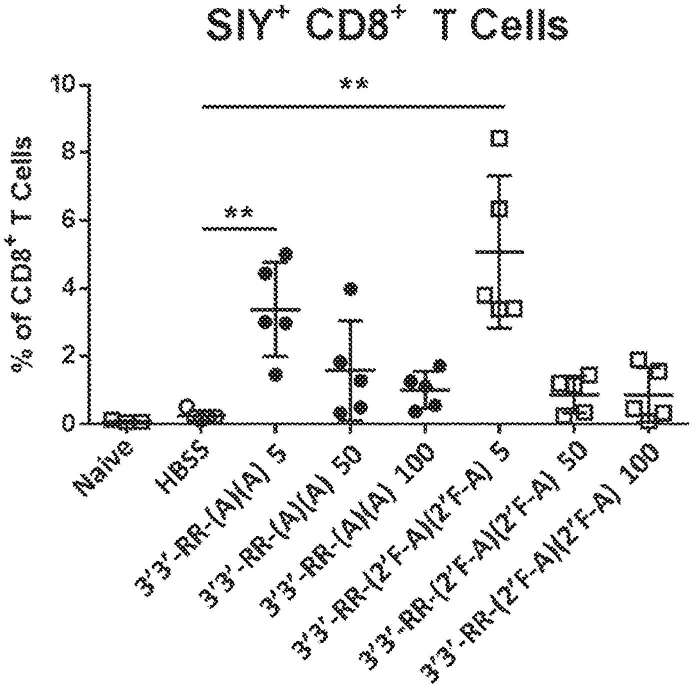

As shown in FIG. 14A, unlike the OH reference 3',3'-RR-(A)(A) compound, all mice treated with the 3',3'-RR-(2'F-A)(2'F-A) compound rejected the growth of established B16-SIY melanomas at all doses. To demonstrate that the effect is mediated by adaptive T cell immune responses, day 7 post-IT injection PBMCs were assessed for the percentage of SIY-specific $CD8^+$ T cells by flow cytometry. As shown in FIG. 14B. PBMCs isolated from mice treated with 5 μg of either the OH reference compound 3',3'-RR-(A)(A) or di-F compound 3',3'-RR-(2'F-A)(2'F-A) elicited significantly SIY-specific $CD8^+$ T cells, as compared to the HBSS-treated control group (** P<0.01, student's 1-test). These data demonstrate the ability of the di-F derivative compound 3',3'-RR-(2'F-A)(2'F-A) to elicit T cell-mediated anti-tumor immunity, in an antigen-specific manner.

Example 16: Di-F-CDN Derivatives Induce Potent Anti-Tumor Efficacy in Diverse Murine Tumor Models To assess the ability of the fluorinated derivative compounds to promote anti-tumor immunity in diverse murine tumor models, tumor cells were implanted (in 100 μL PBS) subcutaneously on the lower back of 6-8 week old C57BL/6 female mice. Treatments began when tumors reached a volume of approximately 100 $mm^3$, on approximately day 14 post tumor implantation (see table below for tumor type, number of cells, and day of IT injection). The CDN compounds were administered by IT injection (10 or 100 μg in a total volume of 40 μL HBSS), and repeated every three days for a total of three injections. The compounds 3',3'-RR-(2'F-A)(2'F-A) and 3',3'-RR-(2'F-G)(2'F-A) and control mice given vehicle only (40 μL HBSS) were dosed. Tumors were measured twice weekly.

| Tumor Type | Description | # Cells Implanted | Days CDN IT |
|---|---|---|---|
| B16.F10 | B16 Melanoma | $5\times10^4$ | 14, 17, 22 |
| MC38 | Colon Carcinoma | $1\times10^5$ | 10, 14, 18 |

Figure 15A:
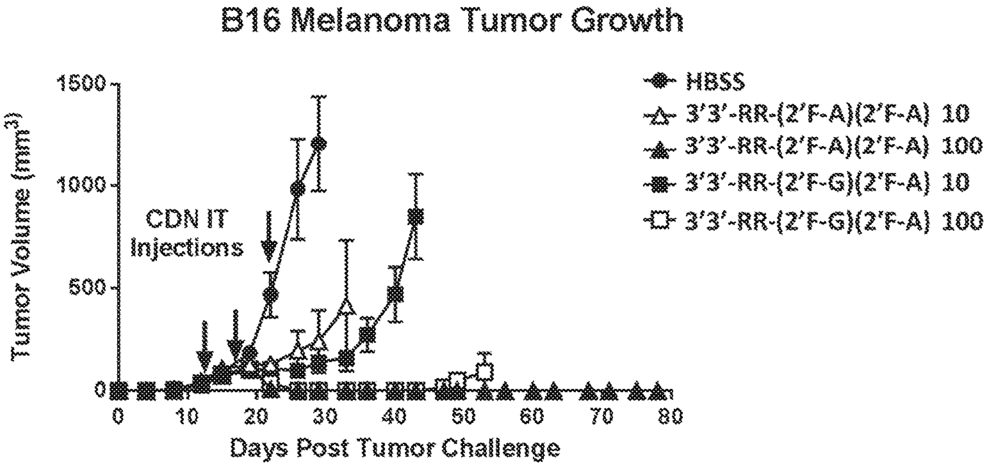
FIG. 15A-B depicts the tumor volume in a B16 melanoma (15A) or MC38 colon carcinoma (15B) mouse model, following intra-tumoral injection of CDNs.
Figure 15B:
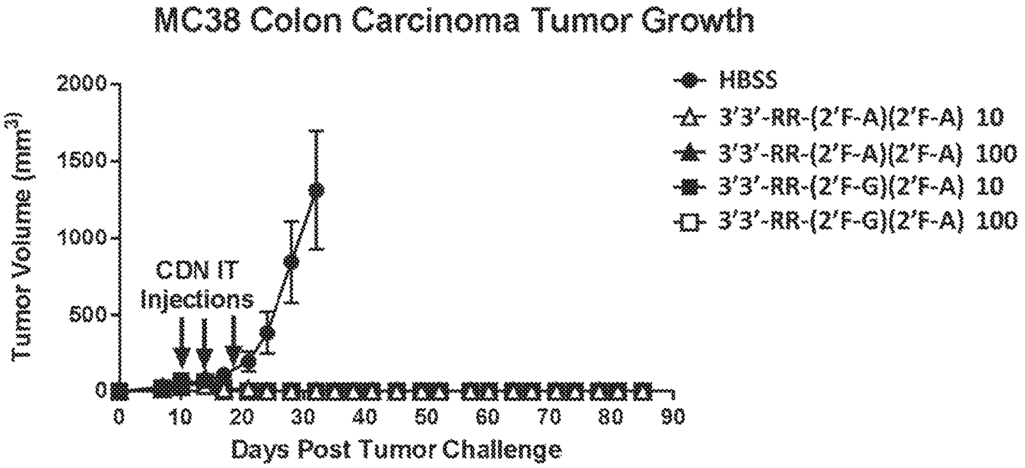

As shown in FIG. 15A, in the aggressive B16.F10 melanoma model the 3',3'-RR-(2'F-A)(2'F-A) and 3',3'-RR-(2'F-G)(2'F-A) compounds induced significant tumor inhibition as compared to HBSS, with the 3',3'-RR-(2'F-A)(2'F-A) molecule eliciting complete tumor regression at the 100 μg dose. In the MC38 colon carcinoma model, as shown in FIG. 15B, both compounds elicited complete tumor regression at all doses tested, compared to HBSS control. These data demonstrate the broad anti-tumor effects of the fluorinated derivatives across diverse tumor models.

Example 17: Comparative Immunogenicity of Di-F-CDN Derivatives

To determine whether the fluorinated derivatives could elicit HIVgag-specific $CD4^+$ and $CD8^+$ T cell responses, BALB/c mice (n=4) were immunized subcutaneously with 0 μg (no CDN), 1 μg or 5 μg of CDN formulated in 2% squalene-and-water (AddaVax, Invivogen) with 5 μg HIV-gag p55 protein. Seven days following the vaccination, spleens were harvested from the mice and splenocytes prepared. $2\times10^5$ splenocytes were stimulated overnight in an IFNγ ELISPOT assay with media alone (unstimulated) or with 1 μM HIVgag p55 $CD4^+$ and $CD8^+$ specific peptides. IFNγ ELISPOTs were developed and quantified using a CTL plate reader and ImmunoSpot software. 3',3'-RR-(2'F-A)(2'F-A) and 3',3'-RR-(2'F-G)(2'F-A) were evaluated for their ability to induce HIVgag-specific immune responses.

Figure 16A:
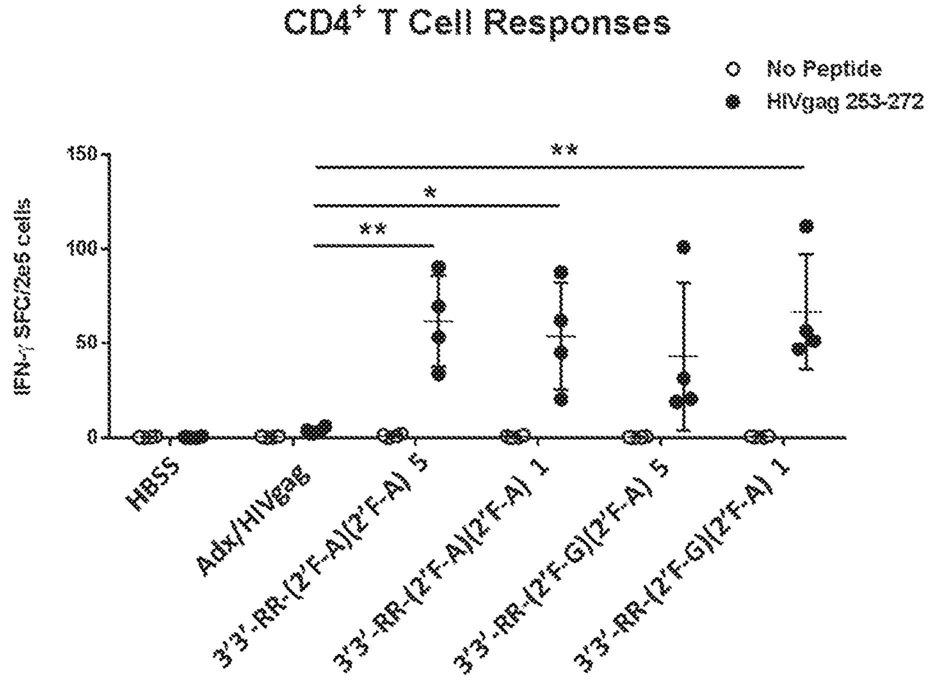
FIG. 16A-B depicts the HIVgag p55 antigen specific CD4+ T-cell response (15A) or $CD8^+$ T cell response (15B) in mice injected with CDN and HIVgag p55 protein.
Figure 16B:
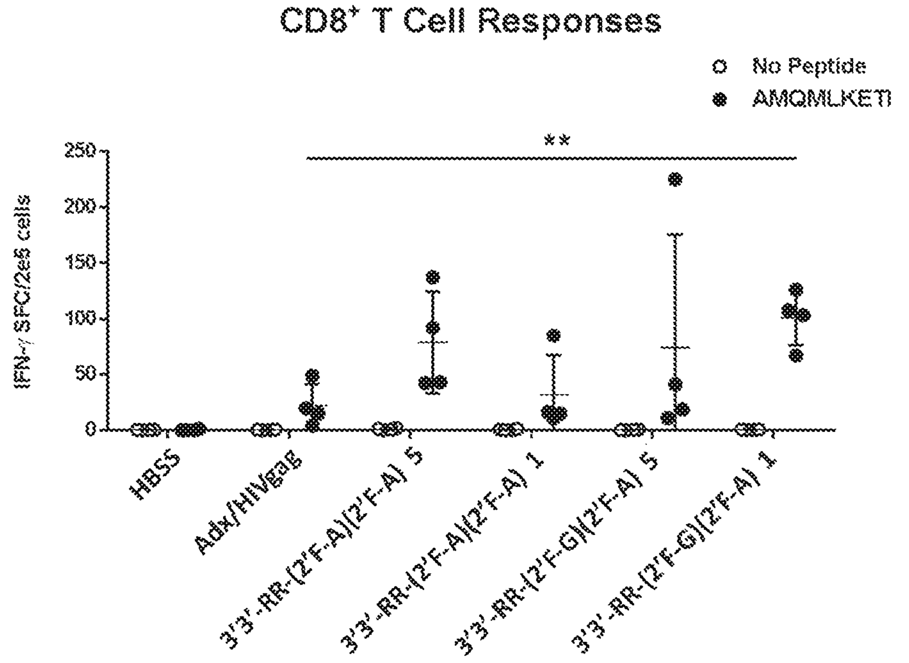

As shown in FIG. 16A, both the 3',3'-RR-(2'F-A)(2'F-A) and 3',3'-RR-(2'F-G)(2'F-A) molecules were capable of eliciting significant $CD4^+$ T cell responses against HIVgag p55, as compared to the no CDN AddaVax+protein control group (*P<0.05.  P<0.01, student's t-test). As shown in FIG. 16**B, the 3',3'-RR-(2'F-G)(2'F-A) compound also elicited significant $CD8^+$ T cell responses against HIVgag p55, as compared to the no CDN control group (*P<0.05, student's t-test). These data demonstrate the ability of the fluorinated compounds to act as potent adjuvants in a vaccine setting against a relevant immunogen.

Example 18: Mono- and Di-F-CDN Binding to hSTING WT

Binding of the mono- and di-F CDN compounds was assessed using Surface Plasmon Resononce to determine a binding constant. An *E. coli* expression construct (human-STING[E149-S379]H232R) was prepared harboring the protein sequence:

```
                                             (SEQ ID NO: 17)
MSGLNDIFEAQKIEWHEEKGNFNVAHGLAWSYYIGYLRLILPELQARIRT

YNQHYNNLLRGAVSQRLYILLPLDCGVPDNLSMADPNIRFLDKLPQQTGD

RAGIKDRVYSNSIYELLENGQRAGTCVLEYATPLQTLFAMSQYSQAGFSR

EDRLEQAKLFCRTLEDILADAPESQNNCRLIAYQEPADDSSFSLSQEVLR

HLRQEEKEEVTVGSLKTSAVPSTSTMSQEPELLISGMEKPLPLRTDFSLE

HHHHHH
```

human-STING[E149-S379]H232R expression in *E. coli* was induced at 18° C. and the protein was subsequently purified using both nickel affinity chromatography and size-exclusion chromatography. Aliquots were prepared and stored at −80° C. in 30 mM Tris pH 7.5/100 mM NaCl/10% glycerol.

N-terminal avi-tagged human-STING(E149-S379) H232R protein was immobilized (~2500 RUs) on a streptavidin chip at 15° C. in a Biacore T200 (GE Healthcare). Titrations of cyclic dinucleotides (CDNs as indicated in Table 6) in 30 mM Tris pH 7.5/50 mM NaCL/0.005% Tween 20/1 mM DTT/2% DMSO, were profiled (30 μLs/min, 180 seconds for sample contact/120 seconds for dissociation) against hSTING at 15° C. Kinetic analysis of the data was performed using Biacore T200 Evaluation software. Steady-state analysis of the data was performed using Graphpad Prism 6.0 software, using one site-specific binding algorithm (Equation is Y=Bmax*X/(Kd+X)). Kd (units of microMolar) are reported in the following Table 6.

TABLE 6

Kd for mono- and di-F CDNs measured by Surface Plasmon Resonance.

| Example/Compound | Compound name | Kd (μM) |
|---|---|---|
| Reference | 3'3'-(2'F-A)(2'F-A) | 0.011 |
| Example 1 Compound 6 | 3'3'-RR-(2'F-A)(2'F-A) | 0.001 |
| Example 1 Compound 6a | 3'3'-RS-(2'F-A)(2'F-A) | 0.029 |
| Example 4 Compound 22 | 3'3'-RR-(A)(2'F-A) | 1.282 |
| Example 2 Compound 14 | 3'3'-RR-(2'F-G)(2'F-A) | 0.093 |
| Example 2 Compound 14a | 3'3'-RS-(2'F-G)(2'F-A) | 0.098 |
| Example 5 Compound 23 | 3'3'-RR-(2'F-G)(A) | 0.311 |
| Example 6 Compound 24 | 3'3'-RR-(G)(2'F-A) | 0.037 |
| Example 6 Compound 24a | 3'3'-RS-(G)(2'F-A) | 0.684 |

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A compound having the structure:

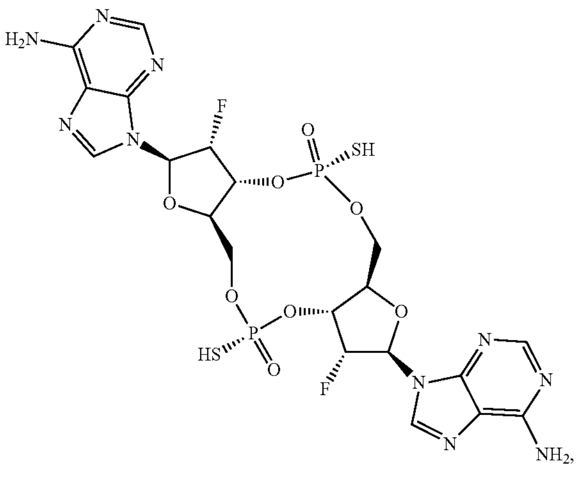 [SMILES: Nc1ncnc2c1ncn2[C@@H]1O[C@@H]2CO[P@@](=O)(S)O[C@H]3[C@@H](F)[C@H](n4cnc5c(N)ncnc54)O[C@@H]3CO[P@@](=O)(S)O[C@H]2[C@H]1F]

or a pharmaceutically acceptable salt, pharmaceutically acceptable solvate or pharmaceutically acceptable hydrate thereof.

2. The compound according to claim 1, wherein the compound is the sodium, potassium, calcium, magnesium, zinc, aluminum, ammonium, diethylamine, olamine, benzathine, benethamine, tromethamine (2-amino-2-(hydroxymethyl)propane-1,3-diol), morpholine, epolamine, piperidine, picoline, dicyclohexylamine, N,N'-dibenzylethylenediamine, 2-hydroxyethylamine, tri-(2-hydroxyethyl)amine, chloroprocaine, choline, deanol, imidazole, diethanolamine, ethylenediamine, meglumine (N-methylglucamine), procaine, dibenzylpiperidine, dehydroabietylamine, glucamine, collidine, quinine, quinolone, erbumine, lysine or arginine salt thereof.

3. The compound according to claim 1, wherein the compound is the sodium salt thereof.

4. A pharmaceutical composition comprising one or more compounds according to claim 1 and a pharmaceutically acceptable excipient.

5. A pharmaceutical composition comprising one or more compounds according to claim 1, another therapeutic agent and a pharmaceutically acceptable excipient.

6. A method for treating an individual suffering from cancer, comprising:

non-parenterally or parenterally administering to the individual an effective amount of the compound according to claim 1.

7. The method according to claim 6, wherein the method further comprises administering one or more additional cancer therapies to the individual, wherein the one or more additional cancer therapies is selected from the group consisting of radiation therapy, surgery, a chemotherapy, or an immunotherapy.

8. A method of treating a disease in an individual, comprising: administering to the individual in need thereof i) an effective amount of the compound according to claim 1; and ii) an effective amount of one or more therapeutic antibodies that induce antibody-dependent cellular cytotoxicity, wherein the disease is selected from the group consisting of a cancer, acute rejection of an organ transplant, Type I diabetes mellitus, rheumatoid arthritis, psoriasis, Crohn's disease, restenosis and allergic asthma.

9. A method according to claim 7, wherein the one or more additional cancer therapies comprises administering a checkpoint inhibitor.

10. A method according to claim 9, wherein the immune checkpoint inhibitor is selected from the group consisting of a CTLA-4 pathway antagonist, a PD-1 pathway antagonist, a Tim-3 pathway antagonist, a Vista pathway antagonist, a BTLA pathway antagonist, a LAG-3 pathway antagonist, and a TIGIT pathway antagonist.

* * * * *

SEQUENCE LISTING

```
<160> NUMBER OF SEQ ID NOS: 17

<210> SEQ ID NO 1
<211> LENGTH: 379
<212> TYPE: PRT
<213> ORGANISM: Homo sapiens

<400> SEQUENCE: 1

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
```

-continued

```
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser
    370                 375


<210> SEQ ID NO 2
<211> LENGTH: 440
<212> TYPE: PRT
<213> ORGANISM: Artificial Sequence
<220> FEATURE:
<223> OTHER INFORMATION: Synthetic: heavy chain amino acid sequence of
      nivolumab

<400> SEQUENCE: 2

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45
```

```
Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440
```

<210> SEQ ID NO 3
<211> LENGTH: 214
<212> TYPE: PRT

<213> ORGANISM: Artificial Sequence
<220> FEATURE:
<223> OTHER INFORMATION: Synthetic: light chain amino acid sequence of nivolumab

<400> SEQUENCE: 3

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 4
<211> LENGTH: 447
<212> TYPE: PRT
<213> ORGANISM: Artificial Sequence
<220> FEATURE:
<223> OTHER INFORMATION: Synthetic: heavy chain amino acid sequences of pembrolizumab

<400> SEQUENCE: 4

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
```

```
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 5
<211> LENGTH: 218
<212> TYPE: PRT
<213> ORGANISM: Artificial Sequence
<220> FEATURE:
<223> OTHER INFORMATION: Synthetic: light chain amino acid sequences of
      pembrolizumab

<400> SEQUENCE: 5

Glu Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 6
<211> LENGTH: 118
<212> TYPE: PRT
<213> ORGANISM: Artificial Sequence
<220> FEATURE:
<223> OTHER INFORMATION: Synthetic: heavy chain amino acid sequence

<400> SEQUENCE: 6

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Ile Lys Leu Gly Thr Val Thr Thr Val Asp Tyr Trp Gly Gln Gly Thr
            100                 105                 110

Leu Val Thr Val Ser Ser
        115
```

<210> SEQ ID NO 7
<211> LENGTH: 110
<212> TYPE: PRT
<213> ORGANISM: Artificial Sequence
<220> FEATURE:

-continued

<223> OTHER INFORMATION: Synthetic: light chain amino acid sequence

<400> SEQUENCE: 7

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110
```

<210> SEQ ID NO 8
<211> LENGTH: 37
<212> TYPE: DNA
<213> ORGANISM: Artificial Sequence
<220> FEATURE:
<223> OTHER INFORMATION: Synthetic: forward primer

<400> SEQUENCE: 8
tacttccaat ccaatgcagc cccagctgag atctctg 37

<210> SEQ ID NO 9
<211> LENGTH: 46
<212> TYPE: DNA
<213> ORGANISM: Artificial Sequence
<220> FEATURE:
<223> OTHER INFORMATION: Synthetic: reverse primer

<400> SEQUENCE: 9
ttatccactt ccaatgttat tattatcaag agaaatccgt gcggag 46

<210> SEQ ID NO 10
<211> LENGTH: 19
<212> TYPE: DNA
<213> ORGANISM: Artificial Sequence
<220> FEATURE:
<223> OTHER INFORMATION: Synthetic: hSTING exon3F

<400> SEQUENCE: 10
gctgagacag gagctttgg 19

<210> SEQ ID NO 11
<211> LENGTH: 19
<212> TYPE: DNA
<213> ORGANISM: Artificial Sequence
<220> FEATURE:
<223> OTHER INFORMATION: Synthetic: hSTING exon3R

<400> SEQUENCE: 11
agccagagag gttcaagga 19

<210> SEQ ID NO 12
<211> LENGTH: 20
<212> TYPE: DNA
<213> ORGANISM: Artificial Sequence
<220> FEATURE:

<223> OTHER INFORMATION: Synthetic: hSTING exon6F

<400> SEQUENCE: 12
ggccaatgac ctgggtctca 20

<210> SEQ ID NO 13
<211> LENGTH: 20
<212> TYPE: DNA
<213> ORGANISM: Artificial Sequence
<220> FEATURE:
<223> OTHER INFORMATION: Synthetic: hSTING exon6R

<400> SEQUENCE: 13
cacccagaat agcatccagc 20

<210> SEQ ID NO 14
<211> LENGTH: 21
<212> TYPE: DNA
<213> ORGANISM: Artificial Sequence
<220> FEATURE:
<223> OTHER INFORMATION: Synthetic: hSTING exon7F

<400> SEQUENCE: 14
tcagagttgg gtatcagagg c 21

<210> SEQ ID NO 15
<211> LENGTH: 21
<212> TYPE: DNA
<213> ORGANISM: Artificial Sequence
<220> FEATURE:
<223> OTHER INFORMATION: Synthetic: hSTING exon7R

<400> SEQUENCE: 15
atctggtgtg ctgggaagag g 21

<210> SEQ ID NO 16
<211> LENGTH: 8
<212> TYPE: PRT
<213> ORGANISM: Artificial Sequence
<220> FEATURE:
<223> OTHER INFORMATION: Synthetic peptide

<400> SEQUENCE: 16

```
Ser Ile Tyr Arg Tyr Tyr Gly Leu
1               5
```

<210> SEQ ID NO 17
<211> LENGTH: 256
<212> TYPE: PRT
<213> ORGANISM: Artificial Sequence
<220> FEATURE:
<223> OTHER INFORMATION: Synthetic: E.coli expression construct

<400> SEQUENCE: 17

```
Met Ser Gly Leu Asn Asp Ile Phe Glu Ala Gln Lys Ile Glu Trp His
1               5                   10                  15

Glu Glu Lys Gly Asn Phe Asn Val Ala His Gly Leu Ala Trp Ser Tyr
            20                  25                  30

Tyr Ile Gly Tyr Leu Arg Leu Ile Leu Pro Glu Leu Gln Ala Arg Ile
        35                  40                  45

Arg Thr Tyr Asn Gln His Tyr Asn Asn Leu Leu Arg Gly Ala Val Ser
    50                  55                  60

Gln Arg Leu Tyr Ile Leu Leu Pro Leu Asp Cys Gly Val Pro Asp Asn
65                  70                  75                  80
```

-continued

```
Leu Ser Met Ala Asp Pro Asn Ile Arg Phe Leu Asp Lys Leu Pro Gln
                85                  90                  95

Gln Thr Gly Asp Arg Ala Gly Ile Lys Asp Arg Val Tyr Ser Asn Ser
            100                 105                 110

Ile Tyr Glu Leu Leu Glu Asn Gly Gln Arg Ala Gly Thr Cys Val Leu
        115                 120                 125

Glu Tyr Ala Thr Pro Leu Gln Thr Leu Phe Ala Met Ser Gln Tyr Ser
    130                 135                 140

Gln Ala Gly Phe Ser Arg Glu Asp Arg Leu Glu Gln Ala Lys Leu Phe
145                 150                 155                 160

Cys Arg Thr Leu Glu Asp Ile Leu Ala Asp Ala Pro Glu Ser Gln Asn
                165                 170                 175

Asn Cys Arg Leu Ile Ala Tyr Gln Glu Pro Ala Asp Asp Ser Ser Phe
            180                 185                 190

Ser Leu Ser Gln Glu Val Leu Arg His Leu Arg Gln Glu Glu Lys Glu
        195                 200                 205

Glu Val Thr Val Gly Ser Leu Lys Thr Ser Ala Val Pro Ser Thr Ser
    210                 215                 220

Thr Met Ser Gln Glu Pro Glu Leu Leu Ile Ser Gly Met Glu Lys Pro
225                 230                 235                 240

Leu Pro Leu Arg Thr Asp Phe Ser Leu Glu His His His His His His
                245                 250                 255
```